US009688756B2

(12) United States Patent
Sun et al.

(10) Patent No.: US 9,688,756 B2
(45) Date of Patent: *Jun. 27, 2017

(54) VARIANT FC-POLYPEPTIDES WITH ENHANCED BINDING TO THE NEONATAL FC RECEPTOR

(71) Applicant: Amgen Inc., Thousand Oaks, CA (US)

(72) Inventors: Jeonghoon Sun, San Diego, CA (US); Seog Joon Han, Simi Valley, CA (US); Susie M Harris, Newbury Park, CA (US); Randal R Ketchem, Snohomish, WA (US); Ji Lu, Thousand Oaks, CA (US); Mark L Michaels, Encino, CA (US); Marc W Retter, Simi Valley, CA (US); Mei-Mei Tsai, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 62 days.

This patent is subject to a terminal disclaimer.

(21) Appl. No.: 14/367,183

(22) PCT Filed: Dec. 17, 2012

(86) PCT No.: PCT/US2012/070146
§ 371 (c)(1),
(2) Date: Jun. 19, 2014

(87) PCT Pub. No.: WO2013/096221
PCT Pub. Date: Jun. 27, 2013

(65) Prior Publication Data
US 2014/0356358 A1 Dec. 4, 2014

Related U.S. Application Data

(60) Provisional application No. 61/578,780, filed on Dec. 21, 2011, provisional application No. 61/585,993, filed on Jan. 12, 2012, provisional application No. 61/729,050, filed on Nov. 21, 2012.

(51) Int. Cl.
C07K 16/00 (2006.01)
C07K 16/28 (2006.01)
G01N 33/68 (2006.01)

(52) U.S. Cl.
CPC .............. *C07K 16/28* (2013.01); *C07K 16/00* (2013.01); *G01N 33/6857* (2013.01); *C07K 2317/30* (2013.01); *C07K 2317/524* (2013.01); *C07K 2317/526* (2013.01); *C07K 2317/72* (2013.01); *C07K 2317/90* (2013.01); *C07K 2317/94* (2013.01); *G01N 2333/705* (2013.01)

(58) Field of Classification Search
CPC .................. C07K 16/468; C07K 16/00; C07K 2317/90–2317/94; C07K 2317/70–2317/72; C07K 2317/52; C07K 2316/52; C07K 2319/30; C07K 7/04; C07K 7/08
See application file for complete search history.

(56) References Cited

U.S. PATENT DOCUMENTS

| 7,695,936 | B2 | 4/2010 | Carter et al. | |
|---|---|---|---|---|
| 7,820,790 | B2 | 10/2010 | Bakker et al. | |
| 9,045,528 | B2* | 6/2015 | Ruker | C07K 16/00 |
| 2003/0078385 | A1 | 4/2003 | Arathoon et al. | |
| 2006/0173170 | A1 | 8/2006 | Chamberlain et al. | |
| 2007/0105199 | A1 | 5/2007 | Yan et al. | |
| 2007/0135620 | A1* | 6/2007 | Chamberlain | C07K 16/32 530/387.3 |
| 2007/0148164 | A1 | 6/2007 | Farrington et al. | |
| 2008/0181887 | A1 | 7/2008 | Dall-Acqua et al. | |
| 2009/0311253 | A1 | 12/2009 | Ghayur et al. | |
| 2010/0189718 | A1* | 7/2010 | Dall'Acqua | A61K 47/48507 424/133.1 |
| 2016/0115241 | A1* | 4/2016 | Yan | C07K 16/2803 424/136.1 |
| 2016/0145340 | A1* | 5/2016 | Borges | C07K 16/28 424/136.1 |

FOREIGN PATENT DOCUMENTS

| WO | WO2004/029207 A2 * | 4/2004 |
|---|---|---|
| WO | 2005-047327 A2 | 5/2005 |
| WO | 2006-036834 A3 | 4/2006 |
| WO | 2008-119096 A1 | 10/2008 |
| WO | WO2008/119096 A1 * | 10/2008 |

(Continued)

OTHER PUBLICATIONS

Wozniak-Knopp et al. Protein Eng Design & Selection, 2010; 23(4):289-97.*
Carayannopoulos, L. and Capra, J., "Immunoglobulins Structure and Function," Fundamental Immunology, 3$^{rd}$ ed. Paul, ed, Raven Press, pp. 282-286, 1993.
Cutler P, "Protein Purification Protocols" (2$^{nd}$ Ed.) in Methods in Molecular Biology; vol. 244, p. 484, Humana Press 2004.
Desmyter, A. et al., "Antigen specificity and high affinity binding provided by one single loop of a camel single-domain antibody," Journal of Biological Chemistry, 276(28): 26285-90; Jul. 2001.
Durocher, Y. et al., "High-level and high-throughput recombinant protein production by transfection of suspension-growing human 293-EBNA1 cells," Nucleic Acids Research; 30(2): e9-e9, 2002 Oxford University Press.

(Continued)

Primary Examiner — Jessica H Roark
(74) Attorney, Agent, or Firm — Raymond M. Doss

(57) ABSTRACT

Described herein are variant Fc-fragments that contain an insertion within or adjacent to a loop that bind to the neonatal Fc receptor (FcRn) with higher affinity and/or higher binding activity at pH 5-6 and approximately the same or lower affinity at a physiologic pH as compared to a control Fc-fragment, that is, little or no binding activity at a physiologic pH. Also described are variant Fc-polypeptides that comprise these variant Fc-fragments. Further described are methods of making and identifying such Fc-fragments and methods for making and using such Fc-polypeptides.

16 Claims, 10 Drawing Sheets

(56) References Cited

FOREIGN PATENT DOCUMENTS

WO 2009-058492 A2 5/2009
WO 2009-089004 A1 7/2009

OTHER PUBLICATIONS

Edelman, G.M. et al., "The covalent structure of an entire γG immunoglobulin molecule," Proceedings of the National Academy of Sciences of the United States, 63(1): 7885, May 1969.
Hunkapiller, T. and Hood, L, "Diversity of the immunoglobulin gene superfamily," Advances in Immunology; 44: 1-63, 1989 Academic Press.
Karatan, E. et al., "Molecular Recognition Properties of FN3 Monobodies that Bind the Src SH3 Domain," Chemistry & Biology, 11(6): 835-844, Jun. 2004.
Muyldermans, S., "Single Domain camel antibodies: current status," J. Biotechnology; Reviews in Molecular Biotechnology, 74: 277-302, 2001.
Nord, K. et al., "A combinatorial library of an α-helical bacterial receptor domain," Protein Engineering, 8(6): 601-608, 1995.
Nuttall, S. et al., "Design and expression of soluble CTLA-4 variable domain as a scaffold for the display of functional polypeptides," Protein Science, 36(2): 217-227, 1999.
Streltsov, V.A. et al., "Structure of a shark IgNAR antibody variable domain and modeling of an early-developmental isotype," Protein Science, 14(11): 2901-2909; Nov. 2005.
Thomas, M. et al, "Full deacylation of polyethylenimine dramatically boosts its gene delivery efficiency and specificity to mouse lung," Proc. of the National Academy of Sciences of the USA, 102(16): 5679-5684, 2005.
Williams, A.F. And Barclay, A.N., "The immunoglobulin superfamily—domains for cell surface recognition," Annual Review of Immunology, vol. 6; pp. 381-405, 1988.
Yeung et al.., "Engineering human IgG1 affinity to human neonatal Fc receptor: impact of affinity improvement on pharmacokinetics in primates," Journal of Immunology, 182 (12): 7663-7671, Jun. 2009.
Koide, A. et al., "The Fibronectin type III domain as a scaffold for novel binding proteins," Journal of Molecular Biology, 284(4): 1141-1151, Dec. 1998.
Kabat et al., *Sequences of Proteins of Immunological Interest*, Public Health Service, N.I.H., Bethesda, MD, 1991 (eBOOK) https://books.google.com/books?id=3jMvZYW2ZtwC&1pg=PA1 &ots=PeNAPXEr3x&lr&pg=PA2164#v=onepage&q&f=false.
Grossman, S. and Turner, J. *Mathematics for the Biological Sciences*, Macmillan Publishing Co., Inc. NY; Chapter 2, Section 2.9, pp. 97-104, Jul. 1974.
Burmeister, W. et al., *Crystal Structure of the Complex of Rate Neonatal Fc Receptor with Fc*, Nature, 372: 379-383, Nov. 1994.
Martin, W. L. et al., *Crystal Structure at 2.8 Å of an FcRn,/ Heterodimeric Fc Complex: Mechanism of pH-Dependent Binding*, Molecular Cell, 7: 867-877, Apr. 2001.

* cited by examiner

```
                               L1
EPKSCDKTHTCPPCPAPELLGGPSVFLFPPKPKDTLMISRTPE          43
                                         L4
VTCVVVDVSHEDPEVKFNWYVDGVEVHNAKTKPREEQYNSTYR          86
       L2A, L2B
VVSVLTVLHQDWLNGKEYKCKVSNKALPAPIEKTISKAKGQPR         129
             L6A  L6B                       L5
EPQVYTLPPSRDELTKNQVSLTCLVKGFYPSDIAVEWESNGQP         172
ENNYKTTPPVLDSDGSFFLYSKLTVDKSRWQQGNVFSCSVMHE         215
    L3
ALHNHYTQKSLSLSPGK(SEQ ID NO:1)    232
```

L1:  L*MISR*T (SEQ ID NO:549) → L(19R)$_6$T (SEQ ID NO:550)
L2A: TV*L*HQDWL (SEQ ID NO:551) → T(19R)$_6$HQDWL(SEQ ID NO:552)
L2B: TV*L*HQDWL (SEQ ID NO:551) → TGGC(19R)$_6$CGGHQDWL (SEQ ID NO:553)
L3:  MH*EALH*MHY(SEQ ID NO:554) → MH(19R)$_5$H(19R)$_1$HY (SEQ ID NO:555)
L4:  EVHN¦A (SEQ ID NO:556) → EVHNGGC(19R)$_6$CGGA (SEQ ID NO:557)
L5:  N¦GQPEN (SEQ ID NO:558) → NGGC(19R)$_6$CGGGQPEN (SEQ ID NO:559)
L6A: DEL¦TKNQ (SEQ ID NO:560) → DELGGC(20R)$_8$CGGTKNQ (SEQ ID NO:561)
L6B: DEL¦TKNQ (SEQ ID NO:560) → DELGGC(19R)$_8$CGGTKNQ (SEQ ID NO:562)

Figure 2

```
                              385  390
                              |    |
Wild type sequence:      WESNGQPENNYKT (SEQ ID NO:563)

Original variant 5-1:    WESNGGCGMPIEFCGGGQPENNYKT
                         (SEQ ID NO:564)

Variant 5-1-1:           WEGGCGMPIEFCGGSNGQPENNYKT
                         (SEQ ID NO:565)

Variant 5-1-2:           WESGGCGMPIEFCGGNGQPENNYKT
                         (SEQ ID NO:566)

Variant 5-1-3:           WESNGGCGMPIEFCGGQPENNYKT
                         (SEQ ID NO:567)

Variant 5-1-4:           WESNGQGGCGMPIEFCGGPENNYKT
                         (SEQ ID NO:568)

Variant 5-1-5:           WESNGQPGGCGMPIEFCGGENNYKT
                         (SEQ ID NO:569)

Variant 5-1-6:           WESNGQPEGGCGMPIEFCGGNNYKT
                         (SEQ ID NO:570)

Variant 5-1-7:           WESNGQPENGGCGMPIEFCGGNYKT
                         (SEQ ID NO:571)

Variant 5-1-8:           WESNGQPENNGGCGMPIEFCGGYKT
                         (SEQ ID NO:572)

Variant 5-1-9:           WESGGCGMPIEFCGGPENNYKT
                         (SEQ ID NO:573)

Variant 5-1-10:          WESGGGCGMPIEFCGGGPENNYKT
                         (SEQ ID NO:574)
```

Figure 5

SEQUENCE LISTING

<160> NUMBER OF SEQ ID NOS: 575

<210> SEQ ID NO 1
<211> LENGTH: 232
<212> TYPE: PRT
<213> ORGANISM: Homo sapiens

<400> SEQUENCE: 1

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro

```
                20                  25                  30
Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 2
<211> LENGTH: 699
<212> TYPE: DNA
<213> ORGANISM: Homo sapiens

<400> SEQUENCE: 2
gagcccaaat cttgtgacaa aactcacaca tgcccaccgt gcccagcacc tgaactcctg      60
gggggaccgt cagtcttcct cttccccca aaacccaagg acaccctcat gatctcccgg     120
acccctgagg tcacatgcgt ggtggtggac gtgagccacg aagaccctga ggtcaagttc     180
aactggtacg tggacggcgt ggaggtgcat aatgccaaga caaagccgcg ggaggagcag     240
tacaacagca cgtaccgtgt ggtcagcgtc ctcaccgtcc tgcaccagga ctggctgaat     300
ggcaaggagt acaagtgcaa ggtctccaac aaagccctcc cagcccccat cgagaaaacc     360
atctccaaag ccaagggca gccccgagag ccacaggtgt acaccctgcc cccatcccgg     420
gatgagctga ccaagaacca ggtcagcctg acctgcctgg tcaaaggctt ctatcccagc     480
gacatcgccg tggagtggga gagcaatggg cagccggaga caactacaa gaccacgcct     540 cccgtgctgg actccgacgg ctccttcttc ctctacagca agctcaccgt ggacaagagc     600
aggtggcagc aggggaacgt cttctcatgc tccgtgatgc atgaggctct gcacaaccac     660
tacacgcaga gagcctctc cctgtctccg ggtaaatga                            699

<210> SEQ ID NO 3
<211> LENGTH: 228
<212> TYPE: PRT
<213> ORGANISM: Homo sapiens
```

<400> SEQUENCE: 3

```
Glu Arg Lys Cys Cys Val Glu Cys Pro Pro Cys Pro Ala Pro Pro Val
 1               5                  10                 15
Ala Gly Pro Ser Val Phe Leu Phe Pro Pro Lys Pro Lys Asp Thr Leu
             20                  25                  30
Met Ile Ser Arg Thr Pro Glu Val Thr Cys Val Val Val Asp Val Ser
         35                  40                  45
His Glu Asp Pro Glu Val Gln Phe Asn Trp Tyr Val Asp Gly Met Glu
     50                  55                  60
Val His Asn Ala Lys Thr Lys Pro Arg Glu Glu Gln Phe Asn Ser Thr
 65                  70                  75                  80
Phe Arg Val Val Ser Val Leu Thr Val Val His Gln Asp Trp Leu Asn
                 85                  90                  95
Gly Lys Glu Tyr Lys Cys Lys Val Ser Asn Lys Gly Leu Pro Ala Pro
             100                 105                 110
Ile Glu Lys Thr Ile Ser Lys Thr Lys Gly Gln Pro Arg Glu Pro Gln
         115                 120                 125
Val Tyr Thr Leu Pro Pro Ser Arg Glu Glu Met Thr Lys Asn Gln Val
     130                 135                 140
Ser Leu Thr Cys Leu Val Lys Gly Phe Tyr Pro Ser Asp Ile Ala Val
145                 150                 155                 160
Glu Trp Glu Ser Asn Gly Gln Pro Glu Asn Asn Tyr Lys Thr Thr Pro
                 165                 170                 175
Pro Met Leu Asp Ser Asp Gly Ser Phe Phe Leu Tyr Ser Lys Leu Thr
             180                 185                 190
Val Asp Lys Ser Arg Trp Gln Gln Gly Asn Val Phe Ser Cys Ser Val
         195                 200                 205
Met His Glu Ala Leu His Asn His Tyr Thr Gln Lys Ser Leu Ser Leu
     210                 215                 220
Ser Pro Gly Lys
225
```

<210> SEQ ID NO 4
<211> LENGTH: 687
<212> TYPE: DNA
<213> ORGANISM: Homo sapiens

<400> SEQUENCE: 4

```
gagcgcaaat gttgtgtcga gtgcccaccg tgcccagcac cacctgtggc aggaccgtca    60
gtcttcctct tccccccaaa acccaaggac accctcatga tctcccggac ccctgaggtc   120
acgtgcgtgg tggtggacgt gagccacgaa gaccccgagg tccagttcaa ctggtacgtg   180
gacggcatgg aggtgcataa tgccaagaca aagccacggg aggagcagtt caacagcacg   240
ttccgtgtgg tcagcgtcct caccgtcgtg caccaggact ggctgaacgg caaggagtac   300
aagtgcaagg tctccaacaa aggcctccca gcccccatcg agaaaaccat ctccaaaacc   360
aaagggcagc ccgagaacc acaggtgtac accctgcccc catcccggga ggagatgacc   420
aagaaccagg tcagcctgac ctgcctggtc aaaggcttct accccagcga catcgccgtg   480
gagtgggaga gcaatgggca gccggagaac aactacaaga ccacctcc atgctggac    540
tccgacggct ccttcttcct ctacagcaag ctcaccgtgg acaagagcag gtggcagcag   600
gggaacgtct tctcatgctc cgtgatgcat gaggctctgc acaaccacta cacacagaag   660
agcctctccc tgtctccggg taaatga                                       687
```

<210> SEQ ID NO 5
<211> LENGTH: 279
<212> TYPE: PRT
<213> ORGANISM: Homo sapiens

<400> SEQUENCE: 5

```
Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Ala Pro
    50                  55                  60

Glu Leu Leu Gly Gly Pro Ser Val Phe Leu Phe Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Tyr
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
    210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
        275
```

<210> SEQ ID NO 6
<211> LENGTH: 840
<212> TYPE: DNA
<213> ORGANISM: Homo sapiens

<400> SEQUENCE: 6

```
gagctcaaaa ccccacttgg tgacacaact cacacatgcc cacggtgccc agagcccaaa      60
tcttgtgaca cacctccccc gtgcccacgg tgcccagagc ccaaatcttg tgacacacct     120
cccccatgcc cacggtgccc agagcccaaa tcttgtgaca cacctccccc gtgcccaagg     180
tgcccagcac ctgaactcct gggaggaccg tcagtcttcc tcttcccccc aaaacccaag     240
gataccctta tgatttcccg gacccctgag gtcacgtgcg tggtggtgga cgtgagccac     300
```

```
gaagacccca aggtccagtt caagtggtac gtggacggcg tggaggtgca taatgccaag      360
acaaagccgc gggaggagca gtacaacagc acgttccgtg tggtcagcgt cctcaccgtc      420
ctgcaccagg actggctgaa cggcaaggag tacaagtgca aggtctccaa caaagccctc      480
ccagccccca tcgagaaaac catctccaaa accaaggac agccccgaga ccacaggtg       540 tacaccctgc ccccatcccg ggaggagatg accaagaacc aggtcagcct gacctgcctg      600
gtcaaaggct tctaccccag cgacatcgcc gtggagtggg agagcagcgg gcagccggag      660
aacaactaca acaccacgcc tcccatgctg gactccgacg gctccttctt cctctacagc      720
aagctcaccg tggacaagag caggtggcag caggggaaca tcttctcatg ctccgtgatg      780
catgaggctc tgcacaaccg cttcacgcag aagagcctct ccctgtctcc gggtaaatga      840
```

<210> SEQ ID NO 7
<211> LENGTH: 229
<212> TYPE: PRT
<213> ORGANISM: Homo sapiens

<400> SEQUENCE: 7

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 8
<211> LENGTH: 690
<212> TYPE: DNA
<213> ORGANISM: Homo sapiens

<400> SEQUENCE: 8

```
gagtccaaat atggtccccc atgcccatca tgcccagcac ctgagttcct ggggggacca    60
tcagtcttcc tgttcccccc aaaacccaag gacactctca tgatctcccg gacccctgag   120
gtcacgtgcg tggtggtgga cgtgagccag gaagaccccg aggtccagtt caactggtac   180
gtggatggcg tggaggtgca taatgccaag acaaagccgc gggaggagca gttcaacagc   240
acgtaccgtg tggtcagcgt cctcaccgtc ctgcaccagg actggctgaa cggcaaggag   300
tacaagtgca aggtctccaa caaaggcctc ccgtcctcca tcgagaaaac catctccaaa   360
gccaaagggc agccccgaga gccacaggtg tacaccctgc ccccatccca ggaggagatg   420
accaagaacc aggtcagcct gacctgcctg gtcaaaggct tctacccag cgacatcgcc   480 gtggagtggg agagcaatgg gcagccggag aacaactaca agaccacgcc tcccgtgctg   540
gactccgacg gctccttctt cctctacagc aggctaaccg tggacaagag caggtggcag   600 gagggggaatg tcttctcatg ctccgtgatg catgaggctc tgcacaacca ctacacacag   660
aagagcctct ccctgtctct gggtaaatga                                    690

<210> SEQ ID NO 9
<211> LENGTH: 267
<212> TYPE: PRT
<213> ORGANISM: Homo sapiens

<400> SEQUENCE: 9

Ala Glu Ser His Leu Ser Leu Leu Tyr His Leu Thr Ala Val Ser Ser
1               5                   10                  15

Pro Ala Pro Gly Thr Pro Ala Phe Trp Val Ser Gly Trp Leu Gly Pro
                20                  25                  30

Gln Gln Tyr Leu Ser Tyr Asn Ser Leu Arg Gly Glu Ala Glu Pro Cys
            35                  40                  45

Gly Ala Trp Val Trp Glu Asn Gln Val Ser Trp Tyr Trp Glu Lys Glu
        50                  55                  60

Thr Thr Asp Leu Arg Ile Lys Glu Lys Leu Phe Leu Glu Ala Phe Lys
65                  70                  75                  80

Ala Leu Gly Gly Lys Gly Pro Tyr Thr Leu Gln Gly Leu Leu Gly Cys
                85                  90                  95

Glu Leu Gly Pro Asp Asn Thr Ser Val Pro Thr Ala Lys Phe Ala Leu
                100                 105                 110

Asn Gly Glu Glu Phe Met Asn Phe Asp Leu Lys Gln Gly Thr Trp Gly
            115                 120                 125

Gly Asp Trp Pro Glu Ala Leu Ala Ile Ser Gln Arg Trp Gln Gln Gln
        130                 135                 140

Asp Lys Ala Ala Asn Lys Glu Leu Thr Phe Leu Leu Phe Ser Cys Pro
145                 150                 155                 160

His Arg Leu Arg Glu His Leu Glu Arg Gly Arg Gly Asn Leu Glu Trp
                165                 170                 175

Lys Glu Pro Pro Ser Met Arg Leu Lys Ala Arg Pro Ser Ser Pro Gly
            180                 185                 190

Phe Ser Val Leu Thr Cys Ser Ala Phe Ser Phe Tyr Pro Pro Glu Leu
        195                 200                 205

Gln Leu Arg Phe Leu Arg Asn Gly Leu Ala Ala Gly Thr Gly Gln Gly
    210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His
```

Ala Gly Leu Ala Gln Pro Leu Arg Val Glu Leu
          260                  265

<210> SEQ ID NO 10
<211> LENGTH: 99
<212> TYPE: PRT
<213> ORGANISM: Homo sapiens

<400> SEQUENCE: 10

Ile Gln Arg Thr Pro Lys Ile Gln Val Tyr Ser Arg His Pro Ala Glu
1               5                  10               15

Asn Gly Lys Ser Asn Phe Leu Asn Cys Tyr Val Ser Gly Phe His Pro
           20                  25               30

Ser Asp Ile Glu Val Asp Leu Leu Lys Asn Gly Glu Arg Ile Glu Lys
         35                 40               45

Val Glu His Ser Asp Leu Ser Phe Ser Lys Asp Trp Ser Phe Tyr Leu
50                  55                 60

Leu Tyr Tyr Thr Glu Phe Thr Pro Thr Glu Lys Asp Glu Tyr Ala Cys
65                  70                75               80

Arg Val Asn His Val Thr Leu Ser Gln Pro Lys Ile Val Lys Trp Asp
           85                  90               95

Arg Asp Met

<210> SEQ ID NO 11
<211> LENGTH: 235
<212> TYPE: PRT
<213> ORGANISM: Homo sapiens

<400> SEQUENCE: 11

Leu Pro Ala Gln Val Ala Phe Thr Pro Tyr Ala Pro Glu Pro Gly Ser
1               5                  10               15

Thr Cys Arg Leu Arg Glu Tyr Tyr Asp Gln Thr Ala Gln Met Cys Cys
           20                  25               30

Ser Lys Cys Ser Pro Gly Gln His Ala Lys Val Phe Cys Thr Lys Thr
         35                 40               45

Ser Asp Thr Val Cys Asp Ser Cys Glu Asp Ser Thr Tyr Thr Gln Leu
50                  55                 60

Trp Asn Trp Val Pro Glu Cys Leu Ser Cys Gly Ser Arg Cys Ser Ser
65                  70                75               80

Asp Gln Val Glu Thr Gln Ala Cys Thr Arg Glu Gln Asn Arg Ile Cys
           85                  90               95

Thr Cys Arg Pro Gly Trp Tyr Cys Ala Leu Ser Lys Gln Glu Gly Cys
              100                 105              110

Arg Leu Cys Ala Pro Leu Arg Lys Cys Arg Pro Gly Phe Gly Val Ala
          115                120             125

Arg Pro Gly Thr Glu Thr Ser Asp Val Val Cys Lys Pro Cys Ala Pro
      130                135             140

Gly Thr Phe Ser Asn Thr Thr Ser Ser Thr Asp Ile Cys Arg Pro His
145                150               155             160

Gln Ile Cys Asn Val Val Ala Ile Pro Gly Asn Ala Ser Met Asp Ala
             165               170             175

Val Cys Thr Ser Thr Ser Pro Thr Arg Ser Met Ala Pro Gly Ala Val
         180                185             190

His Leu Pro Gln Pro Val Ser Thr Arg Ser Gln His Thr Gln Pro Thr
      195              200             205

```
Pro Glu Pro Ser Thr Ala Pro Ser Thr Ser Phe Leu Leu Pro Met Gly
    210                 215                 220
Pro Ser Pro Pro Ala Glu Gly Ser Thr Gly Asp
225                 230                 235

<210> SEQ ID NO 12
<211> LENGTH: 124
<212> TYPE: PRT
<213> ORGANISM: Homo sapiens

<400> SEQUENCE: 12

Met His Val Ala Gln Pro Ala Val Val Leu Ala Ser Ser Arg Gly Ile
1               5                   10                  15
Ala Ser Phe Val Cys Glu Tyr Ala Ser Pro Gly Lys Ala Thr Glu Val
            20                  25                  30
Arg Val Thr Val Leu Arg Gln Ala Asp Ser Gln Val Thr Glu Val Cys
        35                  40                  45
Ala Ala Thr Tyr Met Met Gly Asn Glu Leu Thr Phe Leu Asp Asp Ser
    50                  55                  60
Ile Cys Thr Gly Thr Ser Ser Gly Asn Gln Val Asn Leu Thr Ile Gln
65                  70                  75                  80
Gly Leu Arg Ala Met Asp Thr Gly Leu Tyr Ile Cys Lys Val Glu Leu
                85                  90                  95
Met Tyr Pro Pro Pro Tyr Tyr Leu Gly Ile Gly Asn Gly Thr Gln Ile
            100                 105                 110
Tyr Val Ile Asp Pro Glu Pro Cys Pro Asp Ser Asp
        115                 120

<210> SEQ ID NO 13
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(7)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (2)..(7)
<223> OTHER INFORMATION: /note="Residues given in the sequence have no
      preference with respect to those in the annotations for said
      positions"

<400> SEQUENCE: 13

Cys Lys Lys Lys Lys Lys Lys Cys
1               5

<210> SEQ ID NO 14
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(8)
```

```
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (2)..(8)
<223> OTHER INFORMATION: /note="Residues given in the sequence have no
      preference with respect to those in the annotations for said
      positions"

<400> SEQUENCE: 14

Cys Lys Lys Lys Lys Lys Lys Lys Cys
1               5

<210> SEQ ID NO 15
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(9)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (2)..(9)
<223> OTHER INFORMATION: /note="Residues given in the sequence have no
      preference with respect to those in the annotations for said
      positions"

<400> SEQUENCE: 15

Cys Lys Lys Lys Lys Lys Lys Lys Lys Cys
1               5                   10

<210> SEQ ID NO 16
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(8)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (3)..(8)
<223> OTHER INFORMATION: /note="Residues given in the sequence have no
      preference with respect to those in the annotations for said
      positions"

<400> SEQUENCE: 16

Gly Cys Lys Lys Lys Lys Lys Lys Cys Gly
1               5                   10

<210> SEQ ID NO 17
<211> LENGTH: 11
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"
<220> FEATURE:
<221> NAME/KEY: VARIANT
<222> LOCATION: (3)..(9)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (3)..(9)
<223> OTHER INFORMATION: /note="Residues given in the sequence have no
      preference with respect to those in the annotations for said
      positions"

<400> SEQUENCE: 17

Gly Cys Lys Lys Lys Lys Lys Lys Lys Cys Gly
1               5                   10

<210> SEQ ID NO 18
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(10)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (3)..(10)
<223> OTHER INFORMATION: /note="Residues given in the sequence have no
      preference with respect to those in the annotations for said
      positions"

<400> SEQUENCE: 18

Gly Cys Lys Lys Lys Lys Lys Lys Lys Lys Cys Gly
1               5                   10

<210> SEQ ID NO 19
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(9)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (4)..(9)
<223> OTHER INFORMATION: /note="Residues given in the sequence have no
      preference with respect to those in the annotations for said
      positions"

<400> SEQUENCE: 19

Gly Gly Cys Lys Lys Lys Lys Lys Lys Cys Gly Gly
1               5                   10

<210> SEQ ID NO 20
```

```
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(10)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (4)..(10)
<223> OTHER INFORMATION: /note="Residues given in the sequence have no
      preference with respect to those in the annotations for said
      positions"

<400> SEQUENCE: 20

Gly Gly Cys Lys Lys Lys Lys Lys Lys Lys Cys Gly Gly
1               5                   10

<210> SEQ ID NO 21
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(11)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (4)..(11)
<223> OTHER INFORMATION: /note="Residues given in the sequence have no
      preference with respect to those in the annotations for said
      positions"

<400> SEQUENCE: 21

Gly Gly Cys Lys Lys Lys Lys Lys Lys Lys Lys Cys Gly Gly
1               5                   10

<210> SEQ ID NO 22
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(10)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (5)..(10)
<223> OTHER INFORMATION: /note="Residues given in the sequence have no
      preference with respect to those in the annotations for said
      positions"

<400> SEQUENCE: 22
```

```
Gly Gly Gly Cys Lys Lys Lys Lys Lys Lys Cys Gly Gly Gly
1               5                   10
```

<210> SEQ ID NO 23
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(11)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (5)..(11)
<223> OTHER INFORMATION: /note="Residues given in the sequence have no
      preference with respect to those in the annotations for said
      positions"

<400> SEQUENCE: 23

```
Gly Gly Gly Cys Lys Lys Lys Lys Lys Lys Lys Cys Gly Gly Gly
1               5                   10                  15
```

<210> SEQ ID NO 24
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(12)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (5)..(12)
<223> OTHER INFORMATION: /note="Residues given in the sequence have no
      preference with respect to those in the annotations for said
      positions"

<400> SEQUENCE: 24

```
Gly Gly Gly Cys Lys Lys Lys Lys Lys Lys Lys Lys Cys Gly Gly Gly
1               5                   10                  15
```

<210> SEQ ID NO 25
<211> LENGTH: 705
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: Variation
<222> LOCATION: (109)..(111)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (112)..(114)
<223> OTHER INFORMATION: /replace="AAC" or "ACT" or "ATC" or "ATG" or
      "CAG" or "CAT" or "CCG" or "CGT" or "CTG" or "GAA" or "GAC" or

```
            "GCT" or "GGT" or "GTT" or "TAC" or "TCT" or "TGG" or "TTC"
<220> FEATURE:
<221> NAME/KEY: Variation
<222> LOCATION: (115)..(117)
<223> OTHER INFORMATION: /replace="AAC" or "ACT" or "ATC" or "ATG" or
            "CAG" or "CAT" or "CCG" or "CGT" or "CTG" or "GAA" or "GAC" or
            "GCT" or "GGT" or "GTT" or "TAC" or "TCT" or "TGG" or "TTC"
<220> FEATURE:
<221> NAME/KEY: Variation
<222> LOCATION: (118)..(120)
<223> OTHER INFORMATION: /replace="AAC" or "ACT" or "ATC" or "ATG" or
            "CAG" or "CAT" or "CCG" or "CGT" or "CTG" or "GAA" or "GAC" or
            "GCT" or "GGT" or "GTT" or "TAC" or "TCT" or "TGG" or "TTC"
<220> FEATURE:
<221> NAME/KEY: Variation
<222> LOCATION: (121)..(123)
<223> OTHER INFORMATION: /replace="AAC" or "ACT" or "ATC" or "ATG" or
            "CAG" or "CAT" or "CCG" or "CGT" or "CTG" or "GAA" or "GAC" or
            "GCT" or "GGT" or "GTT" or "TAC" or "TCT" or "TGG" or "TTC"
<220> FEATURE:
<221> NAME/KEY: Variation
<222> LOCATION: (124)..(126)
<223> OTHER INFORMATION: /replace="AAC" or "ACT" or "ATC" or "ATG" or
            "CAG" or "CAT" or "CCG" or "CGT" or "CTG" or "GAA" or "GAC" or
            "GCT" or "GGT" or "GTT" or "TAC" or "TCT" or "TGG" or "TTC"
<220> FEATURE:
<221> NAME/KEY: misc_feature
<222> LOCATION: (109)..(126)
<223> OTHER INFORMATION: /note="nucleotides given in the sequence have
            no preference with respect to those in the annotations for said
            positions"
<220> FEATURE:
<221> NAME/KEY: source
<223> OTHER INFORMATION: /note="see specification as filed for detailed
            description of substitutions and preferred embodiments"

<400> SEQUENCE: 25
gagcccaaat cttgtgacaa aactcacaca tgcccaccgt gcccagcacc tgaactcctg      60
gggggaccgt cagtcttcct cttccccca  aaacccaagg acaccctcaa aaaaaaaaaa     120 aaaaaaccc  ctgaggtcac atgcgtggtg gtggacgtga gccacgaaga ccctgaggtc     180
aagttcaact ggtacgtgga cggcgtggag gtgcataatg ccaagacaaa gccgcgggag     240
gagcagtaca acagcacgta ccgtgtggtc agcgtcctca ccgtcctgca ccaggactgg     300
ctgaatggca aggagtacaa gtgcaaggtc tccaacaaag ccctcccagc ccccatcgag     360
aaaaccatct ccaaagccaa agggcagccc cgagagccac aggtgtacac cctgccccca     420
tcccgggatg agctgaccaa gaaccaggtc agcctgacct gcctggtcaa aggcttctat     480
cccagcgaca tcgccgtgga gtgggagagc aatgggcagc cggagaacaa ctacaagacc     540
acgcctcccg tgctggactc cgacggctcc ttcttcctct acagcaagct caccgtggac     600
aagagcaggt ggcagcaggg gaacgtcttc tcatgctccg tgatgcatga ggctctgcac     660
aaccactaca cgcagaagag cctctccctg tctccgggta aatga                    705

<210> SEQ ID NO 26
<211> LENGTH: 234
<212> TYPE: PRT
<213> ORGANISM: Artificial Sequence
<220> FEATURE:
<221> NAME/KEY: source
<223> OTHER INFORMATION: /note="Description of Artificial Sequence:
            Synthetic polypeptide"
<220> FEATURE:
<221> NAME/KEY: VARIANT
<222> LOCATION: (37)..(42)
<223> OTHER INFORMATION: /replace="Phe" or "Asn" or "Arg" or "Ser" or
            "Thr" or "Met" or "Ile" or "Glu" or "Asp" or "Gly" or
            "Ala" or "Val" or "Gln" or "His" or "Pro" or "Leu"
            or "Tyr" or "Trp"
<220> FEATURE:
```

<221> NAME/KEY: misc_feature
<222> LOCATION: (37)..(42)
<223> OTHER INFORMATION: /note="Residues given in the sequence have no preference with respect to those in the annotations for said positions"

<400> SEQUENCE: 26

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Lys Lys Lys Lys Lys Thr Pro Glu Val Thr Cys
        35                  40                  45

Val Val Val Asp Val Ser His Glu Asp Pro Glu Val Lys Phe Asn Trp
50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
                100                 105                 110

Lys Ala Leu Pro Ala Pro Ile Glu Lys Thr Ile Ser Lys Ala Lys Gly
            115                 120                 125

Gln Pro Arg Glu Pro Gln Val Tyr Thr Leu Pro Pro Ser Arg Asp Glu
        130                 135                 140

Leu Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
210                 215                 220

Gln Lys Ser Leu Ser Leu Ser Pro Gly Lys
225                 230
```

<210> SEQ ID NO 27
<211> LENGTH: 711
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: Variation
<222> LOCATION: (277)..(279)
<223> OTHER INFORMATION: /replace="AAC" or "ACT" or "ATC" or "ATG" or "CAG" or "CAT" or "CCG" or "CGT" or "CTG" or "GAA" or "GAC" or "GCT" or "GGT" or "GTT" or "TAC" or "TCT" or "TGG" or "TTC"
<220> FEATURE:
<221> NAME/KEY: Variation
<222> LOCATION: (280)..(282)
<223> OTHER INFORMATION: /replace="AAC" or "ACT" or "ATC" or "ATG" or "CAG" or "CAT" or "CCG" or "CGT" or "CTG" or "GAA" or "GAC" or "GCT" or "GGT" or "GTT" or "TAC" or "TCT" or "TGG" or "TTC"
<220> FEATURE:
<221> NAME/KEY: Variation
<222> LOCATION: (283)..(285)
<223> OTHER INFORMATION: /replace="AAC" or "ACT" or "ATC" or "ATG" or "CAG" or "CAT" or "CCG" or "CGT" or "CTG" or "GAA" or "GAC" or "GCT" or "GGT" or "GTT" or "TAC" or "TCT" or "TGG" or "TTC"
<220> FEATURE:
<221> NAME/KEY: Variation
<222> LOCATION: (286)..(288)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (289)..(291)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (292)..(294)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: misc_feature
<222> LOCATION: (277)..(294)
<223> OTHER INFORMATION: /note="nucleotides given in the sequence have
      no preference with respect to those in the annotations for said
      positions"
<220> FEATURE:
<221> NAME/KEY: source
<223> OTHER INFORMATION: /note="see specification as filed for detailed
      description of substitutions and preferred embodiments"

<400> SEQUENCE: 27
gagcccaaat cttgtgacaa aactcacaca tgcccaccgt gcccagcacc tgaactcctg      60
gggggaccgt cagtcttcct cttcccccca aaacccaagg acaccctcat gatctcccgg    120
accccTgagg tcacatgcgt ggtggtggac gtgagccacg aagaccctga ggtcaagttc    180
aactggtacg tggacggcgt ggaggtgcat aatgccaaga caaagccgcg ggaggagcag    240
tacaacagca cgtaccgtgt ggtcagcgtc ctcaccaaaa aaaaaaaaaa aaaacaccag    300
gactggctga atggcaagga gtacaagtgc aaggtctcca caaagccct cccagccccc     360 atcgagaaaa ccatctccaa agccaaaggg cagccccgag agccacaggt gtacaccctg    420
cccccatccc gggatgagct gaccaagaac caggtcagcc tgacctgcct ggtcaaaggc    480
ttctatccca gcgacatcgc cgtggagtgg gagagcaatg ggcagccgga gaacaactac    540
aagaccacgc ctcccgtgct ggactccgac ggctccttct tcctctacag caagctcacc    600
gtggacaaga gcaggtggca gcaggggaac gtcttctcat gctccgtgat gcatgaggct    660
ctgcacaacc actacacgca gaagagcctc tccctgtctc cgggtaaatg a             711

<210> SEQ ID NO 28
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (93)..(98)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (93)..(98)
<223> OTHER INFORMATION: /note="Residues given in the sequence have no
      preference with respect to those in the annotations for said
      positions"

<400> SEQUENCE: 28

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Lys Lys Lys Lys
                85                  90                  95

Lys Lys His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Ala
        115                 120                 125

Lys Gly Gln Pro Arg Glu Pro Gln Val Tyr Thr Leu Pro Pro Ser Arg
130                 135                 140

Asp Glu Leu Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Asp Ser Asp Gly Ser
            180                 185                 190

Phe Phe Leu Tyr Ser Lys Leu Thr Val Asp Lys Ser Arg Trp Gln Gln
        195                 200                 205

Gly Asn Val Phe Ser Cys Ser Val Met His Glu Ala Leu His Asn His
    210                 215                 220

Tyr Thr Gln Lys Ser Leu Ser Leu Ser Pro Gly Lys
225                 230                 235
```

<210> SEQ ID NO 29
<211> LENGTH: 729
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: Variation
<222> LOCATION: (286)..(288)
<223> OTHER INFORMATION: /replace="AAC" or "ACT" or "ATC" or "ATG" or "CAG" or "CAT" or "CCG" or "CGT" or "CTG" or "GAA" or "GAC" or "GCT" or "GGT" or "GTT" or "TAC" or "TCT" or "TGG" or "TTC"
<220> FEATURE:
<221> NAME/KEY: Variation
<222> LOCATION: (289)..(291)
<223> OTHER INFORMATION: /replace="AAC" or "ACT" or "ATC" or "ATG" or "CAG" or "CAT" or "CCG" or "CGT" or "CTG" or "GAA" or "GAC" or "GCT" or "GGT" or "GTT" or "TAC" or "TCT" or "TGG" or "TTC"
<220> FEATURE:
<221> NAME/KEY: Variation
<222> LOCATION: (292)..(294)
<223> OTHER INFORMATION: /replace="AAC" or "ACT" or "ATC" or "ATG" or "CAG" or "CAT" or "CCG" or "CGT" or "CTG" or "GAA" or "GAC" or "GCT" or "GGT" or "GTT" or "TAC" or "TCT" or "TGG" or "TTC"
<220> FEATURE:
<221> NAME/KEY: Variation
<222> LOCATION: (295)..(297)
<223> OTHER INFORMATION: /replace="AAC" or "ACT" or "ATC" or "ATG" or "CAG" or "CAT" or "CCG" or "CGT" or "CTG" or "GAA" or "GAC" or

```
              "GCT" or "GGT" or "GTT" or "TAC" or "TCT" or "TGG" or "TTC"
<220> FEATURE:
<221> NAME/KEY: Variation
<222> LOCATION: (298)..(300)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (301)..(303)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: misc_feature
<222> LOCATION: (286)..(303)
<223> OTHER INFORMATION: /note="nucleotides given in the sequence have
      no preference with respect to those in the annotations for said
      positions"
<220> FEATURE:
<221> NAME/KEY: source
<223> OTHER INFORMATION: /note="see specification as filed for detailed
      description of substitutions and preferred embodiments"

<400> SEQUENCE: 29
gagcccaaat cttgtgacaa aactcacaca tgcccaccgt gcccagcacc tgaactcctg    60
gggggaccgt cagtcttcct cttccccca aacccaagg acaccctcat gatctcccgg     120
acccctgagg tcacatgcgt ggtggtggac gtgagccacg aagaccctga ggtcaagttc   180
aactggtacg tggacggcgt ggaggtgcat aatgccaaga caaagccgcg ggaggagcag   240
tacaacagca cgtaccgtgt ggtcagcgtc ctcaccggtg ttgtaaaaa aaaaaaaaaa    300 aaatgtggtg gtcaccagga ctggctgaat ggcaaggagt acaagtgcaa ggtctccaac   360
aaagccctcc cagcccccat cgagaaaacc atctccaaag ccaaagggca gccccgagag   420
ccacaggtgt acaccctgcc cccatcccgg gatgagctga ccaagaacca ggtcagcctg   480
acctgcctgg tcaaaggctt ctatcccagc gacatcgccg tggagtggga gagcaatggg   540
cagccggaga acaactacaa gaccacgcct cccgtgctgg actccgacgg ctccttcttc   600
ctctacagca agctcaccgt ggacaagagc aggtggcagc aggggaacgt cttctcatgc   660
tccgtgatgc atgaggctct gcacaaccac tacacgcaga agagcctctc cctgtctccg   720
ggtaaatga                                                           729

<210> SEQ ID NO 30
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (96)..(101)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (96)..(101)
<223> OTHER INFORMATION: /note="Residues given in the sequence have no
      preference with respect to those in the annotations for said
      positions"

<400> SEQUENCE: 30

Glu Pro Lys Ser Cys Asp Lys Thr His Thr Cys Pro Pro Cys Pro Ala
1               5                   10                  15
```

```
Pro Glu Leu Leu Gly Gly Pro Ser Val Phe Leu Phe Pro Pro Lys Pro
         20                  25                  30

Lys Asp Thr Leu Met Ile Ser Arg Thr Pro Glu Val Thr Cys Val Val
         35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Gly Gly Cys Lys
             85                  90                  95

Lys Lys Lys Lys Lys Cys Gly Gly His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Lys

<210> SEQ ID NO 31
<211> LENGTH: 705
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: Variation
<222> LOCATION: (646)..(648)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (649)..(651)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (652)..(654)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (655)..(657)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
```

<221> NAME/KEY: Variation
<222> LOCATION: (658)..(660)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: misc_feature
<222> LOCATION: (646)..(660)
<223> OTHER INFORMATION: /note="nucleotides given in the sequence have
      no preference with respect to those in the annotations for said
      positions"
<220> FEATURE:
<221> NAME/KEY: Variation
<222> LOCATION: (664)..(666)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: misc_feature
<222> LOCATION: (664)..(666)
<223> OTHER INFORMATION: /note="nucleotides given in the sequence have
      no preference with respect to those in the annotations for said
      positions"
<220> FEATURE:
<221> NAME/KEY: source
<223> OTHER INFORMATION: /note="see specification as filed for detailed
      description of substitutions and preferred embodiments"

<400> SEQUENCE: 31
gagcccaaat cttgtgacaa aactcacaca tgcccaccgt gcccagcacc tgaactcctg     60
gggggaccgt cagtcttcct cttccccca aaacccaagg acaccctcat gatctcccgg    120
cacacccctg aggtcacatg cgtggtggtg gacgtgagcc acgaagaccc tgaggtcaag    180
ttcaactggt acgtggacgg cgtggaggtg cataatgcca agacaaagcc gcgggaggag    240
cagtacaaca gcacgtaccg tgtggtcagc gtcctcaccg tcctgcacca ggactggctg    300
aatggcaagg agtacaagtg caaggtctcc aacaaagccc tcccagcccc catcgagaaa    360
accatctcca aagccaaagg gcagccccga gagccacagg tgtacaccct gcccccatcc    420
cgggatgagc tgaccaagaa ccaggtcagc ctgacctgcc tggtcaaagg cttctatccc    480
agcgacatcg ccgtggagtg ggagagcaat gggcagccgg agaacaacta caagaccacg    540
cctcccgtgc tggactccga cggctccttc ttcctctaca gcaagctcac cgtggacaag    600
agcaggtggc agcaggggaa cgtcttctca tgctccgtga tgcataaaaa aaaaaaaaaa    660
cacaaataca cgcagaagag cctctcccctg tctccgggta aatga                  705

<210> SEQ ID NO 32
<211> LENGTH: 234
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (215)..(219)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (215)..(219)
<223> OTHER INFORMATION: /note="Residues given in the sequence have no
      preference with respect to those in the annotations for said
      positions"
<220> FEATURE:
<221> NAME/KEY: VARIANT
<222> LOCATION: (221)..(221)

```
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (221)..(221)
<223> OTHER INFORMATION: /note="Residues given in the sequence have no
      preference with respect to those in the annotations for said
      positions"

<400> SEQUENCE: 32

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Lys Lys Lys Lys His Lys His Tyr Thr
210                 215                 220

Gln Lys Ser Leu Ser Leu Ser Pro Gly Lys
225                 230

<210> SEQ ID NO 33
<211> LENGTH: 735
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: Variation
<222> LOCATION: (223)..(225)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (226)..(228)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
```

```
<220> FEATURE:
<221> NAME/KEY: Variation
<222> LOCATION: (229)..(231)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (232)..(234)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (235)..(237)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (238)..(240)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: misc_feature
<222> LOCATION: (223)..(240)
<223> OTHER INFORMATION: /note="nucleotides given in the sequence have
      no preference with respect to those in the annotations for said
      positions"
<220> FEATURE:
<221> NAME/KEY: source
<223> OTHER INFORMATION: /note="see specification as filed for detailed
      description of substitutions and preferred embodiments"

<400> SEQUENCE: 33
gagcccaaat cttgtgacaa aactcacaca tgcccaccgt gcccagcacc tgaactcctg      60 ggggaccgt cagtcttcct cttcccccca aacccaagg acaccctcat gatctcccgg      120 accctgagg tcacatgcgt ggtggtggac gtgagccacg aagaccctga ggtcaagttc      180
aactggtacg tggacggcgt ggaggtgcat aatggtggtt gtaaaaaaaa aaaaaaaaaa      240
tgtggtggtg ccaagacaaa gccgcgggag gagcagtaca acagcacgta ccgtgtggtc      300
agcgtcctca ccgtcctgca ccaggactgg ctgaatggca aggagtacaa gtgcaaggtc      360
tccaacaaag ccctcccagc ccccatcgag aaaaccatct ccaaagccaa agggcagccc      420
cgagagccac aggtgtacac cctgccccca tcccgggatg agctgaccaa gaaccaggtc      480
agcctgacct gcctggtcaa aggcttctat cccagcgaca tcgccgtgga gtgggagagc      540
aatgggcagc cggagaacaa ctacaagacc acgcctcccg tgctggactc cgacggctcc      600
ttcttcctct acagcaagct caccgtggac aagagcaggt ggcagcaggg gaacgtcttc      660
tcatgctccg tgatgcatga ggctctgcac aaccactaca cgcagaagag cctctccctg      720
tctccgggta aatga                                                       735

<210> SEQ ID NO 34
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (75)..(80)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
```

```
<220> FEATURE:
<221> NAME/KEY: misc_feature
<222> LOCATION: (75)..(80)
<223> OTHER INFORMATION: /note="Residues given in the sequence have no
      preference with respect to those in the annotations for said
      positions"

<400> SEQUENCE: 34

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Gly Gly Cys Lys Lys Lys Lys Lys Lys
65                  70                  75                  80

Cys Gly Gly Ala Lys Thr Lys Pro Arg Glu Gln Tyr Asn Ser Thr
                85                  90                  95

Tyr Arg Val Val Ser Val Leu Thr Val Leu His Gln Asp Trp Leu Asn
                100                 105                 110

Gly Lys Glu Tyr Lys Cys Lys Val Ser Asn Lys Ala Leu Pro Ala Pro
            115                 120                 125

Ile Glu Lys Thr Ile Ser Lys Ala Lys Gly Gln Pro Arg Glu Pro Gln
130                 135                 140

Val Tyr Thr Leu Pro Pro Ser Arg Asp Glu Leu Thr Lys Asn Gln Val
145                 150                 155                 160

Ser Leu Thr Cys Leu Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
                180                 185                 190

Pro Val Leu Asp Ser Asp Gly Ser Phe Phe Leu Tyr Ser Lys Leu Thr
            195                 200                 205

Val Asp Lys Ser Arg Trp Gln Gln Gly Asn Val Phe Ser Cys Ser Val
210                 215                 220

Met His Glu Ala Leu His Asn His Tyr Thr Gln Lys Ser Leu Ser Leu
225                 230                 235                 240

Ser Pro Gly Lys

<210> SEQ ID NO 35
<211> LENGTH: 735
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: Variation
<222> LOCATION: (517)..(519)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (520)..(522)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
```

```
<222> LOCATION: (523)..(525)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (526)..(528)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (529)..(531)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (532)..(534)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: misc_feature
<222> LOCATION: (517)..(534)
<223> OTHER INFORMATION: /note="nucleotides given in the sequence have
      no preference with respect to those in the annotations for said
      positions"
<220> FEATURE:
<221> NAME/KEY: source
<223> OTHER INFORMATION: /note="see specification as filed for detailed
      description of substitutions and preferred embodiments"

<400> SEQUENCE: 35
gagcccaaat cttgtgacaa aactcacaca tgcccaccgt gcccagcacc tgaactcctg    60
gggggaccgt cagtcttcct cttccccca aacccaagg acaccctcat gatctcccgg    120 accctgagg tcacatgcgt ggtggtggac gtgagccacg aagaccctga ggtcaagttc    180
aactggtacg tggacggcgt ggaggtgcat aatgccaaga caaagccgcg ggaggagcag    240
tacaacagca cgtaccgtgt ggtcagcgtc ctcaccgtcc tgcaccagga ctggctgaat    300
ggcaaggagt acaagtgcaa ggtctccaac aaagcccctcc cagcccccat cgagaaaacc    360
atctccaaag ccaaagggca gccccgagag ccacaggtgt acaccctgcc cccatcccgg    420
gatgagctga ccaagaacca ggtcagcctg acctgcctgg tcaaaggctt ctatcccagc    480
gacatcgccg tggagtggga gagcaatggt ggttgtaaaa aaaaaaaaa aaaatgtggt    540 ggtgggcagc cggagaacaa ctacaagacc acgcctcccg tgctggactc cgacggctcc    600
ttcttcctct acagcaagct caccgtggac aagagcaggt ggcagcaggg gaacgtcttc    660
tcatgctccg tgatgcatga ggctctgcac aaccactaca cgcagaagag cctctccctg    720
tctccgggta aatga                                                     735

<210> SEQ ID NO 36
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (173)..(178)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
```

```
<222> LOCATION: (173)..(178)
<223> OTHER INFORMATION: /note="Residues given in the sequence have no
      preference with respect to those in the annotations for said
      positions"

<400> SEQUENCE: 36

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Cys Lys Lys Lys Lys
                165                 170                 175

Lys Lys Cys Gly Gly Gly Gln Pro Glu Asn Asn Tyr Lys Thr Thr Pro
            180                 185                 190

Pro Val Leu Asp Ser Asp Gly Ser Phe Phe Leu Tyr Ser Lys Leu Thr
        195                 200                 205

Val Asp Lys Ser Arg Trp Gln Gln Gly Asn Val Phe Ser Cys Ser Val
210                 215                 220

Met His Glu Ala Leu His Asn His Tyr Thr Gln Lys Ser Leu Ser Leu
225                 230                 235                 240

Ser Pro Gly Lys

<210> SEQ ID NO 37
<211> LENGTH: 735
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: Variation
<222> LOCATION: (439)..(441)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (442)..(444)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (445)..(447)
<223> OTHER INFORMATION: /replace="AAC" or "ACT" or "ATC" or "ATG" or
```

```
        "CAG" or "CAT" or "CCG" or "CGT" or "CTG" or "GAA" or "GAC" or
        "GCT" or "GGT" or "GTT" or "TAC" or "TCT" or "TGG" or "TTC"
<220> FEATURE:
<221> NAME/KEY: Variation
<222> LOCATION: (448)..(450)
<223> OTHER INFORMATION: /replace="AAC" or "ACT" or "ATC" or "ATG" or
        "CAG" or "CAT" or "CCG" or "CGT" or "CTG" or "GAA" or "GAC" or
        "GCT" or "GGT" or "GTT" or "TAC" or "TCT" or "TGG" or "TTC"
<220> FEATURE:
<221> NAME/KEY: Variation
<222> LOCATION: (451)..(453)
<223> OTHER INFORMATION: /replace="AAC" or "ACT" or "ATC" or "ATG" or
        "CAG" or "CAT" or "CCG" or "CGT" or "CTG" or "GAA" or "GAC" or
        "GCT" or "GGT" or "GTT" or "TAC" or "TCT" or "TGG" or "TTC"
<220> FEATURE:
<221> NAME/KEY: Variation
<222> LOCATION: (454)..(456)
<223> OTHER INFORMATION: /replace="AAC" or "ACT" or "ATC" or "ATG" or
        "CAG" or "CAT" or "CCG" or "CGT" or "CTG" or "GAA" or "GAC" or
        "GCT" or "GGT" or "GTT" or "TAC" or "TCT" or "TGG" or "TTC"
<220> FEATURE:
<221> NAME/KEY: misc_feature
<222> LOCATION: (439)..(456)
<223> OTHER INFORMATION: /note="nucleotides given in the sequence have
        no preference with respect to those in the annotations for said
        positions"
<220> FEATURE:
<221> NAME/KEY: source
<223> OTHER INFORMATION: /note="see specification as filed for detailed
        description of substitutions and preferred embodiments"

<400> SEQUENCE: 37
gagcccaaat cttgtgacaa aactcacaca tgcccaccgt gcccagcacc tgaactcctg      60 ggggaccgt  cagtcttcct cttccccca  aacccaagg  acaccctcat gatctcccgg     120 accctgagg  tcacatgcgt ggtggtggac gtgagccacg aagaccctga ggtcaagttc     180
aactggtacg tggacggcgt ggaggtgcat aatgccaaga caaagccgcg ggaggagcag     240
tacaacagca cgtaccgtgt ggtcagcgtc ctcaccgtcc tgcaccagga ctggctgaat     300
ggcaaggagt acaagtgcaa ggtctccaac aaagccctcc cagcccccat cgagaaaacc     360
atctccaaag ccaagggca  gccccgagag ccacaggtgt acaccctgcc cccatcccgg     420
gatgagctgg gtggttgtaa aaaaaaaaa  aaaaaatgtg gtggtaccaa gaaccaggtc     480
agcctgacct gcctggtcaa aggcttctat cccagcgaca tcgccgtgga gtgggagagc     540
aatgggcagc cggagaacaa ctacaagacc acgcctcccg tgctggactc cgacggctcc     600
ttcttcctct acagcaagct caccgtggac aagagcaggt ggcagcaggg gaacgtcttc     660
tcatgctccg tgatgcatga ggctctgcac aaccactaca cgcagaagag cctctccctg     720
tctccgggta aatga                                                     735

<210> SEQ ID NO 38
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic polypeptide"
<220> FEATURE:
<221> NAME/KEY: VARIANT
<222> LOCATION: (147)..(152)
<223> OTHER INFORMATION: /replace="Phe" or "Asn" or "Arg" or "Ser" or
        "Thr" or "Met" or "Ile" or "Glu" or "Asp" or "Gly" or
        "Ala" or "Val" or "Gln" or "His" or "Pro" or "Leu"
        or "Tyr" or "Trp"
<220> FEATURE:
<221> NAME/KEY: misc_feature
<222> LOCATION: (147)..(152)
<223> OTHER INFORMATION: /note="Residues given in the sequence have no
``` preference with respect to those in the annotations for said positions"

<400> SEQUENCE: 38

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Gly
    130                 135                 140

Gly Cys Lys Lys Lys Lys Lys Cys Gly Gly Thr Lys Asn Gln Val
145                 150                 155                 160

Ser Leu Thr Cys Leu Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
            180                 185                 190

Pro Val Leu Asp Ser Asp Gly Ser Phe Phe Leu Tyr Ser Lys Leu Thr
        195                 200                 205

Val Asp Lys Ser Arg Trp Gln Gln Gly Asn Val Phe Ser Cys Ser Val
    210                 215                 220

Met His Glu Ala Leu His Asn His Tyr Thr Gln Lys Ser Leu Ser Leu
225                 230                 235                 240

Ser Pro Gly Lys
```

<210> SEQ ID NO 39
<211> LENGTH: 735
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (439)..(440)
<223> OTHER INFORMATION: a, c, t, g, unknown or other
<220> FEATURE:
<221> NAME/KEY: modified_base
<222> LOCATION: (442)..(443)
<223> OTHER INFORMATION: a, c, t, g, unknown or other
<220> FEATURE:
<221> NAME/KEY: modified_base
<222> LOCATION: (445)..(446)
<223> OTHER INFORMATION: a, c, t, g, unknown or other
<220> FEATURE:
<221> NAME/KEY: modified_base
<222> LOCATION: (448)..(449)
<223> OTHER INFORMATION: a, c, t, g, unknown or other
<220> FEATURE:
<221> NAME/KEY: modified_base

```
<222> LOCATION: (451)..(452)
<223> OTHER INFORMATION: a, c, t, g, unknown or other
<220> FEATURE:
<221> NAME/KEY: modified_base
<222> LOCATION: (454)..(455)
<223> OTHER INFORMATION: a, c, t, g, unknown or other

<400> SEQUENCE: 39
gagcccaaat cttgtgacaa aactcacaca tgcccaccgt gcccagcacc tgaactcctg      60
gggggaccgt cagtcttcct cttccccca aacccaagg acaccctcat gatctcccgg     120
accctgagg tcacatgcgt ggtggtggac gtgagccacg aagaccctga ggtcaagttc      180
aactggtacg tggacggcgt ggaggtgcat aatgccaaga caaagccgcg ggaggagcag     240
tacaacagca cgtaccgtgt ggtcagcgtc ctcaccgtcc tgcaccagga ctggctgaat     300
ggcaaggagt acaagtgcaa ggtctccaac aaagcccctcc cagcccccat cgagaaaacc    360
atctccaaag ccaaagggca gccccgagag ccacaggtgt acaccctgcc cccatcccgg     420
gatgagctgg tggttgtnn knnknnknnk nnknnktgtg gtggtaccaa gaaccaggtc     480
agcctgacct gcctggtcaa aggcttctat cccagcgaca tcgccgtgga gtgggagagc     540
aatgggcagc cggagaacaa ctacaagacc acgcctcccg tgctggactc cgacggctcc     600
ttcttcctct acagcaagct caccgtggac aagagcaggt ggcagcaggg gaacgtcttc     660
tcatgctccg tgatgcatga ggctctgcac aaccactaca cgcagaagag cctctccctg     720
tctccgggta aatga                                                     735

<210> SEQ ID NO 40
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (147)..(152)
<223> OTHER INFORMATION: Any amino acid

<400> SEQUENCE: 40

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Gly
    130                 135                 140

Gly Cys Xaa Xaa Xaa Xaa Xaa Xaa Cys Gly Gly Thr Lys Asn Gln Val
```

```
                145                 150                 155                 160
Ser Leu Thr Cys Leu Val Lys Gly Phe Tyr Pro Ser Asp Ile Ala Val
                    165                 170                 175

Glu Trp Glu Ser Asn Gly Gln Pro Glu Asn Asn Tyr Lys Thr Thr Pro
                    180                 185                 190

Pro Val Leu Asp Ser Asp Gly Ser Phe Phe Leu Tyr Ser Lys Leu Thr
                    195                 200                 205

Val Asp Lys Ser Arg Trp Gln Gln Gly Asn Val Phe Ser Cys Ser Val
                210                 215                 220

Met His Glu Ala Leu His Asn His Tyr Thr Gln Lys Ser Leu Ser Leu
225                 230                 235                 240

Ser Pro Gly Lys

<210> SEQ ID NO 41
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Gly Gly Cys His Leu Pro Phe Ala Val Cys Gly Gly
1               5                   10

<210> SEQ ID NO 42
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Gly Gly Cys Trp Pro Leu Gln Asp Tyr Cys Gly Gly
1               5                   10

<210> SEQ ID NO 43
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Gly Gly Cys Gly His Glu Tyr Met Trp Cys Gly Gly
1               5                   10

<210> SEQ ID NO 44
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gly Gly Cys Val Phe Asn Met Phe Asn Cys Gly Gly
1               5                   10
```

<210> SEQ ID NO 45
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Gly Gly Cys Ala Leu Tyr Pro Thr Asn Cys Gly Gly
1               5                   10

<210> SEQ ID NO 46
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Gly Gly Cys Met Gln Val Trp Gly Ser Cys Gly Gly
1               5                   10

<210> SEQ ID NO 47
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Gly Gly Cys Gln Lys Gly Trp Val Phe Cys Gly Gly
1               5                   10

<210> SEQ ID NO 48
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Gly Gly Cys Met Val Pro Phe Ser Met Cys Gly Gly
1               5                   10

<210> SEQ ID NO 49
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gly Gly Cys Val Asn Thr Trp Trp Ser Cys Gly Gly
1               5                   10

<210> SEQ ID NO 50
<211> LENGTH: 12
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Gly Gly Cys Ile Gly Pro Phe Trp Trp Cys Gly Gly
1               5                   10

<210> SEQ ID NO 51
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Gly Gly Cys Asp Arg Pro Val Trp Phe Cys Gly Gly
1               5                   10

<210> SEQ ID NO 52
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Gly Gly Cys Asn Met Leu Trp Gly Ser Cys Gly Gly
1               5                   10

<210> SEQ ID NO 53
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Gly Gly Cys Tyr Ile Thr Gln Lys Leu Cys Gly Gly
1               5                   10

<210> SEQ ID NO 54
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

His Leu Pro Phe Ala Val
1               5

<210> SEQ ID NO 55
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 55

Trp Pro Leu Gln Asp Tyr
1               5

<210> SEQ ID NO 56
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Gly His Glu Tyr Met Trp
1               5

<210> SEQ ID NO 57
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Val Phe Asn Met Phe Asn
1               5

<210> SEQ ID NO 58
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Ala Leu Tyr Pro Thr Asn
1               5

<210> SEQ ID NO 59
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Met Gln Val Trp Gly Ser
1               5

<210> SEQ ID NO 60
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

```
Gln Lys Gly Trp Val Phe
1               5

<210> SEQ ID NO 61
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Met Val Pro Phe Ser Met
1               5

<210> SEQ ID NO 62
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Val Asn Thr Trp Trp Ser
1               5

<210> SEQ ID NO 63
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Ile Gly Pro Phe Trp Trp
1               5

<210> SEQ ID NO 64
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Asp Arg Pro Val Trp Phe
1               5

<210> SEQ ID NO 65
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Asn Met Leu Trp Gly Ser
1               5
```

```
<210> SEQ ID NO 66
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Tyr Ile Thr Gln Lys Leu
1               5

<210> SEQ ID NO 67
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Gly Gly Cys Gly Met Pro Ile Glu Phe Cys Gly Gly
1               5                   10

<210> SEQ ID NO 68
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 68
gctgtggagt gggagggtgg ttgtggtatg ccgatcgaat tctgtggtgg tagcaatggg    60
cagccg                                                              66

<210> SEQ ID NO 69
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 69
cggctgccca ttgctaccac cacagaattc gatcggcata ccacaaccac cctcccactc    60
cacagc                                                              66

<210> SEQ ID NO 70
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 70
gtggagtggg agagcggtgg ttgtggtatg ccgatcgaat tctgtggtgg taatgggcag    60
ccggag                                                              66

<210> SEQ ID NO 71
```

```
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 71
ctccggctgc ccattaccac cacagaattc gatcggcata ccacaaccac cgctctccca     60
ctccac                                                               66

<210> SEQ ID NO 72
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 72
tgggagagca atgggggtgg ttgtggtatg ccgatcgaat tctgtggtgg tcagccggag     60
aacaac                                                               66

<210> SEQ ID NO 73
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 73
gttgttctcc ggctgaccac cacagaattc gatcggcata ccacaaccac ccccattgct     60
ctccca                                                               66

<210> SEQ ID NO 74
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 74
gagagcaatg ggcagggtgg ttgtggtatg ccgatcgaat tctgtggtgg tccggagaac     60
aactac                                                               66

<210> SEQ ID NO 75
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 75
gtagttgttc tccggaccac cacagaattc gatcggcata ccacaaccac cctgcccatt     60
gctctc                                                               66
```

```
<210> SEQ ID NO 76
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 76
agcaatgggc agccgggtgg ttgtggtatg ccgatcgaat tctgtggtgg tgagaacaac    60
tacaag                                                              66

<210> SEQ ID NO 77
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 77
cttgtagttg ttctcaccac cacagaattc gatcggcata ccacaaccac ccggctgccc    60
attgct                                                              66

<210> SEQ ID NO 78
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 78
aatgggcagc cggagggtgg ttgtggtatg ccgatcgaat tctgtggtgg taacaactac    60
aagacc                                                              66

<210> SEQ ID NO 79
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 79
ggtcttgtag ttgttaccac cacagaattc gatcggcata ccacaaccac cctccggctg    60
cccatt                                                              66

<210> SEQ ID NO 80
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 80
gggcagccgg agaacggtgg ttgtggtatg ccgatcgaat tctgtggtgg taactacaag    60
accacg                                                              66
```

<210> SEQ ID NO 81
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 81
cgtggtcttg tagttaccac cacagaattc gatcggcata ccacaaccac cgttctccgg    60
ctgccc                                                                66

<210> SEQ ID NO 82
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 82
cagccggaga acaacggtgg ttgtggtatg ccgatcgaat tctgtggtgg ttacaagacc    60
acgcct                                                                66

<210> SEQ ID NO 83
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 83
aggcgtggtc ttgtaaccac cacagaattc gatcggcata ccacaaccac cgttgttctc    60
cggctg                                                                66

<210> SEQ ID NO 84
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 84
gtggagtggg agagcggtgg ttgtggtatg ccgatcgaat tctgtggtgg tccggagaac    60
aactac                                                                66

<210> SEQ ID NO 85
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 85
gtagttgttc tccggaccac cacagaattc gatcggcata ccacaaccac cgctctccca    60
ctccac                                                                66

<210> SEQ ID NO 86
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 86
gtggagtggg agagcggtgg tggttgtggt atgccgatcg aattctgtgg tggtggtccg    60
gagaacaact ac                                                        72

<210> SEQ ID NO 87
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 87
gtagttgttc tccggaccac caccacagaa ttcgatcggc ataccacaac caccaccgct    60
ctcccactcc ac                                                        72

<210> SEQ ID NO 88
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"
<220> FEATURE:
<221> NAME/KEY: VARIANT
<222> LOCATION: (4)..(11)
<223> OTHER INFORMATION: /replace="Phe" or "Asn" or "Arg" or "Ser" or
    "Thr" or "Met" or "Ile" or "Glu" or "Asp" or "Gly" or
    "Ala" or "Val" or "Gln" or "His" or "Pro" or "Leu"
    or "Tyr" or "Trp"
<220> FEATURE:
<221> NAME/KEY: misc_feature
<222> LOCATION: (4)..(11)
<223> OTHER INFORMATION: /note="Residues given in the sequence have no
    preference with respect to those in the annotations for said
    positions"

<400> SEQUENCE: 88

Gly Gly Cys Lys Lys Lys Lys Lys Lys Lys Lys Cys Gly Gly
1               5                   10

<210> SEQ ID NO 89
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"
<220> FEATURE:
<221> NAME/KEY: VARIANT
<222> LOCATION: (4)..(13)
<223> OTHER INFORMATION: /replace="Phe" or "Asn" or "Arg" or "Ser" or
    "Thr" or "Met" or "Ile" or "Glu" or "Asp" or "Gly" or
    "Ala" or "Val" or "Gln" or "His" or "Pro" or "Leu"
    or "Tyr" or "Trp"
<220> FEATURE:
<221> NAME/KEY: misc_feature

```
<222> LOCATION: (4)..(13)
<223> OTHER INFORMATION: /note="Residues given in the sequence have no
      preference with respect to those in the annotations for said
      positions"

<400> SEQUENCE: 89

Gly Gly Cys Lys Lys Lys Lys Lys Lys Lys Lys Cys Gly Gly
1               5                   10                  15

<210> SEQ ID NO 90
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Gly Gly Cys His Phe Asp Ile Met Asn Cys Gly Gly
1               5                   10

<210> SEQ ID NO 91
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Gly Gly Cys Val Ile Asp Phe Phe Gly Cys Gly Gly
1               5                   10

<210> SEQ ID NO 92
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Gly Gly Cys Asp Ile Met Ile Phe Glu Cys Gly Gly
1               5                   10

<210> SEQ ID NO 93
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Gly Gly Cys Met Thr Glu Phe Ala Ile Cys Gly Gly
1               5                   10

<210> SEQ ID NO 94
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 94

Gly Gly Cys Ile Gln Tyr Trp Gln Phe Cys Gly Gly
1               5                   10

<210> SEQ ID NO 95
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Gly Gly Cys Pro Phe Ser Trp Ala Phe Cys Gly Gly
1               5                   10

<210> SEQ ID NO 96
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Gly Gly Cys Gly Phe Ala Phe Met Tyr Cys Gly Gly
1               5                   10

<210> SEQ ID NO 97
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Gly Gly Cys Pro Val Leu Leu Phe Asn Cys Gly Gly
1               5                   10

<210> SEQ ID NO 98
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Gly Gly Cys Pro Phe Thr Trp Thr Lys Cys Gly Gly
1               5                   10

<210> SEQ ID NO 99
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Gly Gly Cys Tyr Leu Tyr Trp Gln Phe Cys Gly Gly
```

<210> SEQ ID NO 100
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Gly Gly Cys Val Ile Asn Met Phe Pro Cys Gly Gly
1               5                   10

<210> SEQ ID NO 101
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Gly Gly Cys Pro Phe Thr Trp Asn Thr Cys Gly Gly
1               5                   10

<210> SEQ ID NO 102
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Gly Gly Cys Pro Phe Gln Ile Gly Glu Cys Gly Gly
1               5                   10

<210> SEQ ID NO 103
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Gly Gly Cys Leu Asp Ile Ile Trp Met Cys Gly Gly
1               5                   10

<210> SEQ ID NO 104
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Gly Gly Cys Met Phe Val Phe Pro Ala Cys Gly Gly
1               5                   10

<210> SEQ ID NO 105

-continued

```
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Gly Gly Cys Val Met Glu Gln Leu Trp Cys Gly Gly
1               5                   10

<210> SEQ ID NO 106
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Gly Gly Cys Phe Lys Glu Tyr Thr Trp Cys Gly Gly
1               5                   10

<210> SEQ ID NO 107
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Gly Gly Cys Pro Lys Asp Tyr His Ile Cys Gly Gly
1               5                   10

<210> SEQ ID NO 108
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Gly Gly Cys Glu Val Met Val Phe Pro Cys Gly Gly
1               5                   10

<210> SEQ ID NO 109
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Gly Gly Cys Val Phe Asn Thr Val Phe Cys Gly Gly
1               5                   10

<210> SEQ ID NO 110
<211> LENGTH: 12
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 110

Gly Gly Cys Asn Leu Pro Gln Glu Trp Cys Gly Gly
1               5                   10

<210> SEQ ID NO 111
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Gly Gly Cys Met Ile Ala Pro Met Tyr Cys Gly Gly
1               5                   10

<210> SEQ ID NO 112
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Gly Gly Cys Met Met Leu Tyr Pro Met Cys Gly Gly
1               5                   10

<210> SEQ ID NO 113
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Gly Gly Cys Ile Ile Gly Pro Phe Leu Cys Gly Gly
1               5                   10

<210> SEQ ID NO 114
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Gly Gly Cys Thr Gly Met Val Phe Phe Cys Gly Gly
1               5                   10

<210> SEQ ID NO 115
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 115

Gly Gly Cys Leu Met Tyr Lys Asn Val Cys Gly Gly
1               5                   10

<210> SEQ ID NO 116
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Gly Gly Cys Ala Phe Gly Ile Met Trp Cys Gly Gly
1               5                   10

<210> SEQ ID NO 117
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Gly Gly Cys Arg His Arg Lys Lys Trp Cys Gly Gly
1               5                   10

<210> SEQ ID NO 118
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Gly Gly Cys Phe Met Gly Ile Trp Gln Cys Gly Gly
1               5                   10

<210> SEQ ID NO 119
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Gly Gly Cys Pro Ser Leu Pro Gln Phe Cys Gly Gly
1               5                   10

<210> SEQ ID NO 120
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Gly Gly Cys Pro Ser Val Phe Thr Trp Cys Gly Gly
1               5                   10
```

```
<210> SEQ ID NO 121
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Gly Gly Cys Gln Glu Tyr Trp Glu Phe Cys Gly Gly
1               5                   10

<210> SEQ ID NO 122
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Gly Gly Cys Gln Trp Pro Thr Glu Phe Cys Gly Gly
1               5                   10

<210> SEQ ID NO 123
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Gly Gly Cys Ile Lys Phe Phe Asp Trp Cys Gly Gly
1               5                   10

<210> SEQ ID NO 124
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Gly Gly Cys Glu Met Ser Phe Phe Leu Cys Gly Gly
1               5                   10

<210> SEQ ID NO 125
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Gly Gly Cys His Ser Glu Val Glu Tyr Cys Gly Gly
1               5                   10

<210> SEQ ID NO 126
<211> LENGTH: 12
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Gly Gly Cys Trp Glu His Pro His Tyr Cys Gly Gly
1               5                   10

<210> SEQ ID NO 127
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Gly Gly Cys Glu Thr Tyr Trp Leu Phe Cys Gly Gly
1               5                   10

<210> SEQ ID NO 128
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Gly Gly Cys Arg Val Pro Tyr Pro Ser Cys Gly Gly
1               5                   10

<210> SEQ ID NO 129
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

Gly Gly Cys Gly Trp Pro Phe Val Met Cys Gly Gly
1               5                   10

<210> SEQ ID NO 130
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130

Gly Gly Cys Met Leu Phe Leu Glu Ser Cys Gly Gly
1               5                   10

<210> SEQ ID NO 131
<211> LENGTH: 12
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 131

Gly Gly Cys Phe His Val Lys Arg Trp Cys Gly Gly
1               5                   10

<210> SEQ ID NO 132
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

Gly Gly Cys Val Trp Glu Gln Glu His Cys Gly Gly
1               5                   10

<210> SEQ ID NO 133
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

Gly Gly Cys Ile Leu His Phe Lys Asp Cys Gly
1               5                   10

<210> SEQ ID NO 134
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 134

Gly Gly Cys His Phe Glu Val Phe Gln Cys Gly Gly
1               5                   10

<210> SEQ ID NO 135
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Gly Gly Cys Val Phe Glu Val Met Gln Cys Gly Gly
1               5                   10

<210> SEQ ID NO 136
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136
```

```
Gly Gly Cys Met Thr Glu Phe Ser Trp Cys Gly Gly
1               5                   10

<210> SEQ ID NO 137
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Gly Gly Cys Glu Gly Asn Met Arg Phe Cys Gly Gly
1               5                   10

<210> SEQ ID NO 138
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Gly Gly Cys Lys Gly His Met Trp Tyr Cys Gly Gly
1               5                   10

<210> SEQ ID NO 139
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

Gly Gly Cys Glu Ala Tyr Trp Gln Phe Cys Gly Gly
1               5                   10

<210> SEQ ID NO 140
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Gly Gly Cys Val Phe Ser Arg Phe Trp Cys Gly Gly
1               5                   10

<210> SEQ ID NO 141
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Gly Gly Cys Met Met Pro Phe Trp Pro Cys Gly Gly
1               5                   10
```

```
<210> SEQ ID NO 142
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Gly Gly Cys Ile Phe Gln Phe Glu Met Cys Gly Gly
1               5                   10

<210> SEQ ID NO 143
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Gly Gly Cys Lys Arg Gln Met Trp Tyr Cys Gly Gly
1               5                   10

<210> SEQ ID NO 144
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

Gly Gly Cys Lys Thr Pro Asn Pro Trp Cys Gly Gly
1               5                   10

<210> SEQ ID NO 145
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Gly Gly Cys Lys Ala Phe Tyr Pro Trp Cys Gly Gly
1               5                   10

<210> SEQ ID NO 146
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Gly Gly Cys Lys Met Tyr Gln Tyr Asp Cys Gly Gly
1               5                   10

<210> SEQ ID NO 147
<211> LENGTH: 12
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Gly Gly Cys Tyr Pro Asp Asn Met Phe Cys Gly Gly
1               5                   10

<210> SEQ ID NO 148
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 148

Gly Gly Cys Gln Val Lys Ile Phe Trp Cys Gly Gly
1               5                   10

<210> SEQ ID NO 149
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 149

Gly Gly Cys Ser Ile Pro Gln Glu Trp Cys Gly Gly
1               5                   10

<210> SEQ ID NO 150
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Gly Gly Cys Lys Met Tyr Gln Ala Thr Cys Gly Gly
1               5                   10

<210> SEQ ID NO 151
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Gly Gly Cys Gln Tyr Glu Arg Trp His Cys Gly Gly
1               5                   10

<210> SEQ ID NO 152
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 152

Gly Gly Cys Arg Phe Gln His Gln Trp Cys Gly Gly
1               5                   10

<210> SEQ ID NO 153
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Gly Gly Cys Gln Asn Met Phe Trp Gln Cys Gly Gly
1               5                   10

<210> SEQ ID NO 154
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Gly Gly Cys Val Met Glu Ile Val Phe Cys Gly Gly
1               5                   10

<210> SEQ ID NO 155
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Gly Gly Cys Ile Leu Asn Phe Asn Met Cys Gly Gly
1               5                   10

<210> SEQ ID NO 156
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Gly Gly Cys Met His Met Asp Tyr Phe Cys Gly Gly
1               5                   10

<210> SEQ ID NO 157
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

```
Gly Gly Cys Gln Val Met Val Leu Pro Cys Gly Gly
1               5                   10
```

<210> SEQ ID NO 158
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

```
Gly Gly Cys Leu Phe Asp Trp Pro Ser Cys Gly Gly
1               5                   10
```

<210> SEQ ID NO 159
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 159

```
Gly Gly Cys Lys Met Tyr His Gln Thr Cys Gly Gly
1               5                   10
```

<210> SEQ ID NO 160
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 160

```
Gly Gly Cys Gln Trp Leu Tyr Glu Ser Cys Gly Gly
1               5                   10
```

<210> SEQ ID NO 161
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

```
Gly Gly Cys Phe Thr Asn Phe Trp Leu Cys Gly Gly
1               5                   10
```

<210> SEQ ID NO 162
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 162

```
Gly Gly Cys Trp Glu Pro Thr His Trp Cys Gly Gly
1               5                   10
```

-continued

```
<210> SEQ ID NO 163
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 163

Gly Gly Cys Ala Phe Ala Met Leu Gln Cys Gly Gly
1               5                   10

<210> SEQ ID NO 164
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 164

Gly Gly Cys Met Tyr Gln Arg Gln Ala Trp Cys Gly Gly
1               5                   10

<210> SEQ ID NO 165
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

Gly Gly Cys Pro Phe Leu Trp Ala Glu Cys Gly Gly
1               5                   10

<210> SEQ ID NO 166
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Gly Gly Cys Met Phe Asp His Lys Val Cys Gly Gly
1               5                   10

<210> SEQ ID NO 167
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Gly Gly Cys Met Glu Ile Phe Asn Phe Cys Gly Gly
1               5                   10

<210> SEQ ID NO 168
<211> LENGTH: 12
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 168

Gly Gly Cys Val Met Glu Arg Leu Trp Cys Gly Gly
1               5                   10

<210> SEQ ID NO 169
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Gly Gly Cys Glu Tyr Tyr Trp Gln Phe Cys Gly Gly
1               5                   10

<210> SEQ ID NO 170
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 170

Gly Gly Cys Pro Phe Ser Trp Asp Gln Cys Gly Gly
1               5                   10

<210> SEQ ID NO 171
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Gly Gly Cys Ile Glu Tyr Phe Ser Trp Cys Gly Gly
1               5                   10

<210> SEQ ID NO 172
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172

Gly Gly Cys Val Phe Glu Ile Met Lys Cys Gly Gly
1               5                   10

<210> SEQ ID NO 173
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 173

Gly Gly Cys Glu Ser Pro Gln Tyr Phe Cys Gly Gly
1               5                   10

<210> SEQ ID NO 174
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Gly Gly Cys His His Asp Phe Glu Trp Cys Gly Gly
1               5                   10

<210> SEQ ID NO 175
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175

Gly Gly Cys Met Phe Pro Phe Ser Trp Cys Gly Gly
1               5                   10

<210> SEQ ID NO 176
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 176

Gly Gly Cys Asn Thr Val Leu Gln Glu Cys Gly Gly
1               5                   10

<210> SEQ ID NO 177
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Gly Gly Cys Val Phe Asp Ile Met Leu Cys Gly Gly
1               5                   10

<210> SEQ ID NO 178
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Gly Gly Cys Met Tyr Gln Gln Pro Trp Cys Gly Gly

```
1               5                   10
```

<210> SEQ ID NO 179
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 179

```
Gly Gly Cys Lys Lys Leu Tyr His Tyr Cys Gly Gly
1               5                   10
```

<210> SEQ ID NO 180
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 180

```
Gly Gly Cys Pro His Trp Pro Phe Glu Cys Gly Gly
1               5                   10
```

<210> SEQ ID NO 181
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 181

```
Gly Gly Cys Pro Ile Phe Pro Met Ile Cys Gly Gly
1               5                   10
```

<210> SEQ ID NO 182
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 182

```
Gly Gly Cys Met Ser Lys Asp Leu Trp Cys Gly Gly
1               5                   10
```

<210> SEQ ID NO 183
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 183

```
Gly Gly Cys Met Phe Gln Met Gly Val Cys Gly Gly
1               5                   10
```

<210> SEQ ID NO 184

```
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 184

Gly Gly Cys Tyr Glu Trp Pro Ser Tyr Cys Gly Gly
1               5                   10

<210> SEQ ID NO 185
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 185

Gly Gly Cys Gln Met Leu Tyr Met Asp Cys Gly Gly
1               5                   10

<210> SEQ ID NO 186
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 186

Gly Gly Cys Thr Val Gln Val Phe Phe Cys Gly Gly
1               5                   10

<210> SEQ ID NO 187
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Gly Gly Cys Ile Thr Phe Pro Met Met Cys Gly Gly
1               5                   10

<210> SEQ ID NO 188
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 188

Gly Gly Cys Val Met Tyr Trp Glu Tyr Cys Gly Gly
1               5                   10

<210> SEQ ID NO 189
<211> LENGTH: 12
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 189

Gly Gly Cys Met Trp Glu Val Leu His Cys Gly Gly
1               5                   10

<210> SEQ ID NO 190
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 190

Gly Gly Cys Met Gln Glu Arg Ser Trp Cys Gly Gly
1               5                   10

<210> SEQ ID NO 191
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 191

Gly Gly Cys Val Phe Glu Thr Ile Gln Cys Gly Gly
1               5                   10

<210> SEQ ID NO 192
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 192

Gly Gly Cys Gln Trp Ala Asn Ser Tyr Cys Gly Gly
1               5                   10

<210> SEQ ID NO 193
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193

Gly Gly Cys Lys Phe Gly Gln Trp Tyr Cys Gly Gly
1               5                   10

<210> SEQ ID NO 194
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 194

Gly Gly Cys Val Phe Asp Gln Met Trp Cys Gly Gly
1               5                   10

<210> SEQ ID NO 195
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 195

Gly Gly Cys Glu Val Met Ile Phe Asn Cys Gly Gly
1               5                   10

<210> SEQ ID NO 196
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 196

Gly Gly Cys Glu Ser Pro Met Phe Val Cys Gly Gly
1               5                   10

<210> SEQ ID NO 197
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 197

Gly Gly Cys Ile Thr Met Phe Gln Asn Cys Gly Gly
1               5                   10

<210> SEQ ID NO 198
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 198

Gly Gly Cys Val Phe Glu Arg Met Phe Cys Gly Gly
1               5                   10

<210> SEQ ID NO 199
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 199

Gly Gly Cys Gly Phe Glu Ile Phe Met Cys Gly
1               5                   10
```

<210> SEQ ID NO 200
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 200

Gly Gly Cys Leu Leu Gln Phe Thr Gly Cys Gly Gly
1               5                   10

<210> SEQ ID NO 201
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Gly Gly Cys His Phe Gln Ile Phe Gln Cys Gly Gly
1               5                   10

<210> SEQ ID NO 202
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

Gly Gly Cys Pro Phe Asp Trp Asp Lys Cys Gly Gly
1               5                   10

<210> SEQ ID NO 203
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Gly Gly Cys Val Thr Pro Leu Pro Phe Cys Gly
1               5                   10

<210> SEQ ID NO 204
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 204

Gly Gly Cys Tyr Met Tyr Met Asp Tyr Cys Gly Gly
1               5                   10

<210> SEQ ID NO 205
<211> LENGTH: 12

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 205

Gly Gly Cys Met Phe Glu Trp Tyr Val Cys Gly Gly
1               5                   10

<210> SEQ ID NO 206
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 206

Gly Gly Cys Pro Phe Thr Trp Arg Ile Cys Gly Gly
1               5                   10

<210> SEQ ID NO 207
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

Gly Gly Cys Glu Asn Asp Trp Lys Met Cys Gly Gly
1               5                   10

<210> SEQ ID NO 208
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 208

Gly Gly Cys Ala Phe Glu Phe Ile Tyr Cys Gly Gly
1               5                   10

<210> SEQ ID NO 209
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 209

Gly Gly Cys Pro Val Ala Val Phe Met Cys Gly Gly
1               5                   10

<210> SEQ ID NO 210
<211> LENGTH: 12
<212> TYPE: PRT
<213> ORGANISM: Artificial Sequence
<220> FEATURE:
<221> NAME/KEY: source
```

-continued

```
<223> OTHER INFORMATION: /note="Description of Artificial Sequence:
      Synthetic peptide"

<400> SEQUENCE: 210

Gly Gly Cys His Phe Asp Ile Phe Asp Cys Gly Gly
1               5                   10

<210> SEQ ID NO 211
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 211

Gly Gly Cys Pro Pro Glu Asn Met Phe Cys Gly Gly
1               5                   10

<210> SEQ ID NO 212
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 212

Gly Gly Cys Pro Phe Gln Met Gly Glu Cys Gly Gly
1               5                   10

<210> SEQ ID NO 213
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 213

Gly Gly Cys Ile Ser Gly Phe Phe Trp Cys Gly Gly
1               5                   10

<210> SEQ ID NO 214
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 214

Gly Gly Cys Pro Phe His Phe Gln Val Cys Gly Gly
1               5                   10

<210> SEQ ID NO 215
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 215
```

Gly Gly Cys Met Phe Gln Ile Ile Asn Cys Gly Gly
1               5                   10

<210> SEQ ID NO 216
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 216

Gly Gly Cys Gln Tyr Phe Leu Pro Cys Gly Gly
1               5                   10

<210> SEQ ID NO 217
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 217

Gly Gly Cys His Phe Ala Val Leu Asp Cys Gly Gly
1               5                   10

<210> SEQ ID NO 218
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 218

Gly Gly Cys Trp Asn Val Met Gly Leu Cys Gly Gly
1               5                   10

<210> SEQ ID NO 219
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219

Gly Gly Cys Tyr Thr Thr His Glu Leu Cys Gly Gly
1               5                   10

<210> SEQ ID NO 220
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Gly Gly Cys Leu Tyr Lys Gln Val Asp Cys Gly Gly
1               5                   10

```
<210> SEQ ID NO 221
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

Gly Gly Cys Val Phe Ser Ala Leu Trp Cys Gly Gly
1               5                   10

<210> SEQ ID NO 222
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 222

Gly Gly Cys Pro Phe Gln Phe Gln Thr Cys Gly Gly
1               5                   10

<210> SEQ ID NO 223
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Gly Gly Cys Ala Phe Leu Met Met Asp Cys Gly Gly
1               5                   10

<210> SEQ ID NO 224
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 224

Gly Gly Cys Glu Val Trp Tyr Glu Phe Cys Gly Gly
1               5                   10

<210> SEQ ID NO 225
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 225

Gly Gly Cys Ala Phe Asp Ile Gly Val Cys Gly Gly
1               5                   10

<210> SEQ ID NO 226
<211> LENGTH: 12
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 226

Gly Gly Cys Leu Ser Pro Leu Met Trp Cys Gly Gly
1               5                   10

<210> SEQ ID NO 227
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 227

Gly Gly Cys Pro Phe Ser Trp Val Ile Cys Gly Gly
1               5                   10

<210> SEQ ID NO 228
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 228

Gly Gly Cys Met Leu Met Phe Gln Gly Cys Gly Gly
1               5                   10

<210> SEQ ID NO 229
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 229

Gly Gly Cys Gln Pro Asn His Trp Leu Cys Gly Gly
1               5                   10

<210> SEQ ID NO 230
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 230

Gly Gly Cys Ile Asp Thr Tyr Val Trp Cys Gly Gly
1               5                   10

<210> SEQ ID NO 231
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 231

Gly Gly Cys His Phe His Leu Met Phe Cys Gly Gly
1               5                   10

<210> SEQ ID NO 232
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 232

Gly Gly Cys Gln Met Ile Phe Ser Thr Cys Gly Gly
1               5                   10

<210> SEQ ID NO 233
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Gly Gly Cys Lys Met Tyr Gln Pro Asp Cys Gly Gly
1               5                   10

<210> SEQ ID NO 234
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 234

Gly Gly Cys Met Trp Gly Val Phe Lys Cys Gly Gly
1               5                   10

<210> SEQ ID NO 235
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 235

Gly Gly Cys Gly Leu Phe Gly Gln Ser Cys Gly Gly
1               5                   10

<210> SEQ ID NO 236
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 236

```
Gly Gly Cys Gln Phe Asn Phe Pro Trp Cys Gly Gly
1               5                   10
```

<210> SEQ ID NO 237
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 237

```
Gly Gly Cys Asn Ile Ala Tyr Pro Trp Cys Gly Gly
1               5                   10
```

<210> SEQ ID NO 238
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238

```
Gly Gly Cys Lys Thr Ile Pro Ile Phe Cys Gly Gly
1               5                   10
```

<210> SEQ ID NO 239
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

```
Gly Gly Cys Gln Met Glu Leu Phe Leu Cys Gly Gly
1               5                   10
```

<210> SEQ ID NO 240
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

```
Gly Gly Cys Leu Gly Ala Phe Tyr Trp Cys Gly Gly
1               5                   10
```

<210> SEQ ID NO 241
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 241

```
Gly Gly Cys Pro Phe Asn Phe Ala Ser Cys Gly Gly
1               5                   10
```

```
<210> SEQ ID NO 242
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 242

Gly Gly Cys Gln Phe Asp Ile Leu Trp Cys Gly Gly
1               5                   10

<210> SEQ ID NO 243
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 243

Gly Gly Cys Tyr Tyr Thr His Glu Leu Cys Gly Gly
1               5                   10

<210> SEQ ID NO 244
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 244

Gly Gly Cys Gln Gln Arg Trp Arg Tyr Cys Gly Gly
1               5                   10

<210> SEQ ID NO 245
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 245

Gly Gly Cys Leu Trp Val Asp Glu Tyr Cys Gly Gly
1               5                   10

<210> SEQ ID NO 246
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 246

Gly Gly Cys Gly Met Leu Gly Trp Phe Cys Gly Gly
1               5                   10

<210> SEQ ID NO 247
<211> LENGTH: 12
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 247

Gly Gly Cys Trp Glu Gln His Tyr Leu Cys Gly Gly
1               5                   10

<210> SEQ ID NO 248
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 248

Gly Gly Cys Lys Thr Trp Gln Leu Leu Ile Phe Cys Gly Gly
1               5                   10

<210> SEQ ID NO 249
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 249

Gly Gly Cys Glu Gln Asn Trp Thr Leu Tyr Met Cys Gly Gly
1               5                   10

<210> SEQ ID NO 250
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 250

Ser Gly Cys Trp Pro Ser Pro Tyr Ile Phe Pro Cys Gly Gly
1               5                   10

<210> SEQ ID NO 251
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 251

Gly Gly Cys Trp Glu Ala Leu Gln Val Asn Asn Cys Gly Gly
1               5                   10

<210> SEQ ID NO 252
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 252

Cys Gly Cys Gln Ala Met Val Val Glu Asp Leu Cys Gly
1               5                   10

<210> SEQ ID NO 253
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 253

Gly Gly Cys Pro Leu Glu Trp Pro Arg Ile Ser Cys Gly Gly
1               5                   10

<210> SEQ ID NO 254
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 254

Gly Gly Cys Glu Pro Trp Ile Met Glu Ala Asn Cys Gly Gly
1               5                   10

<210> SEQ ID NO 255
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 255

Gly Gly Cys Pro Trp Asp Gln His Ile Asn Phe Cys Gly Gly
1               5                   10

<210> SEQ ID NO 256
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 256

Gly Gly Cys Pro Trp Tyr Ile Gln Met Asp His Cys Gly Gly
1               5                   10

<210> SEQ ID NO 257
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 257

Ser Gly Cys Gln Pro Trp Glu Ile Ser Tyr Tyr Cys Gly Gly

<210> SEQ ID NO 258
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 258

Gly Gly Cys Pro Val Met Phe Leu Asp Pro Arg Cys Gly Gly
1               5                   10

<210> SEQ ID NO 259
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 259

Gly Gly Cys Ser Ser Asp Val Leu Met Ile Phe Cys Gly Gly
1               5                   10

<210> SEQ ID NO 260
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 260

Gly Gly Cys Val Asp Glu Met Val Ile Tyr His Cys Gly Gly
1               5                   10

<210> SEQ ID NO 261
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 261

Gly Gly Cys Pro Phe Met Val Asn Leu Tyr Ser Cys Gly Gly
1               5                   10

<210> SEQ ID NO 262
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 262

Gly Gly Cys Glu Ser Asp Thr Met Trp Tyr Phe Cys Gly Gly
1               5                   10

<210> SEQ ID NO 263

```
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 263

Gly Gly Cys Arg Ser Asp Glu Ile Ile Phe Phe Cys Gly Gly
1               5                   10

<210> SEQ ID NO 264
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 264

Gly Gly Cys Pro Trp Asp Leu Leu Leu Pro Leu Cys Gly Gly
1               5                   10

<210> SEQ ID NO 265
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 265

Gly Gly Cys Pro Trp Ala Met Glu Leu Val His Cys Gly Gly
1               5                   10

<210> SEQ ID NO 266
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 266

Ser Gly Cys Thr Ala Ser Met Tyr Trp Glu Tyr Cys Gly Gly
1               5                   10

<210> SEQ ID NO 267
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 267

Gly Gly Cys Gly Leu Tyr Met Asp Pro Pro Tyr Tyr Gly Gly
1               5                   10

<210> SEQ ID NO 268
<211> LENGTH: 14
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic peptide"

<400> SEQUENCE: 268

Gly Gly Cys Pro Val Met Val Met Glu Pro Tyr Cys Gly Gly
1               5                   10

<210> SEQ ID NO 269
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 269

Gly Gly Cys Gln Thr Glu Phe Ile Leu Glu Phe Cys Gly Gly
1               5                   10

<210> SEQ ID NO 270
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 270

Ser Gly Cys Ala Phe Gln Ala His Gly Ala Met Cys Gly Gly
1               5                   10

<210> SEQ ID NO 271
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 271

Gly Gly Cys Pro Asp Phe Met Phe Arg Met Asn Cys Gly Gly
1               5                   10

<210> SEQ ID NO 272
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 272

Ser Gly Cys Ser Val Trp Phe Asp Thr Ile Ser Cys Gly Gly
1               5                   10

<210> SEQ ID NO 273
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 273

Gly Gly Cys Pro Trp Ser Met Glu Ile Ser Asn Cys Gly Gly
1               5                   10

<210> SEQ ID NO 274
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 274

Gly Gly Cys Pro Thr Trp Asn Trp Glu Ile Thr Cys Gly Gly
1               5                   10

<210> SEQ ID NO 275
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 275

Ser Gly Cys Pro Trp Asp Met His Ile Val Asp Cys Gly Gly
1               5                   10

<210> SEQ ID NO 276
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 276

Ser Gly Cys Phe Pro Trp Glu Pro Ala Tyr Phe Cys Gly Gly
1               5                   10

<210> SEQ ID NO 277
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 277

Gly Gly Cys Pro Phe Gly Trp Asn Val Phe His Cys Gly Gly
1               5                   10

<210> SEQ ID NO 278
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 278

Gly Gly Cys Pro Trp His Met Glu Val Asn Glu Cys Gly Gly
1               5                   10

```
<210> SEQ ID NO 279
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 279

Gly Gly Cys Pro Phe Ala Leu Gly Met Gly Glu Cys Gly Gly
1               5                   10

<210> SEQ ID NO 280
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 280

Gly Gly Cys Met Phe Pro Phe Met Leu Ser Asn Cys Gly Gly
1               5                   10

<210> SEQ ID NO 281
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 281

Gly Gly Cys Ala Phe Gln Phe Met Pro Ala His Cys Gly Gly
1               5                   10

<210> SEQ ID NO 282
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 282

Gly Gly Cys Gln Ile Gln Gly Phe Glu Phe Thr Cys Gly Gly
1               5                   10

<210> SEQ ID NO 283
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 283

Gly Gly Cys Pro Met Gly Ile Ile Leu Asp Leu Cys Gly Gly
1               5                   10

<210> SEQ ID NO 284
<211> LENGTH: 14
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 284

Gly Gly Cys Leu Met Leu Glu Pro Thr Val Thr Cys Gly Gly
1               5                   10

<210> SEQ ID NO 285
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 285

Gly Gly Cys Gly Lys Asn Glu Val Ala Met Phe Cys Gly Gly
1               5                   10

<210> SEQ ID NO 286
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 286

Gly Gly Cys Ser Phe Leu Leu Glu Ile Ala Asn Cys Gly Gly
1               5                   10

<210> SEQ ID NO 287
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 287

Gly Gly Cys Asp Val Glu Lys Ile Met Ile Phe Cys Gly Gly
1               5                   10

<210> SEQ ID NO 288
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 288

Gly Gly Cys Phe Pro Met Thr Pro Trp Gly Leu Cys Gly Gly
1               5                   10

<210> SEQ ID NO 289
<211> LENGTH: 15
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 289

Ser Gly Cys Asp Trp Tyr Leu Glu Trp Ser Gly Asn Cys Gly Gly
1               5                   10                  15

<210> SEQ ID NO 290
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 290

Gly Gly Cys Gly Val Glu Ile Met Phe His Gly Cys Gly Gly
1               5                   10

<210> SEQ ID NO 291
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 291

Gly Gly Cys Met Asp Gly Leu His Leu Tyr Phe Cys Gly Gly
1               5                   10

<210> SEQ ID NO 292
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 292

Ser Gly Cys Pro Ile Phe Ile Phe Asp Tyr Tyr Cys Gly Gly
1               5                   10

<210> SEQ ID NO 293
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 293

Gly Gly Cys Ala Val Trp Ile Phe Ser Asp Ala Cys Gly Gly
1               5                   10

<210> SEQ ID NO 294
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 294
```

```
Gly Gly Cys Pro Trp Ser Leu His Ile Gln Gln Cys Gly Gly
1               5                   10
```

<210> SEQ ID NO 295
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 295

```
Ser Gly Cys Ala Phe Ser Met Leu Phe Ile Asn Cys Gly Gly
1               5                   10
```

<210> SEQ ID NO 296
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 296

```
Ser Gly Cys Leu Pro Trp Glu Leu Tyr Met Phe Cys Gly Gly
1               5                   10
```

<210> SEQ ID NO 297
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 297

```
Ser Gly Cys Pro Phe Thr Ile Asn Phe Tyr Thr Cys Gly Gly
1               5                   10
```

<210> SEQ ID NO 298
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 298

```
Gly Gly Cys Pro Ile Trp Phe Thr Trp Ser Thr Cys Gly Gly
1               5                   10
```

<210> SEQ ID NO 299
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 299

```
Gly Gly Cys Gln Ile Gln Val Val Asn Pro Tyr Cys Gly Gly
1               5                   10
```

<210> SEQ ID NO 300
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 300

Gly Gly Cys Ala Phe Gln Ile Glu Phe Leu Met Cys Gly Gly
1               5                   10

<210> SEQ ID NO 301
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 301

Gly Gly Cys Ala Trp Glu Ile Arg Ile Leu Gly Cys Gly Gly
1               5                   10

<210> SEQ ID NO 302
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 302

Gly Gly Cys Pro Tyr Gln Leu Val Ile Met Trp Cys Gly Gly
1               5                   10

<210> SEQ ID NO 303
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 303

Gly Gly Cys Met Phe Ala Met His Val Phe Gly Cys Gly Gly
1               5                   10

<210> SEQ ID NO 304
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 304

Ser Gly Cys Thr Val Met Tyr Thr Leu Gln Ile Phe Gly Gly
1               5                   10

<210> SEQ ID NO 305
<211> LENGTH: 14
<212> TYPE: PRT

<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 305

Ser Gly Cys Ala His Gln Val Tyr Trp Ala Phe Cys Gly Gly
1               5                   10

<210> SEQ ID NO 306
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 306

Gly Gly Cys Pro Asn Phe Phe Asn Phe Trp Phe Cys Gly Gly
1               5                   10

<210> SEQ ID NO 307
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 307

Gly Gly Cys Ala Phe Glu Phe Ser Ser Ala Phe Asn Cys Gly Gly
1               5                   10                  15

<210> SEQ ID NO 308
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 308

Ser Gly Cys Gln Thr Met Leu Thr Ala Glu Gly Glu Trp Cys Gly Gly
1               5                   10                  15

<210> SEQ ID NO 309
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 309

Gly Gly Cys Val Met Asp Leu Trp Pro Asp Leu Glu Ile Cys Gly Gly
1               5                   10                  15

<210> SEQ ID NO 310
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:

-continued

```
      Synthetic peptide"

<400> SEQUENCE: 310

Gly Gly Cys Gln Pro Leu Phe Asp Asp His Asp Thr Trp Cys Gly Gly
1               5                   10                  15

<210> SEQ ID NO 311
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 311

Gly Gly Cys Pro Phe Glu Leu Val Met Ser Asp Glu Gln Cys Gly Gly
1               5                   10                  15

<210> SEQ ID NO 312
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 312

Ser Gly Cys Gly His Gly Met Gln Met Asp Ser Val Phe Cys Gly Gly
1               5                   10                  15

<210> SEQ ID NO 313
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 313

Ser Gly Cys Asp Glu Thr Gln Ser Ala Ile Trp Tyr Phe Cys Gly Gly
1               5                   10                  15

<210> SEQ ID NO 314
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 314

Gly Gly Cys Arg Glu Pro Glu Gln Tyr Trp Thr Val Trp Cys Gly Gly
1               5                   10                  15

<210> SEQ ID NO 315
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 315
```

Ser Gly Cys Gln Glu Lys Lys Asp Leu Tyr Trp Glu Tyr Cys Gly Gly
1               5                   10                  15

<210> SEQ ID NO 316
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 316

Ser Gly Cys Gly Gln Asp Asn Asp Leu Pro Trp Glu Trp Cys Gly Gly
1               5                   10                  15

<210> SEQ ID NO 317
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 317

Gly Gly Cys Val Phe Gln Leu Ser Phe Ser Arg Ser Asp Cys Gly Gly
1               5                   10                  15

<210> SEQ ID NO 318
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 318

Ser Gly Cys Ala Phe Asp Met Ile Trp Phe Glu Gly Val Cys Gly Gly
1               5                   10                  15

<210> SEQ ID NO 319
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 319

Ser Gly Cys Ala Phe Tyr Trp Gln Pro Trp Glu His Ser Cys Gly Gly
1               5                   10                  15

<210> SEQ ID NO 320
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 320

Gly Gly Cys Gln Leu Ser Ile Ile Leu Thr Gly Leu Pro Cys Gly Gly
1               5                   10                  15

-continued

```
<210> SEQ ID NO 321
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 321

Gly Gly Cys Gly Met Leu Glu Trp Ser Gly Leu Gln Phe Cys Gly Gly
1               5                   10                  15

<210> SEQ ID NO 322
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 322

Ser Gly Cys His Glu Lys Ala Leu Thr Tyr Trp Glu Phe Cys Gly Gly
1               5                   10                  15

<210> SEQ ID NO 323
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 323

Gly Gly Cys Phe Glu Asn Met Gln Val Trp Tyr Asn Glu Cys Gly Gly
1               5                   10                  15

<210> SEQ ID NO 324
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 324

Gly Gly Cys Pro Glu Trp Glu Asn Gln Ile Leu Leu Phe Cys Gly Gly
1               5                   10                  15

<210> SEQ ID NO 325
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 325

Ser Gly Cys Glu Ser Trp Gln Arg Asp Met Asn Tyr Phe Cys Gly Gly
1               5                   10                  15

<210> SEQ ID NO 326
<211> LENGTH: 16
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 326

Ser Gly Cys Asn Asp Gln Phe Pro Met Tyr Tyr Leu Phe Cys Gly Gly
1               5                   10                  15

<210> SEQ ID NO 327
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 327

Gly Gly Cys Phe Glu Asp Met Ala Leu Gln Pro Thr Gln Cys Gly Gly
1               5                   10                  15

<210> SEQ ID NO 328
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 328

Ser Gly Cys Lys Gly Pro Trp Gln Phe Glu Phe Leu Val Cys Gly Gly
1               5                   10                  15

<210> SEQ ID NO 329
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 329

Gly Gly Cys Glu Ala Phe Ser Met Lys Phe Asn Asp Phe Cys Gly Gly
1               5                   10                  15

<210> SEQ ID NO 330
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 330

Gly Gly Cys Val Gln Pro Ala Ile Ala Met Trp Pro Phe Cys Gly Gly
1               5                   10                  15

<210> SEQ ID NO 331
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 331

Gly Gly Cys Thr Asp Gln Gly Arg Phe Val Leu Tyr Glu Cys Gly Gly
1               5                   10                  15

<210> SEQ ID NO 332
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 332

Gly Gly Cys Pro Val Gln Glu Phe Leu Trp Gly Val Tyr Cys Gly Gly
1               5                   10                  15

<210> SEQ ID NO 333
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 333

Gly Gly Cys Ser Asn Ser Trp Glu Trp Thr Leu Tyr Ala Cys Gly Gly
1               5                   10                  15

<210> SEQ ID NO 334
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 334

Ser Gly Cys His Gly Leu Val Glu Trp Gly Tyr Met Ala Cys Gly Gly
1               5                   10                  15

<210> SEQ ID NO 335
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 335

Ser Gly Cys Glu Ala Phe Gly Leu Ile Phe Glu Asp Phe Cys Gly Gly
1               5                   10                  15

<210> SEQ ID NO 336
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 336

Gly Gly Cys Ala Asn Pro Glu Phe Gln Met Trp Tyr Phe Cys Gly Gly

```
<210> SEQ ID NO 337
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 337

Ser Gly Cys Gly Tyr Glu Val Pro Ile Pro Leu Phe Thr Cys Gly Gly
1               5                   10                  15

<210> SEQ ID NO 338
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 338

Gly Gly Cys Trp Phe Gln Gln Phe Ala Trp Arg Ala Thr Cys Gly Gly
1               5                   10                  15

<210> SEQ ID NO 339
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 339

Gly Gly Cys Gly Phe Glu Leu Asn Met Ile Ser Gln Tyr Cys Gly Gly
1               5                   10                  15

<210> SEQ ID NO 340
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 340

Gly Gly Cys Glu Pro Phe Glu Leu Arg Phe Tyr His Glu Gly Cys Gly
1               5                   10                  15

Gly

<210> SEQ ID NO 341
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 341

Gly Gly Cys Pro Phe Gln Leu Val Trp Ser Pro Ala Phe Cys Gly Gly
1               5                   10                  15
```

-continued

```
<210> SEQ ID NO 342
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 342

Ser Gly Cys Ala Trp Glu Ile Lys Gly Ile Trp Cys Gly Gly
1               5                   10

<210> SEQ ID NO 343
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 343

Ser Gly Cys Ser Ser Ile Gln Ser Trp Arg Leu Trp Leu Cys Gly Gly
1               5                   10                  15

<210> SEQ ID NO 344
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 344

Gly Gly Cys Gly Val Met Gln Val Leu Asn Arg Ala His Cys Gly Gly
1               5                   10                  15

<210> SEQ ID NO 345
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 345

Arg Gly Cys Gln Val Lys Tyr Tyr Met Gly Glu Gly Asp Cys Gly Gly
1               5                   10                  15

<210> SEQ ID NO 346
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 346

Gly Gly Cys Pro Val Trp Ile Pro Phe His Trp Glu Glu Cys Gly Gly
1               5                   10                  15

<210> SEQ ID NO 347
<211> LENGTH: 16
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 347

Ser Gly Cys Leu Leu Trp Gln Gln Ser Met Leu Leu Phe Cys Gly Gly
1               5                   10                  15

<210> SEQ ID NO 348
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 348

Ser Gly Cys Glu Gln Gln Trp Ser Trp Arg Leu Tyr Leu Cys Gly Gly
1               5                   10                  15

<210> SEQ ID NO 349
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 349

Gly Gly Cys Ser Val Gln Ser Thr Trp Gln Leu Trp Ala Cys Gly Gly
1               5                   10                  15

<210> SEQ ID NO 350
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 350

Ser Gly Cys Lys Tyr Pro Ile Phe Trp Asp Thr Ile Asp Cys Gly Gly
1               5                   10                  15

<210> SEQ ID NO 351
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 351

Ser Gly Cys Val Glu Tyr Gln Tyr Gln Met Val Tyr Phe Cys Gly Gly
1               5                   10                  15

<210> SEQ ID NO 352
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                                 Synthetic peptide"

<400> SEQUENCE: 352

Gly Gly Cys Thr Asp Gln Arg Trp Phe Val Leu Tyr Glu Cys Gly Gly
1               5                   10                  15

<210> SEQ ID NO 353
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 353

Gly Gly Cys Pro Phe Trp Gln Glu Trp His Leu Ser Tyr Cys Gly Gly
1               5                   10                  15

<210> SEQ ID NO 354
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 354

Ser Gly Cys Tyr Met Gly Tyr Met His Leu Ile Ala Glu Cys Gly Gly
1               5                   10                  15

<210> SEQ ID NO 355
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 355

Gly Gly Cys Phe Met Gly Ser Phe Ser Leu Val Tyr Gly Cys Gly Gly
1               5                   10                  15

<210> SEQ ID NO 356
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 356

Ser Gly Cys Pro Trp Gly Phe Met Phe Pro Ile Ser Tyr Cys Gly Gly
1               5                   10                  15

<210> SEQ ID NO 357
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 357
```
ggaaaagtcg actagaccac catgga 26

<210> SEQ ID NO 358
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 358
ctttgcggcc gctcattatt t 21

<210> SEQ ID NO 359
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 359

Gly Gly Cys Gly Lys His Trp His Gln Cys Gly Gly
1               5                   10

<210> SEQ ID NO 360
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 360

Gly Gly Cys His Ser Phe Lys His Phe Cys Gly Gly
1               5                   10

<210> SEQ ID NO 361
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 361

Gly Gly Cys Glu Arg Phe His His Ala Cys Gly Gly
1               5                   10

<210> SEQ ID NO 362
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 362

Gly Gly Cys Ala Gln Gln Trp His His Glu Tyr Cys Gly Gly
1               5                   10

<210> SEQ ID NO 363
<211> LENGTH: 12

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 363

Gly Gly Cys Asp Gly Arg Thr Lys Tyr Cys Gly Gly
1               5                   10

<210> SEQ ID NO 364
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 364

Gly Gly Cys Met Gln Met Asn Lys Trp Cys Gly Gly
1               5                   10

<210> SEQ ID NO 365
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 365

Gly Gly Cys Trp Gly Ser Arg Ser Gln Cys Gly Gly
1               5                   10

<210> SEQ ID NO 366
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 366

Gly Gly Cys Gln Gly Met Trp Thr Trp Cys Gly Gly
1               5                   10

<210> SEQ ID NO 367
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 367

Gly Gly Cys Phe Pro Leu Gln Asp Tyr Cys Gly Gly
1               5                   10

<210> SEQ ID NO 368
<211> LENGTH: 12
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 368

Gly Gly Cys Tyr Pro Leu Gln Asp Tyr Cys Gly Gly
1               5                   10

<210> SEQ ID NO 369
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 369

Gly Gly Cys Val Phe Asn Ala Phe Asn Cys Gly Gly
1               5                   10

<210> SEQ ID NO 370
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 370

Gly Gly Cys Val Phe Asn Gly Phe Asn Cys Gly Gly
1               5                   10

<210> SEQ ID NO 371
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 371

Gly Gly Cys Val Phe Asn His Phe Asn Cys Gly Gly
1               5                   10

<210> SEQ ID NO 372
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 372

Gly Gly Cys Val Phe Asn Ile Phe Asn Cys Gly Gly
1               5                   10

<210> SEQ ID NO 373
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 373
```

Gly Gly Cys Val Phe Asn Leu Phe Asn Cys Gly Gly
1               5                   10

<210> SEQ ID NO 374
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 374

Gly Gly Cys Val Phe Asn Asn Phe Asn Cys Gly Gly
1               5                   10

<210> SEQ ID NO 375
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 375

Gly Gly Cys Val Phe Asn Gln Phe Asn Cys Gly Gly
1               5                   10

<210> SEQ ID NO 376
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 376

Gly Gly Cys Val Phe Asn Ser Phe Asn Cys Gly Gly
1               5                   10

<210> SEQ ID NO 377
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 377

Gly Gly Cys Val Phe Asn Thr Phe Asn Cys Gly Gly
1               5                   10

<210> SEQ ID NO 378
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 378

Gly Gly Cys Val Phe Asn Val Phe Asn Cys Gly Gly
1               5                   10

<210> SEQ ID NO 379
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 379

Gly Gly Cys Trp Gly Ser Arg Ser Gln Cys Gly Gly
1               5                   10

<210> SEQ ID NO 380
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 380
gagtgggaga gcaatggtgg ttgtccggtt ctgctgttca actgtggtgg tgggcagccg    60
gagaac                                                              66

<210> SEQ ID NO 381
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 381
gttctccggc tgcccaccac cacagttgaa cagcagaacc ggacaaccac cattgctctc    60
ccactc                                                              66

<210> SEQ ID NO 382
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 382
gagtgggaga gcaatggtgg ttgtgttttc tctgctctgt ggtgtggtgg tgggcagccg    60
gagaac                                                              66

<210> SEQ ID NO 383
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 383
gttctccggc tgcccaccac cacaccacag agcagagaaa acacaaccac cattgctctc    60
ccactc                                                              66

<210> SEQ ID NO 384
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 384
gagtgggaga gcaatggtgg ttgtgaaact tactggttgt tctgtggtgg tgggcagccg     60
gagaac                                                                66

<210> SEQ ID NO 385
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 385
gttctccggc tgcccaccac cacagaacaa ccagtaagtt tcacaaccac cattgctctc     60
ccactc                                                                66

<210> SEQ ID NO 386
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 386
gagtgggaga gcaatggtgg ttgtccgcat tggccgttcg aatgtggtgg tgggcagccg     60
gagaac                                                                66

<210> SEQ ID NO 387
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 387
gttctccggc tgcccaccac cacattcgaa cggccaatgc ggacaaccac cattgctctc     60
ccactc                                                                66

<210> SEQ ID NO 388
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 388
gagtgggaga gcaatggtgg ttgtgctttc gaattcatct actgtggtgg tgggcagccg     60
gagaac                                                                66

<210> SEQ ID NO 389
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 389
gttctccggc tgcccaccac cacagtagat gaattcgaaa gcacaaccac cattgctctc     60
ccactc                                                                66

<210> SEQ ID NO 390
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 390
gagtgggaga gcaatggtgg ttgtcagtac ttcttgccgt gtggtggtgg gcagccggag     60
aac                                                                  63

<210> SEQ ID NO 391
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 391
gttctccggc tgcccaccac cacacggcaa gaagtactga caaccaccat tgctctccca     60
ctc                                                                  63

<210> SEQ ID NO 392
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 392

Gly Gly Cys Pro His Met Phe Pro Trp Cys Gly Gly
1               5                   10

<210> SEQ ID NO 393
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 393

Gly Gly Cys Gly His Gly Trp Ile Phe Cys Gly Gly
1               5                   10

```
<210> SEQ ID NO 394
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 394

Gly Gly Cys Val Phe Asn Met Phe Asn Cys Gly Gly
1               5                   10

<210> SEQ ID NO 395
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 395

Gly Gly Cys Ile Leu Asn Phe Tyr Gly Cys Gly Gly
1               5                   10

<210> SEQ ID NO 396
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 396

Gly Gly Cys Arg Glu Pro His Pro Phe Cys Gly Gly
1               5                   10

<210> SEQ ID NO 397
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 397

Gly Gly Cys Pro Phe Glu Phe Thr Gln Cys Gly Gly
1               5                   10

<210> SEQ ID NO 398
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 398

Gly Gly Cys Gln Leu Gly Ser Met His Cys Gly Gly
1               5                   10

<210> SEQ ID NO 399
<211> LENGTH: 12
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 399

Gly Gly Cys Tyr Glu Asn Lys Thr Leu Cys Gly Gly
1               5                   10

<210> SEQ ID NO 400
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 400

Gly Gly Cys Arg Ala Gly Tyr Gly Asp Ala Ser Cys Gly Gly
1               5                   10

<210> SEQ ID NO 401
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 401

Gly Gly Cys Met Val Pro Phe Ser Met Cys Gly Gly
1               5                   10

<210> SEQ ID NO 402
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 402

Gly Gly Cys Glu Leu Gln Glu Arg Trp Cys Gly Gly
1               5                   10

<210> SEQ ID NO 403
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 403

Gly Gly Cys Pro Ala Asn Trp Gly Thr Cys Gly Gly
1               5                   10

<210> SEQ ID NO 404
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 404

Gly Gly Cys Met Met Glu Phe Ala Gln Cys Gly Gly
1               5                   10

<210> SEQ ID NO 405
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 405

Gly Gly Cys Gln His His Ile Met Gln Cys Gly Gly
1               5                   10

<210> SEQ ID NO 406
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 406

Gly Gly Cys Tyr Gln His His Met Glu Cys Gly Gly
1               5                   10

<210> SEQ ID NO 407
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 407

Gly Gly Cys Met Val Pro Phe Ser Met Cys Gly Gly
1               5                   10

<210> SEQ ID NO 408
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 408

Gly Gly Cys Gln Lys Gly Trp Val Phe Cys Gly Gly
1               5                   10

<210> SEQ ID NO 409
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 409

```
Gly Gly Cys Val Tyr Asp Val Lys Lys Cys Gly Gly
1               5                   10
```

<210> SEQ ID NO 410
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 410

```
Gly Gly Cys Leu Lys Gly Met His Gly Ser Ala Cys Gly Gly
1               5                   10
```

<210> SEQ ID NO 411
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 411

```
Gly Gly Cys Asn Met Leu Trp Gly Ser Cys Gly Gly
1               5                   10
```

<210> SEQ ID NO 412
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 412

```
Gly Gly Cys Met Gln Pro Trp Ala Phe Cys Gly Gly
1               5                   10
```

<210> SEQ ID NO 413
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 413

```
Gly Gly Cys Met Thr Gln Tyr Asn Trp Cys Gly Gly
1               5                   10
```

<210> SEQ ID NO 414
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 414

```
Gly Gly Cys Val Asn Thr Trp Trp Ser Cys Gly Gly
1               5                   10
```

```
<210> SEQ ID NO 415
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 415

Gly Gly Cys Tyr Ile Thr Gln Lys Leu Cys Gly Gly
1               5                   10

<210> SEQ ID NO 416
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 416

Gly Gly Cys Glu Thr His Tyr Thr Tyr Cys Gly Gly
1               5                   10

<210> SEQ ID NO 417
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 417

Gly Gly Cys Thr Glu Gln Val Met Trp Cys Gly Gly
1               5                   10

<210> SEQ ID NO 418
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 418

Gly Gly Cys Ile Thr Glu Phe Ser His Cys Gly Gly
1               5                   10

<210> SEQ ID NO 419
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 419

Gly Gly Cys Gln Asn Arg Ser Tyr Trp Cys Gly Gly
1               5                   10

<210> SEQ ID NO 420
<211> LENGTH: 12
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 420

Gly Gly Cys His Gly Thr Lys Gln Phe Cys Gly Gly
1               5                   10

<210> SEQ ID NO 421
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 421

Gly Gly Cys Asn Pro His Arg Thr Pro Cys Gly Gly
1               5                   10

<210> SEQ ID NO 422
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 422

Gly Gly Cys Gln His Ser Pro Pro Leu Cys Gly Gly
1               5                   10

<210> SEQ ID NO 423
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 423

Gly Gly Cys Asn His Glu Glu Thr Phe Cys Gly Gly
1               5                   10

<210> SEQ ID NO 424
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 424

Gly Gly Cys Gln Tyr Pro Arg Lys Leu Cys Gly Gly
1               5                   10

<210> SEQ ID NO 425
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

-continued

<400> SEQUENCE: 425

Gly Gly Cys Ile Gly Pro Phe Trp Trp Cys Gly Gly
1               5                   10

<210> SEQ ID NO 426
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 426

Gly Gly Cys Met Gln Pro Trp Ile Asn Cys Gly Gly
1               5                   10

<210> SEQ ID NO 427
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 427

Gly Gly Cys Val Gln His Lys Met Gly Val Val Cys Gly Gly
1               5                   10

<210> SEQ ID NO 428
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 428

Gly Gly Cys Glu Met Glu Asn Ala Trp Cys Gly Gly
1               5                   10

<210> SEQ ID NO 429
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 429

Gly Gly Cys Pro Pro Trp Pro Glu Arg Cys Gly Gly
1               5                   10

<210> SEQ ID NO 430
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 430

Gly Gly Cys His Asp Pro Glu Pro Phe Cys Gly Gly

<210> SEQ ID NO 431
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 431

Gly Gly Cys Asn Glu Pro Lys Tyr Val Cys Gly Gly
1               5                   10

<210> SEQ ID NO 432
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 432

Gly Gly Cys Asp Arg Pro Val Trp Phe Cys Gly Gly
1               5                   10

<210> SEQ ID NO 433
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 433

Gly Gly Cys Glu Ile Pro His Ser Phe Cys Gly Gly
1               5                   10

<210> SEQ ID NO 434
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 434

Gly Gly Cys Met Pro Tyr Glu Met His Cys Gly Gly
1               5                   10

<210> SEQ ID NO 435
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 435

Gly Gly Cys Lys Arg Glu Asn Pro Tyr Cys Gly Gly
1               5                   10

<210> SEQ ID NO 436

```
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 436

Gly Gly Cys Ala Glu Arg Gln Tyr Tyr Cys Gly Gly
1               5                   10

<210> SEQ ID NO 437
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 437

Gly Gly Cys Asn Val Leu Asp Leu Phe Cys Gly Gly
1               5                   10

<210> SEQ ID NO 438
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 438

Gly Gly Cys Lys Ser Met Ile Ser Met Cys Gly Gly
1               5                   10

<210> SEQ ID NO 439
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 439

Gly Gly Cys His His Lys Gln Asp Gln Cys Gly Gly
1               5                   10

<210> SEQ ID NO 440
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 440

Gly Gly Cys Asn Ala Thr Leu Ser Gly Tyr Leu Cys Gly Gly
1               5                   10

<210> SEQ ID NO 441
<211> LENGTH: 12
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 441

Gly Gly Cys Glu Ala Thr Met Thr Trp Cys Gly Gly
1               5                   10

<210> SEQ ID NO 442
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 442

Gly Gly Cys Asn Val Leu Asp Leu Phe Cys Gly Gly
1               5                   10

<210> SEQ ID NO 443
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 443

Gly Gly Cys Ser Arg Val Phe Lys Tyr Cys Gly Gly
1               5                   10

<210> SEQ ID NO 444
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 444

Gly Gly Cys His Ala Pro Gln Trp Glu Cys Gly Gly
1               5                   10

<210> SEQ ID NO 445
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 445

Gly Gly Cys Pro Leu Val Arg Ala Asp Cys Gly Gly
1               5                   10

<210> SEQ ID NO 446
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 446

Gly Gly Cys Met His Asn Glu Glu Phe Cys Gly Gly
1               5                   10

<210> SEQ ID NO 447
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 447

Gly Gly Cys Met Phe Glu Thr Lys Trp Cys Gly Gly
1               5                   10

<210> SEQ ID NO 448
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 448

Gly Gly Cys Asn Met Asn Glu Trp Lys Ser Gly Cys Gly Gly
1               5                   10

<210> SEQ ID NO 449
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 449

Gly Gly Cys Leu Gln Asn Leu Tyr Val Cys Gly Gly
1               5                   10

<210> SEQ ID NO 450
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 450

Gly Gly Cys Gln Thr Ser Met Lys Asn Cys Gly Gly
1               5                   10

<210> SEQ ID NO 451
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 451

Gly Gly Cys Asn Leu Gly His Met Pro Cys Gly Gly
1               5                   10

```
<210> SEQ ID NO 452
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 452

Gly Gly Cys Trp Met Trp Ala Glu Glu Cys Gly Gly
1               5                   10

<210> SEQ ID NO 453
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 453

Gly Gly Cys Val His Asn Asp Lys Leu Cys Gly Gly
1               5                   10

<210> SEQ ID NO 454
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 454

Gly Gly Cys Tyr Gly Lys Ala Gly Met Arg Asp Cys Gly Gly
1               5                   10

<210> SEQ ID NO 455
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 455

Gly Gly Cys Val Ser Ala Ala Thr Ser Arg Thr Cys Gly Gly
1               5                   10

<210> SEQ ID NO 456
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 456

Gly Gly Cys Tyr Pro Gln Lys Glu Ile Cys Gly Gly
1               5                   10

<210> SEQ ID NO 457
<211> LENGTH: 14
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 457

Gly Gly Cys Asn Gln Ser Ser Ser Arg Glu Ala Cys Gly Gly
1               5                   10

<210> SEQ ID NO 458
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 458

Gly Gly Cys Asn Pro Val Ser Thr Gly Ala Tyr Cys Gly Gly
1               5                   10

<210> SEQ ID NO 459
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 459

Gly Gly Cys Pro Gly His Glu Phe Arg Cys Gly Gly
1               5                   10

<210> SEQ ID NO 460
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 460

Gly Gly Cys Gly Glu Tyr Asn Tyr Val Gly Gly Cys Gly Gly
1               5                   10

<210> SEQ ID NO 461
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 461

Gly Gly Cys Lys Trp Ser Met Thr Lys Cys Gly Gly
1               5                   10

<210> SEQ ID NO 462
<211> LENGTH: 12
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 462

Gly Gly Cys Asp Trp His Arg Met Lys Cys Gly Gly
1               5                   10

<210> SEQ ID NO 463
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 463

Gly Gly Cys Met His Ser Pro His Ala Cys Gly Gly
1               5                   10

<210> SEQ ID NO 464
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 464

Gly Gly Cys Met Met Trp Lys Val Asn Cys Gly Gly
1               5                   10

<210> SEQ ID NO 465
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 465

Gly Gly Cys Phe Thr Asn Tyr Ala Ser Glu Lys Cys Gly Gly
1               5                   10

<210> SEQ ID NO 466
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 466

Gly Gly Cys Asp Arg Phe Gln Asn Val Asn Val Cys Gly Gly
1               5                   10

<210> SEQ ID NO 467
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 467
```

```
Gly Gly Cys Glu Arg His Phe Pro Ala Leu Phe Cys Gly Gly
1               5                   10
```

<210> SEQ ID NO 468
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 468

```
Gly Gly Cys Thr Leu Gly Ser Ala Pro Thr Leu Cys Gly Gly
1               5                   10
```

<210> SEQ ID NO 469
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 469

```
Gly Gly Cys Glu Met Met Lys Asn Lys Ser Gly Cys Gly Gly
1               5                   10
```

<210> SEQ ID NO 470
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 470

```
Gly Gly Cys Glu Ala Ser Gly Gln Ile Cys Gly Gly
1               5                   10
```

<210> SEQ ID NO 471
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 471

```
Gly Gly Cys Leu Arg Asn Phe Met Lys Gln Ser Cys Gly Gly
1               5                   10
```

<210> SEQ ID NO 472
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 472

```
Gly Gly Cys Pro Asn Asp Thr Val Arg Asp Ala Cys Gly Gly
1               5                   10
```

```
<210> SEQ ID NO 473
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 473

Gly Gly Cys Ser Phe Ser Arg His Met Gly Ala Cys Gly Gly
1               5                   10

<210> SEQ ID NO 474
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 474

Gly Gly Cys Ala Lys Asp Gln His Thr Gly Ser Cys Gly Gly
1               5                   10

<210> SEQ ID NO 475
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 475

Gly Gly Cys Leu Gly Leu Arg Gln Glu Cys Gly Gly
1               5                   10

<210> SEQ ID NO 476
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 476

Gly Gly Cys Asn Met Asn Glu Trp Lys Ser Gly Cys Gly Gly
1               5                   10

<210> SEQ ID NO 477
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 477

Gly Gly Cys Gln Gln Ile Lys Glu Trp Cys Gly Gly
1               5                   10

<210> SEQ ID NO 478
<211> LENGTH: 12
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 478

Gly Gly Cys Asp Leu Pro Asn Glu Met Cys Gly Gly
1               5                   10

<210> SEQ ID NO 479
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 479

Gly Gly Cys Met Phe Ser His Pro His Cys Gly Gly
1               5                   10

<210> SEQ ID NO 480
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 480

Gly Gly Cys Ala Gly Pro Tyr Trp Ala Cys Gly Gly
1               5                   10

<210> SEQ ID NO 481
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 481

Gly Gly Cys Glu Gln Gln Phe Val Thr Cys Gly Gly
1               5                   10

<210> SEQ ID NO 482
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 482

Gly Gly Cys Met Gly Trp Trp His Leu Cys Gly Gly
1               5                   10

<210> SEQ ID NO 483
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 483

Gly Gly Cys Pro Gln His Gly Glu Met Cys Gly Gly
1               5                   10

<210> SEQ ID NO 484
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 484

Gly Gly Cys Tyr Ala Ser Pro His Glu Cys Gly Gly
1               5                   10

<210> SEQ ID NO 485
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 485

Gly Gly Cys Met Pro Pro Gln Trp Met Cys Gly Gly
1               5                   10

<210> SEQ ID NO 486
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 486

Gly Gly Cys Asp Thr Ile Gly Trp Phe Cys Gly Gly
1               5                   10

<210> SEQ ID NO 487
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 487

Gly Gly Cys Gly Ile Phe Glu Ser Trp Cys Gly Gly
1               5                   10

<210> SEQ ID NO 488
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 488

```
Gly Gly Cys Gly Pro Tyr Lys Thr Glu Cys Gly Gly
1               5                   10
```

<210> SEQ ID NO 489
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 489

```
Gly Gly Cys Gln Pro Gln Ala Ser Trp Cys Gly Gly
1               5                   10
```

<210> SEQ ID NO 490
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 490

```
Gly Gly Cys Asp Arg Gln Val Thr Gly Phe Cys Gly Gly
1               5                   10
```

<210> SEQ ID NO 491
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 491

```
Gly Gly Ser Gln Arg Ala Pro Ala Ser Cys Gly Gly
1               5                   10
```

<210> SEQ ID NO 492
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 492

```
Gly Gly Cys Met Met Arg Glu Gln Gly Cys Gly Gly
1               5                   10
```

<210> SEQ ID NO 493
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 493

```
Gly Gly Cys Leu Leu Pro Asn Met Phe Cys Gly Gly
1               5                   10
```

<210> SEQ ID NO 494
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 494

Gly Gly Cys Cys Pro Val Tyr Gln His Cys Gly Gly
1               5                   10

<210> SEQ ID NO 495
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 495

Gly Gly Cys Leu Met Ser Gln Asp Leu Cys Gly Gly
1               5                   10

<210> SEQ ID NO 496
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 496

Gly Gly Cys Gly Gly Pro Tyr Val Phe Cys Gly Gly
1               5                   10

<210> SEQ ID NO 497
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 497
gagagcaatg gtggttgttt cccgctgcag gactac                              36

<210> SEQ ID NO 498
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 498
gtagtcctgc agcgggaaac aaccaccatt gctctc                              36

<210> SEQ ID NO 499
<211> LENGTH: 36
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 499
gagagcaatg gtggttgtta cccgctgcag gactac                                    36

<210> SEQ ID NO 500
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 500
gtagtcctgc agcgggtaac aaccaccatt gctctc                                    36

<210> SEQ ID NO 501
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 501
ggtggttgtg ttttcaacgc gttcaactgt ggtggtggg                                 39

<210> SEQ ID NO 502
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 502
cccaccacca cagttgaacg cgttgaaaac acaaccacc                                 39

<210> SEQ ID NO 503
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 503
ggtggttgtg ttttcaacgg gttcaactgt ggtggtggg                                 39

<210> SEQ ID NO 504
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 504
cccaccacca cagttgaacc cgttgaaaac acaaccacc                                 39

<210> SEQ ID NO 505
```

```
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 505
ggtggttgtg ttttcaacca tttcaactgt ggtggtggg                              39

<210> SEQ ID NO 506
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 506
cccaccacca cagttgaaat ggttgaaaac acaaccacc                              39

<210> SEQ ID NO 507
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 507
ggtggttgtg ttttcaacat cttcaactgt ggtggtggg                              39

<210> SEQ ID NO 508
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 508
cccaccacca cagttgaaga tgttgaaaac acaaccacc                              39

<210> SEQ ID NO 509
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 509
ggtggttgtg ttttcaactt gttcaactgt ggtggtggg                              39

<210> SEQ ID NO 510
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 510
```

```
cccaccacca cagttgaaca agttgaaaac acaaccacc                                    39
```

<210> SEQ ID NO 511
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 511

```
ggtggttgtg ttttcaacaa cttcaactgt ggtggtggg                                    39
```

<210> SEQ ID NO 512
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 512

```
cccaccacca cagttgaagt tgttgaaaac acaaccacc                                    39
```

<210> SEQ ID NO 513
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 513

```
ggtggttgtg ttttcaacca gttcaactgt ggtggtggg                                    39
```

<210> SEQ ID NO 514
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 514

```
cccaccacca cagttgaact ggttgaaaac acaaccacc                                    39
```

<210> SEQ ID NO 515
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 515

```
ggtggttgtg ttttcaactc gttcaactgt ggtggtggg                                    39
```

<210> SEQ ID NO 516
<211> LENGTH: 39
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 516
cccaccacca cagttgaacg agttgaaaac acaaccacc                             39

<210> SEQ ID NO 517
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 517
ggtggttgtg ttttcaacac gttcaactgt ggtggtggg                             39

<210> SEQ ID NO 518
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 518
cccaccacca cagttgaacg tgttgaaaac acaaccacc                             39

<210> SEQ ID NO 519
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 519
ggtggttgtg ttttcaacgt gttcaactgt ggtggtggg                             39

<210> SEQ ID NO 520
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 520
cccaccacca cagttgaaca cgttgaaaac acaaccacc                             39

<210> SEQ ID NO 521
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 521
gttcctttct attctcac                                                    18
```

```
<210> SEQ ID NO 522
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 522
gagggtgtcc ttgggttttg gggg                                              24

<210> SEQ ID NO 523
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 523
ggtgaggacg ctgaccacac ggta                                              24

<210> SEQ ID NO 524
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 524
atgcatcacg gagcatgaga agac                                              24

<210> SEQ ID NO 525
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 525
attatgcacc tccacgccgt ccac                                              24

<210> SEQ ID NO 526
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 526
attgctctcc cactccacgg cgat                                              24

<210> SEQ ID NO 527
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 527
cccattcaga tcctcttc                                                    18

<210> SEQ ID NO 528
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: Variation
<222> LOCATION: (19)..(21)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (22)..(24)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (25)..(27)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (28)..(30)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (31)..(33)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (34)..(36)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: misc_feature
<222> LOCATION: (19)..(36)
<223> OTHER INFORMATION: /note="nucleotides given in the sequence have
      no preference with respect to those in the annotations for said
      positions"
<220> FEATURE:
<221> NAME/KEY: source
<223> OTHER INFORMATION: /note="see specification as filed for detailed
      description of substitutions and preferred embodiments"

<400> SEQUENCE: 528
aaacccaagg acaccctcaa aaaaaaaaaa aaaaaaaccc ctgaggtcac atgc            54

<210> SEQ ID NO 529
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: Variation
<222> LOCATION: (19)..(21)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"

```
<220> FEATURE:
<221> NAME/KEY: Variation
<222> LOCATION: (22)..(24)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (25)..(27)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (28)..(30)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (31)..(33)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (34)..(36)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: misc_feature
<222> LOCATION: (19)..(36)
<223> OTHER INFORMATION: /note="nucleotides given in the sequence have
      no preference with respect to those in the annotations for said
      positions"
<220> FEATURE:
<221> NAME/KEY: source
<223> OTHER INFORMATION: /note="see specification as filed for detailed
      description of substitutions and preferred embodiments"

<400> SEQUENCE: 529
gtggtcagcg tcctcaccaa aaaaaaaaaa aaaaaacacc aggactggct gaat          54

<210> SEQ ID NO 530
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: Variation
<222> LOCATION: (28)..(30)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (31)..(33)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (34)..(36)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (37)..(39)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
```

```
<221> NAME/KEY: Variation
<222> LOCATION: (40)..(42)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (43)..(45)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: misc_feature
<222> LOCATION: (28)..(45)
<223> OTHER INFORMATION: /note="nucleotides given in the sequence have
      no preference with respect to those in the annotations for said
      positions"
<220> FEATURE:
<221> NAME/KEY: source
<223> OTHER INFORMATION: /note="see specification as filed for detailed
      description of substitutions and preferred embodiments"

<400> SEQUENCE: 530
gtggtcagcg tcctcaccgg tggttgtaaa aaaaaaaaaa aaaaatgtgg tggtcaccag    60
gactggctga at                                                       72

<210> SEQ ID NO 531
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: Variation
<222> LOCATION: (19)..(21)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (22)..(24)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (25)..(27)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (28)..(30)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (31)..(33)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: misc_feature
<222> LOCATION: (19)..(33)
<223> OTHER INFORMATION: /note="nucleotides given in the sequence have
      no preference with respect to those in the annotations for said
      positions"
<220> FEATURE:
<221> NAME/KEY: Variation
<222> LOCATION: (37)..(39)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
```

```
<220> FEATURE:
<221> NAME/KEY: misc_feature
<222> LOCATION: (37)..(39)
<223> OTHER INFORMATION: /note="nucleotides given in the sequence have
      no preference with respect to those in the annotations for said
      positions"
<220> FEATURE:
<221> NAME/KEY: source
<223> OTHER INFORMATION: /note="see specification as filed for detailed
      description of substitutions and preferred embodiments"

<400> SEQUENCE: 531
tcatgctccg tgatgcataa aaaaaaaaaa aaacacaaac actacacgca gaagagc         57

<210> SEQ ID NO 532
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: Variation
<222> LOCATION: (28)..(30)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (31)..(33)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (34)..(36)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (37)..(39)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (40)..(42)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (43)..(45)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: misc_feature
<222> LOCATION: (28)..(45)
<223> OTHER INFORMATION: /note="nucleotides given in the sequence have
      no preference with respect to those in the annotations for said
      positions"
<220> FEATURE:
<221> NAME/KEY: source
<223> OTHER INFORMATION: /note="see specification as filed for detailed
      description of substitutions and preferred embodiments"

<400> SEQUENCE: 532
ggcgtggagg tgcataatgg tggttgtaaa aaaaaaaaaa aaaatgtgg tggtgccaag       60 acaaagccgc gg                                                         72

<210> SEQ ID NO 533
```

```
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: Variation
<222> LOCATION: (28)..(30)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (31)..(33)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (34)..(36)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (37)..(39)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (40)..(42)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (43)..(45)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: misc_feature
<222> LOCATION: (28)..(45)
<223> OTHER INFORMATION: /note="nucleotides given in the sequence have
      no preference with respect to those in the annotations for said
      positions"
<220> FEATURE:
<221> NAME/KEY: source
<223> OTHER INFORMATION: /note="see specification as filed for detailed
      description of substitutions and preferred embodiments"

<400> SEQUENCE: 533
gtggagtggg agagcaatgg tggttgtaaa aaaaaaaaaa aaaaatgtgg tggtgggcag      60
ccggagaaca ac                                                         72

<210> SEQ ID NO 534
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 534
gttcctttct attctcac                                                   18

<210> SEQ ID NO 535
<211> LENGTH: 18
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic primer"

<400> SEQUENCE: 535
cccattcaga tcctcttc                                                         18

<210> SEQ ID NO 536
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: Variation
<222> LOCATION: (31)..(33)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (34)..(36)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (37)..(39)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (40)..(42)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (43)..(45)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (46)..(48)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (49)..(51)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: Variation
<222> LOCATION: (52)..(54)
<223> OTHER INFORMATION: /replace="AAC" or "ACT" or "ATC" or "ATG" or
      "CAG" or "CAT" or "CCG" or "CGT" or "CTG" or "GAA" or "GAC" or
      "GCT" or "GGT" or "GTT" or "TAC" or "TCT" or "TGG" or "TTC"
<220> FEATURE:
<221> NAME/KEY: misc_feature
<222> LOCATION: (31)..(54)
<223> OTHER INFORMATION: /note="nucleotides given in the sequence have
      no preference with respect to those in the annotations for said
      positions"
<220> FEATURE:
<221> NAME/KEY: source
<223> OTHER INFORMATION: /note="see specification as filed for detailed
      description of substitutions and preferred embodiments"

<400> SEQUENCE: 536
```
ctgcccccat ctcgagatga gctgggttgt aaaaaaaaaa aaaaaaaaaa aaaatgtggt    60
ggtaccaacc aggtcagcct gacc                                          84

<210> SEQ ID NO 537
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: modified_base
<222> LOCATION: (40)..(41)
<223> OTHER INFORMATION: a, c, t, g, unknown or other
<220> FEATURE:
<221> NAME/KEY: modified_base
<222> LOCATION: (43)..(44)
<223> OTHER INFORMATION: a, c, t, g, unknown or other
<220> FEATURE:
<221> NAME/KEY: modified_base
<222> LOCATION: (46)..(47)
<223> OTHER INFORMATION: a, c, t, g, unknown or other
<220> FEATURE:
<221> NAME/KEY: modified_base
<222> LOCATION: (49)..(50)
<223> OTHER INFORMATION: a, c, t, g, unknown or other
<220> FEATURE:
<221> NAME/KEY: modified_base
<222> LOCATION: (52)..(53)
<223> OTHER INFORMATION: a, c, t, g, unknown or other

<400> SEQUENCE: 537
ctgcccccat ctcgagatga gctgggttgt nnknnknnkn nknnknnknn knnktgtggt    60
ggtaccaacc aggtcagcct gacc                                          84

<210> SEQ ID NO 538
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 538
ggccccgtga tggtgatgat g                                             21

<210> SEQ ID NO 539
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 539
gagtgggaga gcaatggtgg ttgtcatctg ccgttcgctg tttgtggtgg tgggcagccg    60

```
gagaac                                                              66

<210> SEQ ID NO 540
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 540
gttctccggc tgcccaccac cacaaacagc gaacggcaga tgacaaccac cattgctctc    60
ccactc                                                              66

<210> SEQ ID NO 541
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 541
gagtgggaga gcaatggtgg ttgttggccg ctgcaggact actgtggtgg tgggcagccg    60
gagaac                                                              66

<210> SEQ ID NO 542
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 542
gttctccggc tgcccaccac cacagtagtc ctgcagcggc caacaaccac cattgctctc    60
ccactc                                                              66

<210> SEQ ID NO 543
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 543
gagtgggaga gcaatggtgg ttgtggtcat gaatacatgt ggtgtggtgg gcagccggag    60
aac                                                                 63

<210> SEQ ID NO 544
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 544
```

```
gttctccggc tgcccaccac accacatgta ttcatgacca caaccaccat tgctctccca    60
ctc                                                                  63
```

<210> SEQ ID NO 545
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 545

```
gagtgggaga gcaatggtgg ttgtgttttc aacatgttca actgtggtgg tgggcagccg    60
gagaac                                                               66
```

<210> SEQ ID NO 546
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 546

```
gttctccggc tgcccaccac cacagttgaa catgttgaaa acacaaccac cattgctctc    60
ccactc                                                               66
```

<210> SEQ ID NO 547
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 547

```
gagtgggaga gcaatggtgg ttgtgctctg tacccgacta actgtggtgg tgggcagccg    60
gagaac                                                               66
```

<210> SEQ ID NO 548
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 548

```
gttctccggc tgcccaccac cacagttagt cgggtacaga gcacaaccac cattgctctc    60
ccactc                                                               66
```

<210> SEQ ID NO 549
<211> LENGTH: 6
<212> TYPE: PRT
<213> ORGANISM: Homo sapiens
<400> SEQUENCE: 549

```
Leu Met Ile Ser Arg Thr
1               5
```

```
<210> SEQ ID NO 550
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(7)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (2)..(7)
<223> OTHER INFORMATION: /note="Residues given in the sequence have no
      preference with respect to those in the annotations for said
      positions"

<400> SEQUENCE: 550

Leu Lys Lys Lys Lys Lys Lys Thr
1               5

<210> SEQ ID NO 551
<211> LENGTH: 8
<212> TYPE: PRT
<213> ORGANISM: Homo sapiens

<400> SEQUENCE: 551

Thr Val Leu His Gln Asp Trp Leu
1               5

<210> SEQ ID NO 552
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(7)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (2)..(7)
<223> OTHER INFORMATION: /note="Residues given in the sequence have no
      preference with respect to those in the annotations for said
      positions"

<400> SEQUENCE: 552

Thr Lys Lys Lys Lys Lys Lys His Gln Asp Trp Leu
1               5                   10

<210> SEQ ID NO 553
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(10)
```

-continued

```
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (5)..(10)
<223> OTHER INFORMATION: /note="Residues given in the sequence have no
      preference with respect to those in the annotations for said
      positions"

<400> SEQUENCE: 553

Thr Gly Gly Cys Lys Lys Lys Lys Lys Cys Gly Gly His Gln Asp
1               5                   10                  15

Trp Leu

<210> SEQ ID NO 554
<211> LENGTH: 9
<212> TYPE: PRT
<213> ORGANISM: Homo sapiens

<400> SEQUENCE: 554

Met His Glu Ala Leu His Asn His Tyr
1               5

<210> SEQ ID NO 555
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(7)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (3)..(7)
<223> OTHER INFORMATION: /note="Residues given in the sequence have no
      preference with respect to those in the annotations for said
      positions"
<220> FEATURE:
<221> NAME/KEY: VARIANT
<222> LOCATION: (9)..(9)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (9)..(9)
<223> OTHER INFORMATION: /note="Residue given in the sequence has no
      preference with respect to the annotations for said position"

<400> SEQUENCE: 555

Met His Lys Lys Lys Lys Lys His Lys His Tyr
1               5                   10

<210> SEQ ID NO 556
<211> LENGTH: 5
<212> TYPE: PRT
<213> ORGANISM: Homo sapiens

<400> SEQUENCE: 556

Glu Val His Asn Ala
1               5
```

```
<210> SEQ ID NO 557
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (8)..(13)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (8)..(13)
<223> OTHER INFORMATION: /note="Residues given in the sequence have no
      preference with respect to those in the annotations for said
      positions"

<400> SEQUENCE: 557

Glu Val His Asn Gly Gly Cys Lys Lys Lys Lys Lys Cys Gly Gly
1               5                   10                  15

Ala

<210> SEQ ID NO 558
<211> LENGTH: 6
<212> TYPE: PRT
<213> ORGANISM: Homo sapiens

<400> SEQUENCE: 558

Asn Gly Gln Pro Glu Asn
1               5

<210> SEQ ID NO 559
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(10)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (5)..(10)
<223> OTHER INFORMATION: /note="Residues given in the sequence have no
      preference with respect to those in the annotations for said
      positions"

<400> SEQUENCE: 559

Asn Gly Gly Cys Lys Lys Lys Lys Lys Lys Cys Gly Gly Gly Gln Pro
1               5                   10                  15

Glu Asn

<210> SEQ ID NO 560
<211> LENGTH: 7
<212> TYPE: PRT
<213> ORGANISM: Homo sapiens

<400> SEQUENCE: 560
```

```
Asp Glu Leu Thr Lys Asn Gln
1               5

<210> SEQ ID NO 561
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(14)
<223> OTHER INFORMATION: Any amino acid

<400> SEQUENCE: 561

Asp Glu Leu Gly Gly Cys Xaa Xaa Xaa Xaa Xaa Xaa Xaa Xaa Cys Gly
1               5                   10                  15

Gly Thr Lys Asn Gln
            20

<210> SEQ ID NO 562
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (7)..(14)
<223> OTHER INFORMATION: /replace="Phe" or "Asn" or "Arg" or "Ser" or
      "Thr" or "Met" or "Ile" or "Glu" or "Asp" or "Gly" or
      "Ala" or "Val" or "Gln" or "His" or "Pro" or "Leu"
      or "Tyr" or "Trp"
<220> FEATURE:
<221> NAME/KEY: misc_feature
<222> LOCATION: (7)..(14)
<223> OTHER INFORMATION: /note="Residues given in the sequence have no
      preference with respect to those in the annotations for said
      positions"

<400> SEQUENCE: 562

Asp Glu Leu Gly Gly Cys Lys Lys Lys Lys Lys Lys Lys Lys Cys Gly
1               5                   10                  15

Gly Thr Lys Asn Gln
            20

<210> SEQ ID NO 563
<211> LENGTH: 13
<212> TYPE: PRT
<213> ORGANISM: Homo sapiens

<400> SEQUENCE: 563

Trp Glu Ser Asn Gly Gln Pro Glu Asn Asn Tyr Lys Thr
1               5                   10

<210> SEQ ID NO 564
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 564
```

Trp Glu Ser Asn Gly Gly Cys Gly Met Pro Ile Glu Phe Cys Gly Gly
1               5                   10                  15

Gly Gln Pro Glu Asn Asn Tyr Lys Thr
            20                  25

<210> SEQ ID NO 565
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 565

Trp Glu Gly Gly Cys Gly Met Pro Ile Glu Phe Cys Gly Gly Ser Asn
1               5                   10                  15

Gly Gln Pro Glu Asn Asn Tyr Lys Thr
            20                  25

<210> SEQ ID NO 566
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 566

Trp Glu Ser Gly Gly Cys Gly Met Pro Ile Glu Phe Cys Gly Gly Asn
1               5                   10                  15

Gly Gln Pro Glu Asn Asn Tyr Lys Thr
            20                  25

<210> SEQ ID NO 567
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 567

Trp Glu Ser Asn Gly Gly Gly Cys Gly Met Pro Ile Glu Phe Cys Gly
1               5                   10                  15

Gly Gln Pro Glu Asn Asn Tyr Lys Thr
            20                  25

<210> SEQ ID NO 568
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 568

Trp Glu Ser Asn Gly Gln Gly Gly Cys Gly Met Pro Ile Glu Phe Cys
1               5                   10                  15

Gly Gly Pro Glu Asn Asn Tyr Lys Thr
            20                  25

<210> SEQ ID NO 569
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 569

Trp Glu Ser Asn Gly Gln Pro Gly Gly Cys Gly Met Pro Ile Glu Phe
1               5                   10                  15

Cys Gly Gly Glu Asn Asn Tyr Lys Thr
            20                  25

<210> SEQ ID NO 570
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 570

Trp Glu Ser Asn Gly Gln Pro Glu Gly Gly Cys Gly Met Pro Ile Glu
1               5                   10                  15

Phe Cys Gly Gly Asn Asn Tyr Lys Thr
            20                  25

<210> SEQ ID NO 571
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 571

Trp Glu Ser Asn Gly Gln Pro Glu Asn Gly Gly Cys Gly Met Pro Ile
1               5                   10                  15

Glu Phe Cys Gly Gly Asn Tyr Lys Thr
            20                  25

<210> SEQ ID NO 572
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 572

Trp Glu Ser Asn Gly Gln Pro Asn Asn Gly Gly Cys Gly Met Pro
1               5                   10                  15

Ile Glu Phe Cys Gly Gly Tyr Lys Thr
            20                  25

<210> SEQ ID NO 573
<211> LENGTH: 22
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 573

Trp Glu Ser Gly Gly Cys Gly Met Pro Ile Glu Phe Cys Gly Gly Pro
1               5                   10                  15

Glu Asn Asn Tyr Lys Thr
            20

<210> SEQ ID NO 574
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 574

Trp Glu Ser Gly Gly Gly Cys Gly Met Pro Ile Glu Phe Cys Gly Gly
1               5                   10                  15

Gly Pro Glu Asn Asn Tyr Lys Thr
            20

<210> SEQ ID NO 575
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 575

Tyr Pro Tyr Asp Val Pro Asp Tyr Ala
1               5
```

VARIANT FC-POLYPEPTIDES WITH ENHANCED BINDING TO THE NEONATAL FC RECEPTOR

PRIORITY

This application is a national stage application under 35 U.S.C. 371 of International Application No. PCT/US2012/070146, having an international filing date of Dec. 17, 2012 and which is incorporated herein in its entirety; which claims the benefit of U.S. Provisional Application Nos. 61/578,780, 61/585,993, and 61/729,050 filed Dec. 21, 2011, Jan. 12, 2012, and Nov. 21, 2012, respectively, each of which is incorporated herein in its entirety.

REFERENCE TO THE SEQUENCE LISTING

The present application is being filed along with a Sequence Listing in electronic format. The Sequence Listing is provided as a file entitled A-1688-US-PCT_sequence_listing.txt, created Jun. 19, 2014, which is 235 KB in size. The information in the electronic format of the Sequence Listing is incorporated herein by reference in its entirety.

FIELD

The invention relates to polypeptides comprising variant Fc-fragments that bind to the neonatal Fc receptor with higher affinity and/or greater binding activity compared to a control Fc-fragment. The invention further relates to methods of isolating, making, and using such polypeptides.

BACKGROUND

Therapeutic monoclonal antibodies have been used successfully as treatments for a variety of diseases. The relatively long in vivo half life of antibodies is mediated at least in part by the interaction of the Fc region of the antibody with the neonatal Fc receptor (FcRn). See, e.g., Ghetie et al. (1996), Eur. J. Immunol. 26: 690-96. FcRn binds to the Fc region of IgG antibodies with nanomolar affinity ($K_D \approx 100$ nM) at a pH of less than or equal to 6.0, but does not bind at the pH of blood, i.e., about pH 7.4. Tesar and Björkman (2001), Curr. Opin. Struct. Biol. 20(2): 226-233. Upon internalization of an antibody by a cell, for example by pinocytosis, an IgG can be bound by FcRn in the acidic environment of an endosome. Id. When bound by FcRn within the endosome, the IgG will be directed back to the cell surface, as opposed to entering a default catabolic pathway within the endosome. Id. In the generally physiologic pH environment at the cell surface, the IgG can dissociate from FcRn and re-enter the circulation. This process allows the antibody to return to the circulation following internalization within a cell, as opposed to being degraded in the cell within an endosome.

There is a need in the art for therapeutic antibodies with increased in vivo half lives so as to decrease dosing amounts and/or frequencies. Such antibodies are advantageous because of increased patient convenience, and therefore also possibly increased patient compliance, and/or decreased cost. In the current cost-conscious health care environment, cost can be a determining factor in the practical utility of a therapeutic product.

SUMMARY

Provided are variant Fc-fragments that bind to FcRn with higher affinity and/or higher binding activity than does a control Fc-fragment at a slightly acidic pH and that bind to FcRn with about the same affinity as or lower than a control Fc-fragment, that is, little or no binding activity, at a physiologic pH. Also provided are variant Fc-polypeptides, which contain a variant Fc-fragment as well as a binding region that binds to a target molecule. It is demonstrated herein that variant Fc-polypeptides containing variant Fc-fragments with the binding properties mentioned above also have longer in vivo half lives than control Fc-polypeptides. Further provided are nucleic acids that encode these Fc-fragments and Fc-polypeptides and methods of making these proteins using these nucleic acids. Also included are methods for extending the in vivo half life of an Fc-polypeptide and methods for identifying variant Fc-fragments that bind to FcRn with higher affinity at pH 5-6 and bind FcRn with comparable or lower affinity at physiologic pH as compared to a control Fc-fragment.

Described here is a variant Fc-polypeptide comprising a human IgG1, IgG2, IgG3, or IgG4 variant Fc-fragment, wherein the variant Fc-fragment comprises an insertion of 3 to 20, 10 to 20, 20 to 40, 40 to 60, or 60 to 80 amino acids within or adjacent to Loop 5, 8, and/or 10 of the variant Fc-fragment, wherein the variant Fc-polypeptide binds to a human neonatal Fc receptor (hFcRn) with higher affinity and/or higher binding activity at a pH from about 5.0 to about 6.0 and/or at a pH of about 5.0, 5.2, 5.5, 5.7, or 6.0 than a control Fc-polypeptide that has the same amino acid sequence as the variant Fc-polypeptide except that it does not contain the insertion within or adjacent to Loop 5, 8, and/or 10 and wherein the variant Fc-polypeptide binds to the human neonatal Fc receptor (hFcRn) with approximately the same or lower affinity or binding activity as compared to the control Fc-polypeptide, that is, little or no binding activity, at a physiologic pH and/or at a pH of about 7.4, 7.5, or 7.6. The insertion within or adjacent to the variant Fc-fragment can be at least six amino acids long, not more than 25 amino acids long, from 6 to 16 amino acids long, and/or at least 12 amino acids long. In some embodiments, the insertion does not contain methionine and/or tryptophan residues. The insertion within or adjacent to the variant Fc-fragment can comprise at least one cysteine among the first four inserted amino acids and at least one cysteine among the last four inserted amino acids. Optionally, the insertion can lack cysteine residues other than any cysteine residues occurring in the first or last four amino acids of the insertion. In some embodiments, the insertion is within or adjacent to Loop 10 of the variant Fc-fragment, optionally between amino acids 384 and 385 of the variant Fc-fragment using the EU numbering system shown in Table 1. The insertion can be within amino acids 383 to 387 using the EU numbering system. In some embodiments, the insertion in the variant human Fc-fragment can be between amino acids 382 and 383, 383 and 384, 385 and 386, 386 and 387, 387 and 388, 388 and 389, 389 and 390, or 390 and 391 using the EU numbering system shown in Table 1. Alternatively, amino acids 384-386 can be deleted, and the insertion can be between amino acids 383 and 387 using the EU numbering system shown in Table 1. The insertion in the variant Fc-fragment can comprise the amino acid sequence of any one of SEQ ID NO:13, 14, 15, 16, 17, 18, 19, 20, 21, 22, 23, 24, 41, 42, 43, 44, 45, 46, 47, 48, 49, 50, 51, 52, 53, 54, 55, 56, 57, 58, 59, 60, 61, 62, 63, 64, 65, 66, 67, 90-356, and 359-379. Further, the insertion in the variant Fc-fragment can comprise the amino acid sequence of any one of the following: SEQ ID NOs:41-67; SEQ ID NOs:90-246; SEQ ID NOs:247-356; SEQ ID NOs:367, 369, 372, 373, and 375-379; amino acids 4-9 of any one of SEQ ID NOs:41-53, 67, 90-162, 90-163, 165-215, 164-214, 217-247, 216-246, 359-379 and 392-399, 401-409, 411-426, 428-439, 441-447, 449-453, 456, 459, 461, 464, and 470, 475, 477-489, 491-496; amino acids 4-10 of SEQ ID NO:164, 252, and 490, and amino acids 4-8 of SEQ ID NO:215 or 216; amino acids 4-11 of any one of SEQ ID NOs: 248-288, 290-306, 342, 400, 410, 427, 440, 448, 454, 455, 457, 458, 460, 465-469, 471-474, and 476; amino acids 4-12 of SEQ ID NO:289 or 307; and amino acids 4-13 of any one of SEQ ID NOs:308-341 and 343-356.

Further described herein is a variant Fc-polypeptide comprising a human IgG1, IgG2, IgG3 or IgG4 variant Fc-fragment, wherein the variant Fc-fragment comprises an insertion of 3 to 20, 10 to 20, 20 to 40, 40 to 60, or 60 to 80 amino acids within or adjacent to Loop 10, wherein the variant Fc-polypeptide binds to a hFcRn with higher affinity and/or higher binding activity at a pH in a range from about 5.0 to about 6.0 and/or at a pH of about 5.0, 5.2, 5.5, 5.7, or 6.0 than a control Fc-polypeptide that is the same as the variant Fc-polypeptide except that it does not contain the insertion within or adjacent to Loop 10 and wherein the variant Fc-polypeptide binds to the hFcRn with approximately the same or lower affinity as compared to the control Fc-polypeptide, that is, with little or no binding activity, at a physiologic pH and/or at a pH of about 7.4, 7.5, or 7.6. The insertion can be at least six amino acids long, can be not more than 25 amino acids long, can be from 6 to 16 amino acids long, can be at least 12 amino acids long, and/or can contain at least one cysteine among the first four amino acids of the insertion and at least one cysteine among the last four amino acids of the insertion. The insertion can lack cysteine residues at other positions within the insertion. The insertion can lack methionine and/or tryptophan residues. The insertion in the variant Fc-fragment can be within amino acids 383-387 according to the EU numbering system. The insertion in the variant Fc-fragment can be between amino acids 382 and 383, 383 and 384, 384 and 385, 385 and 386, 386 and 387, 387 and 388, 388 and 389, 389 and 390, or 390 and 391 using the EU numbering system shown in Table 1. Alternatively amino acids 384-386 can be deleted, and the insertion can occur between amino acids 383 and 387, using the EU numbering system. The insertion in the variant Fc-fragment can comprise the amino acid sequence of any one of SEQ ID NO:13, 14, 15, 16, 17, 18, 19, 20, 21, 22, 23, 24, 41, 42, 43, 44, 45, 46, 47, 48, 49, 50, 51, 52, 53, 54, 55, 56, 57, 58, 59, 60, 61, 62, 63, 64, 65, 66, 67, 90-356, 359-379, and 392-496. Further, the insertion in the variant Fc-fragment can comprise the amino acid sequence of any one of the following: SEQ ID NOs:41-67; SEQ ID NOs: 90-246; SEQ ID NOs:247-356; SEQ ID NOs:367, 369, 372, 373, and 375-379; amino acids 4-9 of any one of SEQ ID NOs:41-53, 67, 90-162, 90-163, 165-215, 164-214, 217-247, 216-246, 359-379 and 392-399, 401-409, 411-426, 428-439, 441-447, 449-453, 456, 459, 461, 464, and 470, 475, 477-489, 491-496; amino acids 4-10 of SEQ ID NO:164, 252, and 490, and amino acids 4-8 of SEQ ID NO:215 or 216; amino acids 4-11 of any one of SEQ ID NOs: 248-288, 290-306, 342, 400, 410, 427, 440, 448, 454, 455, 457, 458, 460, 465-469, 471-474, and 476; amino acids 4-12 of SEQ ID NO:289 or 307; and amino acids 4-13 of any one of SEQ ID NOs:308-341 and 343-356. The variant Fc-polypeptide can be a variant Fc fusion protein comprising a non-antibody polypeptide. In particular embodiments, a control Fc fusion protein for the variant Fc fusion protein can be alefacept, rilonacept, aflibercept, etanercept, romiplostim, or abatacept. In other embodiments, the variant Fc-polypeptide can comprise a heavy chain variable region ($V_H$) and/or a light chain variable region ($V_L$) of any antibody and may also comprise a first heavy chain constant region ($C_H1$) and a light chain constant region ($C_L$). In some embodiments, the variant Fc-polypeptide can comprise (a) a heavy chain comprising a $V_H$ region, a first heavy chain constant region ($C_H1$), a hinge region, a $C_H2$ region, and a $C_H3$ region, and (b) a light chain comprising a $V_L$ region and a light chain constant region ($C_L$). The variant Fc-polypeptide can be monovalent. The variant Fc-polypeptide can be a dimer or can be a tetramer.

In further embodiments, described herein are nucleic acids encoding the variant Fc-polypeptides or the variant Fc-fragments described herein, as well as the insertions within or adjacent to the loops of the variant Fc-fragments. Also described are host cells containing such nucleic acids. Also contemplated are methods of making a variant Fc-polypeptide or variant Fc-fragment comprising (a) introducing a nucleic acid encoding the variant Fc-polypeptide or Fc-fragment into a host cell, (b) culturing the host cell comprising the nucleic acid under conditions such that the nucleic acid is expressed, and (c) recovering the expressed variant Fc-polypeptide or Fc-fragment from the culture medium or the cell mass, wherein the variant Fc-fragment, or the variant Fc-polypeptide that contains a variant Fc-fragment, comprises an insertion of 3 to 20, 10 to 20, 20 to 40, 40 to 60, or 60 to 80 amino acids within or adjacent to Loop 5, 8, and/or 10 of the variant Fc-fragment, and wherein the variant Fc-polypeptide or Fc-fragment binds to a hFcRn with higher affinity and or higher binding activity at a pH in a range from about 5.0 to about 6.0 and/or at a pH of about 5.0, 5.2, 5.5, 5.7, or 6.0 than a control Fc-polypeptide or Fc-fragment and wherein the variant Fc-polypeptide or Fc-fragment binds to the human neonatal Fc receptor (hFcRn) with approximately the same or lower affinity or binding activity as compared to the control Fc-polypeptide or control Fc-fragment, that is, with little or no binding activity, at a physiologic pH and/or at a pH of about 7.4, 7.5, or 7.6.

Also described are methods for making any of the variant Fc-fragments or Fc-polypeptides described herein comprising (a) introducing a nucleic acid encoding the variant Fc-polypeptide or Fc-fragment into a host cell, (b) culturing the host cell comprising the nucleic acid under conditions such that the nucleic acid is expressed, and (c) recovering the expressed variant Fc-polypeptide or Fc-fragment from the culture medium or the cell mass.

In a further embodiment, described herein is a method for extending the half life of an Fc-polypeptide comprising a human IgG Fc-fragment comprising the following steps: selecting a site within or adjacent to Loop 5, 8, and/or 10 for insertion; and inserting a peptide into the selected site, wherein the peptide comprises an amino acid sequence selected from the group consisting of: SEQ ID NOs:41-67; SEQ ID NOs:90-246; SEQ ID NOs:247-356; SEQ ID NOs: 367, 369, 372, 373, and 375-379; amino acids 4-9 of any one of SEQ ID NOs:41-53, 67, 90-162, 90-163, 165-215, 164-214, 217-247, 216-246, 359-379 and 392-399, 401-409, 411-426, 428-439, 441-447, 449-453, 456, 459, 461, 464, and 470, 475, 477-489, 491-496; amino acids 4-10 of SEQ ID NO:164, 252, and 490, and amino acids 4-8 of SEQ ID NO:215 or 216; amino acids 4-11 of any one of SEQ ID NOs: 248-288, 290-306, 342, 400, 410, 427, 440, 448, 454, 455, 457, 458, 460, 465-469, 471-474, and 476; amino acids 4-12 of SEQ ID NO:289 or 307; and amino acids 4-13 of any one of SEQ ID NOs:308-341 and 343-356. The selected site can be within or adjacent to Loop 10, and the insertion site can be between amino acids 384 and 385, numbered according to the EU numbering system. The insertion site can be within amino acids 383 to 387 using the EU numbering system. The insertion in the variant Fc-fragment can be between amino acids 382 and 383, 383 and 384, 384 and 385, 385 and 386, 386 and 387, 387 and 388, 388 and 389, 389 and 390, or 390 and 391 using the EU numbering system shown in Table 1. Alternatively amino acids 384-386 can be deleted, and the insertion can occur between amino acids 383 and 387, using the EU numbering system.

Further provided herein is a method for identifying a human IgG variant Fc-fragment that confers a longer in vivo half life on a variant Fc-polypeptide that comprises the variant Fc-fragment, as compared to a control Fc-polypeptide, comprising the following steps: (a) creating a library of nucleic acids encoding Fc-fragments containing an insertion comprising 4-20, 10 to 20, 20-40, 40-60, or 60-80 randomized amino acids within or adjacent to Loop 10; (b) screening Fc-fragments encoded by the library to identify the variant Fc-fragments that (i) bind to human FcRn with higher affinity and/or higher binding activity at pH 5.5, and/or at a pH from about 5-6, than a control Fc-fragment and (ii) bind to human FcRn at the same or lower affinity or binding activity compared to the control Fc-fragment, that is, with little or no binding activity, at physiologic pH and/or at a pH of 7.4, 7.5, or 7.6; (c) constructing a nucleic acid encoding a variant Fc-polypeptide comprising a variant Fc-fragment identified in (b), wherein the concentration of a control Fc-polypeptide, which comprises a control Fc-fragment rather than the variant Fc-fragment, is known to decrease linearly over time when administered to an animal in vivo; (d) introducing the nucleic acid of (c) into a host cell and culturing the host cell under conditions such that the variant Fc-polypeptide encoded by the nucleic acid can be expressed; (e) recovering the variant Fc-polypeptide from the cell mass or cell culture medium; (f) administering the variant Fc-polypeptide to an animal and administering the control Fc-polypeptide to another animal; and (g) monitoring the concentrations of the variant and control Fc-polypeptides in peripheral blood over time subsequent to administration, thereby identifying a variant Fc-fragment that confers a longer in vivo half life on a variant Fc-polypeptide. The insertion of step (a) can be between positions 384 and 385 using the EU numbering system as illustrated in Table 1. The insertion site can be within amino acids 383 to 387 using the EU numbering system. The insertion in the variant Fc-fragment can be between amino acids 382 and 383, 383 and 384, 384 and 385, 385 and 386, 386 and 387, 387 and 388, 388 and 389, 389 and 390, or 390 and 391 using the EU numbering system shown in Table 1. Alternatively amino acids 384-386 can be deleted, and the insertion can occur between amino acids 383 and 387, using the EU numbering system.

In another aspect, a method is provided for treating a chronic disease comprising administering to a patient in need thereof a variant Fc-polypeptide as described herein.

BRIEF DESCRIPTION OF THE FIGURES

FIG. 2: Format of the insertion libraries. Above is shown the sequence of a human IgG1 Fc-fragment (SEQ ID NO:1). Amino acids within loops in which, or adjacent to which, insertions were made are indicated by underlining and boldface type. Library names, i.e., L1, L2A, etc., appear above the region into which insertions were made for that particular library. The format of the insertions is indicated below. At far left are the library names, i.e., L1, L2A, etc. Just to the right of the library names is the original sequence around the insertion site prior to the insertion of any amino acids. Italic letters indicate amino acids that are deleted prior to insertion. A vertical dashed line indicates the insertion site in those libraries in which no amino acids were deleted. At far right is the sequence around the insertion site with the insertion in place. The designations "(19R)$_5$" or "(19R)$_6$" means five or six, respectively, randomized amino acids, which can be any of the 19 amino acids other than cysteine. The designation "(20R)$_8$" means eight randomized amino acids, which can be any of the twenty amino acids.

FIG. 5: Sequences of variants of Loop 10. The amino acid sequences of wild type or variant versions of a loop in a human IgG1 Fc-fragment, plus three adjacent amino acids on either side, are shown. The amino acid sequence shown is from amino acid residues 166-178, in the numbering scheme of FIG. 2, or amino acids 381-393 according to EU numbering (SEQ ID NO:563) as shown in this figure and in Table 1. The unaltered, wild type loop region sequence is designated "wild type sequence." The sequence of this loop region in Fc variant 5-1 (encoded by an isolate from library L5) is designated "5-1" (SEQ ID NO:564). Inserted amino acid sequences are shown in boldface with underlining. The sequence of this same loop region from various variants of 5-1, which have the same peptide inserted in different locations within or adjacent to this loop, in some cases with some loop amino acids deleted, are shown below.

BRIEF DESCRIPTION OF THE SEQUENCES

Figure 1:
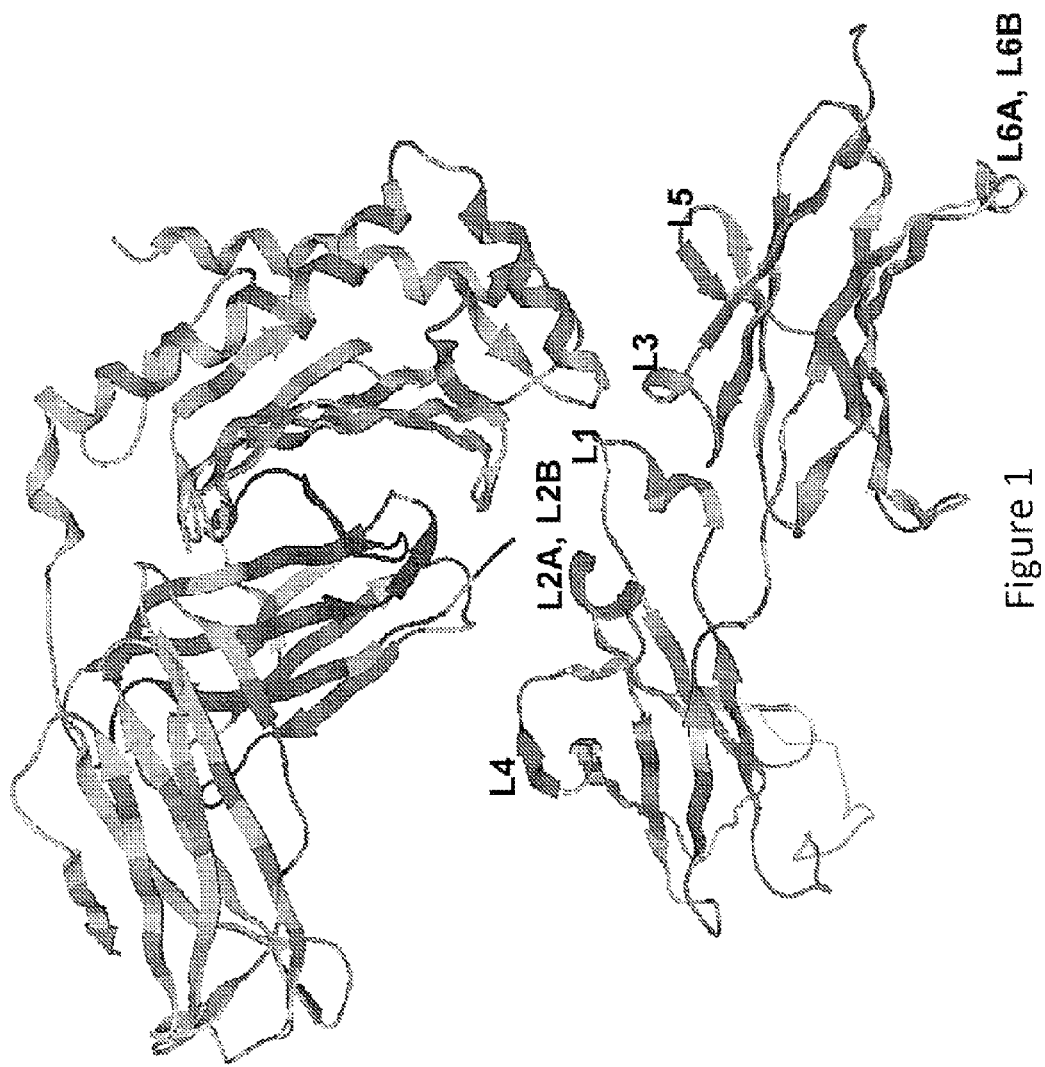
FIG. 1: Ribbon diagram of the predicted three dimensional structure of portions of human FcRn (hFcRn) and a human IgG1 Fc-fragment that come in closest contact upon binding of FcRn to the Fc-fragment. At top is a ribbon diagram of a portion of the tertiary structure of hFcRn. Below is a ribbon diagram of a portion of a human IgG1 Fc-fragment that comes in closest contact with FcRn when FcRn is bound to it. Loops are shown as strings, whereas alpha helices and beta sheets are shown as ribbons. The six sites at which insertions were made are indicated by the names of the eight libraries that were constructed as described below, i.e., L1, L2A, L2B, L3, L4, L5, L6A, and L6B.

| SEQUENCE LISTING NUMBER | DESCRIPTION |
| --- | --- |
| SEQ ID NO: 1 | Amino acid sequence of a human IgG1 Fc region |
| SEQ ID NO: 2 | Nucleotide sequence encoding a human IgG1 Fc region |
| SEQ ID NO: 3 | Amino acid sequence of a human IgG2 Fc region |
| SEQ ID NO: 4 | Nucleotide sequence encoding a human IgG2 Fc region |
| SEQ ID NO: 5 | Amino acid sequence of a human IgG3 Fc region |
| SEQ ID NO: 6 | Nucleotide sequence encoding a human IgG3 Fc region |
| SEQ ID NO: 7 | Amino acid sequence of a human IgG4 Fc region |
| SEQ ID NO: 8 | Nucleotide sequence encoding a human IgG4 Fc region |
| SEQ ID NO: 9 | Amino acid sequence of human FcRn alpha chain |
| SEQ ID NO: 10 | Amino acid sequence of human FcRn β-2-microglobulin chain |
| SEQ ID NO: 11 | Amino acid sequence of the extracellular region of mature human p75 tumor necrosis factor receptor |
| SEQ ID NO: 12 | Amino acid sequence of the extracellular region of mature human (CTLA4) |
| SEQ ID NO: 13 | Amino acid sequence of randomized insertion sequence (CXXXXXXC) |
| SEQ ID NO: 14 | Amino acid sequence of randomized insertion sequence (CXXXXXXXC) |
| SEQ ID NO: 15 | Amino acid sequence of randomized insertion sequence (CXXXXXXXXC) |
| SEQ ID NO: 16 | Amino acid sequence of randomized insertion sequence (GCXXXXXXCG) |
| SEQ ID NO: 17 | Amino acid sequence of randomized insertion sequence (GCXXXXXXXCG) |
| SEQ ID NO: 18 | Amino acid sequence of randomized insertion sequence (GCXXXXXXXXCG) |
| SEQ ID NO: 19 | Amino acid sequence of randomized insertion sequence (GGCXXXXXXCGG) |
| SEQ ID NO: 20 | Amino acid sequence of randomized insertion sequence (GGCXXXXXXXXCGG) |
| SEQ ID NO: 21 | Amino acid sequence of randomized insertion sequence (GGCXXXXXXXXXCGG) |
| SEQ ID NO: 22 | Amino acid sequence of randomized insertion sequence (GGGCXXXXXXCGGG) |
| SEQ ID NO: 23 | Amino acid sequence of randomized insertion sequence (GGGCXXXXXXXXCGGG) |
| SEQ ID NO: 24 | Amino acid sequence of randomized insertion sequence (GGGCXXXXXXXXXCGGG) |
| SEQ ID NO: 25 | Nucleotide sequence of the Fc-fragment-encoding portion of library L1 |
| SEQ ID NO: 26 | Amino acid sequence encoded by SEQ ID NO: 25 |
| SEQ ID NO: 27 | Nucleotide sequence of the Fc-fragment-encoding portion of library L2A |
| SEQ ID NO: 28 | Amino acid sequence encoded by SEQ ID NO: 27 |
| SEQ ID NO: 29 | Nucleotide sequence of the Fc-fragment-encoding portion of library L2B |
| SEQ ID NO: 30 | Amino acid sequence encoded by SEQ ID NO: 29 |
| SEQ ID NO: 31 | Nucleotide sequence of the Fc-fragment-encoding portion of library L3 |
| SEQ ID NO: 32 | Amino acid sequence encoded by SEQ ID NO: 31 |
| SEQ ID NO: 33 | Nucleotide sequence of the Fc-fragment-encoding portion of library L4 |
| SEQ ID NO: 34 | Amino acid sequence encoded by SEQ ID NO: 33 |
| SEQ ID NO: 35 | Nucleotide sequence of the Fc-fragment-encoding portion of library L5 |
| SEQ ID NO: 36 | Amino acid sequence encoded by SEQ ID NO: 35 |
| SEQ ID NO: 37 | Nucleotide sequence of the Fc-fragment-encoding portion of library L6A |
| SEQ ID NO: 38 | Amino acid sequence encoded by SEQ ID NO: 37 |
| SEQ ID NO: 39 | Nucleotide sequence of the Fc-fragment-encoding portion of library L6B |
| SEQ ID NO: 40 | Amino acid sequence encoded by SEQ ID NO: 39 |
| SEQ ID NO: 41 | Amino acid sequence of the insertion in variant Fc-fragment Fc-5-51 |
| SEQ ID NO: 42 | Amino acid sequence of the insertion in variant Fc-fragment Fc-5-69 |
| SEQ ID NO: 43 | Amino acid sequence of the insertion in variant Fc-fragment Fc-5-104 |
| SEQ ID NO: 44 | Amino acid sequence of the insertion in variant Fc-fragment Fc-5-106 |
| SEQ ID NO: 45 | Amino acid sequence of the insertion in variant Fc-fragment Fc-5-112 |
| SEQ ID NO: 46 | Amino acid sequence of the insertion in variant Fc-fragment Fc-5-55 |
| SEQ ID NO: 47 | Amino acid sequence of the insertion in variant Fc-fragment Fc-5-60 |
| SEQ ID NO: 48 | Amino acid sequence of the insertion in variant Fc-fragment Fc-5-70 |
| SEQ ID NO: 49 | Amino acid sequence of the insertion in variant Fc-fragment Fc-5-79 |
| SEQ ID NO: 50 | Amino acid sequence of the insertion in variant Fc-fragment Fc-5-85 |
| SEQ ID NO: 51 | Amino acid sequence of the insertion in variant Fc-fragment Fc-5-95 |
| SEQ ID NO: 52 | Amino acid sequence of the insertion in variant Fc-fragment Fc-5-97 |
| SEQ ID NO: 53 | Amino acid sequence of the insertion in variant Fc-fragment Fc-5-99 |

| SEQUENCE LISTING NUMBER | DESCRIPTION |
|---|---|
| SEQ ID NO: 54 | Amino acid sequence of the middle six amino acids of the insertion in Fc-5-51 |
| SEQ ID NO: 55 | Amino acid sequence of the middle six amino acids of the insertion in Fc-5-69 |
| SEQ ID NO: 56 | Amino acid sequence of the middle six amino acids of the insertion in Fc-5-104 |
| SEQ ID NO: 57 | Amino acid sequence of the middle six amino acids of the insertion in Fc-5-106 |
| SEQ ID NO: 58 | Amino acid sequence of the middle six amino acids of the insertion in Fc-5-112 |
| SEQ ID NO: 59 | Amino acid sequence of the middle six amino acids of the insertion in Fc-5-55 |
| SEQ ID NO: 60 | Amino acid sequence of the middle six amino acids of the insertion in Fc-5-60 |
| SEQ ID NO: 61 | Amino acid sequence of the middle six amino acids of the insertion in Fc-5-70 |
| SEQ ID NO: 62 | Amino acid sequence of the middle six amino acids of the insertion in Fc-5-79 |
| SEQ ID NO: 63 | Amino acid sequence of the middle six amino acids of the insertion in Fc-5-85 |
| SEQ ID NO: 64 | Amino acid sequence of the middle six amino acids of the insertion in Fc-5-95 |
| SEQ ID NO: 65 | Amino acid sequence of the middle six amino acids of the insertion in Fc-5-97 |
| SEQ ID NO: 66 | Amino acid sequence of the middle six amino acids of the insertion in Fc-5-99 |
| SEQ ID NO: 67 | Amino acid sequence of the insertion in variant Fc-fragment 5-1 |
| SEQ ID NO: 68 | Nucleotide sequence of the forward primer used to construct a vector encoding variant Fc-polypeptide 5-1-1 |
| SEQ ID NO: 69 | Nucleotide sequence of the reverse primer used to construct a vector encoding variant Fc-polypeptide 5-1-1 |
| SEQ ID NO: 70 | Nucleotide sequence of the forward primer used to construct a vector encoding variant Fc-polypeptide 5-1-2 |
| SEQ ID NO: 71 | Nucleotide sequence of the reverse primer used to construct a vector encoding variant Fc-polypeptide 5-1-2 |
| SEQ ID NO: 72 | Nucleotide sequence of the forward primer used to construct a vector encoding variant Fc-polypeptide 5-1-3 |
| SEQ ID NO: 73 | Nucleotide sequence of the reverse primer used to construct a vector encoding variant Fc-polypeptide 5-1-3 |
| SEQ ID NO: 74 | Nucleotide sequence of the forward primer used to construct a vector encoding variant Fc-polypeptide 5-1-4 |
| SEQ ID NO: 75 | Nucleotide sequence of the reverse primer used to construct a vector encoding variant Fc-polypeptide 5-1-4 |
| SEQ ID NO: 76 | Nucleotide sequence of the forward primer used to construct a vector encoding variant Fc-polypeptide 5-1-5 |
| SEQ ID NO: 77 | Nucleotide sequence of the reverse primer used to construct a vector encoding variant Fc-polypeptide 5-1-5 |
| SEQ ID NO: 78 | Nucleotide sequence of the forward primer used to construct a vector encoding variant Fc-polypeptide 5-1-6 |
| SEQ ID NO: 79 | Nucleotide sequence of the reverse primer used to construct a vector encoding variant Fc-polypeptide 5-1-6 |
| SEQ ID NO: 80 | Nucleotide sequence of the forward primer used to construct a vector encoding variant Fc-polypeptide 5-1-7 |
| SEQ ID NO: 81 | Nucleotide sequence of the reverse primer used to construct a vector encoding variant Fc-polypeptide 5-1-7 |
| SEQ ID NO: 82 | Nucleotide sequence of the forward primer used to construct a vector encoding variant Fc-polypeptide 5-1-8 |
| SEQ ID NO: 83 | Nucleotide sequence of the reverse primer used to construct a vector encoding variant Fc-polypeptide 5-1-8 |
| SEQ ID NO: 84 | Nucleotide sequence of the forward primer used to construct a vector encoding variant Fc-polypeptide 5-1-9 |
| SEQ ID NO: 85 | Nucleotide sequence of the reverse primer used to construct a vector encoding variant Fc-polypeptide 5-1-9 |
| SEQ ID NO: 86 | Nucleotide sequence of the forward primer used to construct a vector encoding variant Fc-polypeptide 5-1-10 |
| SEQ ID NO: 87 | Nucleotide sequence of the reverse primer used to construct a vector encoding variant Fc-polypeptide 5-1-10 |
| SEQ ID NO: 88 | Amino acid sequence of the insertion in library L-8 |
| SEQ ID NO: 89 | Amino acid sequence of the insertion in library L-10 |
| SEQ ID NO: 90 | Amino acid sequence of insertion in variant Fc-fragment 5y-1 |
| SEQ ID NO: 91 | Amino acid sequence of insertion in variant Fc-fragment 5y-2 |
| SEQ ID NO: 92 | Amino acid sequence of insertion in variant Fc-fragment 5y-3 |
| SEQ ID NO: 93 | Amino acid sequence of insertion in variant Fc-fragment 5y-4 |
| SEQ ID NO: 94 | Amino acid sequence of insertion in variant Fc-fragment 5y-5 |
| SEQ ID NO: 95 | Amino acid sequence of sequence of insertion in variant Fc-fragment 5y-6 |
| SEQ ID NO: 96 | Amino acid sequence of sequence of insertion in variant Fc-fragment 5y-7 |
| SEQ ID NO: 97 | Amino acid sequence of sequence of insertion in variant Fc-fragment 5y-8 |
| SEQ ID NO: 98 | Amino acid sequence of sequence of insertion in variant Fc-fragment 5y-9 |
| SEQ ID NO: 99 | Amino acid sequence of sequence of insertion in variant Fc-fragment 5y-10 |
| SEQ ID NO: 100 | Amino acid sequence of sequence of insertion in variant Fc-fragment 5y-11 |
| SEQ ID NO: 101 | Amino acid sequence of sequence of insertion in variant Fc-fragment 5y-12 |
| SEQ ID NO: 102 | Amino acid sequence of sequence of insertion in variant Fc-fragment 5y-13 |
| SEQ ID NO: 103 | Amino acid sequence of sequence of insertion in variant Fc-fragment 5y-14 |
| SEQ ID NO: 104 | Amino acid sequence of sequence of insertion in variant Fc-fragment 5y-15 |
| SEQ ID NO: 105 | Amino acid sequence of sequence of insertion in variant Fc-fragment 5y-16 |
| SEQ ID NO: 106 | Amino acid sequence of sequence of insertion in variant Fc-fragment 5y-17 |
| SEQ ID NO: 107 | Amino acid sequence of sequence of insertion in variant Fc-fragment 5y-18 |
| SEQ ID NO: 108 | Amino acid sequence of sequence of insertion in variant Fc-fragment 5y-19 |
| SEQ ID NO: 109 | Amino acid sequence of sequence of insertion in variant Fc-fragment 5y-20 |
| SEQ ID NO: 110 | Amino acid sequence of sequence of insertion in variant Fc-fragment 5y-21 |
| SEQ ID NO: 111 | Amino acid sequence of sequence of insertion in variant Fc-fragment 5y-22 |
| SEQ ID NO: 112 | Amino acid sequence of sequence of insertion in variant Fc-fragment 5y-23 |
| SEQ ID NO: 113 | Amino acid sequence of sequence of insertion in variant Fc-fragment 5y-24 |
| SEQ ID NO: 114 | Amino acid sequence of sequence of insertion in variant Fc-fragment 5y-25 |
| SEQ ID NO: 115 | Amino acid sequence of sequence of insertion in variant Fc-fragment 5y-26 |
| SEQ ID NO: 116 | Amino acid sequence of sequence of insertion in variant Fc-fragment 5y-27 |
| SEQ ID NO: 117 | Amino acid sequence of sequence of insertion in variant Fc-fragment 5y-28 |
| SEQ ID NO: 118 | Amino acid sequence of sequence of insertion in variant Fc-fragment 5y-29 |
| SEQ ID NO: 119 | Amino acid sequence of sequence of insertion in variant Fc-fragment 5y-30 |
| SEQ ID NO: 120 | Amino acid sequence of sequence of insertion in variant Fc-fragment 5y-31 |
| SEQ ID NO: 121 | Amino acid sequence of sequence of insertion in variant Fc-fragment 5y-32 |
| SEQ ID NO: 122 | Amino acid sequence of sequence of insertion in variant Fc-fragment 5y-33 |
| SEQ ID NO: 123 | Amino acid sequence of sequence of insertion in variant Fc-fragment 5y-34 |
| SEQ ID NO: 124 | Amino acid sequence of sequence of insertion in variant Fc-fragment 5y-35 |
| SEQ ID NO: 125 | Amino acid sequence of sequence of insertion in variant Fc-fragment 5y-36 |
| SEQ ID NO: 126 | Amino acid sequence of sequence of insertion in variant Fc-fragment 5y-37 |
| SEQ ID NO: 127 | Amino acid sequence of sequence of insertion in variant Fc-fragment 5y-38 |
| SEQ ID NO: 128 | Amino acid sequence of sequence of insertion in variant Fc-fragment 5y-39 |
| SEQ ID NO: 129 | Amino acid sequence of sequence of insertion in variant Fc-fragment 5y-40 |

| SEQUENCE LISTING NUMBER | DESCRIPTION |
|---|---|
| SEQ ID NO: 130 | Amino acid sequence of sequence of insertion in variant Fc-fragment 5y-41 |
| SEQ ID NO: 131 | Amino acid sequence of sequence of insertion in variant Fc-fragment 5y-42 |
| SEQ ID NO: 132 | Amino acid sequence of sequence of insertion in variant Fc-fragment 5y-43 |
| SEQ ID NO: 133 | Amino acid sequence of sequence of insertion in variant Fc-fragment 5y-44 |
| SEQ ID NO: 134 | Amino acid sequence of sequence of insertion in variant Fc-fragment 5y-45 |
| SEQ ID NO: 135 | Amino acid sequence of sequence of insertion in variant Fc-fragment 5y-46 |
| SEQ ID NO: 136 | Amino acid sequence of sequence of insertion in variant Fc-fragment 5y-47 |
| SEQ ID NO: 137 | Amino acid sequence of sequence of insertion in variant Fc-fragment 5y-48 |
| SEQ ID NO: 138 | Amino acid sequence of sequence of insertion in variant Fc-fragment 5y-49 |
| SEQ ID NO: 139 | Amino acid sequence of sequence of insertion in variant Fc-fragment 5y-50 |
| SEQ ID NO: 140 | Amino acid sequence of sequence of insertion in variant Fc-fragment 5y-51 |
| SEQ ID NO: 141 | Amino acid sequence of sequence of insertion in variant Fc-fragment 5y-52 |
| SEQ ID NO: 142 | Amino acid sequence of sequence of insertion in variant Fc-fragment 5y-53 |
| SEQ ID NO: 143 | Amino acid sequence of sequence of insertion in variant Fc-fragment 5y-54 |
| SEQ ID NO: 144 | Amino acid sequence of sequence of insertion in variant Fc-fragment 5y-55 |
| SEQ ID NO: 145 | Amino acid sequence of sequence of insertion in variant Fc-fragment 5y-56 |
| SEQ ID NO: 146 | Amino acid sequence of sequence of insertion in variant Fc-fragment 5y-57 |
| SEQ ID NO: 147 | Amino acid sequence of sequence of insertion in variant Fc-fragment 5y-58 |
| SEQ ID NO: 148 | Amino acid sequence of sequence of insertion in variant Fc-fragment 5y-59 |
| SEQ ID NO: 149 | Amino acid sequence of sequence of insertion in variant Fc-fragment 5y-60 |
| SEQ ID NO: 150 | Amino acid sequence of sequence of insertion in variant Fc-fragment 5y-61 |
| SEQ ID NO: 151 | Amino acid sequence of sequence of insertion in variant Fc-fragment 5y-62 |
| SEQ ID NO: 152 | Amino acid sequence of sequence of insertion in variant Fc-fragment 5y-63 |
| SEQ ID NO: 153 | Amino acid sequence of sequence of insertion in variant Fc-fragment 5y-64 |
| SEQ ID NO: 154 | Amino acid sequence of sequence of insertion in variant Fc-fragment 5y-65 |
| SEQ ID NO: 155 | Amino acid sequence of sequence of insertion in variant Fc-fragment 5y-66 |
| SEQ ID NO: 156 | Amino acid sequence of sequence of insertion in variant Fc-fragment 5y-67 |
| SEQ ID NO: 157 | Amino acid sequence of sequence of insertion in variant Fc-fragment 5y-68 |
| SEQ ID NO: 158 | Amino acid sequence of sequence of insertion in variant Fc-fragment 5y-69 |
| SEQ ID NO: 159 | Amino acid sequence of sequence of insertion in variant Fc-fragment 5y-70 |
| SEQ ID NO: 160 | Amino acid sequence of sequence of insertion in variant Fc-fragment 5y-71 |
| SEQ ID NO: 161 | Amino acid sequence of sequence of insertion in variant Fc-fragment 5y-72 |
| SEQ ID NO: 162 | Amino acid sequence of sequence of insertion in variant Fc-fragment 5y-73 |
| SEQ ID NO: 163 | Amino acid sequence of sequence of insertion in variant Fc-fragment 5y-74 |
| SEQ ID NO: 164 | Amino acid sequence of sequence of insertion in variant Fc-fragment 5y-75 |
| SEQ ID NO: 165 | Amino acid sequence of sequence of insertion in variant Fc-fragment 5y-76 |
| SEQ ID NO: 166 | Amino acid sequence of sequence of insertion in variant Fc-fragment 5y-77 |
| SEQ ID NO: 167 | Amino acid sequence of sequence of insertion in variant Fc-fragment 5y-78 |
| SEQ ID NO: 168 | Amino acid sequence of sequence of insertion in variant Fc-fragment 5y-79 |
| SEQ ID NO: 169 | Amino acid sequence of sequence of insertion in variant Fc-fragment 5y-80 |
| SEQ ID NO: 170 | Amino acid sequence of sequence of insertion in variant Fc-fragment 5y-81 |
| SEQ ID NO: 171 | Amino acid sequence of sequence of insertion in variant Fc-fragment 5y-82 |
| SEQ ID NO: 172 | Amino acid sequence of sequence of insertion in variant Fc-fragment 5y-83 |
| SEQ ID NO: 173 | Amino acid sequence of sequence of insertion in variant Fc-fragment 5y-84 |
| SEQ ID NO: 174 | Amino acid sequence of sequence of insertion in variant Fc-fragment 5y-85 |
| SEQ ID NO: 175 | Amino acid sequence of sequence of insertion in variant Fc-fragment 5y-86 |
| SEQ ID NO: 176 | Amino acid sequence of sequence of insertion in variant Fc-fragment 5y-87 |
| SEQ ID NO: 177 | Amino acid sequence of sequence of insertion in variant Fc-fragment 5y-88 |
| SEQ ID NO: 178 | Amino acid sequence of sequence of insertion in variant Fc-fragment 5y-89 |
| SEQ ID NO: 179 | Amino acid sequence of sequence of insertion in variant Fc-fragment 5y-90 |
| SEQ ID NO: 180 | Amino acid sequence of sequence of insertion in variant Fc-fragment 5y-91 |
| SEQ ID NO: 181 | Amino acid sequence of sequence of insertion in variant Fc-fragment 5y-92 |
| SEQ ID NO: 182 | Amino acid sequence of sequence of insertion in variant Fc-fragment 5y-93 |
| SEQ ID NO: 183 | Amino acid sequence of sequence of insertion in variant Fc-fragment 5y-94 |
| SEQ ID NO: 184 | Amino acid sequence of sequence of insertion in variant Fc-fragment 5y-95 |
| SEQ ID NO: 185 | Amino acid sequence of sequence of insertion in variant Fc-fragment 5y-96 |
| SEQ ID NO: 186 | Amino acid sequence of sequence of insertion in variant Fc-fragment 5y-97 |
| SEQ ID NO: 187 | Amino acid sequence of sequence of insertion in variant Fc-fragment 5y-98 |
| SEQ ID NO: 188 | Amino acid sequence of sequence of insertion in variant Fc-fragment 5y-99 |
| SEQ ID NO: 189 | Amino acid sequence of sequence of insertion in variant Fc-fragment 5y-100 |
| SEQ ID NO: 190 | Amino acid sequence of sequence of insertion in variant Fc-fragment 5y-101 |
| SEQ ID NO: 191 | Amino acid sequence of sequence of insertion in variant Fc-fragment 5y-102 |
| SEQ ID NO: 192 | Amino acid sequence of sequence of insertion in variant Fc-fragment 5y-103 |
| SEQ ID NO: 193 | Amino acid sequence of sequence of insertion in variant Fc-fragment 5y-104 |
| SEQ ID NO: 194 | Amino acid sequence of sequence of insertion in variant Fc-fragment 5y-105 |
| SEQ ID NO: 195 | Amino acid sequence of sequence of insertion in variant Fc-fragment 5y-106 |
| SEQ ID NO: 196 | Amino acid sequence of sequence of insertion in variant Fc-fragment 5y-107 |
| SEQ ID NO: 197 | Amino acid sequence of sequence of insertion in variant Fc-fragment 5y-108 |
| SEQ ID NO: 198 | Amino acid sequence of sequence of insertion in variant Fc-fragment 5y-109 |
| SEQ ID NO: 199 | Amino acid sequence of sequence of insertion in variant Fc-fragment 5y-110 |
| SEQ ID NO: 200 | Amino acid sequence of sequence of insertion in variant Fc-fragment 5y-111 |
| SEQ ID NO: 201 | Amino acid sequence of sequence of insertion in variant Fc-fragment 5y-112 |
| SEQ ID NO: 202 | Amino acid sequence of sequence of insertion in variant Fc-fragment 5y-113 |
| SEQ ID NO: 203 | Amino acid sequence of sequence of insertion in variant Fc-fragment 5y-114 |
| SEQ ID NO: 204 | Amino acid sequence of sequence of insertion in variant Fc-fragment 5y-115 |
| SEQ ID NO: 205 | Amino acid sequence of sequence of insertion in variant Fc-fragment 5y-116 |

| SEQUENCE LISTING NUMBER | DESCRIPTION |
|---|---|
| SEQ ID NO: 206 | Amino acid sequence of sequence of insertion in variant Fc-fragment 5y-117 |
| SEQ ID NO: 207 | Amino acid sequence of sequence of insertion in variant Fc-fragment 5y-118 |
| SEQ ID NO: 208 | Amino acid sequence of sequence of insertion in variant Fc-fragment 5y-119 |
| SEQ ID NO: 209 | Amino acid sequence of sequence of insertion in variant Fc-fragment 5y-120 |
| SEQ ID NO: 210 | Amino acid sequence of sequence of insertion in variant Fc-fragment 5y-121 |
| SEQ ID NO: 211 | Amino acid sequence of sequence of insertion in variant Fc-fragment 5y-122 |
| SEQ ID NO: 212 | Amino acid sequence of sequence of insertion in variant Fc-fragment 5y-123 |
| SEQ ID NO: 213 | Amino acid sequence of sequence of insertion in variant Fc-fragment 5y-124 |
| SEQ ID NO: 214 | Amino acid sequence of sequence of insertion in variant Fc-fragment 5y-125 |
| SEQ ID NO: 215 | Amino acid sequence of sequence of insertion in variant Fc-fragment 5y-126 |
| SEQ ID NO: 216 | Amino acid sequence of sequence of insertion in variant Fc-fragment 5y-127 |
| SEQ ID NO: 217 | Amino acid sequence of sequence of insertion in variant Fc-fragment 5y-128 |
| SEQ ID NO: 218 | Amino acid sequence of sequence of insertion in variant Fc-fragment 5y-129 |
| SEQ ID NO: 219 | Amino acid sequence of sequence of insertion in variant Fc-fragment 5y-130 |
| SEQ ID NO: 220 | Amino acid sequence of sequence of insertion in variant Fc-fragment 5y-131 |
| SEQ ID NO: 221 | Amino acid sequence of sequence of insertion in variant Fc-fragment 5y-132 |
| SEQ ID NO: 222 | Amino acid sequence of sequence of insertion in variant Fc-fragment 5y-133 |
| SEQ ID NO: 223 | Amino acid sequence of sequence of insertion in variant Fc-fragment 5y-134 |
| SEQ ID NO: 224 | Amino acid sequence of sequence of insertion in variant Fc-fragment 5y-135 |
| SEQ ID NO: 225 | Amino acid sequence of sequence of insertion in variant Fc-fragment 5y-136 |
| SEQ ID NO: 226 | Amino acid sequence of sequence of insertion in variant Fc-fragment 5y-137 |
| SEQ ID NO: 227 | Amino acid sequence of sequence of insertion in variant Fc-fragment 5y-138 |
| SEQ ID NO: 228 | Amino acid sequence of sequence of insertion in variant Fc-fragment 5y-139 |
| SEQ ID NO: 229 | Amino acid sequence of sequence of insertion in variant Fc-fragment 5y-140 |
| SEQ ID NO: 230 | Amino acid sequence of sequence of insertion in variant Fc-fragment 5y-141 |
| SEQ ID NO: 231 | Amino acid sequence of sequence of insertion in variant Fc-fragment 5y-142 |
| SEQ ID NO: 232 | Amino acid sequence of sequence of insertion in variant Fc-fragment 5y-143 |
| SEQ ID NO: 233 | Amino acid sequence of sequence of insertion in variant Fc-fragment 5y-144 |
| SEQ ID NO: 234 | Amino acid sequence of sequence of insertion in variant Fc-fragment 5y-145 |
| SEQ ID NO: 235 | Amino acid sequence of sequence of insertion in variant Fc-fragment 5y-146 |
| SEQ ID NO: 236 | Amino acid sequence of sequence of insertion in variant Fc-fragment 5y-147 |
| SEQ ID NO: 237 | Amino acid sequence of sequence of insertion in variant Fc-fragment 5y-148 |
| SEQ ID NO: 238 | Amino acid sequence of sequence of insertion in variant Fc-fragment 5y-149 |
| SEQ ID NO: 239 | Amino acid sequence of sequence of insertion in variant Fc-fragment 5y-150 |
| SEQ ID NO: 240 | Amino acid sequence of sequence of insertion in variant Fc-fragment 5y-151 |
| SEQ ID NO: 241 | Amino acid sequence of sequence of insertion in variant Fc-fragment 5y-152 |
| SEQ ID NO: 242 | Amino acid sequence of sequence of insertion in variant Fc-fragment 5y-153 |
| SEQ ID NO: 243 | Amino acid sequence of sequence of insertion in variant Fc-fragment 5y-154 |
| SEQ ID NO: 244 | Amino acid sequence of sequence of insertion in variant Fc-fragment 5y-155 |
| SEQ ID NO: 245 | Amino acid sequence of sequence of insertion in variant Fc-fragment 5y-156 |
| SEQ ID NO: 246 | Amino acid sequence of sequence of insertion in variant Fc-fragment 5y-157 |
| SEQ ID NO: 247 | Amino acid sequence of sequence of insertion in variant Fc-fragment 5y-158 |
| SEQ ID NO: 248 | Amino acid sequence of sequence of insertion in variant Fc-fragment 8y-1 |
| SEQ ID NO: 249 | Amino acid sequence of sequence of insertion in variant Fc-fragment 8y-2 |
| SEQ ID NO: 250 | Amino acid sequence of sequence of insertion in variant Fc-fragment 8y-3 |
| SEQ ID NO: 251 | Amino acid sequence of sequence of insertion in variant Fc-fragment 8y-4 |
| SEQ ID NO: 252 | Amino acid sequence of sequence of insertion in variant Fc-fragment 8y-5 |
| SEQ ID NO: 253 | Amino acid sequence of sequence of insertion in variant Fc-fragment 8y-6 |
| SEQ ID NO: 254 | Amino acid sequence of sequence of insertion in variant Fc-fragment 8y-7 |
| SEQ ID NO: 255 | Amino acid sequence of sequence of insertion in variant Fc-fragment 8y-8 |
| SEQ ID NO: 256 | Amino acid sequence of sequence of insertion in variant Fc-fragment 8y-9 |
| SEQ ID NO: 257 | Amino acid sequence of sequence of insertion in variant Fc-fragment 8y-10 |
| SEQ ID NO: 258 | Amino acid sequence of sequence of insertion in variant Fc-fragment 8y-11 |
| SEQ ID NO: 259 | Amino acid sequence of sequence of insertion in variant Fc-fragment 8y-12 |
| SEQ ID NO: 260 | Amino acid sequence of sequence of insertion in variant Fc-fragment 8y-13 |
| SEQ ID NO: 261 | Amino acid sequence of sequence of insertion in variant Fc-fragment 8y-14 |
| SEQ ID NO: 262 | Amino acid sequence of sequence of insertion in variant Fc-fragment 8y-15 |
| SEQ ID NO: 263 | Amino acid sequence of sequence of insertion in variant Fc-fragment 8y-16 |
| SEQ ID NO: 264 | Amino acid sequence of sequence of insertion in variant Fc-fragment 8y-17 |
| SEQ ID NO: 265 | Amino acid sequence of sequence of insertion in variant Fc-fragment 8y-18 |
| SEQ ID NO: 266 | Amino acid sequence of sequence of insertion in variant Fc-fragment 8y-19 |
| SEQ ID NO: 267 | Amino acid sequence of sequence of insertion in variant Fc-fragment 8y-20 |
| SEQ ID NO: 268 | Amino acid sequence of sequence of insertion in variant Fc-fragment 8y-21 |
| SEQ ID NO: 269 | Amino acid sequence of sequence of insertion in variant Fc-fragment 8y-22 |
| SEQ ID NO: 270 | Amino acid sequence of sequence of insertion in variant Fc-fragment 8y-23 |
| SEQ ID NO: 271 | Amino acid sequence of sequence of insertion in variant Fc-fragment 8y-24 |
| SEQ ID NO: 272 | Amino acid sequence of sequence of insertion in variant Fc-fragment 8y-25 |
| SEQ ID NO: 273 | Amino acid sequence of sequence of insertion in variant Fc-fragment 8y-26 |
| SEQ ID NO: 274 | Amino acid sequence of sequence of insertion in variant Fc-fragment 8y-27 |
| SEQ ID NO: 275 | Amino acid sequence of sequence of insertion in variant Fc-fragment 8y-28 |
| SEQ ID NO: 276 | Amino acid sequence of sequence of insertion in variant Fc-fragment 8y-29 |
| SEQ ID NO: 277 | Amino acid sequence of sequence of insertion in variant Fc-fragment 8y-30 |
| SEQ ID NO: 278 | Amino acid sequence of sequence of insertion in variant Fc-fragment 8y-31 |
| SEQ ID NO: 279 | Amino acid sequence of sequence of insertion in variant Fc-fragment 8y-32 |
| SEQ ID NO: 280 | Amino acid sequence of sequence of insertion in variant Fc-fragment 8y-33 |
| SEQ ID NO: 281 | Amino acid sequence of sequence of insertion in variant Fc-fragment 8y-34 |

-continued

| SEQUENCE LISTING NUMBER | DESCRIPTION |
|---|---|
| SEQ ID NO: 282 | Amino acid sequence of sequence of insertion in variant Fc-fragment 8y-35 |
| SEQ ID NO: 283 | Amino acid sequence of sequence of insertion in variant Fc-fragment 8y-36 |
| SEQ ID NO: 284 | Amino acid sequence of sequence of insertion in variant Fc-fragment 8y-37 |
| SEQ ID NO: 285 | Amino acid sequence of sequence of insertion in variant Fc-fragment 8y-38 |
| SEQ ID NO: 286 | Amino acid sequence of sequence of insertion in variant Fc-fragment 8y-39 |
| SEQ ID NO: 287 | Amino acid sequence of sequence of insertion in variant Fc-fragment 8y-40 |
| SEQ ID NO: 288 | Amino acid sequence of sequence of insertion in variant Fc-fragment 8y-41 |
| SEQ ID NO: 289 | Amino acid sequence of sequence of insertion in variant Fc-fragment 8y-42 |
| SEQ ID NO: 290 | Amino acid sequence of sequence of insertion in variant Fc-fragment 8y-43 |
| SEQ ID NO: 291 | Amino acid sequence of sequence of insertion in variant Fc-fragment 8y-44 |
| SEQ ID NO: 292 | Amino acid sequence of sequence of insertion in variant Fc-fragment 8y-45 |
| SEQ ID NO: 293 | Amino acid sequence of sequence of insertion in variant Fc-fragment 8y-46 |
| SEQ ID NO: 294 | Amino acid sequence of sequence of insertion in variant Fc-fragment 8y-47 |
| SEQ ID NO: 295 | Amino acid sequence of sequence of insertion in variant Fc-fragment 8y-48 |
| SEQ ID NO: 296 | Amino acid sequence of sequence of insertion in variant Fc-fragment 8y-49 |
| SEQ ID NO: 297 | Amino acid sequence of sequence of insertion in variant Fc-fragment 8y-50 |
| SEQ ID NO: 298 | Amino acid sequence of sequence of insertion in variant Fc-fragment 8y-51 |
| SEQ ID NO: 299 | Amino acid sequence of sequence of insertion in variant Fc-fragment 8y-52 |
| SEQ ID NO: 300 | Amino acid sequence of sequence of insertion in variant Fc-fragment 8y-53 |
| SEQ ID NO: 301 | Amino acid sequence of sequence of insertion in variant Fc-fragment 8y-54 |
| SEQ ID NO: 302 | Amino acid sequence of sequence of insertion in variant Fc-fragment 8y-55 |
| SEQ ID NO: 303 | Amino acid sequence of sequence of insertion in variant Fc-fragment 8y-56 |
| SEQ ID NO: 304 | Amino acid sequence of sequence of insertion in variant Fc-fragment 8y-57 |
| SEQ ID NO: 305 | Amino acid sequence of sequence of insertion in variant Fc-fragment 8y-58 |
| SEQ ID NO: 306 | Amino acid sequence of sequence of insertion in variant Fc-fragment 8y-59 |
| SEQ ID NO: 307 | Amino acid sequence of sequence of insertion in variant Fc-fragment 10y-1 |
| SEQ ID NO: 308 | Amino acid sequence of sequence of insertion in variant Fc-fragment 10y-2 |
| SEQ ID NO: 309 | Amino acid sequence of sequence of insertion in variant Fc-fragment 10y-3 |
| SEQ ID NO: 310 | Amino acid sequence of sequence of insertion in variant Fc-fragment 10y-4 |
| SEQ ID NO: 311 | Amino acid sequence of sequence of insertion in variant Fc-fragment 10y-5 |
| SEQ ID NO: 312 | Amino acid sequence of sequence of insertion in variant Fc-fragment 10y-6 |
| SEQ ID NO: 313 | Amino acid sequence of sequence of insertion in variant Fc-fragment 10y-7 |
| SEQ ID NO: 314 | Amino acid sequence of sequence of insertion in variant Fc-fragment 10y-8 |
| SEQ ID NO: 315 | Amino acid sequence of sequence of insertion in variant Fc-fragment 10y-9 |
| SEQ ID NO: 316 | Amino acid sequence of sequence of insertion in variant Fc-fragment 10y-10 |
| SEQ ID NO: 317 | Amino acid sequence of sequence of insertion in variant Fc-fragment 10y-11 |
| SEQ ID NO: 318 | Amino acid sequence of sequence of insertion in variant Fc-fragment 10y-12 |
| SEQ ID NO: 319 | Amino acid sequence of sequence of insertion in variant Fc-fragment 10y-13 |
| SEQ ID NO: 320 | Amino acid sequence of sequence of insertion in variant Fc-fragment 10y-14 |
| SEQ ID NO: 321 | Amino acid sequence of sequence of insertion in variant Fc-fragment 10y-15 |
| SEQ ID NO: 322 | Amino acid sequence of sequence of insertion in variant Fc-fragment 10y-16 |
| SEQ ID NO: 323 | Amino acid sequence of sequence of insertion in variant Fc-fragment 10y-17 |
| SEQ ID NO: 324 | Amino acid sequence of sequence of insertion in variant Fc-fragment 10y-18 |
| SEQ ID NO: 325 | Amino acid sequence of sequence of insertion in variant Fc-fragment 10y-19 |
| SEQ ID NO: 326 | Amino acid sequence of sequence of insertion in variant Fc-fragment 10y-20 |
| SEQ ID NO: 327 | Amino acid sequence of sequence of insertion in variant Fc-fragment 10y-21 |
| SEQ ID NO: 328 | Amino acid sequence of sequence of insertion in variant Fc-fragment 10y-22 |
| SEQ ID NO: 329 | Amino acid sequence of sequence of insertion in variant Fc-fragment 10y-23 |
| SEQ ID NO: 330 | Amino acid sequence of sequence of insertion in variant Fc-fragment 10y-24 |
| SEQ ID NO: 331 | Amino acid sequence of sequence of insertion in variant Fc-fragment 10y-25 |
| SEQ ID NO: 332 | Amino acid sequence of sequence of insertion in variant Fc-fragment 10y-26 |
| SEQ ID NO: 333 | Amino acid sequence of sequence of insertion in variant Fc-fragment 10y-27 |
| SEQ ID NO: 334 | Amino acid sequence of sequence of insertion in variant Fc-fragment 10y-28 |
| SEQ ID NO: 335 | Amino acid sequence of sequence of insertion in variant Fc-fragment 10y-29 |
| SEQ ID NO: 336 | Amino acid sequence of sequence of insertion in variant Fc-fragment 10y-30 |
| SEQ ID NO: 337 | Amino acid sequence of sequence of insertion in variant Fc-fragment 10y-31 |
| SEQ ID NO: 338 | Amino acid sequence of sequence of insertion in variant Fc-fragment 10y-32 |
| SEQ ID NO: 339 | Amino acid sequence of sequence of insertion in variant Fc-fragment 10y-33 |
| SEQ ID NO: 340 | Amino acid sequence of sequence of insertion in variant Fc-fragment 10y-34 |
| SEQ ID NO: 341 | Amino acid sequence of sequence of insertion in variant Fc-fragment 10y-35 |
| SEQ ID NO: 342 | Amino acid sequence of sequence of insertion in variant Fc-fragment 10y-36 |
| SEQ ID NO: 343 | Amino acid sequence of sequence of insertion in variant Fc-fragment 10y-37 |
| SEQ ID NO: 344 | Amino acid sequence of sequence of insertion in variant Fc-fragment 10y-38 |
| SEQ ID NO: 345 | Amino acid sequence of sequence of insertion in variant Fc-fragment 10y-39 |
| SEQ ID NO: 346 | Amino acid sequence of sequence of insertion in variant Fc-fragment 10y-40 |
| SEQ ID NO: 347 | Amino acid sequence of sequence of insertion in variant Fc-fragment 10y-41 |
| SEQ ID NO: 348 | Amino acid sequence of sequence of insertion in variant Fc-fragment 10y-42 |
| SEQ ID NO: 349 | Amino acid sequence of sequence of insertion in variant Fc-fragment 10y-43 |
| SEQ ID NO: 350 | Amino acid sequence of sequence of insertion in variant Fc-fragment 10y-44 |
| SEQ ID NO: 351 | Amino acid sequence of sequence of insertion in variant Fc-fragment 10y-45 |
| SEQ ID NO: 352 | Amino acid sequence of sequence of insertion in variant Fc-fragment 10y-46 |
| SEQ ID NO: 353 | Amino acid sequence of sequence of insertion in variant Fc-fragment 10y-47 |
| SEQ ID NO: 354 | Amino acid sequence of sequence of insertion in variant Fc-fragment 10y-48 |
| SEQ ID NO: 355 | Amino acid sequence of sequence of insertion in variant Fc-fragment 10y-49 |
| SEQ ID NO: 356 | Amino acid sequence of sequence of insertion in variant Fc-fragment 10y-50 |
| SEQ ID NO: 357 | Nucleotide sequence of a primer |

-continued

| SEQUENCE LISTING NUMBER | DESCRIPTION |
|---|---|
| SEQ ID NO: 358 | Nucleotide sequence of a primer |
| SEQ ID NO: 359 | Amino acid sequence of the peptide insertion in variant Fc-fragment 5-57 |
| SEQ ID NO: 360 | Amino acid sequence of the peptide insertion in variant Fc-fragment 5-64 |
| SEQ ID NO: 361 | Amino acid sequence of the peptide insertion in variant Fc-fragment 5-66 |
| SEQ ID NO: 362 | Amino acid sequence of the peptide insertion in variant Fc-fragment 5-73 |
| SEQ ID NO: 363 | Amino acid sequence of the peptide insertion in variant Fc-fragment 5-92 |
| SEQ ID NO: 364 | Amino acid sequence of the peptide insertion in variant Fc-fragment 5-96 |
| SEQ ID NO: 365 | Amino acid sequence of the peptide insertion in variant Fc-fragment 5-110 |
| SEQ ID NO: 366 | Amino acid sequence of the peptide insertion in variant Fc-fragment 5-113 |
| SEQ ID NO: 367 | Amino acid sequence of the peptide insertion in variant Fc-fragment Fc-5-69-WIF |
| SEQ ID NO: 368 | Amino acid sequence of the peptide insertion in variant Fc-fragment Fc-5-69-WIY |
| SEQ ID NO: 369 | Amino acid sequence of the peptide insertion in variant Fc-fragment Fc-5-106-M4A |
| SEQ ID NO: 370 | Amino acid sequence of the peptide insertion in variant Fc-fragment Fc-5-106-M4G |
| SEQ ID NO: 371 | Amino acid sequence of the peptide insertion in variant Fc-fragment Fc-5-106-M4H |
| SEQ ID NO: 372 | Amino acid sequence of the peptide insertion in variant Fc-fragment Fc-5-106-M4I |
| SEQ ID NO: 373 | Amino acid sequence of the peptide insertion in variant Fc-fragment Fc-5-106-M4L |
| SEQ ID NO: 374 | Amino acid sequence of the peptide insertion in variant Fc-fragment Fc-5-106-M4N |
| SEQ ID NO: 375 | Amino acid sequence of the peptide insertion in variant Fc-fragment Fc-5-106-M4Q |
| SEQ ID NO: 376 | Amino acid sequence of the peptide insertion in variant Fc-fragment Fc-5-106-M4S |
| SEQ ID NO: 377 | Amino acid sequence of the peptide insertion in variant Fc-fragment Fc-5-106-M4T |
| SEQ ID NO: 378 | Amino acid sequence of the peptide insertion in variant Fc-fragment Fc-5-106-M4V |
| SEQ ID NO: 379 | Amino acid sequence of the peptide insertion in variant Fc-fragment Fc-5-110 |
| SEQ ID NO: 380 | Nucleotide sequence of forward PCR primer used to make Antibody X-5y-8 |
| SEQ ID NO: 381 | Nucleotide sequence of reverse PCR primer used to make Antibody X-5y-8 |
| SEQ ID NO: 382 | Nucleotide sequence of forward PCR primer used to make Antibody X-5y-132 |
| SEQ ID NO: 383 | Nucleotide sequence of reverse PCR primer used to make Antibody X-5y-132 |
| SEQ ID NO: 384 | Nucleotide sequence of forward PCR primer used to make Antibody X-5y-38 |
| SEQ ID NO: 385 | Nucleotide sequence of reverse PCR primer used to make Antibody X-5y-38 |
| SEQ ID NO: 386 | Nucleotide sequence of forward PCR primer used to make Antibody X-5y-91 |
| SEQ ID NO: 387 | Nucleotide sequence of reverse PCR primer used to make Antibody X-5y-91 |
| SEQ ID NO: 388 | Nucleotide sequence of forward PCR primer used to make Antibody X-5y-119 |
| SEQ ID NO: 389 | Nucleotide sequence of reverse PCR primer used to make Antibody X-5y-119 |
| SEQ ID NO: 390 | Nucleotide sequence of forward PCR primer used to make Antibody X-5y-127 |
| SEQ ID NO: 391 | Nucleotide sequence of reverse PCR primer used to make Antibody X-5y-127 |
| SEQ ID NO: 392 | Amino acid sequence of a peptide insertion in a variant Fc polypeptide with a positive ELISA score |
| SEQ ID NO: 393 | Amino acid sequence of a peptide insertion in a variant Fc polypeptide with a positive ELISA score |
| SEQ ID NO: 394 | Amino acid sequence of a peptide insertion in a variant Fc polypeptide with a positive ELISA score |
| SEQ ID NO: 395 | Amino acid sequence of a peptide insertion in a variant Fc polypeptide with a positive ELISA score |
| SEQ ID NO: 396 | Amino acid sequence of a peptide insertion in a variant Fc polypeptide with a positive ELISA score |
| SEQ ID NO: 397 | Amino acid sequence of a peptide insertion in a variant Fc polypeptide with a positive ELISA score |
| SEQ ID NO: 398 | Amino acid sequence of a peptide insertion in a variant Fc polypeptide with a positive ELISA score |
| SEQ ID NO: 399 | Amino acid sequence of a peptide insertion in a variant Fc polypeptide with a positive ELISA score |
| SEQ ID NO: 400 | Amino acid sequence of a peptide insertion in a variant Fc polypeptide with a positive ELISA score |
| SEQ ID NO: 401 | Amino acid sequence of a peptide insertion in a variant Fc polypeptide with a positive ELISA score |
| SEQ ID NO: 402 | Amino acid sequence of a peptide insertion in a variant Fc polypeptide with a positive ELISA score |
| SEQ ID NO: 403 | Amino acid sequence of a peptide insertion in a variant Fc polypeptide with a positive ELISA score |
| SEQ ID NO: 404 | Amino acid sequence of a peptide insertion in a variant Fc polypeptide with a positive ELISA score |
| SEQ ID NO: 405 | Amino acid sequence of a peptide insertion in a variant Fc polypeptide with a positive ELISA score |
| SEQ ID NO: 406 | Amino acid sequence of a peptide insertion in a variant Fc polypeptide with a positive ELISA score |
| SEQ ID NO: 407 | Amino acid sequence of a peptide insertion in a variant Fc polypeptide with a positive ELISA score |
| SEQ ID NO: 408 | Amino acid sequence of a peptide insertion in a variant Fc polypeptide with a positive ELISA score |
| SEQ ID NO: 409 | Amino acid sequence of a peptide insertion in a variant Fc polypeptide with a positive ELISA score |
| SEQ ID NO: 410 | Amino acid sequence of a peptide insertion in a variant Fc polypeptide with a positive ELISA score |
| SEQ ID NO: 411 | Amino acid sequence of a peptide insertion in a variant Fc polypeptide with a positive ELISA score |
| SEQ ID NO: 412 | Amino acid sequence of a peptide insertion in a variant Fc polypeptide with a positive ELISA score |
| SEQ ID NO: 413 | Amino acid sequence of a peptide insertion in a variant Fc polypeptide with a positive ELISA score |
| SEQ ID NO: 414 | Amino acid sequence of a peptide insertion in a variant Fc polypeptide with a positive ELISA score |
| SEQ ID NO: 415 | Amino acid sequence of a peptide insertion in a variant Fc polypeptide with a positive ELISA score |
| SEQ ID NO: 416 | Amino acid sequence of a peptide insertion in a variant Fc polypeptide with a positive ELISA score |
| SEQ ID NO: 417 | Amino acid sequence of a peptide insertion in a variant Fc polypeptide with a positive ELISA score |
| SEQ ID NO: 418 | Amino acid sequence of a peptide insertion in a variant Fc polypeptide with a positive ELISA score |
| SEQ ID NO: 419 | Amino acid sequence of a peptide insertion in a variant Fc polypeptide with a positive ELISA score |
| SEQ ID NO: 420 | Amino acid sequence of a peptide insertion in a variant Fc polypeptide with a positive ELISA score |
| SEQ ID NO: 421 | Amino acid sequence of a peptide insertion in a variant Fc polypeptide with a positive ELISA score |
| SEQ ID NO: 422 | Amino acid sequence of a peptide insertion in a variant Fc polypeptide with a positive ELISA score |
| SEQ ID NO: 423 | Amino acid sequence of a peptide insertion in a variant Fc polypeptide with a positive ELISA score |
| SEQ ID NO: 424 | Amino acid sequence of a peptide insertion in a variant Fc polypeptide with a positive ELISA score |
| SEQ ID NO: 425 | Amino acid sequence of a peptide insertion in a variant Fc polypeptide with a positive ELISA score |
| SEQ ID NO: 426 | Amino acid sequence of a peptide insertion in a variant Fc polypeptide with a positive ELISA score |
| SEQ ID NO: 427 | Amino acid sequence of a peptide insertion in a variant Fc polypeptide with a positive ELISA score |
| SEQ ID NO: 428 | Amino acid sequence of a peptide insertion in a variant Fc polypeptide with a positive ELISA score |
| SEQ ID NO: 429 | Amino acid sequence of a peptide insertion in a variant Fc polypeptide with a positive ELISA score |
| SEQ ID NO: 430 | Amino acid sequence of a peptide insertion in a variant Fc polypeptide with a positive ELISA score |
| SEQ ID NO: 431 | Amino acid sequence of a peptide insertion in a variant Fc polypeptide with a positive ELISA score |
| SEQ ID NO: 432 | Amino acid sequence of a peptide insertion in a variant Fc polypeptide with a positive ELISA score |
| SEQ ID NO: 433 | Amino acid sequence of a peptide insertion in a variant Fc polypeptide with a positive ELISA score |

-continued

| SEQUENCE LISTING NUMBER | DESCRIPTION |
|---|---|
| SEQ ID NO: 434 | Amino acid sequence of a peptide insertion in a variant Fc polypeptide with a positive ELISA score |
| SEQ ID NO: 435 | Amino acid sequence of a peptide insertion in a variant Fc polypeptide with a positive ELISA score |
| SEQ ID NO: 436 | Amino acid sequence of a peptide insertion in a variant Fc polypeptide with a positive ELISA score |
| SEQ ID NO: 437 | Amino acid sequence of a peptide insertion in a variant Fc polypeptide with a positive ELISA score |
| SEQ ID NO: 438 | Amino acid sequence of a peptide insertion in a variant Fc polypeptide with a positive ELISA score |
| SEQ ID NO: 439 | Amino acid sequence of a peptide insertion in a variant Fc polypeptide with a positive ELISA score |
| SEQ ID NO: 440 | Amino acid sequence of a peptide insertion in a variant Fc polypeptide with a positive ELISA score |
| SEQ ID NO: 441 | Amino acid sequence of a peptide insertion in a variant Fc polypeptide with a positive ELISA score |
| SEQ ID NO: 442 | Amino acid sequence of a peptide insertion in a variant Fc polypeptide with a positive ELISA score |
| SEQ ID NO: 443 | Amino acid sequence of a peptide insertion in a variant Fc polypeptide with a positive ELISA score |
| SEQ ID NO: 444 | Amino acid sequence of a peptide insertion in a variant Fc polypeptide with a positive ELISA score |
| SEQ ID NO: 445 | Amino acid sequence of a peptide insertion in a variant Fc polypeptide with a positive ELISA score |
| SEQ ID NO: 446 | Amino acid sequence of a peptide insertion in a variant Fc polypeptide with a positive ELISA score |
| SEQ ID NO: 447 | Amino acid sequence of a peptide insertion in a variant Fc polypeptide with a positive ELISA score |
| SEQ ID NO: 448 | Amino acid sequence of a peptide insertion in a variant Fc polypeptide with a positive ELISA score |
| SEQ ID NO: 449 | Amino acid sequence of a peptide insertion in a variant Fc polypeptide with a positive ELISA score |
| SEQ ID NO: 450 | Amino acid sequence of a peptide insertion in a variant Fc polypeptide with a positive ELISA score |
| SEQ ID NO: 451 | Amino acid sequence of a peptide insertion in a variant Fc polypeptide with a positive ELISA score |
| SEQ ID NO: 452 | Amino acid sequence of a peptide insertion in a variant Fc polypeptide with a positive ELISA score |
| SEQ ID NO: 453 | Amino acid sequence of a peptide insertion in a variant Fc polypeptide with a positive ELISA score |
| SEQ ID NO: 454 | Amino acid sequence of a peptide insertion in a variant Fc polypeptide with a positive ELISA score |
| SEQ ID NO: 455 | Amino acid sequence of a peptide insertion in a variant Fc polypeptide with a positive ELISA score |
| SEQ ID NO: 456 | Amino acid sequence of a peptide insertion in a variant Fc polypeptide with a positive ELISA score |
| SEQ ID NO: 457 | Amino acid sequence of a peptide insertion in a variant Fc polypeptide with a positive ELISA score |
| SEQ ID NO: 458 | Amino acid sequence of a peptide insertion in a variant Fc polypeptide with a positive ELISA score |
| SEQ ID NO: 459 | Amino acid sequence of a peptide insertion in a variant Fc polypeptide with a positive ELISA score |
| SEQ ID NO: 460 | Amino acid sequence of a peptide insertion in a variant Fc polypeptide with a positive ELISA score |
| SEQ ID NO: 461 | Amino acid sequence of a peptide insertion in a variant Fc polypeptide with a positive ELISA score |
| SEQ ID NO: 462 | Amino acid sequence of a peptide insertion in a variant Fc polypeptide with a positive ELISA score |
| SEQ ID NO: 463 | Amino acid sequence of a peptide insertion in a variant Fc polypeptide with a positive ELISA score |
| SEQ ID NO: 464 | Amino acid sequence of a peptide insertion in a variant Fc polypeptide with a positive ELISA score |
| SEQ ID NO: 465 | Amino acid sequence of a peptide insertion in a variant Fc polypeptide with a positive ELISA score |
| SEQ ID NO: 466 | Amino acid sequence of a peptide insertion in a variant Fc polypeptide with a positive ELISA score |
| SEQ ID NO: 467 | Amino acid sequence of a peptide insertion in a variant Fc polypeptide with a positive ELISA score |
| SEQ ID NO: 468 | Amino acid sequence of a peptide insertion in a variant Fc polypeptide with a positive ELISA score |
| SEQ ID NO: 469 | Amino acid sequence of a peptide insertion in a variant Fc polypeptide with a positive ELISA score |
| SEQ ID NO: 470 | Amino acid sequence of a peptide insertion in a variant Fc polypeptide with a positive ELISA score |
| SEQ ID NO: 471 | Amino acid sequence of a peptide insertion in a variant Fc polypeptide with a positive ELISA score |
| SEQ ID NO: 472 | Amino acid sequence of a peptide insertion in a variant Fc polypeptide with a positive ELISA score |
| SEQ ID NO: 473 | Amino acid sequence of a peptide insertion in a variant Fc polypeptide with a positive ELISA score |
| SEQ ID NO: 474 | Amino acid sequence of a peptide insertion in a variant Fc polypeptide with a positive ELISA score |
| SEQ ID NO: 475 | Amino acid sequence of a peptide insertion in a variant Fc polypeptide with a positive ELISA score |
| SEQ ID NO: 476 | Amino acid sequence of a peptide insertion in a variant Fc polypeptide with a positive ELISA score |
| SEQ ID NO: 477 | Amino acid sequence of a peptide insertion in a variant Fc polypeptide with a positive ELISA score |
| SEQ ID NO: 478 | Amino acid sequence of a peptide insertion in a variant Fc polypeptide with a positive ELISA score |
| SEQ ID NO: 479 | Amino acid sequence of a peptide insertion in a variant Fc polypeptide with a positive ELISA score |
| SEQ ID NO: 480 | Amino acid sequence of a peptide insertion in a variant Fc polypeptide with a positive ELISA score |
| SEQ ID NO: 481 | Amino acid sequence of a peptide insertion in a variant Fc polypeptide with a positive ELISA score |
| SEQ ID NO: 482 | Amino acid sequence of a peptide insertion in a variant Fc polypeptide with a positive ELISA score |
| SEQ ID NO: 483 | Amino acid sequence of a peptide insertion in a variant Fc polypeptide with a positive ELISA score |
| SEQ ID NO: 484 | Amino acid sequence of a peptide insertion in a variant Fc polypeptide with a positive ELISA score |
| SEQ ID NO: 485 | Amino acid sequence of a peptide insertion in a variant Fc polypeptide with a positive ELISA score |
| SEQ ID NO: 486 | Amino acid sequence of a peptide insertion in a variant Fc polypeptide with a positive ELISA score |
| SEQ ID NO: 487 | Amino acid sequence of a peptide insertion in a variant Fc polypeptide with a positive ELISA score |
| SEQ ID NO: 488 | Amino acid sequence of a peptide insertion in a variant Fc polypeptide with a positive ELISA score |
| SEQ ID NO: 489 | Amino acid sequence of a peptide insertion in a variant Fc polypeptide with a positive ELISA score |
| SEQ ID NO: 490 | Amino acid sequence of a peptide insertion in a variant Fc polypeptide with a positive ELISA score |
| SEQ ID NO: 491 | Amino acid sequence of a peptide insertion in a variant Fc polypeptide with a positive ELISA score |
| SEQ ID NO: 492 | Amino acid sequence of a peptide insertion in a variant Fc polypeptide with a positive ELISA score |
| SEQ ID NO: 493 | Amino acid sequence of a peptide insertion in a variant Fc polypeptide with a positive ELISA score |
| SEQ ID NO: 494 | Amino acid sequence of a peptide insertion in a variant Fc polypeptide with a positive ELISA score |
| SEQ ID NO: 495 | Amino acid sequence of a peptide insertion in a variant Fc polypeptide with a positive ELISA score |
| SEQ ID NO: 496 | Amino acid sequence of a peptide insertion in a variant Fc polypeptide with a positive ELISA score |
| SEQ ID NO: 497 | Nucleotide sequence of a forward PCR primer used to make Fc variant Fc-5-69-W1F |
| SEQ ID NO: 498 | Nucleotide sequence of a reverse PCR primer used to make Fc variant Fc-5-69-W1F |
| SEQ ID NO: 499 | Nucleotide sequence of a forward PCR primer used to make Fc variant Fc-5-69-W1Y |
| SEQ ID NO: 500 | Nucleotide sequence of a reverse PCR primer used to make Fc variant Fc-5-69-W1Y |
| SEQ ID NO: 501 | Nucleotide sequence of a forward PCR primer used to make Fc variant Fc-5-106-M4A |
| SEQ ID NO: 502 | Nucleotide sequence of a reverse PCR primer used to make Fc variant Fc-5-106-M4A |
| SEQ ID NO: 503 | Nucleotide sequence of a forward PCR primer used to make Fc variant Fc-5-106-M4G |
| SEQ ID NO: 504 | Nucleotide sequence of a reverse PCR primer used to make Fc variant Fc-5-106-M4G |
| SEQ ID NO: 505 | Nucleotide sequence of a forward PCR primer used to make Fc variant Fc-5-106-M4H |
| SEQ ID NO: 506 | Nucleotide sequence of a reverse PCR primer used to make Fc variant Fc-5-106-M4H |
| SEQ ID NO: 507 | Nucleotide sequence of a forward PCR primer used to make Fc variant Fc-5-106-M4I |
| SEQ ID NO: 508 | Nucleotide sequence of a reverse PCR primer used to make Fc variant Fc-5-106-M4I |
| SEQ ID NO: 509 | Nucleotide sequence of a forward PCR primer used to make Fc variant Fc-5-106-M4L |

| SEQUENCE LISTING NUMBER | DESCRIPTION |
|---|---|
| SEQ ID NO: 510 | Nucleotide sequence of a reverse PCR primer used to make Fc variant Fc-5-106-M4L |
| SEQ ID NO: 511 | Nucleotide sequence of a forward PCR primer used to make Fc variant Fc-5-106-M4N |
| SEQ ID NO: 512 | Nucleotide sequence of a reverse PCR primer used to make Fc variant Fc-5-106-M4N |
| SEQ ID NO: 513 | Nucleotide sequence of a forward PCR primer used to make Fc variant Fc-5-106-M4Q |
| SEQ ID NO: 514 | Nucleotide sequence of a reverse PCR primer used to make Fc variant Fc-5-106-M4Q |
| SEQ ID NO: 515 | Nucleotide sequence of a forward PCR primer used to make Fc variant Fc-5-106-M4S |
| SEQ ID NO: 516 | Nucleotide sequence of a reverse PCR primer used to make Fc variant Fc-5-106-M4S |
| SEQ ID NO: 517 | Nucleotide sequence of a forward PCR primer used to make Fc variant Fc-5-106-M4T |
| SEQ ID NO: 518 | Nucleotide sequence of a reverse PCR primer used to make Fc variant Fc-5-106-M4T |
| SEQ ID NO: 519 | Nucleotide sequence of a forward PCR primer used to make Fc variant Fc-5-106-M4V |
| SEQ ID NO: 520 | Nucleotide sequence of a reverse PCR primer used to make Fc variant Fc-5-106-M4V |
| SEQ ID NO: 521 | Nucleotide sequence of a forward PCR primer used to construct libraries L1, L2A, L2B, L3, L4, and L5 |
| SEQ ID NO: 522 | Nucleotide sequence of a reverse PCR primer used to construct library L1 |
| SEQ ID NO: 523 | Nucleotide sequence of a reverse PCR primer used to construct libraries L2A and L2B |
| SEQ ID NO: 524 | Nucleotide sequence of a reverse PCR primer used to construct library L3 |
| SEQ ID NO: 525 | Nucleotide sequence of a reverse PCR primer used to construct library L4 |
| SEQ ID NO: 526 | Nucleotide sequence of a reverse PCR primer used to construct library L5 |
| SEQ ID NO: 527 | Nucleotide sequence of a reverse PCR primer used to construct libraries L1, L2A, L2B, L3, L4, and L5 |
| SEQ ID NO: 528* | Nucleotide sequence of a forward PCR primer used to construct library L1 |
| SEQ ID NO: 529* | Nucleotide sequence of a forward PCR primer used to construct library L2A |
| SEQ ID NO: 530* | Nucleotide sequence of a forward PCR primer used to construct library L2B |
| SEQ ID NO: 531* | Nucleotide sequence of a forward PCR primer used to construct library L3 |
| SEQ ID NO: 532* | Nucleotide sequence of a forward PCR primer used to construct library L4 |
| SEQ ID NO: 533* | Nucleotide sequence of a forward PCR primer used to construct library L5 |
| SEQ ID NO: 534 | Nucleotide sequence of a forward PCR primer used to construct libraries L1, L2A, L2B, L3, L4, and L5 |
| SEQ ID NO: 535 | Nucleotide sequence of a reverse PCR primer used to construct libraries L1, L2A, L2B, L3, L4, and L5 |
| SEQ ID NO: 536 | Nucleotide sequence of a forward PCR primer used to construct library L6A |
| SEQ ID NO: 537# | Nucleotide sequence of a forward PCR primer used to construct library L6B |
| SEQ ID NO: 538 | Nucleotide sequence of a reverse PCR primer used to construct libraries L6A and L6B |
| SEQ ID NO: 539 | Nucleotide sequence of forward PCR primer used to construct Antibody X-5-51 |
| SEQ ID NO: 540 | Nucleotide sequence of reverse PCR primer used to construct Antibody X-5-51 |
| SEQ ID NO: 541 | Nucleotide sequence of forward PCR primer used to construct Antibody X-5-69 |
| SEQ ID NO: 542 | Nucleotide sequence of reverse PCR primer used to construct Antibody X-5-69 |
| SEQ ID NO: 543 | Nucleotide sequence of forward PCR primer used to construct Antibody X-5-104 |
| SEQ ID NO: 544 | Nucleotide sequence of reverse PCR primer used to construct Antibody X-5-104 |
| SEQ ID NO: 545 | Nucleotide sequence of forward PCR primer used to construct Antibody X-5-106 |
| SEQ ID NO: 546 | Nucleotide sequence of reverse PCR primer used to construct Antibody X-5-106 |
| SEQ ID NO: 547 | Nucleotide sequence of forward PCR primer used to construct Antibody X-5-112 |
| SEQ ID NO: 548 | Nucleotide sequence of reverse PCR primer used to construct Antibody X-5-112 |
| SEQ ID NO: 549 | Amino acid sequence of amino acids 36-41 of SEQ ID NO: 1, which correspond to amino acids 251-256 in the EU numbering scheme |
| SEQ ID NO: 550 | Amino acid sequence from amino acid 251-256 in the EU numbering scheme in the Fc fragments encoded by Library L1 |
| SEQ ID NO: 551 | Amino acid sequence of amino acids 92-99 of SEQ ID NO: 1, which correspond to amino acids 307-314 in the EU numbering system |
| SEQ ID NO: 552 | Amino acid sequence from amino acid 307-314 in the EU numbering scheme in the Fc fragments encoded by Library L2A |
| SEQ ID NO: 553 | Amino acid sequence from amino acid 307-314 in the EU numbering scheme in the Fc fragments encoded by Library L2B |
| SEQ ID NO: 554 | Amino acid sequence of amino acids 213-221 of SEQ ID NO: 1, which correspond to 428-436 in the EU numbering scheme |
| SEQ ID NO: 555 | Amino acid sequence from amino acid 428-436 in the EU numbering scheme in the Fc fragments encoded by Library L3 |
| SEQ ID NO: 556 | Amino acid sequence of amino acids 68-72 of SEQ ID NO: 1, which correspond to amino acids 283-287 in the EU numbering scheme |
| SEQ ID NO: 557 | Amino acid sequence from amino acid 283-287 in the EU numbering scheme in the Fc fragments encoded by Library L4 |
| SEQ ID NO: 558 | Amino acid sequence of amino acids 169-174 of SEQ ID NO: 1, which correspond to amino acids 384-389 in the EU numbering system |
| SEQ ID NO: 559 | Amino acid sequence from amino acid 384-389 in the EU numbering scheme in the Fc fragments encoded by Library L5 |
| SEQ ID NO: 560 | Amino acid sequence of amino acids 141-147 of SEQ ID NO: 1, which correspond to amino acids 356-362 in the EU numbering system |
| SEQ ID NO: 561 | Amino acid sequence from amino acid 356-362 in the EU numbering scheme in the Fc fragments encoded by Library L6A |
| SEQ ID NO: 562 | Amino acid sequence from amino acid 356-362 in the EU numbering scheme in the Fc fragments encoded by Library L6B |
| SEQ ID NO: 563%* | Amino acid sequence of amino acids 166 to 178 of SEQ ID NO: 1, corresponding to amino acids 381 to 393 in the EU numbering system |
| SEQ ID NO: 564%* | Amino acid sequence corresponding to amino acids 381 to 393 is the EU numbering system of variant Fc fragment 5-1 |
| SEQ ID NO: 565%* | Amino acid sequence corresponding to amino acids 381 to 393 is the EU numbering system of variant Fc fragment 5-1-1 |
| SEQ ID NO: 566%* | Amino acid sequence corresponding to amino acids 381 to 393 is the EU numbering system of variant Fc fragment 5-1-2 |

| SEQUENCE LISTING NUMBER | DESCRIPTION |
|---|---|
| SEQ ID NO: 567* | Amino acid sequence corresponding to amino acids 381 to 393 is the EU numbering system of variant Fc fragment 5-1-3 |
| SEQ ID NO: 568* | Amino acid sequence corresponding to amino acids 381 to 393 is the EU numbering system of variant Fc fragment 5-1-4 |
| SEQ ID NO: 569* | Amino acid sequence corresponding to amino acids 381 to 393 is the EU numbering system of variant Fc fragment 5-1-5 |
| SEQ ID NO: 570* | Amino acid sequence corresponding to amino acids 381 to 393 is the EU numbering system of variant Fc fragment 5-1-6 |
| SEQ ID NO: 571* | Amino acid sequence corresponding to amino acids 381 to 393 is the EU numbering system of variant Fc fragment 5-1-7 |
| SEQ ID NO: 572* | Amino acid sequence corresponding to amino acids 381 to 393 is the EU numbering system of variant Fc fragment 5-1-8 |
| SEQ ID NO: 573* | Amino acid sequence corresponding to amino acids 381 to 393 is the EU numbering system of variant Fc fragment 5-1-9 |
| SEQ ID NO: 574* | Amino acid sequence corresponding to amino acids 381 to 393 is the EU numbering system of variant Fc fragment 5-1-10 |

DETAILED DESCRIPTION

Changes in a therapeutic protein that increase in vivo half-life can be useful because such proteins can be dosed in lower amounts and/or less frequently. The instant invention provides variant Fc-polypeptides comprising variant Fc-fragments that bind to FcRn with increased affinity and/or binding activity at slightly acidic pHs, such as, for example, pH 5.0-6.0, and do not bind well to FcRn at physiologic pHs of about 7.2 to 7.6. As demonstrated herein, such variant Fc-polypeptides containing the variant Fc-fragments can have longer in vivo half lives as compared to control Fc-polypeptides. Provided are variant Fc-polypeptides comprising variant human Fc-fragments, which contain at least one insertion within or adjacent to a loop, which bind to FcRn with enhanced affinity and/or binding activity at a pH of from about 5 to 6 as compared to control Fc-polypeptides that differ only in that they do not contain the insertion(s). Also provided are nucleic acids encoding proteins containing such variant Fc-fragments and variant Fc-polypeptides, host cells containing such nucleic acids, and methods of making variant Fc-polypeptides and variant Fc-fragments. Further, methods of extending the half life of an Fc-polypeptide are provided, and methods of identifying variant Fc-fragments that bind to FcRn with higher affinity and/or binding activity at pH 5-6 with lower or comparable affinity and/or binding activity at a physiologic pH as compared to control Fc-fragments are also provided.

A variant Fc-fragment as described herein contains short insertions at selected sites in loops. FcRn interacts with an Fc-fragment. An immunoglobulin domain, such as the $C_H2$ or $C_H3$ domain, has a barrel-shaped structure comprising beta sheet portions alternating with loops. Hunkapiller and Hood (1989), Adv. Immunol. 44: 1-63; Williams and Barclay (1988), Ann. Rev. Immunol. 6: 381-405. Insertion sites in an Fc-fragment were chosen in loops that are part of the area that comes into relatively close contact with FcRn when it is bound to the Fc-fragment or in loops that are adjacent to these areas. FIG. 1 shows ribbon diagrams of portions of FcRn (top) and an Fc-fragment (bottom) and indicates the positions in the Fc-fragment of the sites selected for insertions.

As will be shown below, many insertions in library L5 have the desired properties of enhanced binding to FcRn at pH 5 to 6 and little or no binding to FcRn at physiologic pH. Other libraries, including libraries L1, L2B, L3, and L4 (see FIGS. 1 and 2), yielded no insertions that had the desired properties even though approximately the same number of variants were screened. Libraries L2A, L6A, and L6B yielded some insertions having the desired properties, although the numbers were much smaller than the numbers obtained from library L5. Surprisingly, the library that produced the most numerous insertions with the desired properties, i.e., library L5, lay in a loop region that is not part of the area that comes in to closest contact with FcRn. FIG. 1.

DEFINITIONS

The term "affinity," as meant herein, refers to binding affinity measured as an $EC_{50}$ measured using a BIAcore® T100 (or a similar instrument) as explained in Example 3. "Higher affinity" of a variant Fc-polypeptide (containing a variant Fc-fragment), as compared to an control Fc-polypeptide (containing a control Fc-fragment), for FcRn means that the variant Fc-polypeptide has an $EC_{50}$ that is no more than 50% of the $EC_{50}$ of the control Fc-polypeptide. Similarly, "lower affinity" of a variant Fc-polypeptide, as compared to a control Fc-polypeptide, means that the variant Fc-polypeptide has an $EC_{50}$ that is more than 150% of that of a control Fc-polypeptide. Affinity of a variant Fc-polypeptide is considered "substantially the same" as that of a control Fc-polypeptide if its $EC_{50}$ is 50-150% of the $EC_{50}$ of the control Fc-polypeptide.

The term "binding activity," as meant herein, refers to binding activity of an Fc-polypeptide to an FcRn measured using streptavidin biosensors coated with biotinylated human FcRn (hFcRn) in the Octet Red® system as described in Example 4 where association occurs at pH 6 and dissociation occurs at pH 7.4. Binding activity of a variant Fc-polypeptide at pH 6 is considered to be "higher than" that of a control Fc-polypeptide if the maximal response observed is at least 1.5, 1.75, or 2.0 times the maximal response observed for the control Fc-polypeptide. The very small amount of residual binding response, i.e., the binding response remaining after most of the protein has dissociated from hFcRn at pH 7.4, observed using a control Fc-polypeptide comprising a wild type Fc-fragment is referred to as "little or no binding activity." A variant Fc-polypeptide is also considered to have "little or no binding activity" at pH 7.4 if the residual binding response detected after some or all of the protein has dissociated at pH 7.4 is no more than 0.2 or 0.1 nanometers more than that detected using a control Fc-polypeptide using the ForteBio system as described in Example 4.

An "amino acid," as meant herein, refers to any one of the twenty L-amino acids commonly found in human proteins, which are the following: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

An "antibody," as meant herein, is a protein containing at least one heavy or light chain immunoglobulin variable region. For example, an scFv, a molecule comprising two or more scFv's, and the domain antibodies consisting essentially of a single immunoglobulin variable region (as described in, e.g., U.S. Pat. No. 7,563,443) are "antibodies" as meant herein. In many cases, an antibody includes a heavy and a light chain variable region plus a human IgG Fc region. Thus, the term "antibody" encompasses full length antibodies containing two full length heavy and two full length light chains, such as naturally-occurring IgG, IgA, IgD, IgD, or IgM antibodies found in mammals. Carayannopoulos and Capra, Ch. 9 in FUNDAMENTAL IMMUNOLOGY, $3^{rd}$ ed., Paul, ed., Raven Press, New York, 1993, pp. 284-286); the portions of this reference that describe antibodies are incorporated herein by reference. Exemplary antibodies include adalimumab, (HUMIRA®, Abbott Laboratories), infliximab (REMICADE®, Centocor Ortho Biotech Inc.), ustekinumab (STELLARA®, Centocor), golimumab (SIMPONI®, Centocor Ortho Biotech), canakinumab (ILARIS®, Novartis Pharmaceuticals Corporation), ofatumumab (ARZERRA®, Glaxo Group Ltd.), tocilizumab (ACTEMRA®, Chugai Seiyaku Kabushiki Corp., Japan), belimumab (BENLYSTA®, LYMPHOSTAT-B®, Human Genome Sciences, Inc.), bevacizumab (AVASTIN®, Genentech), cetuximab (ERBITUX®, ImClone Systems Inc.), efungumab (MYCOGRAB®, Novartis AB Corp.), efalizumab, (RAPTIVA®, Genentech Inc.), etaracizumab (ABEGRIN®, Medimmune LLC), gemtuzumab ozogamicin (MYLOTARG®, Wyeth), girentuximab (RENCAREX®, Wilex AG Corp., Germany), natalizumab (TYSABRI®, Elan Pharmaceuticals, Inc.), omalizumab (XOLAIR®, Novartis AG Corp., Switzerland), oregovomab (OVAREX®, AltaRex Corp., Canada), palivizumab (SYNAGIS®, ABBOSYNAGIS®, Medimmune Inc.). panitumumab (VECTIBIX®, Amgen Inc.), ranibizumab (LUCENTIS®, Genentech Inc.), rituximab (MABTHERA®, RITUXAN®, Idec Pharmaceuticals Corp.) tefibazumab (AUREXIS®, Inhibitex Corp.), tositumomab, (BEXXAR®, GlaxoSmithKline Beecham Corp.), trastuzumab (HERCEPTIN®, Genentech Inc.) and denosumab (PROLIA® or XGEVA®, Amgen Inc.), among many others. Such IgG antibodies can be of the IgG1, IgG2, IgG3, or IgG4 isotype and can be chimeric, human or humanized antibodies. Further, the term "antibody" includes dimeric antibodies containing two heavy chains and no light chains, such as the naturally-occurring antibodies found in camels, other dromedary species, and sharks. See, e.g., Muyldermans et al., 2001, J. Biotechnol. 74:277-302; Desmyter et al., 2001, J. Biol. Chem. 276:26285-90; Streltsov et al. (2005), Protein Science 14: 2901-2909. An antibody can be monospecific (that is, binding to only one kind of antigen) or multispecific (that is, binding to more than one kind of antigen). In some embodiments, an antibody can be bispecific (that is, binding to two different kinds of antigen). Further, an antibody can be monovalent, bivalent, or multivalent, meaning that it can bind to one or two or more antigen molecules at once. Some of the possible formats for such antibodies include monospecific or bispecific full length antibodies, monospecific monovalent antibodies (as described in International Application WO 2009/089004 and US Application Publication 2007/0105199, the relevant portions of which are incorporated herein by reference, and in US Application Publication 2005/0227324, the relevant portions of which are incorporated herein by reference) that may inhibit or activate the molecule to which they bind, bivalent monospecific or bispecific dimeric Fv-Fc, scFv-Fc, or diabody Fc, monospecific monovalent scFv-Fc/Fc's, and the multispecific binding proteins and dual variable domain immunoglobulins described in US Publication 2009/0311253 (the relevant portions of which are incorporated herein by reference), among many other possible antibody formats.

A "binding region," as meant herein, is a region included in an "Fc-polypeptide," a "control Fc-polypeptide," or "variant Fc-polypeptide," as described herein, that binds to a target molecule, such as, for example, a protein that is expressed at high levels on a cancer cell, a cell mediating an autoimmune or inflammatory condition, an infected cell, an infectious agent, or a cell mediating an immune effector function, for example, an NK cell. A binding region can contain a heavy and/or light chain immunoglobulin variable ($V_H$ and/or $V_L$) region or a non-immunoglobulin polypeptide. Exemplary binding regions include, for example, an Fv (which comprises a $V_H$ and a $V_L$ region joined by a linker) or a soluble form of a human receptor that binds to a target molecule.

An "Fc-fragment," as meant herein, is a polypeptide that consists of part or all of a hinge region plus the $C_H2$ and $C_H3$ regions of an antibody plus, optionally, regions found downstream from the $C_H3$ region in some naturally occurring isotypes such as IgA or IgM antibodies. The antibody can be of the IgG isotype, including IgG1, IgG2, IgG3, or IgG4 isotypes, or of the IgM, IgE, IgD or IgA isotype. The antibody can be of human or animal origin. For example, the antibody can be from a mammal, such as a mouse, rat, hamster, rabbit, goat, or sheep, or from a camelid species or a shark. Sequences of human IgG1, IgG2, IgG3, and IgG4 Fc-fragments are disclosed in SEQ ID NOs: 1, 3, 5, and 7, respectively. These sequences are also shown in Table 1 below. In general, Fc-fragments form dimers via interactions between $C_H3$ domains within two Fc-fragments, which are stabilized by disulfide bonds occurring between cysteine residues in the hinge regions. An Fc-fragment referred to herein as an "Fc region" is specifically defined as a dimeric Fc-fragment, although it is recognized that Fc-fragments will generally dimerize under physiologic conditions. Dimers can be dissociated in strongly reducing conditions.

An "Fc-polypeptide," as meant herein, is a protein that comprises an Fc-fragment and a binding region. Fc-polypeptides include antibodies, Fc fusion proteins, and antibodies or fusion proteins that contain an additional "pharmacologically active moiety," which is a non-peptide organic moiety (i.e., "small molecule") or a peptide, which can act as a toxin and/or can mimic, antagonize, or agonize the activity of a biological pathway, covalently conjugated or fused to the Fc-polypeptide. Fc-polypeptides, like Fc-fragments, ordinarily form dimers that are stabilized by disulfide bonds between cysteine residues in the hinge regions of two Fc-polypeptides.

A "control Fc-fragment," as meant herein, is an Fc-fragment that is the same as the "variant Fc-polypeptide" to which it is being compared except that it does not have an insertion in a loop as the variant Fc-fragment does. Thus, the "control Fc-fragment" has unmodified sequence found in a naturally-occurring Fc-fragment in the loop where the variant Fc-fragment has an insertion that increases the affinity of the variant Fc-fragment for FcRn at pH 5 to 6. A control Fc-fragment may contain modifications relative to a naturally-occurring Fc-fragment other than the insertion(s). For example, the heterodimerizing alterations or other minor modifications described below can be present in both the variant Fc-fragment and the control Fc-fragment to which it is being compared. Hence, the only difference between a "control Fc-fragment" and a "variant Fc-fragment" is the insertion within or adjacent to a loop in the variant Fc-fragment. A "control Fc region" is defined a dimer comprising two control Fc-fragments, although a control Fc-fragment would generally be expected to exist in a dimeric form.

A "variant Fc-fragment," as meant herein is an Fc-fragment that includes an insertion of no more than 80, no more than 60, no more than 40, or no more than 20 amino acids within or adjacent to a loop of the Fc-fragment. The loops in a human IgG Fc-fragment are shown in Table 1, and the loops into which insertions were made are shown in FIG. 2. Loops in other Fc-fragments are known in the art. Numerous sequences are known in the art. See, e.g., Kabat et al., Sequences of Proteins of Immunological Interest, Public Health Service N.I.H., Bethesda, Md., 1991, the portions of which relate to the sequences and tertiary structure of hinge, $C_H2$, and $C_H3$ regions are incorporated herein reference. Kabat et al. provides alignments of numerous sequences. Given the alignments provided in Kabat et al., the highly conserved structure of immunoglobulin domains, and the locations of loops provided herein, as well as abundant further information available in the art, loops could be located in an Fc-fragment of any isotype from any species. For example, the Protein Data Bank website contains abundant information on tertiary structures of many proteins. In some embodiments, the inserted amino acids can replace from one to ten amino acids that naturally occur in the loop. The inserted amino acids can be of a fewer, greater, or the same in number as the amino acids that are removed. In other embodiments, all amino acids originally in the loop remain, and the inserted amino acids are simply added. In some embodiments, a variant human IgG Fc-fragment can comprise other "additional minor modifications," that is, the insertion, deletion, or substitution of no more than sixteen amino acids at locations other than the loop in which the insertion occurs. In some embodiments, there can be no more than 1, 2, 3, 4, 5, 6, 7, 8, 9, 10, 11, 12, 13, 14, or 15 insertions, deletions, or substitutions of a single amino acid at locations other than the loop in which the insertion occurs. In other embodiments, a variant Fc-fragment does not comprise any additional minor modifications. In some embodiments, the additional minor modifications can be, for example the "heterodimerizing alterations" described below, which facilitate the formation of heterodimeric Fc regions. In some embodiments, these additional minor modifications can include conservative amino acid substitutions.

Conservative amino acid substitutions include the following: (1) valine, leucine or isoleucine for alanine; (2) lysine, glutamine, or asparagine for arginine; (3) glutamine, glutamate, or aspartate for asparagine; (4) glutamate, asparagine, or glutamine for aspartate; (5) serine or alanine for cysteine; (6) asparagine, glutamate, or aspartate for glutamine; (7) aspartate, gluatamine, or asparagine for glutamate; (8) proline or alanine for glycine; (9) asparagine, glutamine, lysine, or arginine for histidine; (10) leucine, valine, methionine, alanine, or phenylalanine for isoleucine; (11) isoleucine, valine, methionine, alanine, or phenylalanine for leucine; (12) arginine, asparagine, or glutamine for lysine; (13) leucine, phenylalanine, or isoleucine for methionine; (14) leucine, valine, isoleucine, alanine, or tyrosine for phenylalanine; (15) alanine for proline; (16) threonine, alanine, or cysteine for serine; (17) serine for threonine; (18) tyrosine or phenylalanine for tryptophan; (19) tryptophan, phenylalanine, threonine, or serine for tyrosine; and (20) isoleucine, methionine, leucine, phenylalanine, or alanine for valine.

In addition, in some embodiments, a variant Fc-fragment can contain an additional "pharmacologically active moiety," which is a non-peptide organic moiety (i.e., "small molecule") or a peptide, which can act as a toxin and/or can mimic, antagonize, or agonize the activity of a biological pathway, covalently conjugated or fused to the Fc-fragment. If a variant Fc-fragment contains such a pharmacologically active moiety, then its "control Fc-fragment" also contains such a moiety.

In other embodiments, the variant human IgG Fc-fragment comprises no alteration outside of those occurring in the loop at which the insertion occurs. Like an "Fc-fragment," a "variant Fc-fragment" can be of the IgG isotype, including IgG1, IgG2, IgG3, or IgG4 isotypes, or of the IgM, IgE, IgD or IgA isotype. It can be of human or animal origin. For example, an Fc-fragment can be from a mammal, such as a mouse, rat, hamster, rabbit, goat, or sheep, or from a camelid species or a shark can be modified to produce a variant Fc-fragment. As with other Fc-fragments, a variant Fc-fragment is normally dimeric, and a "variant Fc region" is specifically defined as a dimeric variant Fc-fragment.

A "variant Fc-polypeptide," as meant herein, comprises a variant Fc-fragment and a binding region. Optionally, a variant Fc-polypeptide can contain multiple binding regions. A variant Fc-polypeptide can be a multimer, such as a dimer, trimer, tetramer, or higher order multimer. In many cases, the variant Fc-fragment portion of the Fc-polypeptide can form disulfide bonds so as to dimerize. Variant Fc-polypeptides include, for example, dimeric Fc fusion proteins, tetrameric full length antibodies (containing two heavy and two light chains), dimeric scFv-Fc's, etc. They can be heteromultimers or homomultimers, such as heterodimers or homodimers. A variant Fc-polypeptide can be an antibody, an Fc-fusion protein, or in some embodiments an antibody or an Fc-fusion protein comprising an additional, non-antibody pharmacologically active moiety. Such a "pharmacologically active moiety" can be covalently conjugated or fused to the Fc-polypeptide and can be a non-peptide organic moiety (i.e., "small molecule") or a peptide, which can act as a toxin and/or can mimic, antagonize, or agonize the activity of a biological pathway.

An "Fc fusion protein," as meant herein, is a protein containing an Fc-fragment fused to another, non-antibody polypeptide. The non-antibody polypeptide comprises a binding region that binds to a target molecule and does not comprise a heavy or light chain variable region of an antibody. The binding region of an Fc fusion protein can comprise a non-antibody polypeptide such as a soluble portion of a receptor or one or more peptides that bind to a target molecule (such as, for example, a "monomer domain" as defined in U.S. Pat. No. 7,820,790 that binds to a target protein, which can be selected as discussed in U.S. Pat. No. 7,820,790), or other polypeptides. The portions of U.S. Pat. No. 7,820,790 describing monomer domains and how they are selected are incorporated herein by reference. In specific embodiments, an Fc fusion protein can be etanercept (ENBREL® sold by Amgen Inc.), romiplostim (NPLATE® sold by Amgen Inc.), alefacept (AMEVIVE®, Biogen Corp.), abatacept (ORENCIA® sold by Bristol-Myers Squibb), rilonacept (ARCALYST®, sold by Regeneron), or aflibercept (EYLEA™, sold by Regeneron). Other polypeptides that can be part of a binding region of an Fc fusion protein include polypeptides comprising scaffold domains that have been randomized in certain positions and subjected to selection for binding to a certain target molecule. Such scaffold domains include, for example, T-lymphocyte associated protein-4 (CTLA-4; Nuttall et al. (1999), Proteins 36: 217-227), the Z domain of Staphylococcal protein 1 (Nord et al. (1995), Protein Eng. 8: 601-608), green fluorescent protein, and the tenth type III domain of human fibronectin (FN3; Koide et al. (1998), J. Mol. Biol. 284: 1141-1151; Karatan et al. (2004), Chem. & Biol. 11: 835-844). The portions of these references describing the scaffold domains and their use to generate binding domains are incorporated herein by reference. Fc fusion proteins, like other proteins containing Fc-fragments can form multimers, which can be dimers. These multimers can be heteromultimers or homomultimers. An Fc fusion protein can be heterodimeric or homodimeric and bispecific or monospecific.

A "variant Fc fusion protein," as meant herein, is an Fc fusion protein that includes a variant Fc-fragment.

A "control Fc fusion protein," as meant herein, is Fc fusion protein that has the same amino acid sequence as the variant Fc fusion protein to which it is being compared except for the insertion in the loop of the Fc-fragment portion of the variant Fc fusion protein.

A "full length IgG antibody," as meant herein, is an IgG antibody comprising two complete heavy chains and two complete light chains.

"Heterodimerizing alterations" generally refer to alterations in the two chains, that is, the A and B chains, of a dimeric Fc region that facilitate the formation of heterodimeric Fc regions, that is, Fc regions in which the A chain and the B chain of the Fc region do not have identical amino acid sequences. Heterodimerizing alterations can be asymmetric, that is, an A chain having a certain alteration can pair with a B chain having a different alteration. These alterations facilitate heterodimerization and disfavor homodimerization. Whether hetero- or homo-dimers have formed can be assessed by size differences as determined by polyacrylamide gel electrophoresis in situations where one polypeptide chain is an Fc-fragment (that is, lacking sequences other than the hinge, $C_H2$ and $C_H3$ regions) and the other is an scFv-Fc. One example of such paired heterodimerizing alterations are the so-called "knobs and holes" substitutions. See, e.g., U.S. Pat. No. 7,695,936 and US Patent Application Publication 2003/0078385, the portions of which describe such mutations are incorporated herein by reference. As meant herein, an Fc region that contains one pair of knobs and holes substitutions, contains one substitution in one Fc-fragment (designated the A chain) and another in the other Fc-fragment (designated the B chain). For example, the following knobs and holes substitutions in the A and B chains of an IgG1 Fc region have been found to increase heterodimer formation as compared with that found with unmodified A and B chains: 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; and 9) T366W in one polypeptide of the Fc and T366S, L368A, and Y407V in the other. As meant herein, mutations are denoted in the following way. The amino acid (using the one letter code) normally present at a given position in the Fc-fragment using the EU numbering system (see Table 1 below) is followed by the EU position, which is followed by the alternate amino acid that is present at that position. For example, Y407T means that the tyrosine normally present at EU position 407 is replaced by a threonine. Alternatively or in addition to such alterations, substitutions creating new disulfide bridges can facilitate heterodimer formation. See, e.g., US Patent Application Publication 2003/0078385, the portions of which describe such mutations are incorporated herein by reference. Such alterations in an IgG1 Fc region include, for example, the following substitutions: Y349C in one Fc-fragment and S354C in the other; Y349C in one Fc-fragment and E356C in the other; Y349C in one Fc-fragment and E357C in the other; L351C in one Fc-fragment and S354C in the other; T394C in one Fc-fragment and E397C in the other; or D399C in one Fc-fragment and K392C in the other. Similarly, substitutions changing the charge of a one or more residue, for example, in the $C_H3$-$C_H3$ interface, can enhance heterodimer formation as explained in WO 2009/089004, the portions of which describe such substitutions are incorporated herein by reference. Such substitutions are referred to herein as "charge pair substitutions," and an Fc region containing one pair of charge pair substitutions contains one substitution in the A chain and a different substitution in the B chain. General examples of charge pair substitutions include the following: 1) K409D or K409E in one chain plus D399K or D399R in the other; 2) K392D or K392E in one chain plus D399K or D399R in the other; 3) K439D or K439E in one chain plus D356K or D356R in the other; and 4) K370D or K370E in one chain plus E357K or E357R in the other. In addition, the substitutions R355D, R355E, K360D, or K360R in both chains can stabilize heterodimers when used with other heterodimerizing alterations. Specific charge pair substitutions can be used either alone or with other charge pair substitutions. Specific examples of single pairs of charge pair substitutions and combinations thereof include the following: 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; and 17) K409D and K439D on one chain plus D399K and E356K on the other. Any of the these heterodimerizing alterations can be part of a variant Fc region as described herein, which can bind to FcRn with a higher affinity than does a control Fc region.

A "loop," as meant herein, is a portion of a tertiary structure in an Fc-fragment that links beta strands that make up the beta sheets of the core immunoglobulin fold. A loop may contain no more than two consecutive residues designated as being involved in a beta sheet (as in Loops 10 and 11; see Table 1 below) and can also contain residues designated as a helix, a turn, an isolated β bridge, or a bend. The loop regions of human IgG Fc regions, as meant herein, are shown in Table 1.

An "insertion within a loop" or "within" any stretch of amino acids, for example, an insertion within Loop 10, is an insertion of 3-35, 3-20, 6-20, 6-15, 6-12, 3-15, 5, 6, 7, 8, 9, 10, 11, 12, 13, 14, 15, or 16 amino acids between two adjacent amino acids within a loop or between an amino acid within a loop and an adjacent amino acid that is not part of the loop. An "insertion within a loop" also encompasses situations where amino acids are removed from a loop, and other amino acids are inserted into the loop. The number of amino acids inserted into the loop can be 3-35, 3-22, 4-20, 6-18, 6-15, 6-12, 3-15, 5, 6, 7, 8, 9, 10, 11, 12, 13, 14, 15, or 16 amino acids, and the number of amino acids removed from the loop can be less than, the same as, or more than the number of amino acids inserted into the loop. For example, 1, 2, 3, 4, 5, 6, 7, 8, 9, or 10 amino acids can be removed from the loop. In addition, an "insertion within a loop" encompasses embodiments where more than one insertion occurs within the same loop, such as insertions between two different pairs of amino acids that are within or adjacent to a loop, as described above, or where one or more non-adjacent amino acids within the loop are deleted and replaced with fewer, the same number, or more amino acids than were deleted. Library L3 (as shown in FIG. 2) is one example of such an insertion scheme.

An "insertion within or adjacent to a loop," is like an "insertion within a loop," as described above, except that it also includes situations where the insertion is between a first amino acid that is adjacent to the loop and another amino acid that is adjacent to this first amino acid and is outside the loop.

A "physiologic pH," as meant herein, is a pH from about 7.2-7.6.

An "scFv-Fc/Fc" is a dimeric protein consisting essentially of an scFv-Fc plus an Fc-fragment that are linked by one or more disulfide bonds. Further, the Fc region formed by the Fc-fragment and the scFv-Fc can contain "heterodimerizing alterations" in the $C_H3$ domains, such as one, two, three, or more pairs of charge pair substitutions, as described.

A "peptide," as meant herein, is a short polypeptide. Generally, a peptide is from 2 to 80, 2 to 60, 2 to 50, 2 to 40, 2 to 30, or 2-20 amino acids in length.

A "target molecule," as meant herein, is a molecule to which the binding region of an Fc-polypeptide, as described herein, binds. In some embodiments, a target molecule is, for example, a protein that is expressed at high levels on a cancer cell or is expressed on a cell mediating an autoimmune or inflammatory condition or on an infected cell, on an infectious agent, or on a cell mediating an immune effector function, for example, an NK cell.

A "therapeutically effective amount" of a variant Fc-polypeptide that has higher affinity for FcRn than a control Fc-polypeptide, as described herein, is an amount that has the effect of, for example, reducing or eliminating the tumor burden of a cancer patient or reducing or eliminating the symptoms of any disease condition that the protein is used to treat. A therapeutically effective amount need not completely eliminate all symptoms of the condition, but may reduce severity of one or more symptoms or delay the onset of more serious symptoms or a more serious disease that can occur with some frequency following the treated condition. Alternatively, a therapeutically effective amount of a protein containing a modified Fc-polypeptide is sufficient to detectably affect the expression of a relevant biomarker when it is administered to a patient in need of treatment in vivo.

"Treatment" of any disease mentioned herein encompasses an alleviation of at least one symptom of the disease, a reduction in the severity of the disease, or the delay or prevention of disease progression to more serious symptoms that may, in some cases, accompany the disease or lead to at least one other disease. Treatment need not mean that the disease is totally cured. A useful therapeutic agent needs only to reduce the severity of a disease, reduce the severity of one or more symptoms associated with the disease or its treatment, or delay the onset of more serious symptoms or a more serious disease that can occur with some frequency following the treated condition.

Variant Fc-Polypeptides

Provided are variant Fc-polypeptides that bind to FcRn with greater affinity and/or binding activity at pHs from 5.0 to 6.0 than do control Fc-polypeptides. Such variant Fc-polypeptides, like control Fc-polypeptides, bind to FcRn with low affinity and/or binding activity, if at all, at pHs from about 7.2 to about 7.6. These variant Fc-polypeptides can (before modification) be of human or animal origin and can be of an IgG isotype, including IgG1, IgG2, IgG3, or IgG4. The FcRn can also be of human or animal origin. These variant Fc-polypeptides further comprise a binding region that can bind to a target molecule, as described herein, and can be used to treat a condition that is mediated, at least in part, by the target molecule. In some embodiments, the target molecule may not directly mediate the condition treated, but binding to the target molecule can serve to localize the Fc-polypeptide or target molecule(s) it binds to. For example, a bispecific Fc-polypeptide could bridge two different cell types, e.g., a cancer cell and an immune system cell, each of which expresses a target molecule on its surface that the Fc-polypeptide can bind to. The variant Fc-polypeptides can be antibodies or Fc fusion proteins comprising a variant Fc-fragment. A variant Fc-polypeptide could, in addition, be an antibody that contains an additional, non-antibody binding region. Optionally, a variant Fc-polypeptide can contain a human IgG variant Fc-fragment.

In Table 1 below, the amino acid sequences of human IgG1, IgG2, IgG3, and IgG4 Fc-polypeptides (SEQ ID NOs: 1, 3, 5, and 7, respectively) are aligned. Sequences are numbered according to the EU system of Edelman et al. (1969), Proc. Natl. Acad. Sci. 63: 78-85, the relevant portions of which are incorporated herein by reference. As shown in Table 1, a single number can be used to refer to a position that is analogous in all four human IgG isotypes, even though a linear numbering scheme would force one to name a different number for this position in each isotype. For example, the asparagine at position 297 is a well-known and highly conserved glycosylation site present in all human IgG antibodies that is referred to as asparagine 297, regardless of the human IgG isotype under discussion.

Human IgG3 antibodies have a much longer hinge region than other human IgG isotypes, and only the most carboxy-terminal portion of this hinge region is shown in Table 1. The human IgG1, IgG2, and IgG4 sequences shown in Table 1 include the entire hinge region. As is apparent in Table 1, the hinge region of a human IgG4 antibody is three amino acids shorter than that of an IgG1 antibody. Human IgG2 antibodies have a slightly shorter hinge region and a gap of one amino acid near the amino terminal end of the $C_H2$ region as compared to human IgG1. Amino acids 216-447 shown in the IgG1 line and amino acids 224-447 in the IgG4 line of Table 1 correspond to amino acids 1-232 of SEQ ID NO:1 and 6-229 of SEQ ID NO:7, respectively. Amino acids 216 to 447 in the IgG3 line of Table 1 correspond to amino acids 48-279 of SEQ ID NO:5. Amino acids 237 to 447 in the IgG2 line of Table 1 correspond to amino acids 18 to 228 of SEQ ID NO:3.

In Table 1, amino acids that are located in loops, as meant herein, are shown in boldface and are underlined. Each loop is labeled with a number, i.e., "Loop 1," "Loop 2," etc., beneath it. In more detail, loops occur the following locations: Loop 1, amino acids 29-43 of SEQ ID NO:1, amino acids 25-39 of SEQ ID NO:3, amino acid 76-90 of SEQ ID NO:5, and amino acids 26-40 of SEQ ID NO:7; Loop 2, amino acids 50-58 of SEQ ID NO:1, amino acids 46-54 of SEQ ID NO:3, amino acids 97-105 of SEQ ID NO:5, and amino acids 47-55 of SEQ ID NO:7; Loop 3, amino acids 70-72 of SEQ ID NO:1, amino acids 66-68 of SEQ ID NO:3, amino acids 117-119 of SEQ ID NO:5, and amino acids 67-69 of SEQ ID NO:7; Loop 4, amino acids 80-84 of SEQ ID NO:1, amino acids 76-80 of SEQ ID NO:3, amino acids 127-131 of SEQ ID NO:5, and amino acids 77-81 of SEQ ID NO:7; Loop 5, amino acids 92-103 of SEQ ID NO:1, amino acids 88-99 of SEQ ID NO:3, amino acids 139-150 of SEQ ID NO:5, and amino acids 89-100 of SEQ ID NO:7; Loop 6, amino acids 110-116 of SEQ ID NO:1, amino acids 106-112 of SEQ ID NO:3, amino acids 157-163 of SEQ ID NO:5, and amino acids 107-113 of SEQ ID NO:7; Loop 7, amino acids 122-131 of SEQ ID NO:1, amino acids 118-127 of SEQ ID NO:3, amino acids 169-178 of SEQ ID NO:5, and amino acids 119-128 of SEQ ID NO:7; Loop 8, amino acids 137-146 of SEQ ID NO:1, amino acids 133-142 of SEQ ID NO:3, amino acids 184-193 of SEQ ID NO:5, and amino acids 134-143 of SEQ ID NO:7; Loop 9, amino acids 158-162 of SEQ ID NO:1, amino acids 154-158 of SEQ ID NO:3, amino acids 205-209 of SEQ ID NO:5, and amino acids 155-159 of SEQ ID NO:7; Loop 10, amino acids 169-175 of SEQ ID NO:1, amino acids 165-171 of SEQ ID NO:3, amino acids 216-222 of SEQ ID NO:5, and amino acids 166-172 of SEQ ID NO:7; Loop 11, amino acids 179-188 of SEQ ID NO:1, amino acids 175-184 of SEQ ID NO:3, amino acids 226-235 of SEQ ID NO:5, and amino acids 176-185 of SEQ ID NO:7; Loop 12, amino acids 199-207 of SEQ ID NO:1, amino acids 195-203 of SEQ ID NO:3, amino acids 246-254 of SEQ ID NO:5, and amino acids 196-204 of SEQ ID NO:7; Loop 13, amino acids 214-221 of SEQ ID NO:1, amino acids 210-217 of SEQ ID NO:3, amino acids 261-268 of SEQ ID NO:5, and amino acids 211-218 of SEQ ID NO:7.

TABLE 1

Alignment of human IgG Fc regions (alignment discloses SEQ ID NOS 1 and 3, residues 48-279 of SEQ ID NO: 5, and SEQ ID NO: 7, respectively, in order of appearance)

```
               225        235        245        255        265        275
                *          *          *          *          *          *
IgG1  EPKSCDKTHTCPPCPAPELLGGPSVFLFPPKPKDTLMISRTPEVTCVVVDVSHEDPEVKF
IgG2  ERKCCVE---CPPCPAPPVA-GPSVFLFPPKPKDTLMISRTPEVTCVVVDVSHEDPEVQF
IgG3  EPKSCDTPPPCPRCPAPELLGGPSVFLFPPKPKDTLMISRTPEVTCVVVDVSHEDPEVQF
IgG4  ESKYG---PPCPSCPAPEFLGGPSVFLFPPKPKDTLMISRTPEVTCVVVDVSQEDPEVQF
DSSP      S SS S  S         SSS EEEEE    HHHHH TTS    EEEEEE    TT     EE
                                        Loop 1                    Loop 2

285        295        305        315        325        335
                *          *          *          *          *          *
IgG1  NWYVDGVEVHNAKTKPREEQYNSTYRVVSVLTVLHQDWLNGKEYKCKVSNKALPAPIEKT
IgG2  NWYVDGMEVHNAKTKPREEQFNSTFRVVSVLTVHHQDWLNGKEYKCKVSNKGLPAPIEKT
IgG3  KWYVDGVEVHNAKTKPREEQYNSTFRVVSVLTVLHQDWLNGKEYKCKVSNKALPAPIEKT
IgG4  NWYVDGVEVHNAKTKPREEQFNSTYRVVSVLTVLHQDWLNGKEYKCKVSNKGLPSSIEKT
DSSP  EEEETTEEE     EEEEEEE TTS EEEEEEE     HHHHHHT  EEEEEE TTSSS  EEEE
                    Loop 3     Loop 4         Loop 5           Loop 6

345        355        365        375        385        395
                *          *          *          *          *          *
IgG1  ISKAKGQPREPQVYTLPPSRDELTKNQVSLTCLVKGFYPSDIAVEWESNGQPENNYKTTP
IgG2  ISKTKGQPREPQVYTLPPSREEMTKNQVSLTCLVKGFYPSDIAVEWESNGQPENNYKTTP
IgG3  ISKTKGQPREPQVYTLPPSREEMTKNQVSLTCLVKGFYPSDIAVEWESSGQPENNYNTTP
IgG4  ISKAKGQPREPQVYTLPPSQEEMTKNQVSLTCLVKGFYPSDIAVEWESNGQPENNYKTTP
DSSP  E       B    EEEEE    GGGGGSSEEEEEEEEEEEBSS   EEEEEETTEE   EEE
       Loop 7          Loop 8                Loop 9         Loop 10

405        415        425        435        445
                *          *          *          *          *
IgG1  PVLDSDGSFFLYSKLTVDKSRWQQGNVFSCSVMHEALHNHYTQKSLSLSPGK
IgG2  PMLDSDGSFFLYSKLTVDKSRWQQGNVFSCSVMHEALHNHYTQKSLSLSPGK
IgG3  PMLDSDGSFFLYSKLTVDKSRWQQGNIFSCSVMHEALHNRFTQKSLSLSPGK
IgG4  PVLDSDGSFFLYSRLTVDKSRWQEGNVFSCSVMHEALHNHYTQKSLSLSLGK
DSSP  EE TTS EEEEEEEEEEHHHHHTT  EEEEEE TTSGGG EEEEE    S
      Loop 11          Loop 12       Loop 13
```

The markings in the fifth line of each aligned group, designated "DSSP" (which stands for Dictionary of Protein Secondary Structure) were taken from the 1 HZH (chain H) structure available from the Protein Data Bank, have the following meanings: "G" designates a 3-turn helix (310 helix), which has a minimum length 3 residues; "H" designates a 4-turn helix (α helix), which has a minimum length of 4 residues; "I" designates a 5-turn helix (π helix), which has a minimum length of 5 residues; "T" designates a hydrogen bonded turn (3, 4 or 5 turn); "E" designates an extended strand in parallel and/or anti-parallel β-sheet conformation, which has a minimum length of 2 residues; "B" designates a residue in an isolated β-bridge (single pair β-sheet hydrogen bond formation); "S" designates a bend (the only non-hydrogen-bond based assignment). Amino acid residues that are not in any of the above conformations are assigned a blank space in the "DSSP" line. These designations are standard in the art and available in the website for the Protein Data Bank (PDB).

The hinge region of the human IgG Fc-fragments runs from amino acid 216 to 230 as numbered in Table 1. The $C_H2$ region extends from amino acid 231 to 340, and the $C_H3$ region extends from amino acid 341 to 447. It is apparent from the alignment of Table 1 that the sequences of the human IgG Fc-fragments are highly conserved. Most of the sequence differences occur in the hinge region, and very few sequence differences occur in the $C_H2$ and $C_H3$ regions. Thus, results obtained using variant Fc-polypeptides comprising a human IgG variant Fc-fragment comprising insertions in the $C_H2$ or $C_H3$ region of one human IgG subtype will likely be applicable to other human IgG subtypes.

The insertions in the variant human IgG Fc-polypeptides described herein can occur at locations known to be in loops. The insertions can occur within or adjacent to any of Loops 1-13 (as shown in Table 1 above) of an Fc-fragment portion of the Fc-polypeptide. In some embodiments, insertions of 1, 2, 3, 4, 5, 6, 7, 8, 9, 10, 11, 12, 13, 14, 15, or 16 or 1-18, 6-16, 10-16, 12-14, 3-20, 20-30, 30-50, or 50-80 amino acids can be made between two adjacent amino acids, at least one of which is included in a loop of an Fc-fragment. In some embodiments, two cysteines are non-randomly included in the insertion, one each among the first and last four amino acids of the insertion, so as to constrain the amino acids between the cysteines into a tight loop bounded by a disulfide bond. In some embodiments the first three amino acids of the insertion are Gly-Gly-Cys, and the last three amino acids are Cys-Gly-Gly. An insertion of an additional 4, 5, 6, 7, 8, 9, 10, 11, 12, 13, 14, 15, 16, or 10-30 amino acids can be inserted between these two cysteines. In still other embodiments, 1, 2, 3, 4, 5, 6, 7, 8, 9, or 10 amino acids from the loop are deleted and replaced by an insertion of 1, 2, 3, 4, 5, 6, 7, 8, 9, 10, 11, 12, 13, 14, 15, or 16 or 1-18, 6-16, 10-16, 12-14, 15-30, 30-50, or 50-80 amino acids and/or by an insertion that contains two cysteines among the first and last four amino acids of the insertion. The number of amino acids deleted can be the same, less, or greater in number than the amino acids inserted. In other embodiments, more than one insertion can occur in a single loop. The variant Fc-polypeptides, which contain the insertions, can bind to human FcRn with a higher affinity at pH 5 to 6 than does a control Fc-polypeptide. The inserted amino acids can include any of all 20 amino acids or any of all amino acids other than cysteine. Further, a variant Fc-fragment can comprise an insertion in only one loop or in more than one loop, such as in 2, 3, or 4 loops.

Insertions within or adjacent to Loops 5, 8, or 10 of an Fc-fragment can increase the binding affinity of such a variant Fc-fragment for human FcRn at pH 5 to 6. In specific embodiments, an insertion can be made in a human IgG Fc-fragment within or adjacent to Loop 8 between amino acids 358 and 359 or within or adjacent to Loop 10 between amino acids 384 and 385 (using the EU numbering scheme as illustrated in Table 1). The insertion can contain from 4-20, 1-18, 6-16, 10-16, 12-14, 1, 2, 3, 4, 5, 6, 7, 8, 9, 10, 11, 12, 13, 14, 15, or 16 or amino acids. Optionally, the amino acids may be limited to all amino acids other than cysteine. In some embodiments, the insertion can contain a cysteine among the first and the last four amino acids of the insertion, and the inserted amino acids can otherwise be limited to amino acids other than cysteine. In some embodiments, the insertion can contain no cysteines. In some embodiments, the insertion can have a formula selected from the group consisting of CXXXXXXC (SEQ ID NO:13), CXXXXXXXC (SEQ ID NO:14), CXXXXXXXXC (SEQ ID NO:15), GCXXXXXXCG (SEQ ID NO:16), GCXXXXXXXCG (SEQ ID NO:17), GCXXXXXXXXCG (SEQ ID NO:18), GGCXXXXXXCGG (SEQ ID NO:19), GGCXXXXXXXCGG (SEQ ID NO:20), and GGCXXXXXXXXCGG (SEQ ID NO:21), GGGCXXXXXXCGGG (SEQE ID NO:22), GGGCXXXXXXXCGGG (SEQ ID NO:23), and GGGCXXXXXXXXCGGG (SEQ ID NO:24), where X represents any amino acid except cysteine. Since the actual insertion results from a screening process as described in the examples below, it is the randomized amino acids that likely play a dominant role in the observed changes in the properties of the Fc-fragment. As such, it is contemplated that a variant Fc-fragment having an insertion containing only the randomized portions of insertions which, like those above, contain some non-random amino acids can also have the desired properties. Examples of such sequence include the middle six amino acids from SEQ ID NOs: 41-53, which are shown as SEQ ID NOs: 54-66.

In another embodiment, amino acids 308 and 309 (using the EU numbering as shown in Table 1) within or adjacent to Loop 5 are deleted and replaced from 4-20, 1-18, 6-16, 10-16, 12-14, 1, 2, 3, 4, 5, 6, 7, 8, 9, 10, 11, 12, 13, 14, 15, 16, 15-20, 20-40, 40-60, or 60-80 amino acids, which may be limited to all amino acids other than cysteine. In some embodiments, the insertion can contain a cysteine among the first and the last four amino acids of the insertion, and the inserted amino acids can otherwise be limited to amino acids other than cysteine. The insertion can have a formula selected from the group consisting of SEQ ID NO:13-24.

These variant Fc-fragments, as well as Fc-polypeptides that contain them, comprising the amino acid insertions described above and below, can bind to human FcRn at pH 5 to 6 with higher affinity and/or binding activity as compared to a control Fc-fragment and can bind to human FcRn at physiologic pH with an affinity and/or binding activity comparable to or lower than that of control Fc-fragments. Further, these variant Fc-fragments can be further altered and screened for alterations that confer even higher affinity and/or binding activity for human FcRn at pH 5 to 6, lower affinity and/or binding activity for human FcRn at physiologic pH, or other desirable properties, such as stability upon storage. In the Examples below, insertions of particular amino acid sequences (e.g, SEQ ID NOs:41-66 and 90-246) at defined sites within an Fc-fragment are shown to be effective at increasing affinity and/or binding activity of the Fc-fragment for human FcRn at pH 5 to 6.

Variant Fc-polypeptides comprising human IgG variant Fc-fragments also comprise a binding region that binds to a target molecule. Binding of such variant Fc-polypeptides to the target molecule can modulate, optionally antagonize or agonize, the biological activity of the target molecule and/or can serve to localize the Fc-polypeptide to a location where the target molecule is expressed. An Fc-polypeptide can include more than one binding region, such as two, three, or four binding regions in an Fc-polypeptide. Since an Fc-polypeptide can multimerize forming, in some cases, dimers, trimers, or tetramers, multimerization of different Fc-polypeptides can form multimeric Fc-polypeptides that can bind to more than one target molecule. If there are plural binding regions in an Fc-polypeptide, they can bind to the same or different target molecules or portions of a target molecule. Modulation of the activity of the target molecule can affect the course of a disease or condition that is mediated at least in part by the target molecule. Human IgG variant Fc-polypeptides can comprise a binding region that includes one or more antibody variable regions that bind to one or more target molecules. Such human IgG variant Fc-polypeptides can, for example, be full length antibodies, such as human, humanized, or chimeric IgG antibodies, scFc-Fv's, monovalent forms of antibodies such as those described in International Application Publication WO 2005/063816 and US Application Publication 2007/0105199 (the relevant portions of which are incorporated herein by reference), which comprise a dimeric Fc region, as well as $V_H$, $C_H1$, $V_L$, $C_L$ and hinge regions. Further forms are described, for example, in FIG. 2 of US Application Publication 2010/0286374, which is incorporated herein by reference along with the text describing and/or referring to FIG. 2, and in U.S. Pat. No. 5,837,821, which describes "minibodies" comprising an scFv linked to an Fc region. The portions of U.S. Pat. No. 5,837,821 describing minibodies are incorporated herein by reference. Alternatively, the binding region can comprise all or part of a non-antibody protein, optionally a human protein, that binds to the target molecule. For example, the binding region could comprise an extracellular portion a receptor such as, for example, the extracellular region of the human p75 tumor necrosis factor receptor (SEQ ID NO:13) or the human T-lymphocyte associated protein-4 (CTLA4) protein (SEQ ID NO:14).

The binding region can comprise one or more peptides that bind to a target molecule (such as, for example, a "monomer domain" as defined in U.S. Pat. No. 7,820,790 that binds to a target protein, which can be selected as discussed in U.S. Pat. No. 7,820,790), or other peptides. The portions of U.S. Pat. No. 7,820,790 describing monomer domains and how they are selected are incorporated herein by reference. One example of such a peptide is the binding portion of the Fc fusion protein romiplostim (NPLATE®, Amgen Inc., Thousand Oaks, Calif.). Prescribing Information, NPLATE®, Amgen Inc., 2008-2011. Other polypeptides that can be part of a binding region of an Fc fusion protein include polypeptides comprising scaffold domains that have been randomized in certain positions and subjected to selection for binding to a certain target molecule. Such scaffold domains include, for example, CTLA-4 (Nuttall et al. (1999), Proteins 36: 217-227), the Z domain of Staphylococcal protein 1 (Nord et al. (1995), Protein Eng. 8: 601-608), green fluorescent protein, and the tenth type III domain of human fibronectin (FN3; Koide et al. (1998), J. Mol. Biol. 284: 1141-1151; Karatan et al. (2004), Chem. & Biol. 11: 835-844). The portions of these references that describe the scaffold domains and their use to generate binding domains are incorporated herein by reference.

A target molecule, to which a binding region binds, can be a molecule where the modulation of the biological activity of the molecule can affect the course of a disease or condition or can be a molecule localized in a diseased area, for example a protein expressed on the surface of cancer cells. In an autoimmune or inflammatory condition, the target molecule can be a molecule acting in a pathway that plays a role in mediating the condition. A target molecule can be a molecule that is localized such that binding to the target molecule will place an Fc-polypeptide appropriately such that it can affect the course of a disease. For example, if an Fc-polypeptide includes a toxin, placing it near a cancer cell by means of a binding region that binds to a protein highly expressed on the cancer cells can be advantageous. Target molecules include, for example, general classes of proteins such as soluble ligands, receptor bound ligands, soluble receptors, membrane bound receptors, membrane channel proteins, soluble and membrane bound proteins, and non-protein antigens, including extracellular and intracellular target molecules. Exemplary target molecules include, without limitation, the following human proteins: tumor necrosis factor, tumor necrosis factor receptor, interleukin-1, interleukin-6 (IL-6), IL-6 receptor, CD80/86, CD20, CD33, CD52, interleukin-12, interleukin-23, interleukin-17, HER2, HER2 neu receptor, epidermal growth factor receptor (EGFR), vascular endothelial growth factor (VEGF), B cell activating factor (BAFF), RANK ligand, OR51E2, claudins, CDH3, CD22, complement factors, and sclerostin, among many others.

Depending in part on the host cell in which a variant Fc-polypeptide is produced and/or the purification methods used, the variant Fc-polypeptide can further comprise additional amino acid sequences such as, for example, a signal sequence facilitating secretion in eukaryotic cells (which is removed in mature forms of the protein), an N-terminal methionine to facilitate translation in bacteria, and/or a tag sequence (for example, a polyhistidine tag or a FLAG® tag) to facilitate protein purification or identification.

Nucleic Acids Encoding Libraries of Variant Fc-Fragments

Also described herein are libraries of nucleic acids encoding Fc-fragments having insertions, which are at least partially randomized, that occur within or adjacent to loops of the Fc-fragments. FIG. 2 illustrates the format for each of the eight libraries that were made, as described below in the Examples. The sequences of these libraries and the amino acid sequences encoded by them are disclosed in SEQ ID NOs:25-40. Such libraries are useful for panning in order to select individual nucleic acids that encode variant human IgG Fc-fragments that bind with enhanced affinity to FcRn at pH 5.0 to 6.0 as compared to a control Fc-fragment. Such variant human IgG Fc-polypeptides may also bind to FcRn poorly if at all at pH 7.2 to 7.6, as does a control Fc-fragment.

In some embodiments, these libraries of nucleic acids encoding Fc-fragments with insertions in regions encoding loop regions (as set forth in Table 1) can be of human or animal origin, including nucleic acids encoding mouse, rat, rabbit, or monkey Fc-fragments or Fc-fragments from a camelid species. In some embodiments the encoded Fc-fragment can be an IgG Fc-fragment, such as an IgG1, IgG2, IgG3, or IgG4 Fc-fragment, or an Fc-fragment of an IgA, IgE, IgD, or IgM isotype. The insertions in the portions of the nucleic acids encoding loops can be within or adjacent to the nucleotide sequences encoding Loop 1, Loop 2, Loop 3, Loop 4, Loop 5, Loop 6, Loop 7, Loop 8, Loop 9, Loop 10, Loop 11, Loop 12, or Loop 13, as shown in Table 1.

The size of the library as compared to the number of different variants in the library is an important consideration. In a best case, the panning procedure to which the library is subjected will have a high probability of including all different variants that are included in the library. The number of different variants in the library depends on the number of randomized positions in the library and the number of different amino acids that can be used at each randomized position. For example, a library that has six randomized positions that can contain any of 19 different amino acids can theoretically have $19^6 \approx 4.7 \times 10^7$ different variants. If, for example, $10^9$ independent phage or bacteria expressing these variants are panned, there is a very high probability that all isolates with the properties selected for in the screen will be recovered. See, e.g., Grossman and Turner, Mathematics for the Biological Sciences, Chapter 2, Section 2.9, pp. 97-104, Macmillan Publishing Co., Inc., New York and Collier Macmillan Publishers, London, 1974, which section is incorporated herein by reference. Libraries of a size that make it possible to screen enough isolates to detect rare isolates with the desired properties are contemplated. Thus, libraries encoding from $10^5$ to $10^{13}$, $10^6$ to $10^{12}$, or $10^7$ to $10^{10}$ different variants are contemplated.

Libraries with randomized insertions within or adjacent to nucleotide sequences encoding Loops 5, 8, and 10 of the Fc-fragment-encoding portion can be advantageous. Such libraries can encode Fc-fragments with insertions within or adjacent to Loops 5, 8, or 10 that contain 20-40, 4-20, 1-18, 6-16, 10-16, 12-14, 1, 2, 3, 4, 5, 6, 7, 8, 9, 10, 11, 12, 13, 14, 15, or 16 randomized amino acids. These randomized amino acids can be flanked by cysteine residues. In some embodiments, additional non-randomized amino acids can also be inserted before or after the randomized amino acids. In some embodiments, the encoded randomized amino acids can be preceded by a Gly-Gly-Cys and followed by a Cys-Gly-Gly.

Nucleic Acids Encoding Variant Fc-Polypeptides, Fc-Fragments, and Insertions

Also described are nucleic acids encoding specific variant Fc-fragments, which can be part of a variant Fc-polypeptide, and nucleic acids encoding insertions within or adjacent to loops of variant Fc-fragments. Nucleotide sequences encoding Fc-fragments are known in the art (see, e.g., Kabat et al., Sequences of Proteins of Immunological Interest, Public Health Service N.I.H., Bethesda, Md., 1991), and sequences encoding human IgG1, IgG2, IgG3, and IgG4 Fc-fragments (SEQ ID NOs: 2, 4, 6, and 8, respectively) are reported herein. The locations of loops within Fc-fragments are delineated (Table 1), and various kind of insertions into these regions are described herein. Sequences encoding amino acid insertions that increase binding to FcRn at pHs in the range of 5 to 6 are also reported (see, e.g., SEQ ID NOs:41-53).

More generally, described herein are nucleic acids encoding a variant Fc-fragment having an insertion within or adjacent to a loop, wherein the Fc-fragment can bind to human FcRn with higher affinity at pH 5-6 than a control Fc-fragment. The positions at which such insertions occur in include Loops 1, 2, 3, 4, 5, 6, 7, 8, 9, 10, 11, 12, or 13 within the Fc-polypepetide.

Nucleic acids encoding variant Fc-polypeptides can be used to produce variant Fc-polypeptides by introducing the nucleic acids into host cells, including prokaryotic or eukaryotic host cells, and culturing the cells under conditions such that the protein(s) encoded by the nucleic acids will be expressed. The variant Fc-polypeptide can be recovered from the cell mass or the culture supernatant. Such polypeptides can be purified by methods well known in the art such as, for example, Protein A or Protein G affinity chromatography, size exclusion chromatography, ion exchange chromatography, and hydrophobic interaction chromatography, among other available methods.

Methods of Isolating and Making Variant Fc-Fragments and Fc-Polypeptides

Variant Fc-fragments can be isolated using screening procedures described in detail in the Examples below. In broad terms, a library of nucleic acids encoding Fc-fragments with insertions including randomized amino acids within or adjacent to a loop is prepared. This library is then introduced into a virus or a cell, which is cultured under conditions such that the nucleic acids from the library can be expressed, so that the virus (which can, for example, be a baculovirus or a filamentous phage) or cell (which can, for example, be a bacterial, yeast, or mammalian cell), can display the Fc-fragments containing the insertions. In an alternate embodiment, the library can be translated in vitro in a ribosome display system such that Fc-fragments with the desired properties, and the nucleic acids encoding them, can be selected out from this mixture. Alternatively, a CIS display system can be used. See, e.g., Odegrip et al. (2004), Proc. Natl. Acad. Sci. 101(9): 2806-2810, the relevant portions of which are incorporated herein by reference. In the methods of the invention, variant Fc-fragments that can bind to human FcRn with higher affinity as compared to a control Fc-fragment within the pH range from to 6 can be enriched for by panning with FcRn as described in the examples below and screened for using, for example, enzyme-linked immunosorbent assay (ELISA), which may be performed initially on groups of isolates or on single isolates. If ELISA is initially performed on groups of isolates, these isolates can be amplified and rescreened individually to obtain individual isolates expressing a variant Fc-fragment with enhanced affinity to human FcRn at pH 5-6 and with lower or about the same affinity for human FcRn at physiologic pH as compared to a control Fc-fragment.

In further steps, nucleic acids encoding the variant Fc-fragments can be isolated from phage or cells, such as bacteria, yeast or mammalian cells, or amplified from RNA in the case of ribosome display. These nucleic acids can be sequenced to determine the exact position and nature of the insertion. Using this information, nucleic acids encoding a desired variant Fc-polypeptide or variant Fc-fragment can be constructed using methods well-known in the art. Further modification of the nucleic acid encoding the variant Fc-fragment or Fc-polypeptide can be undertaken if desired.

Such nucleic acids can be inserted into vectors appropriate for the host cell in which the Fc-polypeptide or Fc-fragment will be expressed. These nucleic acids can be introduced into the host cells by any of the methods well-known in the art. Host cells that could be used include bacteria, including *Escherichia coli*t, yeast, including *Saccharomyces cerevisiae* or *Pichia pastoris*, insect cells, plant cells, and mammalian cells, including Chinese hamster ovary (CHO) cells, 293 cells, and baby hamster kidney (BHK) cells, among many others. These host cells can be cultured under conditions such that the introduced nucleic acids will be expressed, and the Fc-polypeptide or Fc-fragment can be recovered from the culture supernatant or the cell mass.

Generally, the procedure used to introduce the nucleic acids into the host cells may depend upon the host cell into which the nucleic acids are to be introduced. Methods of introducing nucleic acids into bacteria are well-known in the art. For example, electroporation or calcium chloride transformation are commonly used. Methods for introduction of nucleic acids into yeast are well-known in the art and include, for example, transformation methods using lithium acetate and polyethylene glycol. Methods for introducing heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Expression vectors used in any of the host cells will contain sequences for plasmid maintenance and for cloning and expression of exogenous nucleotide sequences. Such sequences will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element.

Therapeutic Uses of Variant Fc-Polypeptides

Variant Fc-polypeptides described herein can be used as human therapeutics for a variety of conditions. Which variant Fc-polypeptide is appropriate for which condition can be determined by the binding region(s) of the Fc-polypeptide, as well as possibly other aspects of its structure such as, for example, an attached toxic moiety. Variant Fc-polypeptides can have increased in vivo half lives as compared to control Fc-polypeptides and may therefore require lower and/or less frequent dosing than control Fc-polypeptides. Thus, variant Fc-polypeptides might be well suited to treat chronic conditions, where less frequent dosing is particularly desirable. However, a variant Fc-polypeptide can be used as a treatment of most or all conditions that a control Fc-polypeptide (which has the same amino acid sequence as the variant Fc-polypeptide except that it does not have the insertion in a loop) can be used to treat. The variant Fc-polypeptides described herein can also be used concurrently with other medications used for treating the condition being treated.

For example, an Fc fusion protein that is a variant Fc-polypeptide which contains an insertion in a loop can be used as a treatment for the same conditions that a control Fc-polypeptide is used. However, dosing amount and/or frequency of the variant Fc-polypeptide may be different because of its increased half-life. For example, a variant Fc-polypeptide could be made starting from a therapeutic Fc fusion protein such as etanercept (which is indicated for moderate to severe rheumatoid arthritis, polyarticular juvenile idiopathic arthritis, psoriatic arthritis, ankylosing spondylitis, and moderate to severe plaque psoriasis), abatacept (which is indicated for moderate to severe rheumatoid arthritis, moderate to severe polyarticular juvenile idiopathic arthritis), or romiplostim (which is indicated for chronic immune thrombocytopenic purpura) by inserting one of the insertions that enhance FcRn binding disclosed herein, e.g., SEQ ID NOs: 41-53, in a loop in the Fc-fragment portion of each of these molecules. The insertion could, for example, be made within or adjacent to Loops 5, 8, or 10 of the Fc-fragment portion of the Fc fusion protein. Such variant forms of etanercept, abatacept, or romiplostim could be used to treat the same diseases as unaltered etanercept, abatacept, or romiplostim can be used to treat.

Similarly, if the variant Fc-polypeptide is a therapeutic antibody, such as, for example, adalimumab, ustikinumab, golimumab, natalizumab, infliximab, or denosumab, such a variant form of the antibody comprising a variant Fc-fragment can be used to treat the same diseases that these antibodies, in an unaltered form, are used to treat. Thus, a variant Fc-fragment, as described herein, can change the dosage amount or frequency of treatment, but not the condition the Fc-polypeptide is used to treat.

Generally, Fc-polypeptides are used to treat a wide variety of diseases including oncologic indications, autoimmune and inflammatory conditions, bone-related conditions, conditions, metabolic conditions, and neurologic conditions such as, for example, chronic pain, among many others.

Pharmaceutical Compositions

The invention includes pharmaceutical compositions comprising the variant Fc-fragments or variant Fc-polypeptides described herein. Such compositions can comprise a therapeutically effective amount of a variant Fc-polypeptide or variant Fc-fragment with one or more additional components such as a physiologically acceptable carrier, excipient, or diluent. Such additional components can include buffers, carbohydrates, polyols, amino acids, chelating agents, stabilizers, and/or preservatives, among many possibilities.

Methods of Administration

The variant Fc-polypeptides or variant Fc-fragments, or pharmaceutical compositions containing these molecules, can be administered by any feasible method. Therapeutics that comprise a protein will ordinarily be administered by injection since oral administration, in the absence of some special formulation or circumstance, would lead to hydrolysis of the protein in the acid environment of the stomach. Subcutaneous, intramuscular, intravenous, intraarterial, intralesional, or peritoneal injection are possible routes of administration. Topical administration is also possible, especially for diseases involving the skin. Alternatively, variant Fc-polypeptides or variant Fc-fragments can be administered through contact with a mucus membrane, for example by intra-nasal, sublingual, vaginal, or rectal administration or as an inhalant. Alternatively, certain pharmaceutical compositions comprising a variant Fc-polypeptide or variant Fc-fragment can be administered orally.

Having described the invention in general terms above, the following examples are offered by way of illustration and not limitation.

EXAMPLES

Example 1

Creation of a Model of the Tertiary Structure of Human FcRn:Human IgG1 Fc

To aid design of the libraries described below, a homology model of the tertiary structure a human FcRn in a complex with a human IgG1 Fc-fragment was created based on the structure of a complex of a rat FcRn and a rat IgG Fc-fragment available in Protein Data Bank (PDB Accession No. 1FRT). The Protein Data Bank (PDB) was searched with amino acid sequences of human IgG1 Fc-fragment (SEQ ID NO:1) and human FcRn α and β-2-microglobulin (β2m) chains, SEQ ID NOs:9 and 10, respectively. Several templates were obtained based on amino acid sequence homology and tertiary structure. FcRn α chain structures (1 EXU (chain A), 1FRT (chain A), and 1I1A (chain A)), FcRn β2m chain structures (1CE6 (chain B), 1HSA (chain B), 1YPZ (chain B), 1HHG (chain B) and 1I1A (chain B)), and Fc structures 1 HZH (chain H), 1I1A (chain C), 1OQO (chain A), 1T83 (chain A) and 2J6E (chain A)) were selected. The FcRn α structures 1 EXU (chain A), 1FRT (chain A) and 1I1A (chain A) were superimposed and the resulting root mean square deviation (RMSD), that is, the average distance between analogous atoms in superimposed protein structures, values are 0.30 Å to 0.76 Å, with the mean value 0.59 Å. The RMSD values between the FcRn β2m domain structures 1CE6 (chain B), 1HSA (chain B), 1YPZ (chain B), 1HHG (chain B), and 1I1A (chain B) range from 0.30 Å to 0.76 Å with the mean value 0.59 Å. The RMSD values between the Fc structures 1 HZH (chain H), 1I1A (chain C), 1OQO (chain A), 1T83 (chain A) and 2J6E (chain A) range from 0.30 Å to 0.76 Å with the mean value 0.59 Å. These RMSD values indicate that the template FcRn and Fc structures from different sources share very similar tertiary structures.

Based on these template structures and the amino acid sequences of human FcRn (hFcRn) and human IgG1 Fc-fragment (hIgG1 Fc), a homology model of hFcRn:hIgG1 Fc complex was created using a linux-based molecular modeling module of the computational software Molecular Operating Environment (MOE; Chemical Computing Group, Montreal, Quebec, Canada). FIG. 1 shows the portion of this modeled complex where the hIgG1 Fc (below) and the hFcRn (above) come into closest contact, as well as some adjacent areas of these proteins.

Example 2

Construction of the Insertion Libraries

Eight libraries encoding variant human IgG1 Fc regions, each library having different kinds of insertions, were constructed. FIG. 2 shows the sequence of a human IgG1 Fc region and the positions and the format of the six insertion libraries. The positions of the loops into which insertion libraries described below were inserted are indicated in FIGS. 1 and 2 as L1, L2A, L2B, L3, L4, L5, L6A and L6B. Some insertion sites in the Fc were among the closest points of contact between hIgG1 Fc and hFcRn (such as L1, L2A, L2B, and L3), and others (L4, L5, L6A, and L6B) were at some distance from the closest points of contact between hFc and hFcRn.

As shown in FIG. 2, in some of the libraries, such as L1, L2A, L2B, and L3, amino acids within a loop were deleted and replaced with randomized amino acids, in most cases with a slightly greater number of amino acids than had been deleted. The randomized amino acids included all amino acids other than cysteine. In library L2B, six randomized amino acids were preceded by the sequence Gly-Gly-Cys and followed by the sequence Cys-Gly-Gly. Since the two cysteines would be expected to form a disulfide bridge given their proximity, it would be expected that the six randomized amino acids between the cysteines would form a spatially constrained loop. For example, in L2B, six randomized amino acids were preceded by the sequence Gly-Gly-Cys and followed by the sequence Cys-Gly-Gly, thus creating spatially constrained loops containing the randomized amino acids. In other libraries, i.e., L4 and L5, randomized amino acids were inserted without deleting any amino acids normally present.

Two rounds of PCR were used to construct L1, L2A, L2B, L3, L4 and L5 libraries encoding a group of human IgG1 variant Fc-fragments. The template used in the first and second sets of PCR reactions in the first round of reactions was a phagemid vector into which DNA encoding a human IgG1 Fc-fragment (SEQ ID NO:2) had been inserted so as to allow its expression as part of a phage coat protein in appropriate bacterial strains (pIgG1-Fc). The first set of PCR reactions in the first round of reactions used to generate the libraries utilized forward and reverse primers in order to create PCR fragments that contain an ApaLI restriction enzyme site at the upstream end. The following forward primer, which matched vector sequences upstream of the region encoding the Fc-fragment, was used for all of the first set of PCR reactions in the first round of reactions: 5'-GT-TCCT TTC TAT TCTCAC-3' (SEQ ID NO:521). The reverse primers, which were within Fc-encoding sequences, were the following: 5'-GAG GGT GTC CTT GGG TTT TGG GGG-3' (SEQ ID NO:522; Library L1); 5'-GGT GAG GAC GCT GAC CAC ACG GTA-3' (SEQ ID NO:523; Libraries L2A and L2B); 5'-ATG CAT CAC GGA GCA TGA GAA GAC-3' (SEQ ID NO:524; Library L3); 5'-ATT ATG CAC CTC CAC GCC GTC CAC-3'(SEQ ID NO:525; Library 4); and 5'-ATT GCT CTC CCA CTC CAC GGC GAT-3' (SEQ ID NO:526; Library L5).

A second set of PCR reactions in the first round of reactions also used pIgG1-Fc as a template and used an oligonucleotide that matched the complement of vector sequences downstream from the Fc-encoding sequences as a reverse primer. This reverse primer had the following sequence: 5'-CCC ATT CAG ATC CTC TTC-3' (SEQ ID NO:527). The forward primers used for these reactions were as follows: Library L1,5'-AAA CCC AAG GAC ACC CTC (TRIM)$_6$ACC CCT GAG GTC ACA TGC-3' (SEQ ID NO:528); Library L2A, 5'-GTG GTC AGC GTC CTC ACC (TRIM)$_6$ CAC CAG GAC TGG CTG MT-3' (SEQ ID NO:529); Library L2B, 5'-GTG GTC AGC GTC CTC ACC GGT GGT TGT (TRIM)$_6$ TGT GGT GGT CAC CAG GAC TGG CTG AAT-3' (SEQ ID NO:530); Library L3: 5'-TCA TGC TCC GTG ATG CAT (TRIM)$_5$ CAC (TRIM)$_1$ CAC TAC ACG CAG AAG AGC-3' (SEQ ID NO:531); Library L4: 5'-GGC GTG GAG GTG CAT AAT GGT GGT TGT (TRIM)$_6$TGT GGT GGT GCC AAG ACA AAG CCG CGG-3' (SEQ ID NO:532); and Library L5: 5'-GTG GAG TGG GAG AGC AAT GGT GGT TGT (TRIM)$_6$ TGT GGT GGT GGG CAG CCG GAG AAC AAC-3' (SEQ ID NO:533). In these oligonucleotides, "TRIM" represents a mixture of trinucleotides encoding all amino acids except cysteine (Trimer Phosphoramidite Mix 2, Glen Research Catalog No. 13-1992-95). The mixture is an equimolar mixture of the following trinucleotides: AAA, AAC, ACT, ATC, ATG, CAG, CAT, CCG, CGT, CTG, GAA, GAC, GCT, GGT, GTT, TAC, TCT, TGG, TTC. Hence, codons encoding all amino acids except cysteine to were represented approximately equally in the TRIM mixture. Thus, "(TRIM)$_6$" means that six random trinucleotides encoding any amino acid except cysteine are included in the oligo.

In a second round of PCR reactions (one for each library), the products from the first and second sets of PCR reactions from the first round described above served as templates. The primers used were the same for all libraries and were the following: 5'-GTT CCT TTC TAT TCT CAC-3' (forward; SEQ ID NO:534) and 5'-CCC ATT CAG ATC CTC TTC-3' (reverse; SEQ ID NO:535).

Libraries L6A and L6B were constructed in one round of PCR, using pIgG1-Fc as a template. In the PCR reaction described below, an XmaI restriction site (5'-CCCGGG-3') in the coding region for the Fc-fragment was changed to a XhoI restriction site (5'-CTCGAG-3") due to the sequences of the primers. These alterations were silent mutations that did not encode different amino acids from the unmodified pIgG1-Fc and were made because an XhoI plus NotI restriction digestion was more efficient than an XmaI plus NotI digestion. The forward primers used for these reactions were as follows: Library L6A: 5'-CTG CCC CCA TCT CGA GAT GAG CTG GGT TGT (TRIM)$_8$ TGT GGT GGT ACC AAC CAG GTC AGC CTG ACC-3' (SEQ ID NO:536); and library L6B: 5'-CTG CCC CCA TCT CGA GAT GAG CTG GGT TGT (NNK)$_8$TGT GGT GGT ACC AAC CAG GTC AGC CTG ACC-3' (SEQ ID NO:537). The reverse primer sequence was 5'-GGC CCC GTG ATG GTG ATG ATG-3' (SEQ ID NO:538). In L6B a mixture of trinucleotides called NNK, which contains trinucleotides encoding all twenty amino acids in 32 degenerate codons, was used. In this trinucleotide mixture, "N" represents a randomized position that is either adenosine, guanidine, cytidine, or thymidine and "K" represents a partially constrained position that is either guanidine or thymidine.

For all PCR reactions, PCR core kits were used (Roche, Catalog No. 11 578 553 001) with the following reaction conditions: 95° C. for 5 minutes, followed by 30 cycles of 95° C. for 45 seconds-55° C. for 45 seconds-72° C. for 90 seconds, and finally 72° C. 10 minutes. DNA from the PCR reactions was purified using QIAquick PCR Purification Kits (QIAGEN, 28104). About 200 µg of phagemid vector DNA and 10 µg of purified PCR product (from the third round of PCR reactions) were digested with ApaLI and NotI (for Libraries L1-L5) and XhoI and NotI (for Libraries L6A and L6B). The digested DNA was gel purified with QIAquick Gel Purification Kits (QIAGEN, 28704).

Digested vector DNA and library PCR products in a molar ratio of 1:2 were ligated using T4 DNA ligase (New England Biolabs). The mixture was incubated at 16° C. overnight. DNA was purified by ethanol precipitation. A total of 25 µg DNA was electroporated into 1000 µl of electrocompetent XL1 blue $E.$ $coli$ cells (Stratagene) in a 2.5 kV field using 200Ω resistance and 25 µF capacitance to obtain about $1 \times 10^9$ $E.$ $coli$ transformants. Exact sizes of libraries ranged from $7 \times 10^8$ (for L5) to $1.8 \times 10^9$ (for L4). Cells were inoculated in 1000 mL of 2×YT medium (which contains 16 g/L Bacto Tryptone, 10 g/L Bacto Yeast Extract, and 5 g/L NaCl at a pH of 7.0-7.2) containing 100 µg/mL ampicillin and 2% glucose and grown until the $OD_{600}$ was about 0.5. About $3 \times 10^9$ plaque-forming units per milliliter (PFU/mL) of M13 helper phage were then added, and the culture was incubated at 37° C. for 1 hr. Infected cells were then spun down and resuspended with 1000 mL of 2×YT medium containing 100 µg/ml ampicillin and 40 µg/mL kanamycin. Cells were grown at 30° C. overnight. The phage were then precipitated with PEG 6000.

All libraries used in these transformations, other than L6A and L6B, contained six randomized codons, each of which encoded any of nineteen different amino acids, and therefore would be expected to encode about $4.7 \times 10^7$ ($19^6$) different variant Fc-fragments. Similarly, L6A would be expected to encode about $1.76 \times 10^{10}$ ($20^8$) different variant Fc-fragments, since it contained eight randomized codons that encoded any of 20 different amino acids. For libraries other than Libraries L6A and L6B, given the expected number of different variants in each library, the library sizes of about $10^9$ (ranging from $7 \times 10^8$ to $1.8 \times 10^9$) were 7-33 times the number of variants.

Example 3

Screening of the Fc Loop Libraries

Two rounds of panning for phage expressing variant Fc-fragments that bind to FcRn with increased affinity as compared a wild type Fc-fragment at pH 6.0 (and having a low binding affinity at pH 7.4) were performed as follows. In the first round, phage were resuspended in a liquid containing 0.4 ml 20 mM MES, pH 6.0, 5% skim milk, 0.05% Tween 20. Each of four wells of a MAXISORP™ immunoplate (Nunc, Rochester, N.Y.) was coated with 10 µg of hFcRn and blocked with 5% skim milk, and 100 µL of phage at $5 \times 10^{11}$ PFU/mL were added. After a 1 hr incubation at 37° C., wells were washed 3-10 times with 20 mM MES, pH 6.0, 0.2% Tween 20. The phage were eluted by adding 100 µL phosphate buffered saline (PBS), pH 7.4 to each well and incubating the plate for 1 hr at 37° C. These phage were used to reinfect an exponentially growing $E.$ $coli$ XL1-blue culture, which was cultured until it reached an $OD_{600}$ of about 0.5. About $3 \times 10^9$ PFU/mL of M13 helper phage were then added, and the culture was incubated at 37° C. for 1 hr. Infected cells were then spun down and resuspended with 1000 ml of 2×YT medium containing 100 µg/ml ampicillin and 40 µg/ml kanamycin. Cells were grown at 30° C. overnight. The phage were then precipitated with PEG6000.

Using these phage, a second round of panning was performed using essentially the same methods used in the first round. Stringency of the panning was increased slightly by reducing the concentration of FcRn coated onto the microtiter plates slightly and increasing the number of washes. The eluted phage, after washing several times, were used to reinfect an exponentially growing $E.$ $coli$ XL1-blue culture at an $OD_{600}$ of about 0.5, which was then cultured for an hour at 37° C. and plated on plates containing about 100 µg/ml ampicillin and kanamycin to obtain colonies.

Single colonies were inoculated into 96-well tissue culture plates containing 120 µL/well 2×YT medium containing 100 µg/mL ampicillin and 2% glucose. The cells were grown at 37° C. on a shaker until an $OD_{600}$ of about 0.5 was reached. Then $3 \times 10^9$/mL M13 helper phage were added to each well and incubated for 1 hr. The cells then were spun down and resuspended with 180 µL/well 2×YT medium containing 100 µg/mL ampicillin and 40 µg/mL kanamycin. The culture was then incubated at 30° C. overnight on a shaker.

Approximately 100 µL of biotinylated human FcRn at 2 µg/mL was added to the wells of MAXISORP™ plates coated with 10 µg/mL streptavidin. After washing with PBS plus 0.05% Tween 20 (PBST) five times, phage from the overnight cultures in MES buffer at pH 6.0 or pH 7.4 were added to the plates and incubated at room temperature for 1 hr. A horseradish peroxidase (HRP)-conjugated anti-M13 antibody was used to detect the binding phage, and the plates were scored by a microtiter plate reader using a wavelength in the visible range. Positives were selected based on a higher signal at pH 5.5 (approximately 150% of the signal generated by a control Fc-fragment) and a signal that was comparable to that of a control Fc-fragment or lower at pH 7.4. In a second round of screening in which a single 96 well microtiter plate of isolated colonies was tested for each library, no positives were detected for libraries L2B, L3, or L4. About 20% of the colonies picked for Library L2A were positive, as were about 10% of the colonies picked for libraries L6A and L6B. Library L5 was clearly distinguishable from all other libraries since about 90% of the colonies picked were positive. Hence, library L5 was, by a large margin, the library that produced the most positives. These data indicate that the site at which library 5 is inserted is particularly favorable for isolation of variants that increase binding to FcRn at pH 5-6, while maintaining the low affinity of the Fc-fragment for FcRn at physiologic pHs.

We selected positives from libraries L2A, L5, L6A, and L6B, which were sequenced and further characterized as described below. Binding was assessed by a quantitative enzyme-linked immunoadsorbent assay (ELISA). The ELISA scores reflect binding affinity, with higher scores meaning higher affinity. Typically, scores higher than about 3~5 indicate binding above background. The sequences of the insertions of these positives and their scores in an ELISA are shown in Table 2 below. For library L5, the insertions are between the N169 and G170 according to the numbering in FIG. 2. For libraries 6A and 6B, the insertions are between L143 and T144 according to the numbering in FIG. 2.

TABLE 2

Sequences and ELISA scores of selected positives

| Library Control | ELISA score pH 6 | ELISA score pH 7.4 | Insertion sequence (SEQ ID NO:) | Isolate identifier |
|---|---|---|---|---|
| L5 | 95.4 | 2.8 | GGCVFNMFNCGG (SEQ ID NO: 44) | 5-106 |
| L5 | 95.1 | 15.1 | GGCPHMFPWCGG (SEQ ID NO: 392) | |
| L5 | 92.1 | 28.4 | GGCGHGWIFCGG (SEQ ID NO: 393) | |
| L5 | 91.0 | 4.4 | GGCVFNMFNCGG (SEQ ID NO: 394) | |
| L5 | 89.5 | 23.5 | GGCILNFYGCGG (SEQ ID NO: 395) | |
| L5 | 88.6 | 8.9 | GGCREPHPFCGG (SEQ ID NO: 396) | |
| L5 | 87.3 | 1.8 | GGCPFEFTQCGG (SEQ ID NO: 397) | |
| L5 | 86.5 | 0.4 | GGCQLGSMHCGG (SEQ ID NO: 398) | |
| L5 | 86.3 | 1.6 | GGCYENKTLCGG (SEQ ID NO: 399) | |
| L5 | 82.5 | 0.4 | GGCHLPFAVCGG (SEQ ID NO: 41) | 5-51 |
| L5 | 82.4 | 2.0 | GGCGHEYMWCGG (SEQ ID NO: 43) | 5-104 |
| L6A | 79.5 | 0.7 | GGCRAGYGDASCGG (SEQ ID NO: 400) | |
| L5 | 79.2 | 0.6 | GGCMVPFSMCGG (SEQ ID NO: 401) | |
| L5 | 76.7 | 0.6 | GGCWPLQDYCGG (SEQ ID NO: 42) | 5-69 |
| L5 | 75.5 | 0.3 | GGCELQERWCGG (SEQ ID NO: 402) | |
| L5 | 74.8 | 0.5 | GGCPANWGTCGG (SEQ ID NO: 403) | |
| L5 | 74.2 | 2.3 | GGCMMEFAQCGG (SEQ ID NO: 404) | |
| L5 | 73.4 | 0.4 | GGCQHHIMQCGG (SEQ ID NO: 405) | |
| L5 | 73.1 | 0.4 | GGCYQHHMECGG (SEQ ID NO: 406) | |
| L5 | 72.7 | 0.5 | GGCMQMNKWCGG (SEQ ID NO: 364) | 5-96 |
| L5 | 72.3 | 0.6 | GGCMVPFSMCGG (SEQ ID NO: 407) | |
| L5 | 72 | 0.4 | GGCQKGWVFCGG (SEQ ID NO: 408) | |
| L5 | 71.2 | 0.7 | GGCVYDVKKCGG (SEQ ID NO: 409) | |
| L6B | 68.9 | 0.8 | GGCLKGMHGSACGG (SEQ ID NO: 410) | |
| L5 | 68.6 | 0.6 | GGCNMLWGSCGG (SEQ ID NO: 411) | |
| L5 | 67.4 | 0.4 | GGCMQPWAFCGG (SEQ ID NO: 412) | |
| L5 | 65.6 | 0.5 | GGCMTQYNWCGG (SEQ ID NO: 413) | |
| L5 | 65.2 | 0.3 | GGCVNTWWSCGG (SEQ ID NO: 414) | |
| L5 | 64.1 | 0.5 | GGCDGRTKYCGG (SEQ ID NO: 363) | 5-92 |
| L5 | 63.6 | 0.7 | GGCYITQKLCGG (SEQ ID NO: 415) | |
| L5 | 63 | 0.5 | GGCETHYTYCGG (SEQ ID NO: 416) | |
| L5 | 62.7 | 0.4 | GGCALYPTNCGG (SEQ ID NO: 45) | 5-112 |
| L5 | 62.2 | 0.3 | GGCTEQVMWCGG (SEQ ID NO: 417) | |
| L5 | 61.2 | 0.4 | GGCITEFSHCGG (SEQ ID NO: 418) | |
| L5 | 61 | 0.3 | GGCQNRSYWCGG (SEQ ID NO: 419) | |
| L5 | 61 | 0.5 | GGCHGTKQFCGG (SEQ ID NO: 420) | |
| L5 | 60.9 | 0.3 | GGCNPHRTPCGG (SEQ ID NO: 421) | |
| L5 | 60.3 | 0.3 | GGCQHSPPLCGG (SEQ ID NO: 422) | |

TABLE 2-continued

Sequences and ELISA scores of selected positives

| Library Control | ELISA score pH 6 | ELISA score pH 7.4 | Insertion sequence (SEQ ID NO:) | Isolate identifier |
|---|---|---|---|---|
| L5 | 60.2 | 0.4 | GGCNHEETFCGG (SEQ ID NO: 423) | |
| L5 | 59.6 | 0.3 | GGCQYPRKLCGG (SEQ ID NO: 424) | |
| L5 | 59.2 | 0.3 | GGCIGPFWWCGG (SEQ ID NO: 425) | |
| L5 | 59.2 | 0.3 | GGCMQPWINCGG (SEQ ID NO: 426) | |
| L6B | 58.9 | 0.8 | GGCVQHKMGVVCGG (SEQ ID NO: 427) | |
| L5 | 58.5 | 0.5 | GGCEMENAWCGG (SEQ ID NO: 428) | |
| L5 | 58.3 | 0.3 | GGCPPWPERCGG (SEQ ID NO: 429) | |
| L5 | 57.8 | 0.3 | GGCGKHWHQCGG (SEQ ID NO: 359) | 5-57 |
| L5 | 57.7 | 0.4 | GGCHDPEPFCGG (SEQ ID NO: 430) | |
| L5 | 57.7 | 0.5 | GGCNEPKYVCGG (SEQ ID NO: 431) | |
| L5 | 57.7 | 0.5 | GGCDRPVWFCGG (SEQ ID NO: 432) | |
| L5 | 57.2 | 0.4 | GGCHSFKHFCGG (SEQ ID NO: 360) | 5-64 |
| L5 | 57.2 | 0.7 | GGCEIPHSFCGG (SEQ ID NO: 433) | |
| L5 | 56.7 | 0.4 | GGCMPYEMHCGG (SEQ ID NO: 434) | |
| L5 | 56.1 | 0.7 | GGCQGMWTWCGG (SEQ ID NO: 366) | 5-113 |
| L5 | 55.6 | 0.7 | GGCKRENPYCGG (SEQ ID NO: 435) | |
| L5 | 55.5 | 1.4 | GGCAERQYYCGG (SEQ ID NO: 436) | |
| L5 | 55.4 | 0.3 | GGCNVLDLFCGG (SEQ ID NO: 437) | |
| L5 | 55.2 | 0.2 | GGCKSMISMCGG (SEQ ID NO: 438) | |
| L5 | 54.9 | 0.6 | GGCHHKQDQCGG (SEQ ID NO: 439) | |
| L6B | 54.9 | 0.6 | GGCNATLSGYLCGG (SEQ ID NO: 440) | |
| L5 | 54.7 | 0.6 | GGCEATMTWCGG (SEQ ID NO: 441) | |
| L5 | 54.6 | 0.3 | GGCNVLDLFCGG (SEQ ID NO: 442) | |
| L5 | 54.5 | 0.3 | GGCAQQWHHEYCGG (SEQ ID NO: 362) | 5-73 |
| L5 | 54.2 | 0.7 | GGCSRVFKYCGG (SEQ ID NO: 443) | |
| L5 | 53.2 | 0.3 | GGCHAPQWECGG (SEQ ID NO: 444) | |
| L5 | 53.2 | 0.4 | GGCPLVRADCGG (SEQ ID NO: 445) | |
| L5 | 53.2 | 0.4 | GGCMHNEEFCGG (SEQ ID NO: 446) | |
| L5 | 52.4 | 1.2 | GGCMFETKWCGG (SEQ ID NO: 447) | |
| L6B | 52.1 | 0.4 | GGCNMNEWKSGCGG (SEQ ID NO: 448) | |
| L5 | 51.6 | 0.4 | GGCLQNLYVCGG (SEQ ID NO: 449) | |
| L5 | 51.3 | 0.2 | GGCQTSMKNCGG (SEQ ID NO: 450) | |
| L5 | 51.2 | 0.5 | GGCERFHHACGG (SEQ ID NO: 361) | 5-66 |
| L5 | 51.1 | 0.4 | GGCNLGHMPCGG (SEQ ID NO: 451) | |
| L5 | 50.5 | 1.0 | GGCWMWAEECGG (SEQ ID NO: 452) | |
| L5 | 50.3 | 0.4 | GGCVHNDKLCGG (SEQ ID NO: 453) | |
| L6B | 50.1 | 0.4 | GGCYGKAGMRDCGG (SEQ ID NO: 454) | |

TABLE 2-continued

Sequences and ELISA scores of selected positives

| Library Control | ELISA score pH 6 | ELISA score pH 7.4 | Insertion sequence (SEQ ID NO:) | Isolate identifier |
|---|---|---|---|---|
| L6B | 50 | 0.3 | GGCVSAATSRTCGG (SEQ ID NO: 455) | |
| L5 | 49.8 | 0.6 | GGCYPQKEICGG (SEQ ID NO: 456) | |
| L6B | 49.2 | 0.4 | GGCNQSSSREACGG (SEQ ID NO: 457) | |
| L6A | 48.5 | 0.2 | GGCNPVSTGAYCGG (SEQ ID NO: 458) | |
| L5 | 48.2 | 1.8 | GGCPGHEFRCGG (SEQ ID NO: 459) | |
| L6B | 47.2 | 0.4 | GGCGEYNYVGGCGG (SEQ ID NO: 460) | |
| L5 | 47.2 | 0.9 | GGCKWSMTKCGG (SEQ ID NO: 461) | |
| L5 | 47 | 1.4 | GGCDWHRMKCGG (SEQ ID NO: 462) | |
| L5 | 46.8 | 3.6 | GGCMHSPHACGG (SEQ ID NO: 463) | |
| L5 | 46.2 | 0.9 | GGCMMWKVNCGG (SEQ ID NO: 464) | |
| L6A | 45.2 | 0.3 | GGCFTNYASEKCGG (SEQ ID NO: 465) | |
| L6A | 44 | 0.2 | GGCDRFQNVNVCGG (SEQ ID NO: 466) | |
| L6A | 43.8 | 0.6 | GGCERHFPALFCGG (SEQ ID NO: 467) | |
| L6B | 43.6 | 0.2 | GGCTLGSAPTLCGG (SEQ ID NO: 468) | |
| L6B | 43.2 | 0.3 | GGCEMMKNKSGCGG (SEQ ID NO: 469) | |
| L5 | 42.4 | 1.6 | GGCEASGQICGG (SEQ ID NO: 470) | |
| L6B | 42.3 | 0.2 | GGCLRNFMKQSCGG (SEQ ID NO: 471) | |
| L6B | 42.2 | 0.4 | GGCPNDTVRDACGG (SEQ ID NO: 472) | |
| L6B | 41.8 | 0.3 | GGCSFSRHMGACGG (SEQ ID NO: 473) | |
| L6A | 41.2 | 0.2 | GGCAKDQHTGSCGG (SEQ ID NO: 474) | |
| L5 | 41.1 | 1.6 | GGCLGLRQECGG (SEQ ID NO: 475) | |
| L6B | 41 | 0.2 | GGCNMNEWKSGCGG (SEQ ID NO: 476) | |
| L5 | 38.7 | 1.6 | GGCQQIKEWCGG (SEQ ID NO: 477) | |
| L5 | 36.1 | 1 | GGCDLPNEMCGG (SEQ ID NO: 478) | |
| L5 | 35.8 | 0.7 | GGCMFSHPHCGG (SEQ ID NO: 479) | |
| L5 | 33.7 | 0.7 | GGCAGPYWACGG (SEQ ID NO: 480) | |
| L5 | 31.1 | 0.8 | GGCEQQFVTCGG (SEQ ID NO: 481) | |
| L5 | 29.5 | 1.2 | GGCMGWWHLCGG (SEQ ID NO: 482) | |
| L5 | 28.4 | 0.5 | GGCPQHGEMCGG (SEQ ID NO: 483) | |
| L5 | 27.7 | 1.0 | GGCYASPHECGG (SEQ ID NO: 484) | |
| L5 | 27.5 | 2.1 | GGCMPPQWMCGG (SEQ ID NO: 485) | |
| L5 | 26.9 | 1.4 | GGCDTIGWFCGG (SEQ ID NO: 486) | |
| L5 | 26.3 | 0.7 | GGCGIFESWCGG (SEQ ID NO: 487) | |
| L5 | 26.1 | 0.9 | GGCGPYKTECGG (SEQ ID NO: 488) | |
| L5 | 25.2 | 0.7 | GGCQPQASWCGG (SEQ ID NO: 489) | |
| L5 | 25 | 0.4 | GGCDRQVTGFCGG (SEQ ID NO: 490) | |
| L5 | 24.9 | 1.2 | GGSQRAPASCGG (SEQ ID NO: 491) | |
| L5 | 23.9 | 1.5 | GGCMMREQGCGG (SEQ ID NO: 492) | |

TABLE 2-continued

Sequences and ELISA scores of selected positives

| Library | Control | ELISA score pH 6 | ELISA score pH 7.4 | Insertion sequence (SEQ ID NO:) | Isolate identifier |
|---------|---------|------------------|--------------------|---------------------------------|--------------------|
| L5 | | 22 | 1.0 | GGCLLPNMFCGG (SEQ ID NO: 493) | |
| L5 | | 21.7 | 0.3 | GGCCPVYQHCGG (SEQ ID NO: 494) | |
| L5 | | 21.5 | 1.0 | GGCLMSQDLCGG (SEQ ID NO: 495) | |
| L5 | | 21.3 | 1.4 | GGCGGPYVFCGG (SEQ ID NO: 496) | |
| | WT* | 13-20 | 0.5-1.3 | | |
| | phg* | 0.4-0.7 | 0.3-1.8 | | |
| | media* | 0.4-0.7 | 0.5-0.6 | | |

*Since these control samples were measured multiple times, these results are reported as a range. "WT," "phg," and "media" mean, respectively, phage expressing a control Fc-fragment, phage expressing no Fc-fragment, and no phage.

Example 4

Studies on Binding Association and Dissociation Rates

To further characterize some of the variant Fc-fragments identified by the phage ELISA, binding of the variant Fc-fragments to FcRn at pH 6 and 7.4 was characterized for a subset of the identified variant Fc-fragments. DNA encoding selected variant Fc-fragment isolates, all from library L5, was introduced into a mammalian expression vector, which was used to transfect 293 6E cells using deacylated PEI essentially as described by Thomas et al. (Proc. Natl. Acad. Sci. 102(16): 5679-5684, 2005), the relevant portions of which are incorporated herein by reference. Isolates having high ELISA scores for binding to FcRn were selected. The concentrations of variant Fc-fragments in conditioned media (CM) were measured using 1:2 and 1:10 diluted CM samples with Protein A Biosensors (ForteBio, Inc., catalog number 18-5010) on Octet Red® (ForteBio Inc., Menlo Park, Calif.). Concentrations were calculated using a standard curve created with a purified Fc fusion protein.

Biotinylated hFcRn at 100 nM was captured on streptavidin (SA) biosensors (ForteBio Inc., 18-5019) off-line at RT for 2 hours. Using these biotinylated hFcRn-coated SA biosensors in the Octet Red® system, association and dissociation of unlabeled proteins can be detected in real time via diffraction of light. Variant and control Fc-fragment CM samples were diluted to 10 μg/mL at pH 6 or pH 7.4. Three association and dissociation conditions were set up: (1) association at pH 6 and dissociation at pH 6; (2) association at pH 6 and dissociation at pH 7.4; and (3) association at pH 7.4 and dissociation at pH 7.4. SA biosensors coated with biotinylated hFcRN were dipped into buffer at a specific pH for 1 min and then soaked in the samples containing variant Fc-fragments or controls at a specific pH for 5 min to allow binding to FcRn. The Fc biosensors were then soaked in buffer at a specific pH for 5 minutes more to allow the bound Fc-fragments to dissociate from FcRn. Detection of binding and dissociation of the Fc-fragments was possible through the use of bio-layer interferometry as implemented using the Octet Red® system, so that binding and dissociation were detected in real time.

Figure 3:
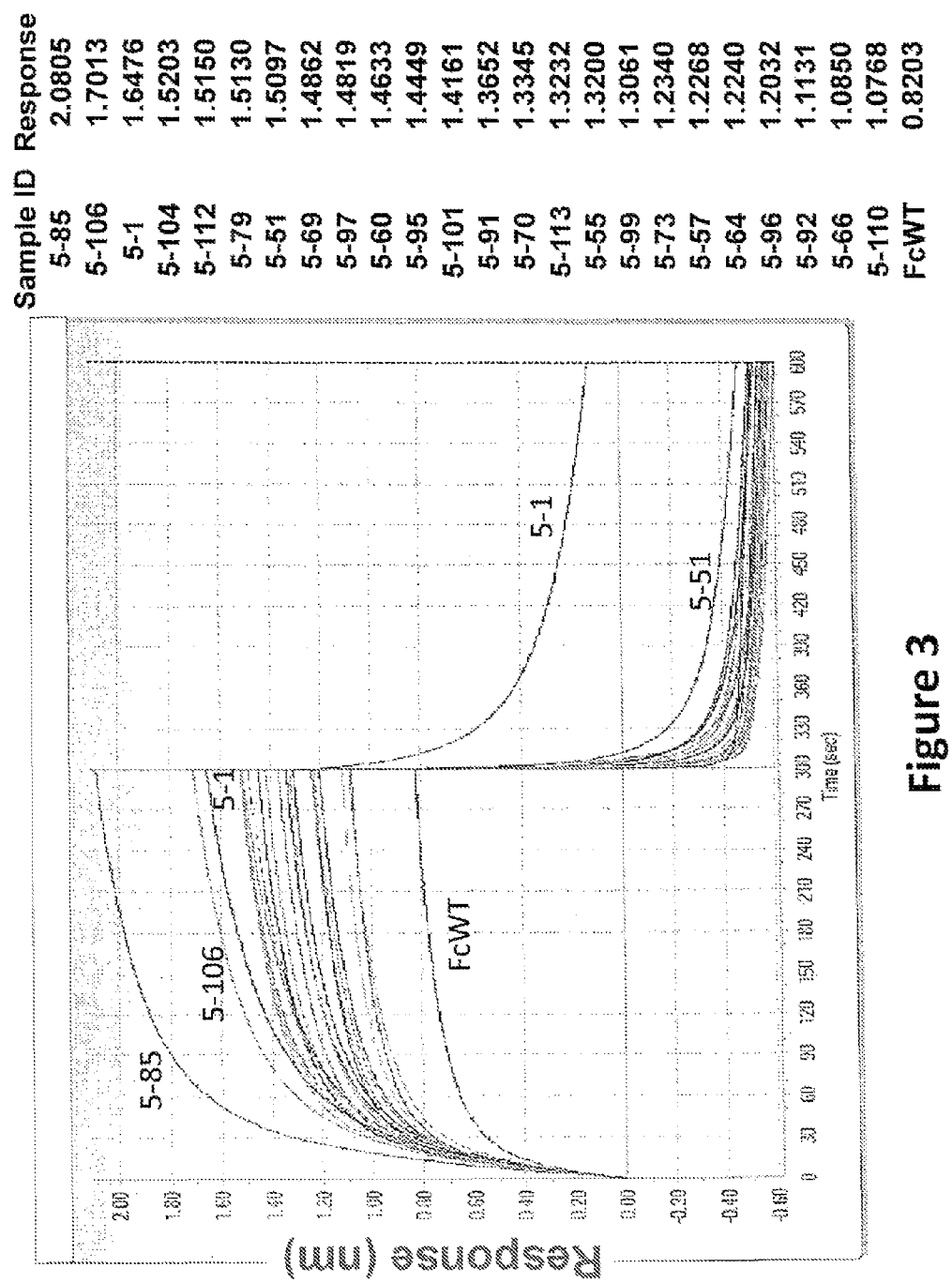
FIG. 3: Association and dissociation curves at pH 6 and pH 7.4, respectively, of variant Fc-fragments from library L5. The curves at left show the response detected using the ForteBio Octet® system as explained in Example 4 where the portions of the curves to the left of the central vertical line show the relative amounts of association of the various Fc-fragments to FcRn at pH 6 and the portions of the curves to the right of the central vertical line show the dissociation of the Fc-fragments from FcRn at pH 7.4. The table at right provides the maximal binding response detected at pH 6 for each variant and for a wild type Fc-fragment (FcWT).

Association and dissociation rates of the variant Fc-fragments at different pHs were compared to the controls. Higher binding at pH 6, slower off-rate at pH 6, very weak binding at pH 7.4, and faster off-rate at pH 7.4 as compared to the control Fc-fragment were the criteria used for selection of variant Fc-fragments for further characterization. A number of the 61 variant Fc-fragments tested showed more binding and slower dissociation at pH 6 and comparable or faster dissociation at pH 7.4 after binding at pH 6 relative to a control Fc-fragment. FIG. 3 shows the binding at pH 6 (to the left of the center vertical line) and dissociation at pH 7.4 (to the right of the center vertical line) curves for 24 variant Fc-fragments tested that had the most favorable properties. To the right of the curves the name of each variant Fc-fragment tested is listed along with the maximal binding response (in nanometers (nm)) observed during the association phase of the experiment. The absolute number for maximal response can vary somewhat from experiment to experiment, and it is not directly proportional to binding constants such as $k_{on}$, $k_{dis}$, or $K_D$ ($k_{dis}/k_{on}$). In FIG. 3, the lowest binding response was observed with a wild type Fc-fragment, and all variants shown had higher responses at pH 6. Most of the variant Fc-fragments dissociated rapidly at pH 7.4, as does a wild type Fc-fragment. However, variant 5-1 clearly dissociated much more slowly at pH 7.4 than any other variant, whereas all other variants tested dissociated rapidly at pH 7.4, as did the wild type Fc-fragment. Fc variant 5-85 stood out as the variant with the largest response at pH 6 that also dissociated rapidly at pH 7.4. A number of other variants, such as 5-106, 5-104, 5-112, 5-79, 5-51, and 5-69, among others, also had high responses at pH 6 and rapid dissociation at pH 7.4. Thus, many variant Fc-fragments with improved properties were isolated from library L5.

Example 5

Production of Variant Fc-Fragments

DNA encoding selected isolates, all from Library L5, was introduced into a mammalian expression vector, which was used to transfect 293 cells using deacylated PEI essentially as described by Thomas et al. (Proc. Natl. Acad. Sci. 102(16): 5679-5684, 2005), the relevant portions of which are incorporated herein by reference. Mammalian cells were chosen due to the ease of expression and post-translational processing in this system. The protein expression and production methods used are described in Durocher et al. (Nucl. Acids Res. 30(2): e9, 2002), the relevant portions of which are incorporated herein by reference. The secreted variant Fc-fragments were purified from the culture media using Protein A affinity chromatograpy and size exclusion chromatography. High performance liquid chromatography (HPLC) was used to check the purity of the Fc-fragments. For general guidance in purification methods, see Methods in Molecular Biology: Protein Purification Protocols v.244, Cultler, ed., Humana, N.J., 2004. Protein titers of the Fc variants were assessed by Coomassie blue staining of a polyacrlamide gel. All isolates were expressed at adequate levels for testing.

Example 6

Thermal Stability of Variant Fc-Fragments

Differential Scanning calorimetry (DSC) measures the enthalpy ($\Delta H$) of unfolding due to heat denaturation. Protein (or other macro-) molecules in solution are in equilibrium between the native, folded populations and denatured, unfolded populations. The higher the thermal transition midpoint ($T_m$), when 50% of the protein molecules are unfolded, the more stable the molecule. DSC is also used to determine the change in heat capacity ($\Delta Cp$) of denaturation. DSC experiments were performed with MicroCal VP-Capillary DSC (GE Helathcare, Piscataway, N.J.) in order to measure $T_m$ of the various Fc-fragments. The concentration of purified control (Fc-WT) or variant Fc-fragment in each experiment was 0.5 mg/mL in 10 mM sodium acetate, 9% sucrose at pH 5. The samples were heated from 20° C. to 95° C. at a heating rate of 60° C./hour. The thermal transition midpoints (Tm) of individual domains were determined when 50% of the individual domain was unfolded. The Tm values of the variant Fc-fragments and the control wild type Fc-fragment are listed in Table 3 below.

TABLE 3

Tm values of the variant Fc-fragments

| Sample Identifier | Tm of $C_H2$ Domain (° C.) | Tm of $C_H3$ Domain (° C.) |
|---|---|---|
| Fc-WT | 67.7 | 84.3 |
| Fc-5-55 | 67.7 | 77.5 |
| Fc-5-60 | 67.7 | 78.4 |
| Fc-5-64 | 67.4 | 79.2 |
| Fc-5-69 | 68.3 | 76.2 |
| Fc-5-70 | 67.3 | 77.7 |
| Fc-5-73 | 67.7 | 78.8 |
| Fc-5-79 | 67.3 | 76.5 |
| Fc-5-85 | 66.5 | 73.4 |
| Fc-5-91 | 67.4 | 77.6 |
| Fc-5-92 | 67.5 | 79.5 |
| Fc-5-95 | 67.1 | 77 |
| Fc-5-96 | 67.0 | 79.2 |
| Fc-5-97 | 67.4 | 78.2 |
| Fc-5-99 | 67.0 | 78.2 |
| Fc-5-101 | 67.0 | 78.6 |
| Fc-5-104 | 67.1 | 78.0 |
| Fc-5-106 | 66.6 | 77.4 |
| Fc-5-112 | 67.2 | 77.1 |
| Fc-5-113 | 68.1 | 77.9 |
| Fc-5-1 | 68.4 | 77.4 |
| Fc-5-51 | 67.4 | 77.4 |
| Fc-5-57 | 67.1 | 79.1 |
| Fc-5-66 | 67.5 | 79 |

These data indicate that the Tm of the $C_H2$ domain was not substantially affected by library L5 insertions, which are in the $C_H3$ domain. Although Tm of the $C_H3$ domain was slightly decreased in variant Fc-fragments as compared to the control Fc-fragment (Fc-WT), the Tm values of the $C_H3$ domain in the variant Fc-fragments are still approximately 10° C. higher than the Tm values of the $C_H2$ domain. Thus, the lower threshold of the thermal stability of the entire Fc domain, that is, the Tm of the $C_H2$ domain, is not affected.

Example 7

Binding of Variant Fc-Fragments to Human or Cynomolgus Monkey FcRn

Binding of variant Fc-fragments to human and cynomolgus monkey FcRn was tested using a BIAcore® T100 analysis system (GE Healthcare Bio-Sciences AB Private Limited Liability Company, Uppsala, Sweden) at both pH 5.5 and pH 7.4. The test consisted of incubating various concentrations of the variant Fc-fragments or control Fc-fragments with a fixed amount of human or cynomolgus monkey FcRn under binding conditions and subsequently measuring the amount of free, unbound FcRn in these mixtures by binding to a surface (in a flow cell of a CM5 (Biacore) chip) on which an Fc-fragment was immobilized. The Fc-fragment immobilized on the chip was sufficient in quantity to bind essentially all of the free, unbound FcRn in the mixture. Thus, the amount of unbound FcRn in the mixture was quantitatively ascertained by surface plasmon resonance through use of the BIAcore® T100 analysis system. From this information, an $EC_{50}$, that is, the concentration of the variant or control Fc-fragment at which 50% of the FcRn in the mixture was bound, was calculated. Initially, a group of 23 variant-Fc-fragments (Fc-5-1 being considered a control) identified in the experiments described above were tested for binding to human FcRn. Based on these data, fourteen variant Fc-fragments were selected and further tested for binding to cynomolgus monkey FcRn.

The experimental protocol is described in more detail below. The Fc-fragments to be tested were produced in 293 cells and purified as described above. A wild-type human control Fc-fragment (Fc-WT) and a variant Fc-fragment (Fc-5-1) were immobilized on the flow cells of a CM5 chip (Biacore) using amine coupling with density around 6000 resonance units (RU). Fc-5-1 was used because it, unlike Fc-WT, binds to FcRn well at pH 7.4. One flow cell with no immobilized protein bound to it was used as a background control. It was possible to use a single flow cell for successive samples by washing between samples with a solution at pH 7.4 to release FcRn bound to the Fc-fragment immobilized on the flow cell.

To obtain a reasonable signal for the different molecules and conditions tested, different assay conditions were used. For assays at pH 5.5, 10 nM of human or cynomolgus monkey FcRn was mixed with serial dilutions of the variant and control Fc-fragments being tested (which ranged from 0.1~2,000 nM) and incubated for 1 hour at room temperature in 10 mM sodium acetate, pH 5.5, 150 mM NaCl, 0.005% P20, 0.1 mg/mL BSA. As positive controls, 10 mM human and cynomolgus monkey FcRn were each incubated in the same solution, for the same time, and at the same temperature described immediately above, but without an added Fc-fragment. In these samples, presumably all FcRn was unbound. Binding of the free, unbound FcRn in each of these mixtures to the immobilized Fc-WT and Fc-5-1 was measured by injecting the mixtures over the surfaces on the flow cells and detecting the FcRn bound to the surfaces via surface plasmon resonance.

For assays at pH 7.4, 10 nM human and cynomolgus monkey FcRn was mixed with serial dilutions of the variant and control Fc-fragments being tested (which ranged from 0.1~2,000 nM) and incubated for 1 hour at room temperature in phosphate buffered saline (PBS) with 0.005% polysorbate 20, 0.1 mg/mL BSA. As positive controls, 10 mM human and cynomolgus monkey FcRn were each incubated in the same solution, for the same time, and at the same temperature described immediately above, but without an added Fc-fragment. Amounts of free, unbound FcRn in these mixtures were determined by binding to immobilized Fc-5-1 Fc-fragment, which was measured by injecting these mixtures over a flow cell surface coated with Fc-5-1 and detecting the FcRn bound to the surfaces via surface plasmon resonance. Fc-5-1 was used in these assays because it binds to FcRn with much greater affinity that Fc-WT at pH 7.4.

A decreased FcRn binding response with increasing concentrations of Fc-fragment in the mixtures indicated that FcRn was bound to the Fc-fragment in solution, which blocked FcRn from binding to the immobilized Fc-fragment on the surfaces of the flow cells. Plotting the FcRn binding signal versus Fc-fragment concentrations, $EC_{50}$'s were calculated using nonlinear regression of one-site competition in GraphPad Prism 5™ software. These results are shown in Table 4.

TABLE 4

$EC_{50}$ of Fc-fragments for binding to FcRn at pH 5.5 and 7.4

| Sample | Human FcRn pH 5.5 $EC_{50}$ (nM) | Human FcRn pH 5.5 95% CI (nM) | Human FcRn pH 7.4 $EC_{50}$ (nM) | Human FcRn pH 7.4 95% CI (nM) | Cynomolgus FcRn pH 5.5 $EC_{50}$ (nM) | Cynomolgus FcRn pH 5.5 95% CI (nM) | Cynomolgus FcRn pH 7.4 $EC_{50}$ (nM) | Cynomolgus FcRn pH 7.4 95% CI (nM) |
|---|---|---|---|---|---|---|---|---|
| Fc-WT | 290 | 200~430 | >2000 | | 270 | 200~360 | >2000 | |
| Fc-5-1 | 2.6 | 1.4~4.7 | 45 | 33~61 | 2.3 | 1.2~4.5 | 42 | 28~63 |
| Fc-5-51 | 16 | 13~19 | >2000 | | 21 | 12~36 | >2000 | |
| Fc-5-55 | 49 | 35~69 | >2000 | | 53 | 46~62 | >2000 | |
| Fc-5-57 | 180 | 110~310 | >2000 | | ND* | | ND | |
| Fc-5-60 | 67 | 48~94 | >2000 | | 60 | 43~85 | >2000 | |
| Fc-5-64 | 210 | 113~375 | >2000 | | ND | | ND | |
| Fc-5-66 | 200 | 170~230 | >2000 | | ND | | ND | |
| Fc-5-69 | 14 | 12~17 | >2000 | | 18 | 14~23 | >2000 | |
| Fc-5-70 | 26 | 20~32 | >2000 | | 27 | 18~39 | >2000 | |
| Fc-5-73 | 190 | 120~290 | >2000 | | ND | | ND | |
| Fc-5-79 | 53 | 45~64 | >2000 | | 63 | 48~81 | >2000 | |
| Fc-5-85 | 18 | 15~21 | >2000 | | 25 | 14~43 | >2000 | |
| Fc-5-91 | 57 | 40~110 | >2000 | | ND | | ND | |
| Fc-5-92 | 75 | 54~106 | >2000 | | ND | | ND | |
| Fc-5-95 | 42 | 31~56 | >2000 | | 50 | 37~67 | >2000 | |
| Fc-5-96 | 76 | 58~110 | >2000 | | ND | | ND | |
| Fc-5-97 | 25 | 19~32 | >2000 | | 31 | 27~36 | >2000 | |
| Fc-5-99 | 15 | 11~19 | >2000 | | 16 | 10~25 | >2000 | |
| Fc-5-101 | 100 | 60~170 | >2000 | | ND | | ND | |
| Fc-5-104 | 15 | 3~67 | >2000 | | 16 | 14~19 | >2000 | |
| Fc-5-106 | 5.3 | 4.5~6.4 | >2000 | | 3.6 | 2.4~5.3 | >2000 | |
| Fc-5-110 | 250 | 140~460 | >2000 | | ND | | ND | |
| Fc-5-112 | 46 | 38~56 | >2000 | | 49 | 34~72 | >2000 | |
| Fc-5-113 | 20 | 12~33 | >2000 | | 27 | 21~35 | >2000 | |

*ND indicates "not determined"

The data in Table 4 indicate that many of the variant Fc-fragments tested have substantially improved binding to human FcRn at pH 5.5 (i.e., have a substantially lower $EC_{50}$ compared to Fc-WT) and maintain low binding at pH 7.4 (i.e., have a high $EC_{50}$, like that of Fc-WT). However, five of them (Fc-5-57, Fc-5-64, Fc-5-66, Fc-5-73, and Fc-5-110) did not show much improved binding at pH 5.5. Eight of them (Fc-5-55, Fc-5-60, Fc-5-79, Fc-5-91, Fc-5-92, Fc-5-96, Fc-5-101, and Fc-5-112) showed only around 2-5× improvement in binding at pH 5.5. These data further indicate that $EC_{50}$'s of the variant Fc-fragments for binding to human and cynomolgus monkey FcRn's are comparable. All variant Fc-fragments tested (other than Fc-5-1, which was considered as a control) maintained low binding to both human and cynomolgus monkey FcRn at pH 7.4.

Example 8

Construction of Further Modified Variant Fc-Fragments

Further modified versions of variant Fc-fragments Fc-5-69 and Fc-5-106 were made. The variants of Fc-5-69 were made as follows. DNA encoding variant Fc-fragment Fc-5-69 was inserted into a mammalian expression vector that could also be propagated in *E. coli*, which was used as a template. For variant Fc-5-69-W1F, the following two primers were used: forward, GAG AGC AAT GGT GGT TGT TTC CCG CTG CAG GAC TAC (SEQ ID NO:497); and reverse, GTA GTC CTG CAG CGG GAA ACA ACC ACC ATT GCT CTC (SEQ ID NO:498). For Fc-5-69-W1Y, the following two primers were used: forward, GAG AGC AAT GGT GGT TGT TAC CCG CTG CAG GAC TAC (SEQ ID NO:499); and reverse, GTA GTC CTG CAG CGG GTA ACA ACC ACC ATT GCT CTC (SEQ ID NO:500). The Quikchange Site-Directed Mutagenesis Kit (Stratagene, 200518) protocol was used. The reaction mixture was 200 nM dNTPs, 100 nM primers, 1 ng DNA template, 1 μL DNA polymerase and water in a total volume of 50 μL. The reaction was run at 95° C. for 30 seconds, then 16 cycles of 95° C. for 30 seconds, 55° C. for 60 seconds, 68° C. for 6 minutes, followed by 68° C. for 10 minutes. Then 1 μL of DpnI was added, and the reaction was incubated at 37° C. for 1 hour. Then 2 μL of the mixture was used to transform 30 μl of XL1-blue supercompetent cells (Stratagene) at 42° C. for 45 seconds. Thereafter, 0.5 mL SOC was added, and the cells were incubated at 37° C. for 1 hour on a shaker at 300 revolutions per minute (rpm). The transformed cells were spread on LB-ampicillin agar plates and incubated at 37° C. overnight.

Individual colonies were picked, and plasmid DNA was prepared and sequenced. The DNA sequences indicated that the variant Fc-fragments had the following inserted amino acid sequences, which differed by one amino acid from the insert in Fc-5-69: Fc-5-69-W1F, GGCFPLQDYCGG (SEQ ID NO:367); and Fc-5-69-W1Y, GGCYPLQDYCGG (SEQ ID NO:368). DNA encoding these variant Fc-fragments was introduced into 293 cells, and purified Fc-fragments were produced as described above for use in Biacore® binding assays performed as described above.

Modified versions of Fc-5-106 were made by similar methods except that the template for the PCR reactions was a DNA encoding Fc-5-106 inserted into a mammalian expression vector. The primers used for the PCR reactions had the following sequences: Fc-5-106-M4A, forward, GGT GGT TGT GTT TTC AAC GCG TTC AAC TGT GGT GGT GGG (SEQ ID NO:501) and reverse, CCC ACC ACC ACA GTT GAA CGC GTT GAA AAC ACA ACC ACC (SEQ ID NO:502); Fc-5-106-M4G, forward, GGT GGT TGT GTT TTC AAC GGG TTC AAC TGT GGT GGT GGG (SEQ ID NO:503), and reverse, CCC ACC ACC ACA GTT GAA CCC GTT GAA AAC ACA ACC ACC (SEQ ID NO:504);

Fc-5-106-M4H, forward, GGT GGT TGT GTT TTC AAC CAT TTC AAC TGT GGT GGT GGG (SEQ ID NO:505), and reverse, CCC ACC ACC ACA GTT GAA ATG GTT GAA AAC ACA ACC ACC (SEQ ID NO:506); Fc-5-106-M4I, forward, GGT GGT TGT GTT TTC AAC ATC TTC AAC TGT GGT GGT GGG (SEQ ID NO:507), and reverse, CCC ACC ACC ACA GTT GAA GAT GTT GAA AAC ACA ACC ACC (SEQ ID NO:508); Fc-5-106-M4L, forward, GGT GGT TGT GTT TTC AAC TTG TTC AAC TGT GGT GGT GGG (SEQ ID NO:509), and reverse, CCC ACC ACC ACA GTT GAA CAA GTT GAA AAC ACA ACC ACC (SEQ ID NO:510); Fc-5-106-M4N, forward, GGT GGT TGT GTT TTC AAC AAC TTC AAC TGT GGT GGT GGG (SEQ ID NO:511), and reverse, CCC ACC ACC ACA GTT GAA GTT GTT GAA AAC ACA ACC ACC (SEQ ID NO:512); Fc-5-106-M4Q, forward, GGT GGT TGT GTT TTC AAC CAG TTC AAC TGT GGT GGT GGG (SEQ ID NO:513), and reverse, CCC ACC ACC ACA GTT GAA CTG GTT GM AAC ACA ACC ACC (SEQ ID NO:514); Fc-5-106-M4S, forward, GGT GGT TGT GTT TTC AAC TCG TTC AAC TGT GGT GGT GGG (SEQ ID NO:515), and reverse, CCC ACC ACC ACA GTT GAA CGA GTT GAA AAC ACA ACC ACC (SEQ ID NO:516); Fc-5-106-M4T, forward, GGT GGT TGT GTT TTC AAC ACG TTC AAC TGT GGT GGT GGG (SEQ ID NO:517), and reverse, CCC ACC ACC ACA GTT GAA CGT GTT GAA AAC ACA ACC ACC (SEQ ID NO:518); Fc-5-106-M4V, forward, GGT GGT TGT GTT TTC AAC GTG TTC AAC TGT GGT GGT GGG (SEQ ID NO:519), and reverse, CCC ACC ACC ACA GTT GAA CAC GTT GAA AAC ACA ACC ACC (SEQ ID NO:520).

PCR reactions were performed as described above and used to transform *E. coli*. Plasmid DNAs from individual colonies were sequenced. Isolates encoding Fc-fragments having the following inserted sequences were selected: Fc-5-106-M4A, GGCVFNAFNCGG (SEQ ID NO:369); Fc-5-106-M4G, GGCVFNGFNCGG (SEQ ID NO:370); Fc-5-106-M4H, GGCVFNHFNCGG (SEQ ID NO:371); Fc-5-106-M4I, GGCVFNIFNCGG (SEQ ID NO:372); Fc-5-106-M4L, GGCVFNLFNCGG (SEQ ID NO:373); Fc-5-106-M4N, GGCVFNNFNCGG (SEQ ID NO:374); Fc-5-106-M4Q, GGCVFNQFNCGG (SEQ ID NO:375); Fc-5-106-M4S, GGCVFNSFNCGG (SEQ ID NO:376); Fc-5-106-M4T, GGCVFNTFNCGG (SEQ ID NO:377); Fc-5-106-M4V, GGCVFNVFNCGG (SEQ ID NO:378).

These derivatives of Fc-5-69 and Fc-5-106 were made and tested for relative binding affinity to human and cynomolgus monkey FcRn at pH 5.5 and 7.4 using the methods described in Example 7.

TABLE 5

Binding of variants of 5-69 and Fc 5-106 to human and cynomolgus monkey FcRn

| Sample | Human FcRn pH 5.5 | | Human FcRn pH 7.4 | | Cynomolgus FcRn pH 5.5 | | Cynomolgus FcRn pH 7.4 | |
|---|---|---|---|---|---|---|---|---|
| | $EC_{50}$ (nM) | 95% Cl (nM) | $EC_{50}$ (nM) | 95% Cl (nM) | $EC_{50}$ (nM) | 95% Cl (nM) | $EC_{50}$ (nM) | 95% Cl (nM) |
| Fc-WT | 270 | 170~440 | >2000 | | 250 | 130~470 | >2000 | |
| Fc-5-69 | 20 | 13~30 | 1100 | 960~1400 | | | | |
| Fc-5-69-WIF | 57 | 36~89 | >2000 | | | | | |
| Fc-5-69-WIY | 140 | 75~240 | >2000 | | | | | |
| Fc-5-106 | 5.4 | 3.7~8.0 | 1400 | 1100~1700 | 4.6 | 3.5~6.1 | >2000 | |
| Fc-5-106-M4A | 27 | 16~45 | >2000 | | | | | |
| Fc-5-106-M4G | 100 | 66~160 | >2000 | | | | | |
| Fc-5-106-M4H | 100 | 48~230 | >2000 | | | | | |
| Fc-5-106-M4I | 2.6 | 1.8~3.6 | 900 | 760~1100 | 3.2 | 2.1~4.8 | 970 | 810~1200 |
| Fc-5-106-M4L | 2.3 | 1.5~3.4 | 650 | 460~920 | 2.8 | 1.6~4.7 | 710 | 460~1100 |
| Fc-5-106-M4N | 100 | 52~180 | >2000 | | | | | |
| Fc-5-106-M4Q | 34 | 17~68 | >2000 | | | | | |
| Fc-5-106-M4S | 58 | 32~106 | >2000 | | | | | |
| Fc-5-106-M4T | 10 | 4.4~21 | >2000 | | 8.3 | 5.3~13 | >2000 | |
| Fc-5-106-M4V | 6.2 | 3.6~11 | >2000 | | 5.0 | 3.4~7.3 | >2000 | |

Both Fc-5-69 derivatives showed weaker binding affinity than Fc-5-69 itself at pH 5.5. Two Fc-5-106 derivatives (Fc-5-106-M4I and Fc-5-106-M4L) showed higher affinity binding to both human and cynomolgus FcRn at pH 7.4 compared to Fc-5-106. Also, four of the Fc-5-106 derivatives including these two (Fc-5-106-M4I, Fc-5-106-M4L, Fc-5-106-M4T and Fc-5-106-M4V) showed improved or approximately the same binding activity at pH 5.5 compared to Fc-5-106 itself. These four were tested for binding affinity to cynomolgus monkey FcRn. All four had $EC_{50}$'s for binding to cynomolgus monkey FcRn that were similar to those for human FcRn at both pH 5.5. and 7.4.

Example 9

In Vivo Characterization of Variant Fc-Fragments

To determine whether antibodies containing the variant Fc-fragments identified above have improved pharmacokinetic (PK) properties in vivo, an unmodified Antibody X (which is a human IgG2 anti-human IL-23 antibody) and variant versions of Antibody X containing variant Fc-fragments were tested in vivo in cynomolgus monkeys to define pharmacokinetic parameters. Antibody X was selected as an appropriate antibody in which to test the pharmacokinetic parameters of the variant Fc-fragments because it was known to have a linear pK profile and because IL-23 was known to be expressed at low levels in vivo. Thus, it was expected that target-related effects on PK parameters would be minimal, making it easier to detect pK effects due to the variant Fc-fragments.

Five variant IgG2 antibodies called (X-5-51, X-5-69, X-5-104, X-5-106, and X-5-112) were made. These IgG2 antibodies had the same insertions at the same positions (according to the alignment in Table 1) as the variant IgG1 Fc-fragments Fc-5-51, Fc-5-69, Fc-5-104, Fc-5-106, and Fc-5-112, respectively. More specifically, the insertions were between amino acids 384 and 385 (EU numbering as in Table 1) in the human IgG2 Fc-fragment. A plasmid containing DNA encoding the heavy chain of Antibody X was used as a template for five PCR reactions done using the following primers: for X-5-51, forward, 5'-GAG TGG GAG AGC AAT GGT GGT TGT CAT CTG CCG TTC GCT GTT TGT GGT GGT GGG CAG CCG GAG AAC-3' (SEQ ID NO:539), and reverse, 5'-GTT CTC CGG CTG CCC ACC ACC ACA AAC AGC GAA CGG CAG ATG ACA ACC ACC ATT GCT CTC CCA CTC-3' (SEQ ID NO:540); for X-5-69, forward, 5'-GAG TGG GAG AGC AAT GGT GGT TGT TGG CCG CTG CAG GAC TAC TGT GGT GGT GGG CAG CCG GAG AAC-3' (SEQ ID NO:541), and reverse, 5'-GTT CTC CGG CTG CCC ACC ACC ACA GTA GTC CTG CAG CGG CCA ACA ACC ACC ATT GCT CTC CCA CTC-3' (SEQ ID NO:542); for X-5-104, forward, 5'-GAG TGG GAG AGC AAT GGT GGT TGT GGT CAT GAA TAC ATG TGG TGT GGT GGG CAG CCG GAG MC-3' (SEQ ID NO:543), and reverse, 5'-GTT CTC CGG CTG CCC ACC ACA CCA CAT GTA TTC ATG ACC ACA ACC ACC ATT GCT CTC CCA CTC-3' (SEQ ID NO:544); for X-5-106, forward, 5'-GAG TGG GAG AGC AAT GGT GGT TGT GTT TTC AAC ATG TTC AAC TGT GGT GGT GGG CAG CCG GAG MC-3' (SEQ ID NO:545), and reverse, 5'-GTT CTC CGG CTG CCC ACC ACC ACA GTT GAA CAT GTT GAA MC ACA ACC ACC ATT GCT CTC CCA CTC-3' (SEQ ID NO:546); and for X-5-112, forward, 5'-GAG TGG GAG AGC AAT GGT GGT TGT GCT CTG TAC CCG ACT AAC TGT GGT GGT GGG CAG CCG GAG MC-3' (SEQ ID NO:547), and reverse, 5'-GTT CTC CGG CTG CCC ACC ACC ACA GTT AGT CGG GTA CAG AGC ACA ACC ACC ATT GCT CTC CCA CTC-3' (SEQ ID NO:548). The Quikchange Site-Directed Mutagenesis Kit (Stratagene, 200518) protocol was used. The reaction mixture was 200 nM dNTPs, 100 nM primers, 1 ng DNA template, 1 µL DNA polymerase and water in a total volume of 50 µL. The reaction was run at 95° C. for 30 seconds, then 16 cycles of 95° C. for 30 seconds, 55° C. for 60 seconds, 68° C. for 6 minutes, followed by 68° C. for 10 minutes. Then 1 µL of DpnI was added, and the reaction was incubated at 37° C. for 1 hour. Then 2 µL of the mixture was used to transform 30 µl of XL1-blue supercompetent cells (Stratagene) at 42° C. for 45 seconds. Thereafter, 0.5 mL SOC was added, and the cells were incubated at 37° C. for 1 hour on a shaker at 300 rpm. The transformed cells were spread on LB-ampicillin agar plates and incubated at 37° C. overnight. Individual colonies were picked, and plasmid DNA was prepared and sequenced to ensure that the isolates chosen had the expected DNA sequence.

Antibodies were prepared in essentially the same way as described above for Fc-fragments, except that the mammalian host cells were transfected with DNAs encoding both the IgG2 heavy chain, including a portion encoding either a variant or a control Fc-fragment, and the light chain of Antibody X. Host cells were incubated under conditions appropriate for expression of the antibodies, and the antibodies were recovered from the culture medium, purified as described above, and used for the following experiments.

Cynomolgus monkeys (n=2/group) received a single intravenous dose of an unmodified or a variant version of Antibody X at a dose of 1 mg/kg and were followed during an 8-week in-life phase. Samples of blood were collected at specified time points over the course of the experiment. Samples were collected at pre-dose, 0.25, 1, 4, 8, 12, 24, 48, 72, 168, 240, 336, 408, 504, 576, 672, 744, 840, 1008, 1176 and 1344 hours post-dose.

An anti-human IgG sandwich ELISA was used to determine systemic concentrations of the injected antibodies by comparison to a standard curve derived from the same molecule. Specifically, a mouse anti-human Fc antibody was diluted in PBS, coated onto plates, and incubated for 2 hours at room temperature. The well contents were discarded, and PBS-Tween 20 (SuperBlock®, Thermo Scientific) was added to the wells as a blocking buffer. After incubation for one hour at room temperature, the plate wells were washed with PBS-Tween-20, and serum samples were added to the wells and incubated for 1 hour with shaking. Wells were again washed, and a horseradish peroxidase labeled mouse anti-human Fc antibody was added to the plates. Following a one hour incubation, wells were washed and developed for 10 minutes using a 3,3',5,5' tetramethylbenzidine (TMB) substrate. The resulting colorimetric reaction was quenched with phosphoric or sulfuric acid added to the plate. Optical densities (ODs) were determined at 450 nm and 650 nm, and the OD at 650 nm was subtracted from the OD at 450 nm. The conversion of OD values into concentrations for the study samples was achieved through data regression using a logistic model with weighting set to $1/Y^2$ in Watson LIMS version 7.0.0.04.

Pharmacokinetic analysis was performed using the PK analytical package provided within Watson LIMS, version 7.0.0.04 by. Exposure (area under the curve (AUC)) and clearance (mL/kg/hr) values were derived from this analysis. Concentration vs. time data for the last 5 sampling time points for each cynomolgus monkey was used to calculate half-life (T½) values.

Figure 4:
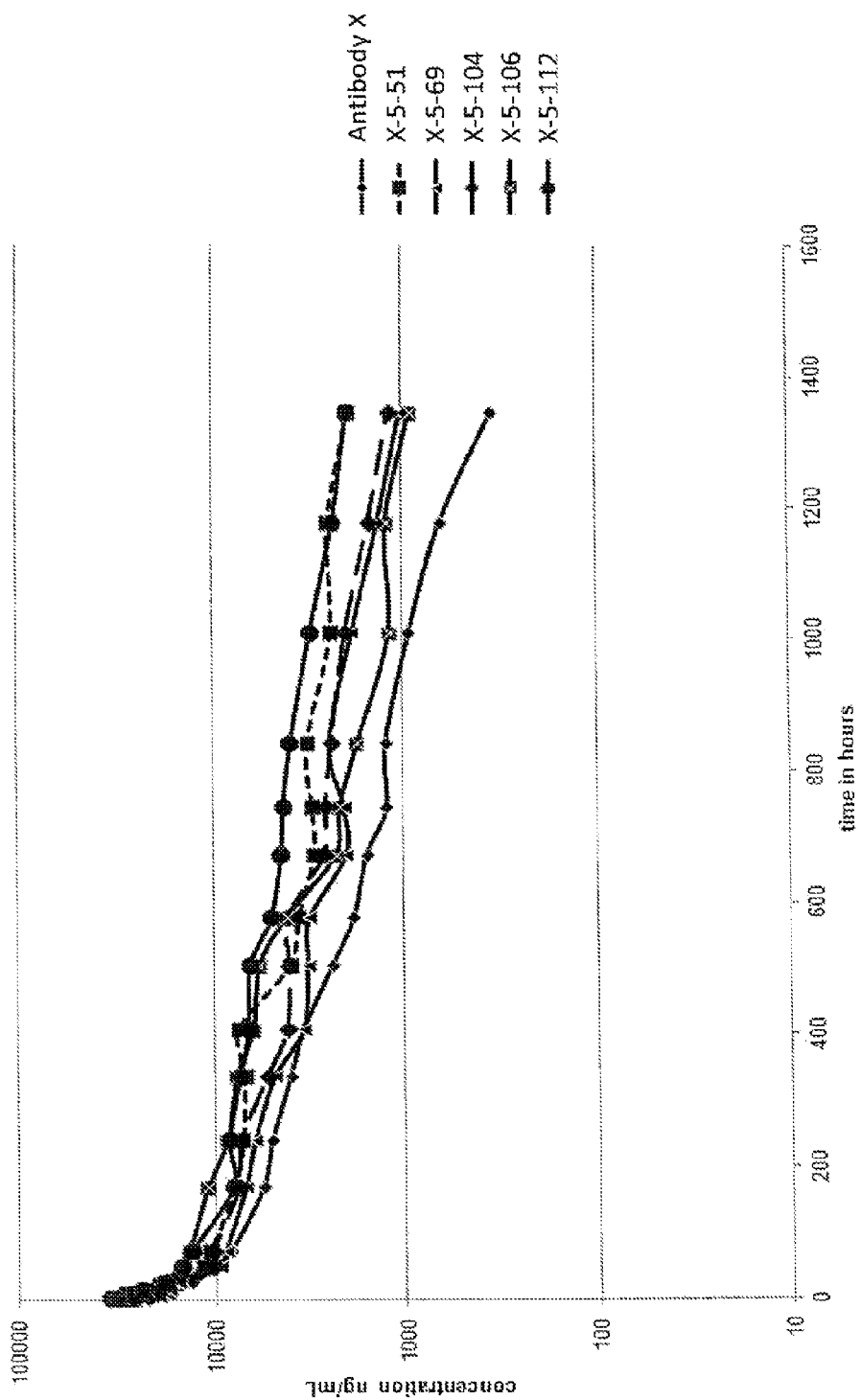
FIG. 4: Average concentrations of antibodies containing variant and control Fc-fragments as a function of time post-injection in cynomolgus monkeys. The x axis indicates time in hours post-injection, and the y axis indicates the concentration of the antibody in nanograms per milliliter (ng/mL) in peripheral blood of cynomolgus monkeys that have been injected with an antibody.

As shown in FIG. 4, variant versions of Antibody X containing variant Fc-fragments X-5-51, X-5-69, X-5-104, X-5-106 and X-5-112 all demonstrated higher mAb concentrations in cynomolgus monkeys at a given sampling time point as compared to unmodified Antibody X. As shown in Table 6, increased exposure values and decreased clearance values were demonstrated for all variant versions of Antibody X tested compared to unmodified Antibody X. In addition, four of the five variant versions of Antibody X had increased half lives. The one variant that did not exhibit an increased half life (X-5-106), may represent a situation where anti-drug antibodies against the injected antibody may have developed in one monkey, since data from one of the two monkeys tested indicated a very short half life (48 hours), whereas data from the other monkey indicated an increased half life (538 hours). Further experimentation to measure the presence of anti-drug antibodies could clarify this issue.

TABLE 6

| | Mean values for half-life, exposure, and clearance | | | | | |
|---|---|---|---|---|---|---|
| | Unmodified Antibody X | X-5-51 | X-5-69 | X-5-104 | X-5-106 | X-5-112 |
| T ½ (hours) | 335 | 910 | 550 | 477 | 191 | 520 |
| AUC-exposure (ug*hr/mL) | 3890 | 6640 | 4960 | 5745 | 6005 | 7810 |

TABLE 6-continued

Mean values for half-life, exposure, and clearance

|  | Unmodified Antibody X | X-5-51 | X-5-69 | X-5-104 | X-5-106 | X-5-112 |
|---|---|---|---|---|---|---|
| Clearance (mL/kg/hr) | 0.247 | 0.109 | 0.173 | 0.153 | 0.154 | 0.108 |

Generally, these data indicate that increased binding of a variant Fc-fragment to FcRn at pH 5.5-6.0 (relative to a control Fc-fragment) and rapid dissociation from FcRn at pH 7.4 correlate with a longer in vivo half-life of an antibody containing the variant Fc-fragment in cynomolgus monkeys. However, an exact quantitative relationship between the degree of improvement in binding at pH 5.5 or 6 of an IgG1 variant Fc-fragment and the degree of improvement in pharmacokinetic parameters for a full length IgG2 antibody having the same insertion as the variant Fc-fragment is not shown by these data. These data do, however, indicate that X-5-51, X-5-69, X-5-104, and X-5-112 have increased half lives relative to an unaltered Antibody X and suggest that the same is true for X-5-106. Moreover, all variant antibodies tested had lower clearance rates and higher exposure as compared to the control antibody.

Example 10

Construction of Variant Fc-Fragments with Insertions at Alternate Sites

The fact that many variants from library L5 had desirable properties indicated that the position of these insertions was favorable. The following experiments were done to determine whether other sites within or adjacent to the same loop as the L5 insertion site might have better properties. To test this idea, one of the selected peptides was inserted at different locations in this loop, and the resulting variant Fc-fragments were tested for FcRn binding. The peptide insertion of variant Fc-fragment 5-1 was chosen as the peptide to insert. This peptide has the following amino acid sequence: GGCGMPIEFCGG (SEQ ID NO:67). As shown in FIG. 5 (which uses the EU numbering system as exemplified in Table 1), this peptide was inserted at sites within or adjacent to the library L5 loop other than the library L5 insertion site. Binding of the resulting Fc-fragments to FcRn was assayed using SA biosensors (ForteBio Inc. 18-5019) coated biotinylated huFcRn as described in Example 4 above.

In more detail, the DNA constructs encoding these variant Fc-fragments were made as follows. The Quikchange® Site-Directed Mutagenesis Kit (Stratagene, 200518) protocol was used. The reaction mixture was composed of 200 nM dNTPs, 100 nM primers, 1 ng DNA template, 1 µL DNA polymerase and water to a total volume of 50 µL. The primers used in these reactions for each variant are shown below in Table 7. The DNA template was a cDNA encoding a wild type human IgG1 Fc-polypeptide inserted into a vector. The reaction was run at 95° C. for 30 seconds, then 16 cycles of 95° C. for 30 seconds, 55° C. for 60 seconds, and 68° C. for 6 minutes, followed by a final cycle of 68° C. for 10 minutes. Then 1 µL of DpnI was then added, and the reaction was incubated at 37° C. for 1 hour. Then 2 µL of the mixture was used to transform 30 µL of XL1-blue supercompetent E. coli cells (Stratagene) at 42° C. for 45 seconds. Thereafter, 0.5 mL Super Optimal Broth with Catabolite repression (SOC; containing 2% bacto-tryptone, 0.5% yeast extract, 10 mM NaCl, 2.5 mM KCl, 10 mM MgCl₂, and 20 mM glucose) was added, and the cells were incubated at 37° C. for 1 hour on a shaker at 300 revolutions per minute (rpm). The transformed cells were spread on LB-ampicillin agar plates and incubated at 37° C. overnight.

TABLE 7

Primers used in PCR reactions for construction variant Fc-fragment-encoding DNAs

| Variant Fc-fragment designation | Forward Primer | Reverse Primer |
|---|---|---|
| 5-1-1 | 5'-GCT GTG GAG TGG GAG GGT GGT TGT GGT ATG CCG ATC GAA TTC TGT GGT GGT AGC AAT GGG CAG CCG-3' (SEQ ID NO: 68) | 5'-CGG CTG CCC ATT GCT ACC ACC ACA GAA TTC GAT CGG CAT ACC ACA ACC ACC CTC CCA CTC CAC AGC-3' (SEQ ID NO: 69) |
| 5-1-2 | 5'-GTG GAG TGG GAG AGC GGT GGT TGT GGT ATG CCG ATC GAA TTC TGT GGT GGT AAT GGG CAG CCG GAG-3' (SEQ ID NO: 70) | 5'-CTC GGC TGC CCA TTA CC ACC ACA GAA TTC GAT CGG CAT ACC ACA ACC ACC GCT CTC CCA CTC CAC-3' (SEQ ID NO: 71) |
| 5-1-3 | 5'-TGG GAG AGC AAT GGG GGT GGT TGT GGT ATG CCG ATC GAA TTC TGT GGT GGT CAG CCG GAG AAC AAC-3' (SEQ ID NO: 72) | 5'-GTT GTT CTC CGG CTG ACC ACC ACA GAA TTC GAT CGG CAT ACC ACA ACC ACC CCC ATT GCT CTC CCA-3' (SEQ ID NO: 73) |
| 5-1-4 | 5'- GAG AGC AAT GGG CAG GGT GGT TGT GGT ATG CCG ATC GAA TTC TGT GGT GGT CCG GAG AAC AAC TAC-3' (SEQ ID NO: 74) | 5'GTA GTT GTT CTC CGG ACC ACC ACA AAM TTC GAT CGG CAT ACC ACA ACC ACC CTG CCC ATT GCT CTC-3' (SEQ ID NO: 75) |

TABLE 7-continued

Primers used in PCR reactions for construction variant Fc-fragment-encoding DNAs

| Variant Fc-fragment designation | Forward Primer | Reverse Primer |
|---|---|---|
| 5-1-5 | 5'-AGC AAT GGG CAG CCG GGT GGT TGT GGT ATG CCG ATC GAA TTC TGT GGT GGT GAG AAC AAC TAC AAG-3' (SEQ ID NO: 76) | 5'-CTT GTA GTT GTT CTC ACC ACC ACA GAA TTC GAT CGG CAT ACC ACA ACC ACC CGG CTG CCC ATT GCT-3' (SEQ ID NO: 77) |
| 5-1-6 | 5'-AAT GGG CAG CCG GAG GGT GGT TGT GGT ATG CCG ATC GAA TTC TGT GGT GGT AAC AAC TAC AAG ACC-3' (SEQ ID NO: 78) | 5'-GGT CTT GTA GTT GTT ACC ACC ACA GAA TTC GAT CGG CAT ACC ACA ACC ACC CTC CGG CTG CCC ATT-3' (SEQ ID NO: 79) |
| 5-1-7 | 5'-GGG CAG CCG GAG AAC GGT GGT TGT GGT ATG CCG ATC GAA TTC TGT GGT GGT AAC TAC AAG ACC ACG-3' (SEQ ID NO: 80) | 5'-CGT GGT CTT GTA GTT ACC ACC ACA GAA TTC GAT CGG CAT ACC ACA ACC ACC GTT CTC CGG CTG CCC-3' (SEQ ID NO: 81) |
| 5-1-8 | 5'-CAG CCG GAG AAC AAC GGT GGT TGT GGT ATG CCG ATC GAA TTC TGT GGT GGT TAC AAG ACC ACG CCT-3' (SEQ ID NO: 82) | 5'-AGG CGT GGT CTT GTA ACC ACC ACA GAA TTC GAT CGG CAT ACC ACA ACC ACC GTT GTT CTC CGG CTG-3' (SEQ ID NO: 83) |
| 5-1-9 | 5'-GTG GAG TGG GAG AGC GGT GGT TGT GGT ATG CCG ATC GAA TTC TGT GGT GGT CCG GAG AAC AAC TAC-3' (SEQ ID NO: 84) | 5'-GTA GTT GTT CTC CGG ACC ACC ACA GAA TTC GAT CGG CAT ACC ACA ACC ACC GCT CTC CCA CTC CAC-3' (SEQ ID NO: 85) |
| 5-1-10 | 5'-GTG GAG TGG GAG AGC GGT GGT GGT TGT GGT ATG CCG ATC GAA TTC TGT GGT GGT GGT CCG GAG AAC AAC TAC-3' (SEQ ID NO: 86) | 5'-GTA GTT GTT CTC CGG ACC ACC ACA GAA TTC GAT CGG CAT ACC ACA ACC ACC ACC GCT CTC CCA CTC CAC-3' (SEQ ID NO: 87) |

Individual colonies were picked, and plasmid DNA was prepared and sequenced. DNA encoding these variant Fc-fragments was introduced into 293-6E cells, and Fc-fragments in conditioned media (CM) from these cells were used in ForteBio binding assays performed as described above. See Example 4.

Figure 6:
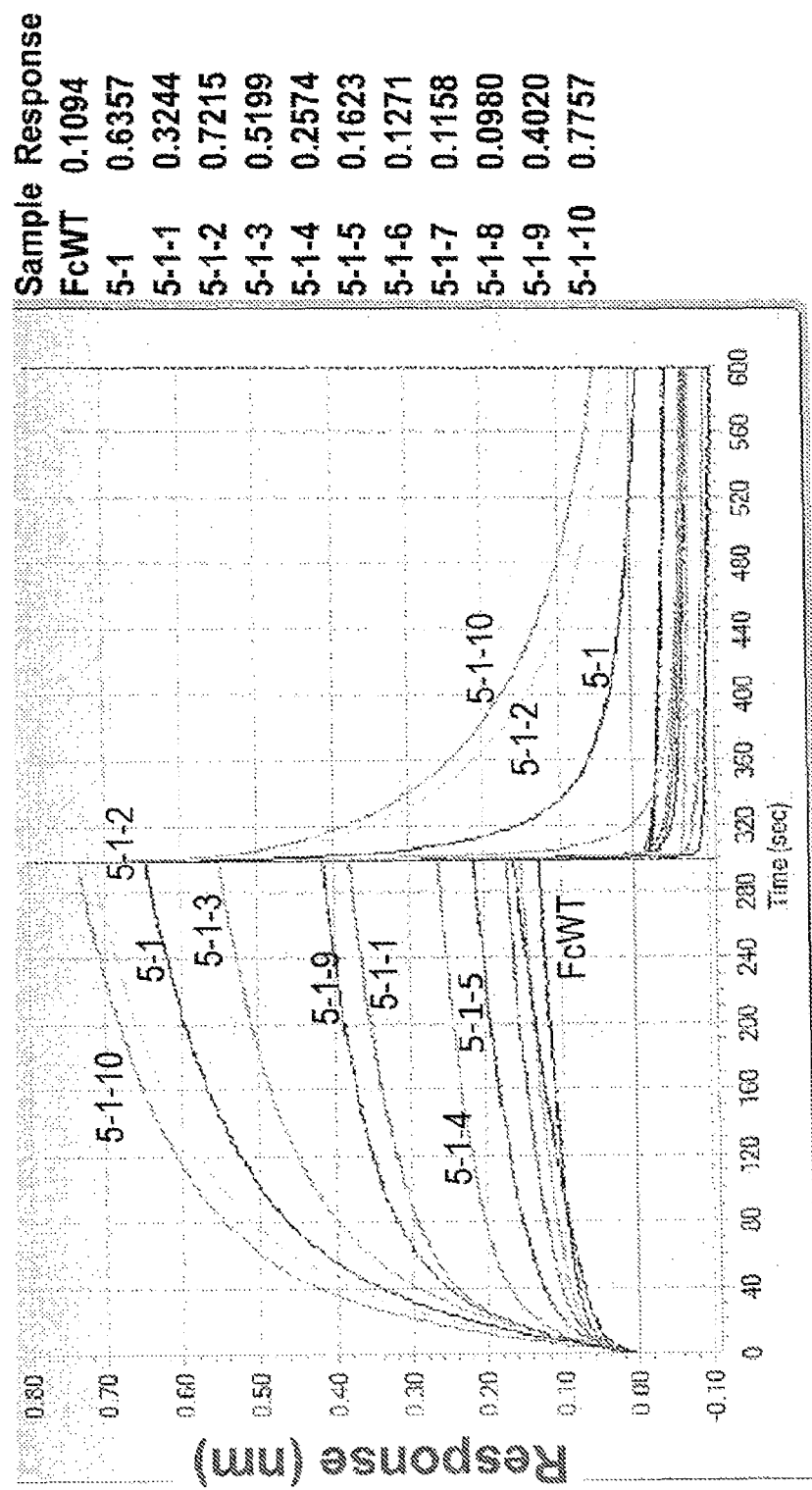
FIG. 6: Association and dissociation curves at pH 6 and pH 7.4, respectively, of variant Fc-fragments having the same insertion at different positions of Loop 10. At left are shown the association curves at pH 6 (to the left of the central vertical line) and dissociation curves at pH 7.4 (to the right of the central vertical line) of the various variant Fc-fragments and a wild type Fc-fragment (FcWT). At right the maximal binding response detected for each variant at pH 6 is shown in tabular form.

The results for binding at pH 6 and dissociation at pH 7 are shown in FIG. 6. Two of the variant Fc-fragments, 5-1-10 and 5-1-2, had a greater maximal response than variant 5-1 at pH 6, but also dissociated more slowly at pH 7.4. See FIG. 6. All other constructs showed a somewhat lesser maximal response, as compared to variant 5-1, at pH 6, but all of these responses were comparable to or higher than that of a wild type Fc-fragment (designated FcWT in FIG. 6). Further, dissociation of these constructs at pH 7.4, unlike that of 5-1, was comparable to that of FcWT. Thus, most of the Fc variants, other than 5-1-2 and 5-1-10 (both of which have an insertion between positions 383 and 384), with insertions within or adjacent to Loop 10 dissociated faster at pH 7.4 than variant 5-1. Also, variants 5-1-1, 5-1-2, 5-1-3, 5-1-9, and 5-1-10 clearly had higher maximal responses that did FcWT at pH 6 variant 5-1, whereas variants 5-1-6, 5-1-7, and 5-1-8 had maximal responses comparable to that of FcWT. Variants 5-1-4 and 5-1-5 had only marginally higher responses than did FcWT. These data indicate that insertion of the peptide had more favorable effects at certain sites within Loop 10. Specifically, insertion between positions 382 and 383, 383 and 384, 384 and 385, 385 and 386 (using the EU numbering system as illustrated in Table 1 and FIG. 5) produced Fc variants that had a greater maximal response at pH 6 than did FcWT plus rapid dissociation at pH 7.4. In contrast, Fc variants having insertions between positions 388 and 389, 389 and 390, or 390 and 391 had properties similar to FcWT. Finally, Fc variants having insertions between 386 and 387 or 387 and 388 showed marginally higher responses at pH 6 than Fc WT and rapid dissociation at pH 7.4. In addition, removal of amino acids 384-386 and insertion of the peptide in their place, as was done in variants 5-1-9 and 5-1-10, also improved the properties of the these Fc variants as compared to FcWT. The slightly longer insertion of 5-1-10, which included three rather than the two glycine residues as in 5-1-9 at the beginning and end of the insertion, had a higher response than any other variant, including 5-1-2, which had an insertion (with no accompanying deletion) between positions 383 and 384. These data indicate that insertions of a peptide that can enhance binding to FcRn within the region between positions 382 and 387 can enhance binding of an Fc-fragment to FcRn at pH 6 while preserving its fast dissociation from FcRn at pH 7.4. On the other hand, insertion of such a peptide between positions 388 and 391 did not substantially enhance binding activity and/or affinity of an Fc-fragment to FcRn at pH 6 as compared to FcWT and also had little or no effect on dissociation at pH 7.4. Thus, these data point to a portion of Loop 10, that is, from position 382 to 386, 387, or 388 (EU numbering), as containing particularly favorable sites for making insertions that can enhance binding activity and/or affinity to FcRn at pH 6.

Example 11

Selection of Variant Fc-Fragment by Yeast Display

To obtain a different group of variant Fc-polypeptides, a selection was performed using yeast display. To make libraries for screening in yeast, three previously made libraries were used as starting points. One of these was library L5, which is described above. See FIG. 2 and Example 2. The two other libraries had insertions at exactly the same site as library L5 and were made using the same general methods that were used to make library L5, but the format of the insertions differed in that library L5 encoded insertions with six randomized amino acids while libraries L-8 and L-10 encoded insertions with eight and ten randomized amino acids, respectively. Specifically, these libraries encoded insertions with the following formats: library L-8, GGC(19R)$_8$CGG (SEQ ID NO:88); and library L-10, GGC(19R)$_{10}$CGG (SEQ ID NO:89). These insertions, like those in library L5, are between the "N" at position 169 and the "G" at position 170 according to the numbering scheme in FIG. 2. The "(19R)$_8$" and "(19R)$_{10}$" indicate eight and ten, respectively, randomized amino acids, which can be any amino acid other than cysteine.

Libraries L5, L-8 and L-10 were digested with SacII and NotI, and the resulting fragments, which encoded the variant Fc-fragments, were purified and ligated into a vector appropriate for expression in both *Escherichia coli* and *Saccharomyces cerevisiae*. The vector also encoded an HA tag (a short peptide sequence (YPYDVPDYA) (SEQ ID NO:575) from human influenza hemagglutinin) in frame with the insertion, which was used to confirm that the Fc regions were displayed on the surface of the yeast cells. These three new libraries were introduced into *E. coli*, specifically, into XL1-Blue supercompetent *E. coli* cells. DNA from about 5×10$^8$ *E. coli* transformants was used to transform about 1–2×10$^9$ *S. cerevisiae* cells using the standard lithium acetate method. An overnight culture of *S. cerevisiae* was diluted to an OD$_{600}$ of 0.2-0.3 in 100 milliliters of yeast extract peptone dextrose medium (which contains 20 g/L bacto-peptone, 10 g/L yeast extract, 2% glucose (YPD)) and grown at 30° C. shaking at 300 revolutions per minute (rpm) until the OD$_{600}$ reached 1.0-2.0. The cells were then washed with 30 milliliters of water and with 30 milliliters of 100 mM LiOAc. For each library, a transformation mixture containing 1M LiOAc, 50% PEG, single stranded carrier DNA, water, and 25 ug of library DNA was added to cells. Each transformation was heat shocked at 42° C. for 45 minutes. The cells were pelleted and then grown in 50 milliliters YPD medium at 30° C. for 1 hour. Cells were pelleted again and washed with 30 milliliters SD-leu medium (14.7 g/L sodium citrate, 4.29 g/L citric acid, 2% dextrose, 6.7 g/L yeast nitrogen base (YNB), 1.6 g/L Yeast Synthetic Drop-out Medium Supplements without Leucine (Sigma, Y1376)). The cells were then resuspended in 10 milliliters of SD-leu media. The 10 milliliters of transformed cells were then inoculated into 300 milliliters SD-leu media and grown overnight at 30° C.

Induction of expression of the variant Fc-fragments in the yeast transformants was accomplished by inoculating an aliquot of an overnight culture (about 10$^8$ cells) into induction medium (5.4 g/L Na$_2$HPO$_4$, 8.56 g/L NaH$_2$PO$_4$, 2% galactose, 6.7 g/L YNB, and 1.6 g/L Yeast Synthetic Drop-out Medium Supplements without Leucine (Sigma, Y1376)) and culturing the cells for about 48 hours at 20° C.

These induced cells were spun down and resuspended in phosphate buffered saline (PBS) buffer (+0.5% BSA) at pH 7.4. Then 0.5-1×10$^8$ induced cells were incubated for one hour with 1 μM biotinylated FcRn (biotin-FcRn). Cells were then washed and incubated with 2 μg/mL labeled streptavidin (streptavidin (SA)-Alexa Fluor® 647 (Catalog number S32357, Invitrogen)) for 15 minutes. Cells were then washed and incubated with anti-Cy5/Anti-Alexa Fluor® 647 Microbeads (Catalog number 130-091-395, MACS Miltenyi Biotec) for 15 minutes. Cells were washed and separated using LS Columns (Catalog number 130-042-401, MACS Miltenyi Biotec) and a QuadroMACS® Separation Unit (Catalog number 130-091-051, MACS Miltenyi Biotec). Aliquots of the pre-column, flow-thru, washes, and elution fractions were collected for FACS analysis. Flow-thru and washes were collected as our depleted population, which contained cells expressing variant Fc-polypeptides that bound to FcRn with very low affinity at pH 7.4.

This depleted population of cells was then grown overnight at 30° C. in SD-leu medium. Cells were then induced for about 48 hours at 20° C. in induction medium as described above. The subsequent wash and incubation steps were performed in MES buffer (20 mM MES, 137 mM NaCl, 0.5% BSA) at pH 5.5. Induced cells were incubated on ice with 250 nM biotin-FcRn for one hour. Subsequently, SA-Alexa Fluor® 647 (2 μg/mL) and anti-HA-FITC (1 μg/mL) were added, and, after being washed and put through a cell strainer, the cells were subjected to FACS analysis at pH 5.5. Gates were set to collect cells that exhibited a robust signal for both FITC and Alexa Fluor®. These cells were then cultured overnight at 30° C. in SD-leu medium and then induced for about 48 hours at 20° C. in induction medium. Then, in a second round, the induced cells were incubated on ice with 25 nM biotin-FcRn for one hour, and the labeling, washing, straining, FACS, culturing, and inductions steps, as described above, were repeated. Finally, in a third round, the induced cells were incubated on ice with 5 nM biotin-FcRn for one hour, followed by the labeling, washing, straining, FACS and culturing steps described above. Hence, the end result was a population of cells expressing Fc-fragments that could bind FcRn with higher affinity than a wild type Fc-fragment could at pH 5.5.

This population of cells was plated, and 500 colonies from Library L5 and 400 colonies from each of Libraries L-8 and L-10 were selected for further analysis. Each of these individual colonies was cultured at 30° C. overnight in SD-leu medium as described above. The sequences of the insertions in each of these isolates was determined from yeast plasmid DNA. In all, 317, 265, and 313 unique sequences were found among these isolates in each of libraries L5, L-8, and L-10, respectively. Cells were then induced at 20° C. for 48 hours in the induction medium described above. The subsequent wash and incubation steps were performed in parallel in MES buffer (20 mM MES, 137 mM NaCl, 0.5% BSA) at pH 5.5 and in PBS buffer (+0.5% BSA) at pH 7.4. About 5×10$^5$ cells per sample were incubated with 250 nM biotin-FcRn and 1 μg/ml anti-HA-FITC for 1 hour. Then cells were washed and incubated with 2 μg/mL SA-Alexa Fluor® 647 for 15 minutes. Cells were washed and analyzed for binding via FACS to determine whether they bound FcRn strongly at pH 5.5 and weakly at pH 7.4. Individual cell lines showing the highest signals for binding to FcRn at pH 5.5, along with a low signal for binding to FcRn at pH 7.4 and few or no methionine or tryptophan residues, were chosen from each library for further analysis. These selected isolates included 158, 59, and 50 cell lines from L5, L-8, and L-10, respectively, and the sequences of the insertions in these isolates are shown in Table 8 below. (Note that the clone named 5y-37 was not included in the further analysis because it was not re-cloned successfully into the appropriate vector.)

TABLE 8

Sequences of variant Fc-polypeptides that bind with high affinity at pH 5.5 and low affinity at pH 7.4

| | LIBRARY L5 | | LIBRARY L-8 | | LIBRARY L-10 |
|---|---|---|---|---|---|
| Clone | INSERTION SEQ (SEQ ID NO) | Clone | INSERTION SEQ (SEQ ID NO) | Clone | INSERTION SEQ (SEQ ID NO) |
| 5y-1 | GGCHFDIMNCGG (SEQ ID NO: 90) | 8y-1 | GGCKTWQLLIFCGG (SEQ ID NO: 248) | 10y-1 | GGCAFEFSSAFNCGG (SEQ ID NO: 307) |
| 5y-2 | GGCVIDFFGCGG (SEQ ID NO: 91) | 8y-2 | GGCEQNWTLYMCGG (SEQ ID NO: 249) | 10y-2 | SGCQTMLTAEGEWCGG (SEQ ID NO: 308) |
| 5y-3 | GGCDIMIFECGG (SEQ ID NO: 92) | 8y-3 | SGCWPSPYIFPCGG (SEQ ID NO: 250) | 10y-3 | GGCVMDLWPDLEICGG (SEQ ID NO: 309) |
| 5y-4 | GGCMTEFAICGG (SEQ ID NO: 93) | 8y-4 | GGCWEALQVNNCGG (SEQ ID NO: 251) | 10y-4 | GGCQPLFDDHDTWCGG (SEQ ID NO: 310) |
| 5y-5 | GGCIQYWQFCGG (SEQ ID NO: 94) | 8y-5 | CGCQAMVVEDLCG (SEQ ID NO: 252) | 10y-5 | GGCPFELVMSDEQCGG (SEQ ID NO: 311) |
| 5y-6 | GGCPFSWAFCGG (SEQ ID NO: 95) | 8y-6 | GGCPLEWPRISCGG (SEQ ID NO: 253) | 10y-6 | SGCGHGMQMDSVFCGG (SEQ ID NO: 312) |
| 5y-7 | GGCGFAFMYCGG (SEQ ID NO: 96) | 8y-7 | GGCEPWIMEANCGG (SEQ ID NO: 254) | 10y-7 | SGCDETQSAIWYFCGG (SEQ ID NO: 313) |
| 5y-8 | GGCPVLLFNCGG (SEQ ID NO: 97) | 8y-8 | GGCPWDQHINFCGG (SEQ ID NO: 255) | 10y-8 | GGCREPEQYWTVWCGG (SEQ ID NO: 314) |
| 5y-9 | GGCPFTWTKCGG (SEQ ID NO: 98) | 8y-9 | GGCPWYIQMDHCGG (SEQ ID NO: 256) | 10y-9 | SGCQEKKDLYWEYCGG (SEQ ID NO: 315) |
| 5y-10 | GGCYLYWQFCGG (SEQ ID NO: 99) | 8y-10 | SGCQPWEISYYCGG (SEQ ID NO: 257) | 10y-10 | SGCGQDNDLPWEWCGG (SEQ ID NO: 316) |
| 5y-11 | GGCVINMFPCGG (SEQ ID NO: 100) | 8y-11 | GGCPVMFLDPRCGG (SEQ ID NO: 258) | 10y-11 | GGCVFQLSFSRSDCGG (SEQ ID NO: 317) |
| 5y-12 | GGCPFTWNTCGG (SEQ ID NO: 101) | 8y-12 | GGCSSDVLMIFCGG (SEQ ID NO: 259) | 10y-12 | SGCAFDMIWFEGVCGG (SEQ ID NO: 318) |
| 5y-13 | GGCPFQIGECGG (SEQ ID NO: 102) | 8y-13 | GGCVDEMVIYHCGG (SEQ ID NO: 260) | 10y-13 | SGCAFYWQPWEHSCGG (SEQ ID NO: 319) |
| 5y-14 | GGCLDIIWMCGG (SEQ ID NO: 103) | 8y-14 | GGCPFMVNLYSCGG (SEQ ID NO: 261) | 10y-14 | GGCQLSIILTGLPCGG (SEQ ID NO: 320) |
| 5y-15 | GGCMFVFPACGG (SEQ ID NO: 104) | 8y-15 | GGCESDTMWYFCGG (SEQ ID NO: 262) | 10y-15 | GGCGMLEWSGLQFCGG (SEQ ID NO: 321) |
| 5y-16 | GGCVMEQLWCGG (SEQ ID NO: 105) | 8y-16 | GGCRSDEIIFFCGG (SEQ ID NO: 263) | 10y-16 | SGCHEKALTYWEFCGG (SEQ ID NO: 322) |
| 5y-17 | GGCFKEYTWCGG (SEQ ID NO: 106) | 8y-17 | GGCPWDLLLPLCGG (SEQ ID NO: 264) | 10y-17 | GGCFENMQVWYNECGG (SEQ ID NO: 323) |
| 5y-18 | GGCPKDYHICGG (SEQ ID NO: 107) | 8y-18 | GGCPWAMELVHCGG (SEQ ID NO: 265) | 10y-18 | GGCPEWENQILLFCGG (SEQ ID NO: 324) |
| 5y-19 | GGCEVMVFPCGG (SEQ ID NO: 108) | 8y-19 | SGCTASMYWEYCGG (SEQ ID NO: 266) | 10y-19 | SGCESWQRDMNYFCGG (SEQ ID NO: 325) |
| 5y-20 | GGCVFNTVFCGG (SEQ ID NO: 109) | 8y-20 | GGCGLYMDPPYYGG (SEQ ID NO: 267) | 10y-20 | SGCNDQFPMYYLFCGG (SEQ ID NO: 326) |
| 5y-21 | GGCNLPQEWCGG (SEQ ID NO: 110) | 8y-21 | GGCPVMVMEPYCGG (SEQ ID NO: 268) | 10y-21 | GGCFEDMALQPTQCGG (SEQ ID NO: 327) |
| 5y-22 | GGCMIAPMYCGG (SEQ ID NO: 111) | 8y-22 | GGCQTEFILEFCGG (SEQ ID NO: 269) | 10y-22 | SGCKGPWQFEFLVCGG (SEQ ID NO: 328) |
| 5y-23 | GGCMMLYPMCGG (SEQ ID NO: 112) | 8y-23 | SGCAFQAHGAMCGG (SEQ ID NO: 270) | 10y-23 | GGCEAFSMKFNDFCGG (SEQ ID NO: 329) |
| 5y-24 | GGCIIGPFLCGG (SEQ ID NO: 113) | 8y-24 | GGCPDFMFRMNCGG (SEQ ID NO: 271) | 10y-24 | GGCVQPAIAMWPFCGG (SEQ ID NO: 330) |

TABLE 8-continued

Sequences of variant Fc-polypeptides that bind with high affinity at pH 5.5 and low affinity at pH 7.4

| LIBRARY L5 | | LIBRARY L-8 | | LIBRARY L-10 | |
|---|---|---|---|---|---|
| Clone | INSERTION SEQ (SEQ ID NO) | Clone | INSERTION SEQ (SEQ ID NO) | Clone | INSERTION SEQ (SEQ ID NO) |
| 5y-25 | GGCTGMVFFCGG (SEQ ID NO: 114) | 8y-25 | SGCSVWFDTISCGG (SEQ ID NO: 272) | 10y-25 | GGCTDQGRFVLYECGG (SEQ ID NO: 331) |
| 5y-26 | GGCLMYKNVCGG (SEQ ID NO: 115) | 8y-26 | GGCPWSMEISNCGG (SEQ ID NO: 273) | 10y-26 | GGCPVQEFLWGVYCGG (SEQ ID NO: 332) |
| 5y-27 | GGCAFGIMWCGG (SEQ ID NO: 116) | 8y-27 | GGCPTWNWEITCGG (SEQ ID NO: 274) | 10y-27 | GGCSNSWEWTLYACGG (SEQ ID NO: 333) |
| 5y-28 | GGCRHRKKWCGG (SEQ ID NO: 117) | 8y-28 | SGCPWDMHIVDCGG (SEQ ID NO: 275) | 10y-28 | SGCHGLVEWGYMACGG (SEQ ID NO: 334) |
| 5y-29 | GGCFMGIWQCGG (SEQ ID NO: 118) | 8y-29 | SGCFPWEPAYFCGG (SEQ ID NO: 276) | 10y-29 | SGCEAFGLIFEDFCGG (SEQ ID NO: 335) |
| 5y-30 | GGCPSLPQFCGG (SEQ ID NO: 119) | 8y-30 | GGCPFGWNVFHCGG (SEQ ID NO: 277) | 10y-30 | GGCANPEFQMWYFCGG (SEQ ID NO: 336) |
| 5y-31 | GGCPSVFTWCGG (SEQ ID NO: 120) | 8y-31 | GGCPWHMEVNECGG (SEQ ID NO: 278) | 10y-31 | SGCGYEVPIPLFTCGG (SEQ ID NO: 337) |
| 5y-32 | GGCQEYWEFCGG (SEQ ID NO: 121) | 8y-32 | GGCPFALGMGECGG (SEQ ID NO: 279) | 10y-32 | GGCWFQQFAWRATCGG (SEQ ID NO: 338) |
| 5y-33 | GGCQWPTEFCGG (SEQ ID NO: 122) | 8y-33 | GGCMFPFMLSNCGG (SEQ ID NO: 280) | 10y-33 | GGCGFELNMISQYCGG (SEQ ID NO: 339) |
| 5y-34 | GGCIKFFDWCGG (SEQ ID NO: 123) | 8y-34 | GGCAFQFMPAHCGG (SEQ ID NO: 281) | 10y-34 | GGCEPFELRFYHEGCGG (SEQ ID NO: 340) |
| 5y-35 | GGCEMSFFLCGG SEQ ID NO: 124) | 8y-35 | GGCQIQGFEFTCGG (SEQ ID NO: 282) | 10y-35 | GGCPFQLVWSPAFCGG (SEQ ID NO: 341) |
| 5y-36 | GGCHSEVEYCGG (SEQ ID NO: 125) | 8y-36 | GGCPMGIILDLCGG (SEQ ID NO: 283) | 10y-36 | SGCAWEIKGIWCGG (SEQ ID NO: 342) |
| 5y-37 | GGCWEHPHYCGG (SEQ ID NO: 126) | 8y-37 | GGCLMLEPTVTCGG (SEQ ID NO: 284) | 10y-37 | SGCSSIQSWRLWLCGG (SEQ ID NO: 343) |
| 5y-38 | GGCETYWLFCGG (SEQ ID NO: 127) | 8y-38 | GGCGKNEVAMFCGG (SEQ ID NO: 285) | 10y-38 | GGCGVMQVLNRAHCGG (SEQ ID NO: 344) |
| 5y-39 | GGCRVPYPSCGG (SEQ ID NO: 128) | 8y-39 | GGCSFLLEIANCGG (SEQ ID NO: 286) | 10y-39 | RGCQVKYYMGEGDCGG (SEQ ID NO: 345) |
| 5y-40 | GGCGWPFVMCGG (SEQ ID NO: 129) | 8y-40 | GGCDVEKIMIFCGG (SEQ ID NO: 287) | 10y-40 | GGCPVWIPFHWEECGG (SEQ ID NO: 346) |
| 5y-41 | GGCMLFLESCGG (SEQ ID NO: 130) | 8y-41 | GGCFPMTPWGLCGG (SEQ ID NO: 288) | 10y-41 | SGCLLWQQSMLLFCGG (SEQ ID NO: 347) |
| 5y-42 | GGCFHVKRWCGG (SEQ ID NO: 131) | 8y-42 | SGCDWYLEWSGNCGG (SEQ ID NO: 289) | 10y-42 | SGCEQQWSWRLYLCGG (SEQ ID NO: 348) |
| 5y-43 | GGCVWEQEHCGG (SEQ ID NO: 132) | 8y-43 | GGCGVEIMFHGCGG (SEQ ID NO: 290) | 10y-43 | GGCSVQSTWQLWACGG (SEQ ID NO: 349) |
| 5y-44 | GGCILHFKDCGG (SEQ ID NO: 133) | 8y-44 | GGCMDGLHLYFCGG (SEQ ID NO: 291) | 10y-44 | SGCKYPIFWDTIDCGG (SEQ ID NO: 350) |
| 5y-45 | GGCHFEVFQCGG (SEQ ID NO: 134) | 8y-45 | SGCPIFIFDYYCGG (SEQ ID NO: 292) | 10y-45 | SGCVEYQYQMVYFCGG (SEQ ID NO: 351) |
| 5y-46 | GGCVFEVMQCGG (SEQ ID NO: 135) | 8y-46 | GGCAVWIFSDACGG (SEQ ID NO: 293) | 10y-46 | GGCTDQRWFVLYECGG (SEQ ID NO: 352) |
| 5y-47 | GGCMTEFSWCGG (SEQ ID NO: 136) | 8y-47 | GGCPWSLHIQQCGG (SEQ ID NO: 294) | 10y-47 | GGCPFWQEWHLSYCGG (SEQ ID NO: 353) |
| 5y-48 | GGCEGNMRFCGG (SEQ ID NO: 137) | 8y-48 | SGCAFSMLFINCGG (SEQ ID NO: 295) | 10y-48 | SGCYMGYMHLIAECGG (SEQ ID NO: 354) |

TABLE 8-continued

Sequences of variant Fc-polypeptides that bind with high affinity at pH 5.5 and low affinity at pH 7.4

| LIBRARY L5 | | LIBRARY L-8 | | LIBRARY L-10 | |
|---|---|---|---|---|---|
| Clone | INSERTION SEQ (SEQ ID NO) | Clone | INSERTION SEQ (SEQ ID NO) | Clone | INSERTION SEQ (SEQ ID NO) |
| 5y-49 | GGCKGHMWYCGG (SEQ ID NO: 138) | 8y-49 | SGCLPWELYMFCGG (SEQ ID NO: 296) | 10y-49 | GGCFMGSFSLVYGCGG (SEQ ID NO: 355) |
| 5y-50 | GGCEAYWQFCGG (SEQ ID NO: 139) | 8y-50 | SGCPFTINFYTCGG (SEQ ID NO: 297) | 10y-50 | SGCPWGFMFPISYCGG (SEQ ID NO: 356) |
| 5y-51 | GGCVFSRFWCGG (SEQ ID NO: 140) | 8y-51 | GGCPIWFTWSTCGG (SEQ ID NO: 298) | | |
| 5y-52 | GGCMMPFWPCGG (SEQ ID NO: 141) | 8y-52 | GGCQIQVVNPYCGG (SEQ ID NO: 299) | | |
| 5y-53 | GGCIFQFEMCGG (SEQ ID NO: 142) | 8y-53 | GGCAFQIEFLMCGG (SEQ ID NO: 300) | | |
| 5y-54 | GGCKRQMWYCGG (SEQ ID NO: 143) | 8y-54 | GGCAWEIRILGCGG (SEQ ID NO: 301) | | |
| 5y-55 | GGCKTPNPWCGG (SEQ ID NO: 144) | 8y-55 | GGCPYQLVIMWCGG (SEQ ID NO: 302) | | |
| 5y-56 | GGCKAFYPWCGG (SEQ ID NO: 145) | 8y-56 | GGCMFAMHVFGCGG (SEQ ID NO: 303) | | |
| 5y-57 | GGCKMYQYDCGG (SEQ ID NO: 146) | 8y-57 | SGCTVMYTLQIFGG (SEQ ID NO: 304) | | |
| 5y-58 | GGCYPDNMFCGG (SEQ ID NO: 147) | 8y-58 | SGCAHQVYWAFCGG (SEQ ID NO: 305) | | |
| 5y-59 | GGCQVKIFWCGG (SEQ ID NO: 148) | 8y-59 | GGCPNFFNFWFCGG (SEQ ID NO: 306) | | |
| 5y-60 | GGCSIPQEWCGG (SEQ ID NO: 149) | | | | |
| 5y-61 | GGCKMYQATCGG (SEQ ID NO: 150) | | | | |
| 5y-62 | GGCQYERWHCGG (SEQ ID NO: 151) | | | | |
| 5y-63 | GGCRFQHQWCGG (SEQ ID NO: 152) | | | | |
| 5y-64 | GGCQNMFWQCGG (SEQ ID NO: 153) | | | | |
| 5y-65 | GGCVMEIVFCGG (SEQ ID NO: 154) | | | | |
| 5y-66 | GGCILNFNMCGG (SEQ ID NO: 155) | | | | |
| 5y-67 | GGCMHMDYFCGG (SEQ ID NO: 156) | | | | |
| 5y-68 | GGCQVMVLPCGG (SEQ ID NO: 157) | | | | |
| 5y-69 | GGCLFDWPSCGG (SEQ ID NO: 158) | | | | |
| 5y-70 | GGCKMYHQTCGG (SEQ ID NO: 159) | | | | |
| 5y-71 | GGCQWLYESCGG (SEQ ID NO: 160) | | | | |
| 5y-72 | GGCFTNFWLCGG (SEQ ID NO: 161) | | | | |

TABLE 8-continued

Sequences of variant Fc-polypeptides that bind with high affinity at pH 5.5 and low affinity at pH 7.4

| LIBRARY L5 | | LIBRARY L-8 | | LIBRARY L-10 | |
|---|---|---|---|---|---|
| Clone | INSERTION SEQ (SEQ ID NO) | Clone | INSERTION SEQ (SEQ ID NO) | Clone | INSERTION SEQ (SEQ ID NO) |
| 5y-73 | GGCWEPTHWCGG (SEQ ID NO: 162) | | | | |
| 5y-74 | GGCAFAMLQCGG (SEQ ID NO: 163) | | | | |
| 5y-75 | GGCMYQRQAWCGG (SEQ ID NO: 164) | | | | |
| 5y-76 | GGCPFLWAECGG (SEQ ID NO: 165) | | | | |
| 5y-77 | GGCMFDHKVCGG (SEQ ID NO: 166) | | | | |
| 5y-78 | GGCMEIFNFCGG (SEQ ID NO: 167) | | | | |
| 5y-79 | GGCVMERLWCGG (SEQ ID NO: 168) | | | | |
| 5y-80 | GGCEYYWQFCGG (SEQ ID NO: 169) | | | | |
| 5y-81 | GGCPFSWDQCGG (SEQ ID NO: 170) | | | | |
| 5y-82 | GGCIEYFSWCGG (SEQ ID NO: 171) | | | | |
| 5y-83 | GGCVFEIMKCGG (SEQ ID NO: 172) | | | | |
| 5y-84 | GGCESPQYFCGG (SEQ ID NO: 173) | | | | |
| 5y-85 | GGCHHDFEWCGG (SEQ ID NO: 174) | | | | |
| 5y-86 | GGCMFPFSWCGG (SEQ ID NO: 175) | | | | |
| 5y-87 | GGCNTVLQECGG (SEQ ID NO: 176) | | | | |
| 5y-88 | GGCVFDIMLCGG (SEQ ID NO: 177) | | | | |
| 5y-89 | GGCMYQQPWCGG (SEQ ID NO: 178) | | | | |
| 5y-90 | GGCKKLYHYCGG (SEQ ID NO: 179) | | | | |
| 5y-91 | GGCPHWPFECGG (SEQ ID NO: 180) | | | | |
| 5y-92 | GGCPIFPMICGG (SEQ ID NO: 181) | | | | |
| 5y-93 | GGCMSKDLWCGG (SEQ ID NO: 182) | | | | |
| 5y-94 | GGCMFQMGVCGG (SEQ ID NO: 183) | | | | |
| 5y-95 | GGCYEWPSYCGG (SEQ ID NO: 184) | | | | |
| 5y-96 | GGCQMLYMDCGG (SEQ ID NO: 185) | | | | |

TABLE 8-continued

Sequences of variant Fc-polypeptides that bind with high affinity at pH 5.5 and low affinity at pH 7.4

| LIBRARY L5 | | LIBRARY L-8 | | LIBRARY L-10 | |
|---|---|---|---|---|---|
| Clone | INSERTION SEQ (SEQ ID NO) | Clone | INSERTION SEQ (SEQ ID NO) | Clone | INSERTION SEQ (SEQ ID NO) |
| 5y-97 | GGCTVQVFFCGG (SEQ ID NO: 186) | | | | |
| 5y-98 | GGCITFPMMCGG (SEQ ID NO: 187) | | | | |
| 5y-99 | GGCVMYWEYCGG (SEQ ID NO: 188) | | | | |
| 5y-100 | GGCMWEVLHCGG (SEQ ID NO: 189) | | | | |
| 5y-101 | GGCMQERSWCGG (SEQ ID NO: 190) | | | | |
| 5y-102 | GGCVFETIQCGG (SEQ ID NO: 191) | | | | |
| 5y-103 | GGCQWANSYCGG (SEQ ID NO: 192) | | | | |
| 5y-104 | GGCKFGQVVYCGG (SEQ ID NO: 193) | | | | |
| 5y-105 | GGCVFDQMWCGG (SEQ ID NO: 194) | | | | |
| 5y-106 | GGCEVMIFNCGG (SEQ ID NO: 195) | | | | |
| 5y-107 | GGCESPMFVCGG (SEQ ID NO: 196) | | | | |
| 5y-108 | GGCITMFQNCGG (SEQ ID NO: 197) | | | | |
| 5y-109 | GGCVFERMFCGG (SEQ ID NO: 198) | | | | |
| 5y-110 | GGCGFEIFMCG (SEQ ID NO: 199) | | | | |
| 5y-111 | GGCLLQFTGCGG (SEQ ID NO: 200) | | | | |
| 5y-112 | GGCHFQIFQCGG (SEQ ID NO: 200) | | | | |
| 5y-113 | GGCPFDWDKCGG (SEQ ID NO: 202) | | | | |
| 5y-114 | GGCVTPLPFCG (SEQ ID NO: 203) | | | | |
| 5y-115 | GGCYMYMDYCGG (SEQ ID NO: 204) | | | | |
| 5y-116 | GGCMFEWYVCGG (SEQ ID NO: 205) | | | | |
| 5y-117 | GGCPFTWRICGG (SEQ ID NO: 206) | | | | |
| 5y-118 | GGCENDWKMCGG (SEQ ID NO: 207) | | | | |
| 5y-119 | GGCAFEFIYCGG (SEQ ID NO: 208) | | | | |
| 5y-120 | GGCPVAVFMCGG (SEQ ID NO: 209) | | | | |

TABLE 8-continued

Sequences of variant Fc-polypeptides that bind with high affinity at pH 5.5 and low affinity at pH 7.4

| LIBRARY L5 | | LIBRARY L-8 | | LIBRARY L-10 | |
|---|---|---|---|---|---|
| Clone | INSERTION SEQ (SEQ ID NO) | Clone | INSERTION SEQ (SEQ ID NO) | Clone | INSERTION SEQ (SEQ ID NO) |
| 5y-121 | GGCHFDIFDCGG (SEQ ID NO: 210) | | | | |
| 5y-122 | GGCPPENMFCGG (SEQ ID NO: 211) | | | | |
| 5y-123 | GGCPFQMGECGG (SEQ ID NO: 212) | | | | |
| 5y-124 | GGCISGFFWCGG (SEQ ID NO: 213) | | | | |
| 5y-125 | GGCPFHFQVCGG (SEQ ID NO: 214) | | | | |
| 5y-126 | GGCMFQIINCGG (SEQ ID NO: 215) | | | | |
| 5y-127 | GGCQYFLPCGG (SEQ ID NO: 216) | | | | |
| 5y-128 | GGCHFAVLDCGG (SEQ ID NO: 217) | | | | |
| 5y-129 | GGCWNVMGLCGG (SEQ ID NO: 218) | | | | |
| 5y-130 | GGCYTTHELCGG (SEQ ID NO: 219) | | | | |
| 5y-131 | GGCLYKQVDCGG (SEQ ID NO: 220) | | | | |
| 5y-132 | GGCVFSALWCGG (SEQ ID NO: 221) | | | | |
| 5y-133 | GGCPFQFQTCGG (SEQ ID NO: 222) | | | | |
| 5y-134 | GGCAFLMMDCGG (SEQ ID NO: 223) | | | | |
| 5y-135 | GGCEVWYEFCGG (SEQ ID NO: 224) | | | | |
| 5y-136 | GGCAFDIGVCGG (SEQ ID NO: 225) | | | | |
| 5y-137 | GGCLSPLMWCGG (SEQ ID NO: 226) | | | | |
| 5y-138 | GGCPFSWVICGG (SEQ ID NO: 227) | | | | |
| 5y-139 | GGCMLMFQGCGG (SEQ ID NO: 228) | | | | |
| 5y-140 | GGCQPNHWLCGG (SEQ ID NO: 229) | | | | |
| 5y-141 | GGCIDTYVWCGG (SEQ ID NO: 230) | | | | |
| 5y-142 | GGCHFHLMFCGG (SEQ ID NO: 231) | | | | |
| 5y-143 | GGCQMIFSTCGG (SEQ ID NO: 232) | | | | |
| 5y-144 | GGCKMYQPDCGG (SEQ ID NO: 233) | | | | |

TABLE 8-continued

Sequences of variant Fc-polypeptides that bind with high affinity at pH 5.5 and low affinity at pH 7.4

| LIBRARY L5 | | LIBRARY L-8 | | LIBRARY L-10 | |
|---|---|---|---|---|---|
| Clone | INSERTION SEQ (SEQ ID NO) | Clone | INSERTION SEQ (SEQ ID NO) | Clone | INSERTION SEQ (SEQ ID NO) |
| 5y-145 | GGCMWGVFKCGG (SEQ ID NO: 234) | | | | |
| 5y-146 | GGCGLFGQSCGG (SEQ ID NO: 235) | | | | |
| 5y-147 | GGCQFNFPWCGG (SEQ ID NO: 236) | | | | |
| 5y-148 | GGCNIAYPWCGG (SEQ ID NO: 237) | | | | |
| 5y-149 | GGCKTIPIFCGG (SEQ ID NO: 238) | | | | |
| 5y-150 | GGCOMELFLOGG (SEQ ID NO: 239) | | | | |
| 5y-151 | GGCLGAFYWCGG (SEQ ID NO: 240) | | | | |
| 5y-152 | GGCPFNFASCGG (SEQ ID NO: 241) | | | | |
| 5y-153 | GGCQFDILWCGG (SEQ ID NO: 242) | | | | |
| 5y-154 | GGCYYTHELCGG (SEQ ID NO: 243) | | | | |
| 5y-155 | GGCQQRWRYCGG (SEQ ID NO: 244) | | | | |
| 5y-156 | GGCLWVDEYCGG (SEQ ID NO: 245) | | | | |
| 5y-157 | GGCGMLGWFCGG (SEQ ID NO: 246) | | | | |
| 5y-158 | GGCWEQHYLCGG (SEQ ID NO: 247) | | | | |

Selected individual clones from each library were pooled and DNA was isolated using the Zymoprep Yeast Plasmid Miniprep II Kit (D2004, Zymo Research). PCR was performed on the pooled DNA using forward primer (5' GGA AAA GTC GAC TAG ACC ACC ATG GA 3' (SEQ ID NO:357)) and reverse primer (5' CTT TGC GGC CGC TCA TTA TTT 3' (SEQ ID NO:358)). A PCR Core Kit (Roche, Catalog No. 11 578 553 001) was used with the following reaction conditions: 95° C. for 5 minutes, followed by 30 cycles of 95° C. for 45 seconds, 55° C. for 45 seconds, 72° C. for 90 seconds, and finally 72° C. 10 minutes. The PCR reaction and a mammalian expression vector were digested overnight at 37° C. with SalI and NotI restriction enzymes (New England Biolabs). The digested DNA was gel purified using the QIAquick Gel Purification Kit (28704, Qiagen). The digested vector DNA and PCR products were ligated using T4 DNA ligase (New England Biolabs) and incubated at 16° C. overnight. The ligated DNA was used to transform XL10-gold Ultracompetent *E. coli* cells (#200315, Stratagene), and individual clones were selected. Plasmid DNA from an *E. coli* clone containing DNA encoding each selected variant Fc-polypeptide were introduced into 293-6E mammalian cells. Specifically, 293-6E cells were seeded at 5×10$^4$ cells/well in poly-D-lysine-coated, 96 well flat bottom microtiter plates and incubated overnight at 37° C. Then 200 ng of plasmid DNA was transfected into the cells using the Fugene® HD transfection reagent (#E2312, Promega) and incubated overnight at 37° C. The following day the growth media was changed to serum free media containing 0.5% Tryptone. Conditioned media was collected after another 6 days of growth at 37° C. The conditioned media, which contained the variant Fc-fragments, was then tested for binding to FcRn using the ForteBio technology described in Example 4. Association and dissociation curves at pH 6 and 7.4, respectively, from variant Fc-fragments having the most favorable binding profiles are shown in FIG. 7.

Figure 7:
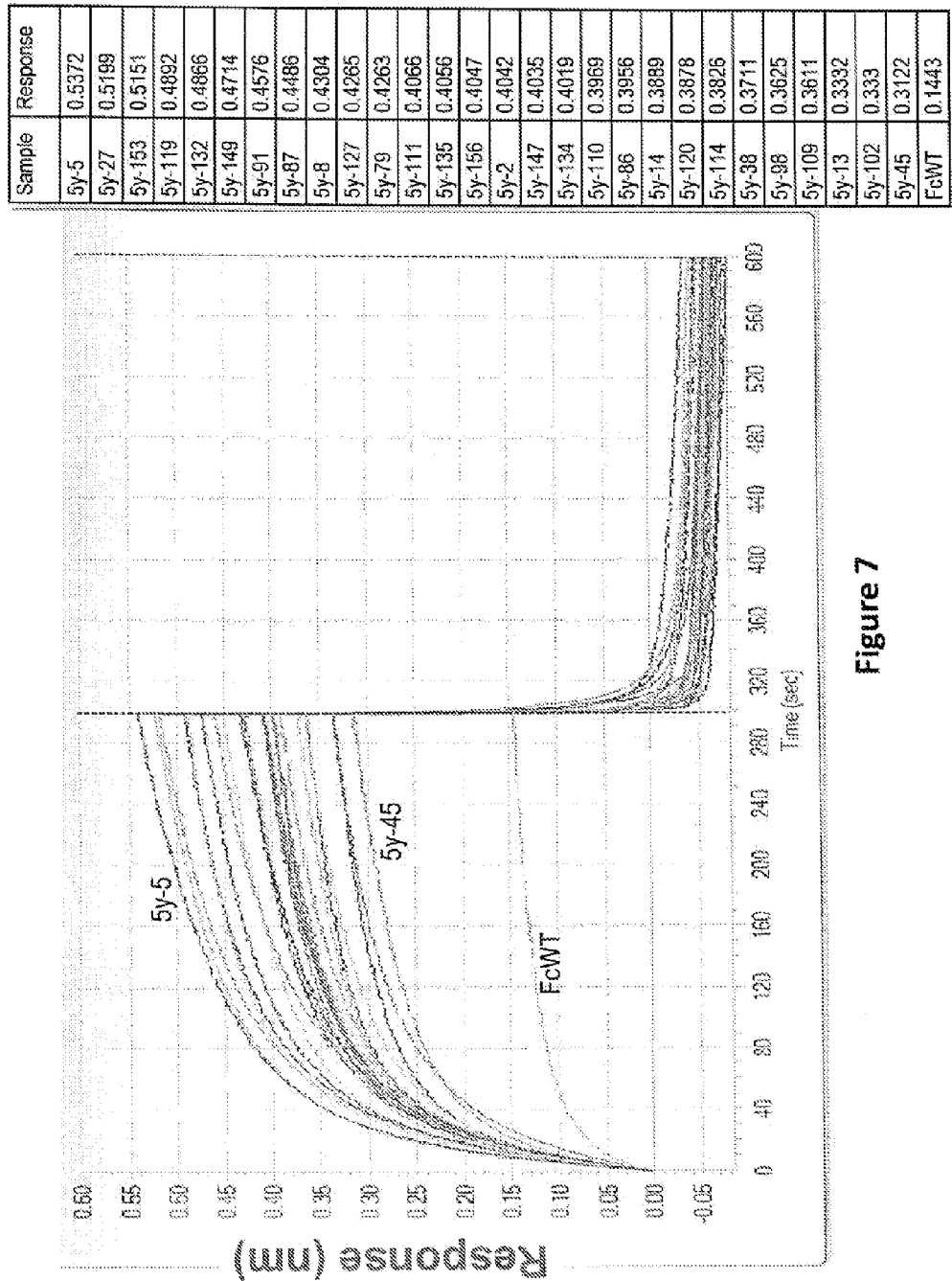
FIG. 7: Association and dissociation curves at pH 6 and pH 7.4 of variant Fc-fragments from library L5 screened in yeast. At left are shown the association curves at pH 6 (to the left of the central vertical line) and dissociation curves at pH 7.4 (to the right of the central vertical line) of the various variant Fc-fragments and a wild type Fc-fragment (FcWT). At right the maximal binding response detected for each variant at pH 6 is shown in tabular form.
Figure 8:
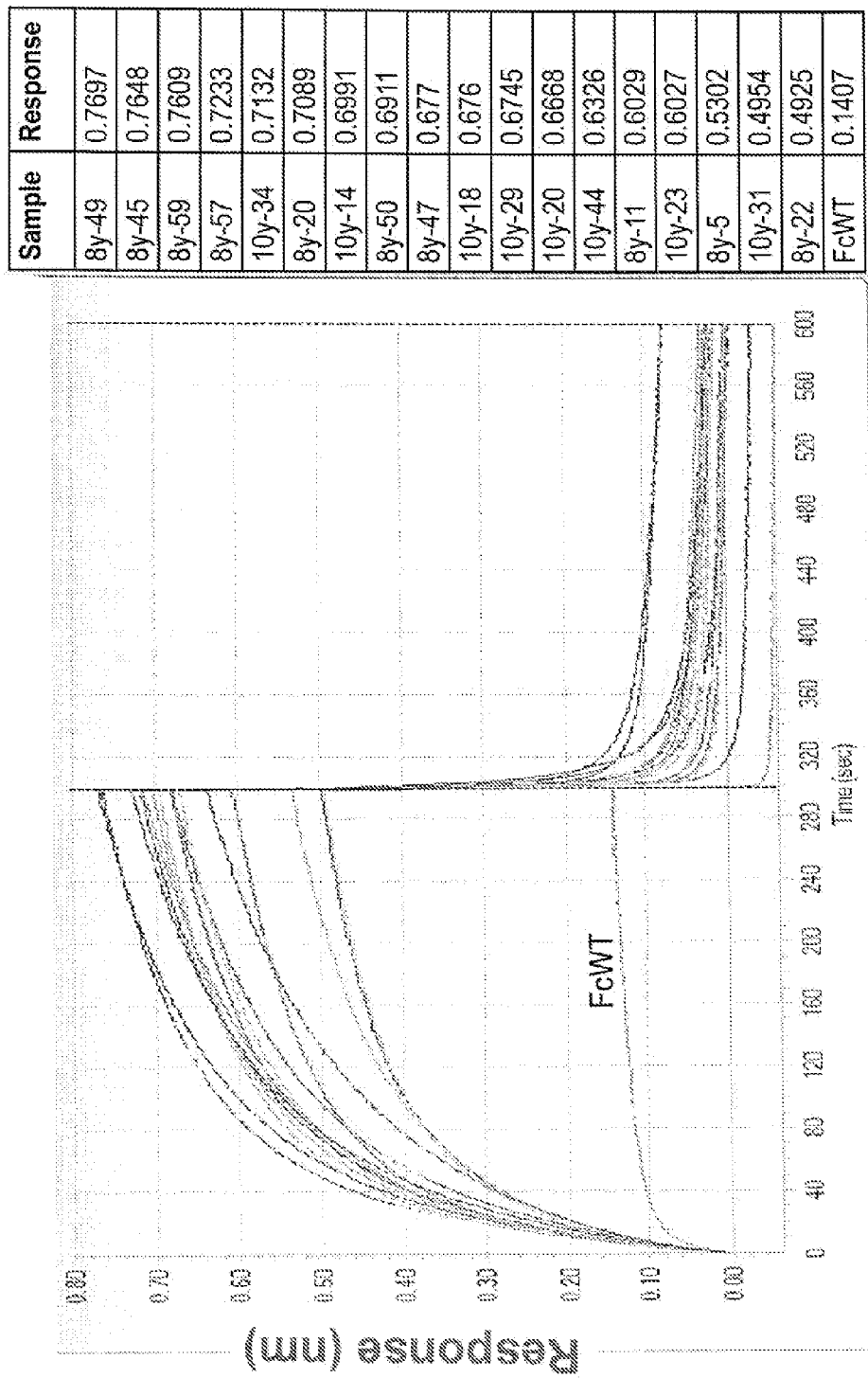
FIG. 8: Association and dissociation curves at pH 6 and pH 7.4 of variant Fc-fragments from library L-8 and L-10 screened in yeast. At left are shown the association curves at pH 6 (to the left of the central vertical line) and dissociation curves at pH 7.4 (to the right of the central vertical line) of the various variant Fc-fragments and a wild type Fc-fragment (FcWT). At right the maximal binding response detected for each variant at pH 6 is shown in tabular form.

FIG. 7 shows association and dissociation profiles for FcRn binding at pH 6 and pH 7.4, respectively, of the 28 best variant Fc-fragments from yeast library L5, as well as a wild type Fc-fragment (FcWT), and FIG. 8 shows FcRn binding profiles for the 18 best variant Fc-fragments selected from yeast libraries L-8 and L-10. All of the L5 variant Fc-fragments had a much higher maximal response at pH 6, that is, higher binding activity, than FcWT. At pH 7.4, all dissociated rapidly, that is, had little or no binding activity, similar to FcWT. All of the L-8 and L-10 variant Fc-fragments had a much higher maximal response at pH 6, that is, higher binding activity, than FcWT. At pH 7.4, all dissociated rapidly, although most showed low levels of residual binding not observed in FcWT. Thus, all of these variant Fc-fragments have favorable properties as compared to FcWT. Therefore, insertions of peptides with different lengths can be successfully used to enhance binding activity to FcRn at pH 6 while preserving rapid dissociation from FcRn at pH 7.4 with little or no residual binding.

Example 12

In Vivo Characterization of Variant Fc-Fragments Selected in Yeast

To determine whether antibodies containing the variant Fc-fragments identified in the yeast screen described above have improved pharmacokinetic (PK) properties in vivo, an unmodified Antibody X (which is a human IgG2 anti-human IL-23 antibody) and variant versions of Antibody X containing variant Fc-fragments were tested in vivo in cynomolgus monkeys to define pharmacokinetic parameters. Antibody X was selected as an appropriate antibody in which to test the pharmacokinetic parameters of the variant Fc-fragments because it was known to have a linear pK profile and because IL-23 was known to be expressed at low levels in viva. Thus, it was expected that target-related effects on PK parameters would be minimal, making it easier to detect pK effects due to the variant Fc-fragments.

Six variant IgG2 antibodies called (X-5y-8, X-5y-132, X-5y-38, X-5y-91, X-5y-119, and X-5y-127) were made. These IgG2 antibodies had the same insertions at the same positions as the variant IgG1 Fc-fragments 5y-8, 5y-132, 5y-38, 5y-91, 5y-119, and 5y-127, respectively. A plasmid containing DNA encoding the heavy chain of Antibody X was used as a template for five PCR reactions done using the following primers: for X-5y-8, forward, 5'-GAG TGG GAG AGC AAT GGT GGT TGT CCG GTT CTG CTG TTC AAC TGT GGT GGT GGG CAG CCG GAG AAC-3' (SEQ ID NO:380), and reverse, 5'-GTT CTC CGG CTG CCC ACC ACC ACA GTT GAA CAG CAG AAC CGG ACA ACC ACC ATT GCT CTC CCA CTC-3'(SEQ ID NO:381); for X-5y-132, forward, 5'-GAG TGG GAG AGC MT GGT GGT TGT GTT TTC TCT GCT CTG TGG TGT GGT GGT GGG CAG CCG GAG AAC-3'(SEQ ID NO:382), and reverse, 5'-GTT CTC CGG CTG CCC ACC ACC ACA CCA CAG AGC AGA GAA MC ACA ACC ACC ATT GCT CTC CCA CTC-3' (SEQ ID NO:383); for X-5y-38, forward, 5'-GAG TGG GAG AGC AAT GGT GGT TGT GAA ACT TAC TGG TTG TTC TGT GGT GGT GGG CAG CCG GAG MC-3' (SEQ ID NO:384), and reverse, 5'-GTT CTC CGG CTG CCC ACC ACC ACA GAA CAA CCA GTA AGT TTC ACA ACC ACC ATT GCT CTC CCA CTC-3' (SEQ ID NO:385); for X-5y-91, forward, 5'-GAG TGG GAG AGC AAT GGT GGT TGT CCG CAT TGG CCG TTC GAA TGT GGT GGT GGG CAG CCG GAG AAC-3' (SEQ ID NO:386), and reverse, 5'-GTT CTC CGG CTG CCC ACC ACC ACA TTC GAA CGG CCA ATG CGG ACA ACC ACC ATT GCT CTC CCA CTC-3' (SEQ ID NO:387); for X-5y-119, forward, 5'-GAG TGG GAG AGC AAT GGT GGT TGT GCT TTC GAA TTC ATC TAC TGT GGT GGT GGG CAG CCG GAG MC-3' (SEQ ID NO:388), and reverse, 5'-GTT CTC CGG CTG CCC ACC ACC ACA GTA GAT GAA TTC GAA AGC ACA ACC ACC ATT GCT CTC CCA CTC-3' (SEQ ID NO:389); and for X-5y-127, forward, 5'-GAG TGG GAG AGC AAT GGT GGT TGT CAG TAC TTC TTG CCG TGT GGT GGT GGG CAG CCG GAG MC-3' (SEQ ID NO:390), and reverse 5'-GTT CTC CGG CTG CCC ACC ACC ACA CGG CM GAA GTA CTG ACA ACC ACC ATT GCT CTC CCA CTC-3' (SEQ ID NO:391). The Quikchange Site-Directed Mutagenesis Kit (Stratagene, 200518) protocol was used. The reaction mixture was 200 nM dNTPs, 100 nM primers, 1 ng DNA template, 1 µL DNA polymerase and water in a total volume of 50 µL. The reaction was run at 95° C. for 30 seconds, then 16 cycles of 95° C. for 30 seconds, 55° C. for 60 seconds, 68° C. for 6 minutes, followed by 68° C. for 10 minutes. Then 1 µL of DpnI was added, and the reaction was incubated at 37° C. for 1 hour. Then 2 µL of the mixture was used to transform 30 µl of XL1-blue supercompetent cells (Stratagene) at 42° C. for 45 seconds. Thereafter, 0.5 mL SOC was added, and the cells were incubated at 37° C. for 1 hour on a is shaker at 300 rpm. The transformed cells were spread on LB-ampicillin agar plates and incubated at 37° C. overnight. Individual colonies were picked, and plasmid DNA was prepared and sequenced to ensure that the isolates chosen had the expected DNA sequence.

Antibodies were prepared in essentially the same way as described above for Fc-fragments, except that the mammalian host cells were transfected with DNAs encoding both the IgG2 heavy chain, including a portion encoding either a variant or a control Fc-fragment, and the light chain of Antibody X. Host cells were incubated under conditions appropriate for expression of the antibodies, and the antibodies were recovered from the culture medium, purified as described above, and used for the following experiments.

Cynomolgus monkeys (n=2/group) received a single intravenous dose of an unmodified or a variant version of Antibody X at a dose of 1 mg/kg and were followed during an 8-week in-life phase. Antibody X-5-112, which was previously tested, was used as a control, as well as Antibody X itself. Samples of blood were collected at specified time points over the course of the experiment. Samples were collected at pre-dose, 0.25, 1, 4, 8, 12, 24, 48, 72, 168, 240, 336, 408, 504, 576, 672, 744, 840, 1008, 1176 and 1344 hours post-dose. The antibodies were detected in blood samples and the pharmacokinetic analysis was performed essentially as described above in Example 9.

Figure 9:
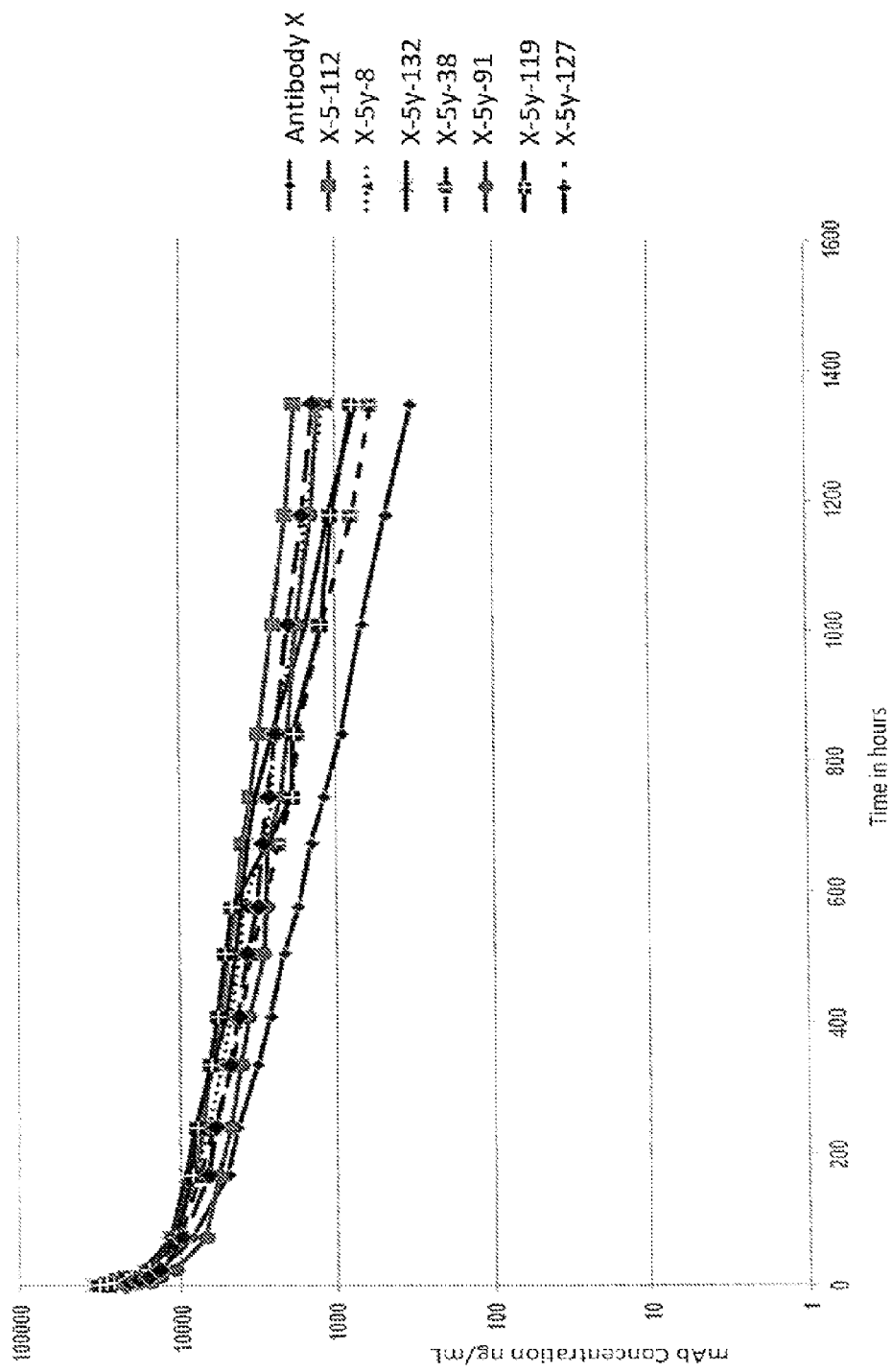
FIG. 9: Average concentrations of antibodies containing variant and control Fc-fragments as a function of time post-injection in cynomolgus monkeys. The x axis indicates time in hours post-injection, and the y axis indicates the concentration of the antibody in nanograms per milliliter (ng/mL) in peripheral blood of cynomolgus monkeys that have been injected with an antibody.

As shown in FIG. 9, variant versions of Antibody X containing all variant Fc-fragments tested demonstrated higher mAb concentrations in cynomolgus monkeys at most sampling time points, including all time points beyond 400 hours, compared to unmodified Antibody X. Further, some variants were comparable to X-5-112, which had previously been tested, including X-5y-8, X-5y-127, and X-5y-91.

Table 11 below shows the half life (T½), exposure (area under the curve (AUC)) and clearance rate(CI) of Antibody X and variants thereof in each of the cynomolgus monkeys in the study.

TABLE 11

Individual values for half life (T½), exposure (AUC), and clearance (CI).

| Antibody (monkey identification number) | T½ (hours) | AUC (µg * hr/mL) | CI (mL/kg/hr) |
|---|---|---|---|
| Antibody X (#201) | 269 | 3356 | 0.29 |
| Antibody X (#202) | 351 | 3745 | 0.253 |
| X-5-112 (#203) | 469 | 5843 | 0.148 |
| X-5-112 (#204) | 677 | 7752 | 0.099 |
| X-5y-8 (#205) | 389 | 5484 | 0.168 |
| X-5y-8 (#206) | 520 | 6611 | 0.13 |
| X-5y-132 (#207) | 139 | 5962 | 0.167 |
| X-5y-132 (#208) | 531 | 6770 | 0.127 |
| X-5y-38 (#209) | 258 | 5454 | 0.178 |
| X-5y-38 (#210) | 428 | 4563 | 0.199 |
| X-5y-91 (#211) | 626 | 3742 | 0.213 |
| X-5y-91 (#212) | 684 | 5162 | 0.151 |
| X-5y-119 (#213) | 39 | 4713 | 0.212 |
| X-5y-119 (#214) | 465 | 7272 | 0.12 |
| X-5y-127 (#215) | 529 | 4825 | 0.176 |
| X-5y-127 (#216) | 679 | 5946 | 0.132 |

All variants showed increased half lives and AUC compared to that of Antibody X in at least one of the two monkeys injected with each. In monkeys #207 and #213, X-5Y132 and X-5y-119, respectively, had shorter half lives than Antibody X. This could be interpreted to mean that these particular monkeys developed anti-drug antibodies, which led to more rapid clearance of the antibodies. AUC values were also greater than those of Antibody X for most of the variants tested.

Averaged data for these pharmacokinetic parameters, which omits monkeys #207 and #213, is shown in Table 12 below. Values from a previous study reported in Table 6 above are included for Antibodies X and X-5-112, which show that the values are relatively constant from one study to the next.

TABLE 12

Mean values for half life (T½), exposure (AUC), and clearance (Cl).

| Antibody (n) | T½ (hours) | AUC (μg * hr/mL) | Cl (mL/kg/hr) |
|---|---|---|---|
| Antibody X (n = 2)* | 335 | 3890 | 0.247 |
| Antibody X (n = 2) | 310 | 3550 | 0.272 |
| X-5-112 (n = 2)* | 529 | 7810 | 0.108 |
| X-5-112 (n = 2) | 573 | 6795 | 0.123 |
| X-5y-8 (n = 2) | 455 | 6044 | 0.149 |
| X-5y-132 (n = 1)# | 531 | 6770 | 0.127 |
| X-5y-38 (n = 2) | 343 | 5008 | 0.185 |
| X-5y-91 (n = 2) | 655 | 4452 | 0.182 |
| X-5y-119 (n = 1)# | 465 | 7272 | 0.12 |
| X = 5y-127 (n = 2) | 604 | 5386 | 0.154 |

*These are values from a previous study reported in Example 9 and Table 6 and included here for comparison.
Only one of the two monkeys tested in this study was included because it is suspected that anti-drug antibodies are the cause of rapid clearance observed in the other monkey.

These data show that pharmacokinetic parameters for Antibody X and for X-5-112 were relatively constant from one study to the next. They also indicate that half life and exposure are increased in all variants tested. Thus, these data generally indicate that increased binding of a variant Fc-fragment to FcRn at pH 5.5-6.0 (relative to a control Fc-fragment) and rapid dissociation from FcRn at pH 7.4 correlate with a longer in vivo half-life of an antibody containing the variant Fc-fragment in cynomolgus monkeys.

Example 13

In Vivo Characterization of a Variant Fc-Containing Antibody Having a Non-Linear PK Profile To determine whether the PK properties of an antibody having a non-linear PK profile could be improved by the insertion of one of peptides described herein, the insertion in variant Fc fragment Fc-5-112 was transferred into Antibody Y, a human IgG2 antibody having a non-linear PK profile. This variant form of Antibody Y, a variant IgG2 antibody called Y-5-112, was made essentially as described above, except using different PCR primers appropriate for making the required alteration in Antibody Y.

Antibodies were prepared as described above in Example 9. Cynomolgus monkeys (n=2/group) received a single intravenous dose of Antibody Y or Antibody Y-5-112 at a dose of 10 mg/kg and were followed during an 8-week in-life phase. Blood samples were collected at pre-dose, and 0.083 (5 min), 0.25, 0.5, 1, 2, 4, 6, 8, 12, 24, 36, 48, 72, 96, 120, 144, 168, 192, 216, 240, 264, 288, 312, 336, 384, 432, 480, 528, 576, 624, 672, 720, 768, 816, 864, 912, 960, 1008, 1056, 1104, 1152, 1200, 1248, 1296, and 1344 hours post dose.

Concentrations in cynomolgus monkey serum were determined using a sandwich ELISA. A mouse anti-human antibody was diluted in PBS and added to the wells of a 96-well microtiter plate. After a nominal 5° C. incubation lasting overnight or up to three days, the well contents were discarded and a blocking buffer comprised of blocker BLOTTO (Thermo® Scientific) was dispensed into plate wells. After a minimum one-hour incubation at ambient room temperature (ART), plate wells were emptied and washed six times with 1× Wash Solution (2 mM imidazole, 0.02% Tween 20, 0.5 mM EDTA, 160 mM NaCl, which is sold by KPL, Inc. as a 20× solution). Study specimens, assay standards and quality control samples prepared in 100% monkey serum, were diluted 50-fold in blocker BLOTTO prior to adding to plate wells. The contents of the plate wells were mixed while incubating for 60 minutes on a plate shaker. Next, plate wells were washed and horseradish peroxidase-labeled mouse anti-human antibody was added to the plate wells. After a final one-hour incubation, plate wells were washed and developed using one component 3,3',5,5'-tetramethylbenzidine (TMB) substrate solution. The resulting colorimetric reaction was quenched by adding sulfuric acid to plate wells. Optical densities were determined at dual wavelengths of 450 nm and 650 nm, and the value obtained at 650 nm was subtracted from the value obtained at 450 nm. The conversion of OD values into concentrations for the diluted study specimens was achieved through data regression using a logistic model with weighting set to $1/Y^2$ in Watson LIMS version 7.0.0.01.

Figure 10:
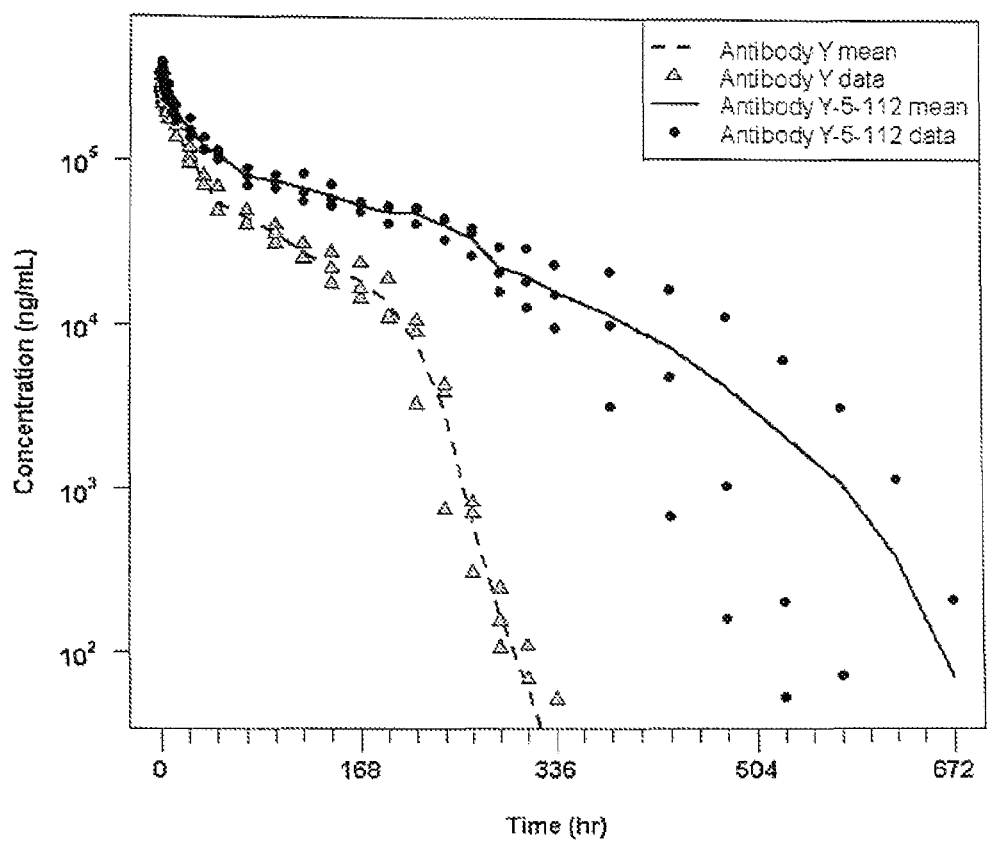
FIG. 10: Average concentrations of antibodies containing variant and control Fc-fragments as a function of time post-injection in cynomolgus monkeys. The x axis indicates time in hours post-injection, and the y axis indicates the concentration of the antibody in nanograms per milliliter (ng/mL) in peripheral blood of cynomolgus monkeys that have been injected with an antibody. As indicated, filled circles represent individual data points for cynomolgus monkeys injected with Y-5-112, and the solid line represents the mean of these data. Similarly, triangles represent individual data points for cynomolgus monkeys injected with Antibody Y, and the dashed line represents the mean of these data.

As shown in FIG. 10, Antibody Y has a biphasic PK profile with an approximately linear phase extending from 0 hours to about 216 hours. Thereafter, Antibody Y concentration drops off precipitously. Antibody Y-5-112 has a similar profile except that the linear, gradually-descending portion of the profile extends from about 0 hours to about 432 hours. Thus, the insertion in Antibody Y-5-112 apparently decreases the slope of the linear portion of the PK profile, thus increasing overall exposure as compared to Antibody Y.

What is claimed is:

1. A variant Fc-polypeptide comprising a human IgG1, IgG2, IgG3, or IgG4 variant Fc-fragment,
   wherein the variant Fc-fragment comprises an insertion:
   between amino acids 382 and 383, amino acids 383 and 384, amino acids 384 and 385, amino acids 385 and 386, amino acids 386 and 387, amino acids 387 and 388, or amino acids 388 and 389, using the EU numbering system shown in Table 1, or
   wherein amino acids 384-386 are deleted and the insertion is between amino acids 383 and 387, using the EU numbering system,
   wherein the insertion is 10-16 amino acids and comprises at least one cysteine among the first four inserted amino acids and at least one cysteine among the last four inserted amino acids,
   wherein the variant Fc-polypeptide binds to a human neonatal Fc receptor (hFcRn) with higher binding activity at pH 6.0 than a control Fc-polypeptide that has the same amino acid sequence as the variant Fc-polypeptide except that it does not contain the insertion, and
   wherein the variant Fc-polypeptide has little or no binding activity for binding to hFcRn at pH 7.4 and any residual binding response detected at pH 7.4 is no more than 0.1 nanometer more than that detected using the control Fc-polypeptide.

2. The variant Fc-polypeptide of claim 1, wherein the insertion in the variant human Fc-fragment is between amino acids 384 and 385, using the EU numbering system.

3. The variant Fc-polypeptide of claim 1, wherein the first three amino acids of the insertion are Gly-Gly-Cys and the last three amino acids of the insertion are Cys-Gly-Gly.

4. The variant Fc-polypeptide of claim 1, wherein the insertion in the variant Fc-fragment comprises the amino acid sequence of any one of SEQ ID NOs: 15-24, 41-53, 90-356, 359-367, 369, 372, 373, and 375-379.

5. The variant Fc-polypeptide of claim 3 or 4, wherein the insertion in the variant Fc-fragment has the amino acid sequence of any one of SEQ ID NOs: 41-45, 97, 127, 180, 208, 216, and 221.

6. The variant Fc-polypeptide of claim 1, wherein the insertion is between amino acids 384 and 385, using the EU numbering system, and wherein the insertion comprises the amino acid sequence of any one of SEQ ID NOs: 15-24, 41-53, 90-356, 359-367, 369, 372, 373, and 375-379.

7. The variant Fc-polypeptide of claim 1, wherein said variant Fc-polypeptide:
   is a variant Fc fusion protein comprising a non-antibody polypeptide,
   is an antibody comprising a $V_H$ region, a $V_L$ region, a $C_H2$ region, and a $C_H3$ region,
   is monovalent or divalent, and/or
   is a dimer or a tetramer.

8. A nucleic acid encoding the variant Fc-polypeptide of claim 1 or 3.

9. A host cell containing the nucleic acid of claim 8.

10. A method for making a variant Fc-polypeptide comprising:
culturing a host cell containing a nucleic acid under conditions such that the nucleic acid is expressed, and
recovering the expressed variant Fc-polypeptide from the culture medium or the cell mass,
wherein the nucleic acid encodes a variant Fc-polypeptide comprising a human IgG1, IgG2, IgG3, or IgG4 variant Fc-fragment,
wherein the variant Fc-fragment comprises an insertion:
between amino acids 382 and 383, amino acids 383 and 384, amino acids 384 and 385, amino acids 385 and 386, amino acids 386 and 387, amino acids 387 and 388, or amino acids 388 and 389, using the EU numbering system shown in Table 1, or
wherein amino acids 384-386 are deleted and the insertion is between amino acids 383 and 387, using the EU numbering system,
wherein the insertion is 10-16 amino acids and comprises at least one cysteine among the first four inserted amino acids and at least one cysteine among the last four inserted amino acids,
wherein the variant Fc-polypeptide binds to a human neonatal Fc receptor (hFcRn) with higher binding activity at pH 6.0 than a control Fc-polypeptide that has the same amino acid sequence as the variant Fc-polypeptide except that it does not contain the insertion, and
wherein the variant Fc-polypeptide has little or no binding activity for binding to hFcRn at pH 7.4 and any residual binding response detected at pH 7.4 is no more than 0.1 nanometer more than that detected using the control Fc-polypeptide.

11. A method for extending the half life of an Fc-polypeptide comprising a human IgG Fc-fragment comprising the following steps:
selecting a site in the Fc-fragment, wherein said site is:
between amino acids 382 and 383, amino acids 383 and 384, amino acids 384 and 385, amino acids 385 and 386, amino acids 386 and 387, amino acids 387 and 388, or amino acids 388 and 389, using the EU numbering system shown in Table 1, or
wherein amino acids 384-386 are deleted and the insertion is between amino acids 383 and 387, using the EU numbering system,
wherein the insertion is 10-16 amino acids and comprises at least one cysteine among the first four inserted amino acids and at least one cysteine among the last four inserted amino acids; and
inserting a peptide into the selected site, wherein the peptide comprises an amino acid sequence selected from the group consisting of: SEQ ID NOs:41-53, 90-356, 359-367, 369, 372, 373, and 375-379.

12. The method of claim 10 or 11,
wherein the insertion is between amino acids 382 and 383, amino acids 383 and 384, amino acids 384 and 385, or amino acids 385 and 386 using the EU numbering system or
wherein amino acids 384-386 are deleted and the insertion is between amino acids 383 and 387 using the EU numbering system.

13. A method for identifying a human IgG variant Fc-fragment that confers a longer in vivo half life on a variant Fc-polypeptide that comprises the variant Fc-fragment, as compared to a control Fc-polypeptide, comprising the following steps:
(a) creating a library of nucleic acids encoding variant Fc-fragments containing an insertion between:
amino acids 382 and 383, amino acids 383 and 384, amino acids 384 and 385, amino acids 385 and 386, amino acids 386 and 387, amino acids 387 and 388, or amino acids 388 and 389 of the variant Fc-fragment, using the EU numbering system shown in Table 1, or
wherein amino acids 384-386 are deleted and the insertion is between amino acids 383 and 387, using the EU numbering system,
wherein the insertion is 10-16 randomized amino acids, and wherein said insertion comprises at least one cysteine among the first four inserted amino acids and at least one cysteine among the last four inserted amino acids;
(b) screening Fc-fragments encoded by the library to identify the variant Fc-fragments that (i) bind to hFcRn with higher binding activity at pH 6 than a control Fc-fragment and (ii) have little or no binding activity for binding to hFcRn at pH 7.4;
(c) constructing a nucleic acid encoding a variant Fc-polypeptide comprising a variant Fc-fragment identified in (b), wherein the concentration of a control Fc-polypeptide, which comprises a control Fc-fragment rather than the variant Fc-fragment, is known to decrease linearly over time when administered to an animal in vivo;
(d) introducing the nucleic acid of (c) into a host cell and culturing the host cell under conditions such that the variant Fc-polypeptide encoded by the nucleic acid can be expressed;
(e) recovering the variant Fc-polypeptide from the cell mass or cell culture medium;
(f) administering the variant Fc-polypeptide to an animal and administering the control Fc-polypeptide to another animal; and
(g) monitoring the concentrations of the variant and control Fc-polypeptides in peripheral blood over time subsequent to administration, thereby identifying a variant Fc-fragment that confers a longer in vivo half life and greater exposure on a variant Fc-polypeptide.

14. The method of claim 13, wherein the insertion of step (a) is between positions 384 and 385 using the EU numbering system as illustrated in Table 1.

15. The variant Fc-polypeptide of claim 1 or 3, wherein the insertion is within amino acids 383 to 387 using the EU numbering system shown in Table 1.

16. The variant Fc-polypeptide of claim 1 or 3, wherein the residual binding response is determined by bio-layer interferometry.

* * * * *

UNITED STATES PATENT AND TRADEMARK OFFICE
CERTIFICATE OF CORRECTION

PATENT NO.        : 9,688,756 B2                                     Page 1 of 1
APPLICATION NO.   : 14/367183
DATED             : June 27, 2017
INVENTOR(S)       : Jeonghoon Sun et al.

It is certified that error appears in the above-identified patent and that said Letters Patent is hereby corrected as shown below:

In the Claims

Claim 4, Line 1, replace "The variant Fc-polypeptide of claim 1, wherein" with -- The variant Fc-polypeptide of claim 1 or 3, wherein --

Claim 5, Line 1, replace "The variant Fc-polypeptide of claim 3 or 4, wherein" with -- The variant Fc-polypeptide of claim 4, wherein --

Claim 6, Line 1, replace "The variant Fc-polypeptide of claim 1, wherein" with -- The variant Fc-polypeptide of claim 1 or 3, wherein --

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*